United States Patent
Kelly et al.

(10) Patent No.: US 10,287,566 B2
(45) Date of Patent: *May 14, 2019

(54) DHAD VARIANTS AND METHODS OF SCREENING

(71) Applicant: Butamax Advanced Biofuels LLC, Wilmington, DE (US)

(72) Inventors: Kristen J. Kelly, Wilmington, DE (US); Rick W. Ye, Hockessin, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 65 days.

This patent is subject to a terminal disclaimer.

(21) Appl. No.: 15/406,876

(22) Filed: Jan. 16, 2017

(65) Prior Publication Data

US 2017/0226497 A1    Aug. 10, 2017

Related U.S. Application Data

(63) Continuation of application No. 14/207,823, filed on Mar. 13, 2014, now Pat. No. 9,580,705.

(60) Provisional application No. 61/789,204, filed on Mar. 15, 2013.

(51) Int. Cl.
| | | |
|---|---|---|
| *C12N 9/88* | (2006.01) | |
| *C12P 7/16* | (2006.01) | |
| *C12P 7/40* | (2006.01) | |
| *B01D 11/04* | (2006.01) | |
| *C12N 15/52* | (2006.01) | |

(52) U.S. Cl.
CPC .............. *C12N 9/88* (2013.01); *B01D 11/04* (2013.01); *C12N 15/52* (2013.01); *C12P 7/16* (2013.01); *C12P 7/40* (2013.01); *C12Y 101/01001* (2013.01); *C12Y 101/01086* (2013.01); *C12Y 202/01006* (2013.01); *C12Y 402/01009* (2013.01); *Y02E 50/10* (2013.01); *Y02P 20/52* (2015.11)

(58) Field of Classification Search
CPC combination set(s) only.
See application file for complete search history.

(56) References Cited

U.S. PATENT DOCUMENTS

| | | | |
|---|---|---|---|
| 4,683,202 A | 7/1987 | Mullis | |
| 5,643,779 A | 7/1997 | Erlich et al. | |
| 6,177,264 B1 | 1/2001 | Eggeling et al. | |
| 6,699,703 B1 | 3/2004 | Doucette-Stamm et al. | |
| 7,541,173 B2 | 6/2009 | Bramucci et al. | |
| 7,659,104 B2 | 2/2010 | Bramucci et al. | |
| 7,851,188 B2 | 12/2010 | Donaldson et al. | |
| 7,910,342 B2 | 3/2011 | Liao et al. | |
| 7,932,063 B2 | 4/2011 | Dunson et al. | |
| 7,993,889 B1 | 8/2011 | Donaldson et al. | |
| 8,017,364 B2 | 9/2011 | Bramucci et al. | |
| 8,017,376 B2 | 9/2011 | Dundon et al. | |
| 8,071,358 B1 | 12/2011 | Dundon et al. | |
| 8,129,162 B2 | 3/2012 | Li et al. | |
| 8,178,328 B2 | 5/2012 | Donaldson et al. | |
| 8,188,250 B2 | 5/2012 | Bramucci et al. | |
| 8,206,970 B2 | 6/2012 | Eliot et al. | |
| 8,222,017 B2 | 7/2012 | Li et al. | |
| 8,232,089 B2 | 7/2012 | Urano et al. | |
| 8,241,878 B2 | 8/2012 | Anthony et al. | |
| 8,273,558 B2 | 9/2012 | Donaldson et al. | |
| 8,273,565 B2 | 9/2012 | Dundon et al. | |
| 8,283,144 B2 | 10/2012 | Donaldson et al. | |
| 8,372,612 B2 | 2/2013 | Larossa et al. | |
| 8,389,252 B2 | 3/2013 | Larossa | |
| 8,455,224 B2 | 6/2013 | Paul | |
| 8,455,225 B2 | 6/2013 | Bramucci et al. | |
| 8,465,964 B2 | 6/2013 | Anthony et al. | |
| 8,518,678 B2 | 8/2013 | Flint et al. | |
| 8,557,562 B2 | 10/2013 | Bramucci et al. | |
| 8,614,085 B2 | 12/2013 | Van Dyk et al. | |
| 8,617,861 B2 | 12/2013 | Grady et al. | |
| 8,637,269 B2 | 1/2014 | Anthony et al. | |
| 8,637,281 B2 | 1/2014 | Paul et al. | |
| 8,652,823 B2 | 2/2014 | Flint et al. | |
| 8,889,385 B2 | 2/2014 | Donaldson et al. | |
| 8,669,094 B2 | 3/2014 | Anthony et al. | |
| 8,691,540 B2 | 4/2014 | Bramucci et al. | |
| 8,735,114 B2 | 5/2014 | Donaldson et al. | |
| 8,765,433 B2 | 7/2014 | Gude et al. | |
| 8,785,166 B2 | 7/2014 | Anthony et al. | |

(Continued)

FOREIGN PATENT DOCUMENTS

| | | |
|---|---|---|
| CA | 2716427 | 8/2009 |
| EP | 1887081 | 2/2008 |

(Continued)

OTHER PUBLICATIONS

Arthur, et al., Contribution of VanY D,D-Carboxypeptidase to Glycopeptide Resistance in Enterococcus faecalis by Hydrolysis of Peptidoglycan Precursors, Antimicrob. Agents Chemother. 38:1899-1903, 1994.
Wycoff, et al., Characterization and sequence analysis of a stable cryptic plasmid from Enterococcus faecium 226 and development of a stable cloning vector, Appi. Environ. Microbiol. 62:1461-1466, 1996.
Zirkle, et al., Analysis of a 108-kb region of the Saccharopolyspora spinosa genome covering the obscurin polyketide synthase locus, DNA Sequence 15:123-134, 2004.
Dickinson, et al., An investigation of the metabolirns of valine to isobutyl alcohol in *Saccharomyces cerevisiae*, J. Biol. Chem. 273: 25751-25756,1998.

(Continued)

*Primary Examiner* — Kagnew H Gebreyesus

(57) ABSTRACT

Methods of screening for dihydroxy-acid dehydratase (DHAD) variants that display increased DHAD activity are disclosed, along with DHAD variants identified by these methods. Such enzymes can result in increased production of compounds from DHAD requiring biosynthetic pathways. Also disclosed are isolated nucleic acids encoding the DHAD variants, recombinant host cells comprising the isolated nucleic acid molecules, and methods of producing butanol.

14 Claims, 3 Drawing Sheets

Specification includes a Sequence Listing.

(56) References Cited

U.S. PATENT DOCUMENTS

| | | | |
|---|---|---|---|
| 8,795,992 | B2 | 8/2014 | Bramucci et al. |
| 8,828,694 | B2 | 9/2014 | Anthony et al. |
| 8,828,695 | B2 | 9/2014 | Grady et al. |
| 8,828,704 | B2 | 9/2014 | Donaldson et al. |
| 8,871,488 | B2 | 10/2014 | Dauner et al. |
| 8,895,307 | B2 | 11/2014 | Li et al. |
| 8,906,666 | B2 | 12/2014 | Alsaker |
| 8,911,981 | B2 | 12/2014 | Li et al. |
| 8,940,511 | B2 | 1/2015 | Larossa |
| 8,945,859 | B2 | 2/2015 | Donaldson et al. |
| 8,945,899 | B2 | 2/2015 | Li et al. |
| 8,951,774 | B2 | 2/2015 | Donaldson et al. |
| 8,951,937 | B2 | 2/2015 | Flint et al. |
| 8,956,850 | B2 | 2/2015 | Anthony et al. |
| 8,962,298 | B2 | 2/2015 | Donaldson et al. |
| 8,969,055 | B2 | 3/2015 | Grady et al. |
| 8,969,065 | B2 | 3/2015 | Anthony et al. |
| 8,980,612 | B2 | 3/2015 | Donaldson et al. |
| 9,068,190 | B2 | 6/2015 | Donaldson et al. |
| 9,080,179 | B2 | 7/2015 | Paul |
| 9,163,266 | B2 | 10/2015 | Anthony |
| 9,169,467 | B2 | 10/2015 | Govindarajan et al. |
| 9,169,499 | B2 | 10/2015 | Paul et al. |
| 9,181,566 | B2 | 11/2015 | Dauner et al. |
| 9,206,447 | B2 | 12/2015 | Anthony et al. |
| 9,238,801 | B2 | 1/2016 | Li et al. |
| 9,238,828 | B2 | 1/2016 | McElvain et al. |
| 9,260,708 | B2 | 2/2016 | Anthony et al. |
| 9,267,157 | B2 | 2/2016 | Anthony et al. |
| 9,273,330 | B2 | 3/2016 | Bramucci et al. |
| 9,284,612 | B2 | 3/2016 | Liao et al. |
| 9,297,016 | B2 | 3/2016 | Flint et al. |
| 9,297,028 | B2 | 3/2016 | Donaldson et al. |
| 9,297,029 | B2 | 3/2016 | Donaldson et al. |
| 9,303,225 | B2 | 4/2016 | Donaldson et al. |
| 9,365,872 | B2 | 6/2016 | Donaldson et al. |
| 9,388,392 | B2 | 7/2016 | Govindarajan et al. |
| 9,404,117 | B2 | 8/2016 | Anthony |
| 9,422,582 | B2 | 8/2016 | Anthony et al. |
| 2003/0166179 | A1 | 9/2003 | Rajgarhia et al. |
| 2007/0031918 | A1 | 2/2007 | Dunson et al. |
| 2008/0293125 | A1 | 11/2008 | Subbian et al. |
| 2009/0081746 | A1 | 3/2009 | Liao et al. |
| 2009/0162911 | A1 | 6/2009 | Larossa et al. |
| 2009/0305369 | A1 | 12/2009 | Donaldson et al. |
| 2010/0081154 | A1 | 4/2010 | Flint et al. |
| 2010/0081182 | A1 | 4/2010 | Paul et al. |
| 2010/0093020 | A1 | 4/2010 | Bramucci et al. |
| 2010/0120105 | A1 | 5/2010 | Anthony et al. |
| 2010/0221802 | A1 | 9/2010 | Grady et al. |
| 2011/0039327 | A1 | 2/2011 | Winkler et al. |
| 2011/0076733 | A1 | 3/2011 | Urano et al. |
| 2011/0195505 | A1 | 8/2011 | Euler et al. |
| 2011/0244536 | A1 | 10/2011 | Nagarajan et al. |
| 2011/0287500 | A1 | 11/2011 | Urano et al. |
| 2011/0294179 | A1 | 12/2011 | Grady et al. |
| 2012/0034666 | A1 | 2/2012 | Hawkins et al. |
| 2012/0058541 | A1 | 3/2012 | Alsaker et al. |
| 2012/0149080 | A1 | 6/2012 | Bramucci et al. |
| 2012/0196341 | A1 | 8/2012 | Donaldson et al. |
| 2012/0258873 | A1 | 10/2012 | Gibson et al. |
| 2013/0035515 | A1 | 2/2013 | Dobson et al. |
| 2013/0252296 | A1 | 9/2013 | Maggio-Hall et al. |
| 2014/0030782 | A1 | 1/2014 | Anthony et al. |
| 2014/0030783 | A1 | 1/2014 | Anthony et al. |
| 2014/0038263 | A1 | 2/2014 | Flint et al. |
| 2014/0038268 | A1 | 2/2014 | Flint et al. |
| 2014/0051137 | A1 | 2/2014 | Flint et al. |
| 2014/0093930 | A1 | 4/2014 | Li et al. |
| 2014/0141479 | A1 | 5/2014 | Anthony et al. |
| 2014/0170732 | A1 | 6/2014 | Bramucci et al. |
| 2014/0186910 | A1 | 7/2014 | Rothman et al. |
| 2014/0186911 | A1 | 7/2014 | Anthony et al. |
| 2014/0273116 | A1 | 9/2014 | Kelly et al. |
| 2014/0273129 | A1 | 9/2014 | Bhalla et al. |
| 2014/0273130 | A1 | 9/2014 | Anthony et al. |
| 2014/0349349 | A1 | 11/2014 | Dauner et al. |
| 2014/0377824 | A1 | 12/2014 | Satagopan et al. |
| 2015/0037855 | A1 | 2/2015 | Bhadra et al. |
| 2015/0111269 | A1 | 4/2015 | Li et al. |
| 2015/0125920 | A1 | 5/2015 | Anthony et al. |
| 2015/0218595 | A1 | 8/2015 | Bhadra et al. |
| 2015/0240267 | A1 | 8/2015 | Anthony et al. |
| 2016/0024534 | A1 | 1/2016 | Anthony et al. |
| 2016/0130612 | A1 | 5/2016 | Anthony et al. |
| 2016/0138050 | A1 | 5/2016 | Bramucci et al. |
| 2016/0222370 | A1 | 8/2016 | Anthony et al. |
| 2016/0319307 | A1 | 11/2016 | Nagarajan et al. |
| 2016/0326551 | A1 | 11/2016 | Van Dyk et al. |
| 2016/0326552 | A1 | 11/2016 | Dauner et al. |

FOREIGN PATENT DOCUMENTS

| | | |
|---|---|---|
| WO | WO2006059111 | 6/2006 |
| WO | WO2007020992 | 2/2007 |
| WO | WO2007106524 | 9/2007 |
| WO | WO2008098227 | 8/2008 |
| WO | WO2009086423 | 7/2009 |
| WO | WO2009149270 | 12/2009 |
| WO | WO2010037111 | 4/2010 |
| WO | WO2010037112 | 4/2010 |
| WO | WO2011019894 | 2/2011 |
| WO | WO2011066356 | 6/2011 |
| WO | WO2011103300 | 8/2011 |
| WO | WO2012071121 | 5/2012 |

OTHER PUBLICATIONS

Durre, New insights and novel developments in ciostridal acetone/butanol/isopropanol fermentation, Appl. Microbial. Biotechnol. 49:639-648, 1998.

Eden, et al., Involvement of branched-chain amino acid aminotransferases in the production of fusel alcohols during fermentation in yeast, Appl. Microbial, Biotechnol. 55:296-300, 2001.

Eichenbaum, et al., Use of the Lactococcal nisA promoter to regulate gene expression in gram-positive bacteria: comparison of induction level and promoter strength Appl. Environ. Microbiol. 64:2763-2769, 1998.

Flint, et al., Dihydroxy acid dehydratase from spinach contains a [2Fe—2S] cluster, J Biol. Chem. 263:3558-3564, 1988.

Flint, et al., Studies on the active site of dihydroxy-acid dehydratase, Bioorganic Chem. 21:367-385, 1993.

Flint, et al., The Inactivation of Fe—S Cluster Containing Hydrolyases by Superoxide, J. Biol. Chem. 268:22369-22376, 1993.

Fujimoto; et al., pAM401-Based Shuttle Vectors That Enable Overexpression of Promaterless Genes and One-Step Purification of Tag Fusion Proteins Directly from Enterococcus faecalis, Appl. Environ. Microbiol. 67:1262-1267, 2001.

Godon, et al., Branched-chain amino acid biosynthesis genes in *Lactococcus lactis* subsp. *lactis*, J. Bacteriol. 174:6580-6589, 1992.

Gossens, et al., Control of diacetyl formation by the intensification of the anabolic flux of acetohydroxyacid intermediates, European Brewery Convention: Proceedings of the 21st Congress, Madrid, 1987, pp. 553-560.

Groot, et al.,Technologies for butanol recovery integrated with fermentations, Process. Biochem. 27:61-75, 1992.

Horton, et al., Engineering hybrid genes without the use of restriction enzymes: gene splicing by overlap extension, Gene 77:61-68, 1989.

Imlay, Iron-sulphur clusters and the problem with oxygen, Mol. Microbial. 59:1073-1082, 2006.

Kim, et al., Catalytic promiscuity in dihydroxy-acid dehydratase from the thermoacidophilic archaean Sulfotobus solfataricus, J. Biochem. 139: 591-596, 2006.

Kleerbezem, et al., Controlled Gene Expression Systems for Lactic Acid Bacteria: Transferable Nisin-Inducible Expression Cassettes for *Lactococcus, Leuconostoc,* and *Lactobacillus* spp. Appl. Environ. Microbiol. 63:4581-4584, 1997.

Maguin, et al., New thermosensitive plasrnid for gram-positive bacteria, J. Bacteriol. 174:5633-5638, 1992.

(56) References Cited

OTHER PUBLICATIONS

Methods in Yeast Genetics, 2005, Cold Spring Harbor Laboratory Press, Cold Spring Harbor, NY, pp. 201-202.
O'Sullivan, et al., High- and low-copy-numbe Lactococcus shuttle cloning vectors with features for clone screening, Gene 137:227-231, 1993.
Polaina, Cloning of the IL V2, IL V3 and IL V 5 Genes of *Saccharomyces cerevisiae*, Carlsberg Res. Commun., 49:577-584, 1984.
Renault, et al., Plasmid vectors for gram-positive bacteria switching from high to low copy number, Gene 183:175-182, 1996.
Rud, et al., A synthetic promoter library for constitutive gene expression in Lactobacillus plantarum, Microbiology 152:1011-1019, 2006.
Rupp, et al., Electron spin relaxation of iron-sulfur proteins studied by microwave power saturation, Biochirn, Biophys. Acta 537:255-269. 1978.
Scott, et al., Sequences of versatile broad-host-range vectors of the RK2 family, Plasmid 50:74-79, 2003.
Seffernick, et al., Melamine deaminase and atrazine chlorohydrolase: 98 percent identical but functionally different, J. Bacteriol. 183:2405-2410, 2001.
Sorvig, et al., Plasmid p256 from Lactobacillus plantarum represents a new type of replicon in lactic acid bacteria, and contains a toxin-antitoxin-like plasmid maintenance system, Microbiology 151:421-431, 2005.
Tanimoto, et al., Analysis of the Conjugal Transfer System of the Pheromone-Independent Highly Transferable Enterococcus Plasmid pMG1: Identification of a tra Gene (traA) Up-Regulated during Conjugation, J. Bacteriol. 184:5800-5804, 2002.
Thompson, et al., Clustal W: improving the sensitivity of progressive multiple sequence alignment through sequence weiahting, position-specific gap penalties and weight matrix choice, Nucleic Acids Research 22:4673-4680, 1994.
Van Kranenburg, et al., Functional Analysis of Three Plasrnids from Lactobacillus plantarum, Appl. Environ. Microbiol. 71:1223-1230, 2005.
Villa, et al., Control of Vicinal Diketone Production by Brewer's Yeast. I. Effects of ilv5 and IL V3 Gene Amplification on Vicinal Diketone Production and IL V Enzyme Activity, Journal of the American Society of Brewing Chemists, 53:49-53, 1995.
Watanabe, et al., Identification and characterization of L-Arabonate dehydratase, L-2-keto-3-deoxyarabonate dehydratase, and L-Arabinolactonase involved in an alternative pathway of L-Arabinose metabolism, J. Biol. Chem. 281:33521-3353, 2006.
Branden, et al., Introduction to Protein Structure, Garland Publishing Inc., New York p. 247, 1991.
Gellissen, et al., Heterologous protein production in yeast, Antonie van Leeuwenhoek 62:79-93, 1992.
Harashima, et al., Heterologous Protein Production by Yeast Host-Vector Systems, Biopress technol, 19:137-156, 1994.
Mendoza-Vega, et al., industrial production of heterologous proteins by fed-batch cultures of the yeast *Saccharomyces cerevisiae*, FEMS Microbiol. Rev. 15:369-410, 1994.
Roggenkamp, et al., Expression and processing of bacterial 8-lactanase in the yeast *Saccharomyces cerevisiae*, Proc. Natl. Acad. Sci. USA 78:4466-4470, 1981.
Romanos, et al., Foreign Gene Expression in Yeast: a Review, Yeast 8: 423-488, 1992.
Russell, et al., Production of Recombinant Products in Yeast: A Review, Australian J. Biotechol. 5:48-55, 1991.
Chica, et al., Semi-rational approaches to engineering enzyme activity: combining the benefits of directed evolution and rational design, Curr. Opin. Biotechnol. 16:378-384, 2005.
Johnson, et al., Structure, Function, and Formation of Biological Iron-Sulfur Clusters, Ann. Rev. Biochern. 74:247-281, 2005.
Chen, et al., Role of NifS in maturation of glutamine phosphoribosylpyrophosphate amidotransferase, J. Bacteriol. 179:7567-7590, 1997.

Flint, *Escherichia coli* Contains a Protein That Is Homologous in Function and N-terminal Sequence to the Protein Encoded by the nifS Gene of Azotobacter vinelandil and That Can Participate in the Synthesis of the Fe—S Cluster of Dihydroxy-acid Dehydratase, J. Biol. Chem, 271:16068-16074, 1996.
Ui, et al., Production of L-2,3-butanediol by a new pathway constructed in *Escherichia coli*, Lett. Appl. Microbiol. 39:533-537, 2004.
Karlin, et al., Comparative analysis of gene expression among low G+C gram-positive genomes, Proc. Natl. Acad. Sci USA 101:6182-6187, 2004.
Henriksen, et al., Redirection of pyruvate catabolism in Lactococcus lactis by selection of mutants with additional growth requirements, Appl. Microbiol. Biotechnol, 56:767-775, 2001.
Neves, et al. Metabolic characterization of Lactococcus lactis deficient in lactate dehydrogenase using in vivo 13CNMR, Eur. J. Biochem. 267:3859-3868, 2000.
Chen, Ph.D. Thesis, McGill University, Montreal, Canada, Formation and Analysis of Fusel Alcohols in Beer, 1978.
Broun, et al., Catalytic Plasticity of Fatty Acid Modification Enzymes Underlying Chemical Diversity of Plant Lipids, Science 282:1315-1317, 1998.
Devos, et al. Practical Limits of Function Prediction, Proteins: Structure, Function and Genetics 41:98-107, 2000.
Kisselev, Polypeptide Release Factors in Prokaryotes and Eukaryotes: Same Function, Different Structure, Structure 10:8-9, 2002.
Madera, et al., A comparison of profile hidden Markov model procedures for remote homology detection, Nuc. Acids Res. 30:4321-4328, 2002.
Sen, et al. Developments in Directed Evolution for Improving Enzyme Functions, Appl. Biochem. Biotechnol. 143:212-223, 2007.
Stanke, et al., Gene prediction with hidden Markov model and a new intron submodel, Bioinformatics 19 Suppl.2: 215-225, 2003.
Whisstock, et al., Prediction of protein function from protein sequence and structure, Quarterly Reviews of Biophysics 36:307-340, 2003.
Wishart, et al., A Single Mutation Converts a Novel Phosphotyrosine Binding Domain into a Dual-specificity Phosphate, J. Biol. Chem. 270:26782-26785, 1995.
Witkowski, et al., Conversion of a beta-Ketoacyl Synthase to a Malonyl Decarboxylase by Replacement of the Active-Site Cysteine with Glutamine, Biochern, 38:11643-11650, 1999.
Chen, et al., Inhibition of Fe—S cluster biosynthesis decreases mitochondrial iron export: Evidence that Yfh1p affects Fe—S cluster synthesis, Proc. Natl. Acad. Sci. 99:12321-12326, 2002.
Jensen, et al., Role of *Saccharomyces cerevisiae* ISA1 and ISA2 in Iron Homeostasis, Mol. Cell Biol. 20:3918-3927, 2000.
Nakamura, et al., Hyperproduction of Recombinant Ferredoxins in *Escherichia coli* by Coexpression of the ORF1-ORF2-iscS-iscU-iscA-hscB-hscA-fdx-ORF3 Gene Cluster, J. Biochem. 126:10-18, 1999.
Garland, et al., *Saccharornyces cerevisiae* ISU1 and ISU2: Members of a Well-conserved Gene Family for Iron-Sulfur Cluster Assembly, J. Mol. Biol. 294:897-907,1999.
Altschul, et al., Basic Local Alignment Search Tool, J. Mol. Biol. 215:403-410, 1990.
Flint, et al., The role and properties of the iron-sulfur cluster in *Escherichia coli* dihydroxy-acid dehydratase. J. Biol. Chem, 268:14732-14742, 1993.
Deshpande, et al., Ethanol Production from Cellulose by Coupled Saccharification/Fermentation using *Saccharomyces cerevisiae* and Cellulase Complex from Sclerotium rolfsii UV-8 Mutant, Appl. Biochern, Biotechnol. 36:227-234, 1992.
Frohman, et al., Rapid production of full-length cDNAs from rare transcripts: Amplification using a single gene-specific oligonucleotide primer, Proc. Natl. Acad. Sci. 85:8998-9002, 1988.
Guo, et al. Pervaporation study on the dehydration of aqueous butanol solution: a comparison of flux vs. permeance, separation factor vs. selectivity, J. Membrane Sci. 245:199-210, 2004.
Hartmanis, et al., Dial Metabolism and Dial Dehydratase in Clostridium glycolicum, Arch. Biochem. Biophys. 245:144-152, 1986.
Higgins, et al., Fast and sensitive multiple sequence alignments on a microcomputer. Cabios Communications 5:151-153, 1989.

(56) References Cited

OTHER PUBLICATIONS

Higgins, et al., Clustal V: improved software for multiple sequence alignment, Cabios 8:189-191, 1992.
Krogh, et al., Hidden Markov Models in Computational Biology, J. Mol. Biol. 235:1501-1531, 1994.
Loh, et al., Polymerase Chain Reaction with Single-Sided Specificity: Analysis of T Cell Receptor Gamma Chain, Science 243:217-220, 1989.
Mnaimneh, et al., Exploration of Essential Gene Functions via Titratable Promoter Alleles, Cell 118:31-44, 2004.
O'Brien, et al., Insight into the Mechanism of the B12-Independent Glycerol Dehydratase from Clostridium butyricum: Preliminary Biochemical and Structural Characterization, Biochemistry 43:4635-4645, 2004.
O'Hara, et al, One-sided polymerase chain reaction: The amplification of cDNA, Proc. Natl. Acad. Sci. 86:5673-5677, 1989.
Scott, et al., Whole-Genome Transcription Profiling Reveals Genes Up-Regulated by Growth on Fucose in the Human Gut Bacterium "Roseburia inulinivorans," J. Bacteriol. 188:4340-4349, 2006.
Sulter, et al., Proliferation and metabolic significance of peroxisomes in Candida boidinii during growth on o-alanine or oleic acid as the sole carbon source, Arch. Microbiol. 153:485-489, 1990.
Tabor, et al., A bacteriophage T7 RNA polymerase/promoter system for controlled exclusive expression of specific genes, Proc. Nat. Acad. Sci. 82:1074-1078, 1985.
Van Ness, et al., The use of oligodeoxynucleotide probes in chaotrope-based hybridization solutions, Nucl. Acid Res. 19:5143-5151, 1991.
Wach, et al., New Heterologous Modules for Classical or PCR-based Gene Disruptions in Saccharomyces cerevisiae, Yeast 10:1793-1808, 1994.
Walker, et al., Isothermal in vitro amplification of DNA by a restriction enzyme/DNA polymerase system, Proc. Natl. Acad. Sci. 89:392-396, 1992.
Aden, et al. Lignoceilulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.
Flint, et al., The Inactivation of Dihydroxy-acid Dehydratase in Escherichia coli Treated with Hyperbaric Oxygen Occurs Because of the Destruction of its Fe-S Cluster, but the Enzyme Remains in the Cell in a FormThat Can Be Reactivated, J. Biol. Chem. 268:25547-25552, 1993.
Bellion, et al., Microb. Growth C1 Compd., [Int. Symp.], 7th (1993), 415 32. Editor(s): Murrell, J. Collin; Kelly, Don P. Publisher: Intercept, Andover, UK.
Connor, et al., Engineering of an Escherichia coli Strain for the Production of 3-Methyl-1-Butanol, Appl. Environ. Microbiol. 74:5769-5775, 2008.
Malkin, et al., The Reconstitution of Clostridial Ferredoxin, Biochem. Biophys. Res. Comm. 23:822-827, 1996.
Liu, et al., Electron Paramagnetic Resonance Evidence for a Novel Interconversion of [3Fe—4S] and [4Fe—4S] Clusters with Endogenous Iron and Sulfide in Anaerobic Ribonucleotide Reductase Activase in Vitro, J. Biol. Chem, 275:12367-12373, 2000.
Tokumoto, et al., Genetic analysis of the isc operon in Escherichia coil involved in the biogenesis of cellular iron sulfur proteins, J. Biochem. 130:63-71, 2001.
Fontecave, et al., Mechanisms of iron-sulfur cluster assembly; the SUF machinery, J. Biol. Inorganic Chem. 10:713-721, 2005.
Elli, et al., Iron requirement of Lactobacillus spp. in completely chemically defined growth media, J. Appl. Microbial, 88:695-703, 2000.
Hebert, et al., Nutritional Requirements of Lactobacillus deibrueckii subsp. lactis in a Chemically Defined Medium. Curr. Microbiol. 49:341-345, 2004.
Duhutrel, et al., Iron Sources Used by the Nonpathogenic Lactic Acid Bacterium Lactobacillus sakei as Revealed by Electron Energy Loss Spectroscopy and Secondary-ion Mass Spectrometry, Appl. Environ. Microbiol. 76:560-565, 2009.

Rychlik, in Methods in Molecular Biology, White, B. A. Ed., (1993) vol. 15, pp. 31 39, PCR Protocols: Current Methods and Applications. Humania: Totowa, NK.
Sambrook, et al., Molecular Cloning: A Laboratory Manual, 2nd ed,, Cold Spring Harbor Laboratory: Cold Spring Harbor, NY (1989).
Imbert, et al. On the Iron Requirement of Lactobacilli Grown in Chemically Defined Medium, Curr. Microbiol. 37:64-66, 1998.
Pandey, et al., Iron requirement and search for siderophores in lactic acid bacteria, Appl. Microbiol. Biotechnol. 40:735-739, 1994.
Archibald, Lactobacillus plantarum, an organism not requiring iron, FEMS Microbiol. Lett. 19:29-32, 1983.
Shrago, et al.,Conjugal Plasmid Transfer (pAMb1) in Lactobacillus plantarum, Appl. Environ. Microbiol. 52:574-576, 1986.
Thein, et al., "The use of oligonucleotides as specific hybridization probes in the Diagnosis of Genetic Disorders," in Human Genetic Diseases: A Practical Approach, K. E. Davis Ed., (1986) pp. 33 50, IRL: Herndon, VA.
Cruz-Rodz, et al., High efficiency introduction of plasmid DNA into glycine treated Enterococcus Faecalis by electroporation, Moi. Gen. Gent. 224:152-154, 1990.
W. R. Pearson, Cornput. Methods Genome Res., [Proc. Int. Symp.] (1994), Meeting Date 1992, 111-120.
Velasco, et al., Cloning of the dihydroxyacid dehydratse-encoding gene (ILV3) from Saccharomyces cerevisiae, Gene 137:179-185, 1993.
Casey, Cloning and Analysis of Two Alleles of the ILV3 Gene from Saccharomyces cerevisiae, Carlsberg Research Communications 51:327-341. 1986.
Guo, et al., Protein tolerance to random amino acid change, Proc. Natl. Acad, Sci, 101:9205-9210, 2004.
Lazar, et al., Transforming Growth Factor alpha: Mutation of Aspartic Acid 47 and Leucine 48 Results in Different Biological Activity Mol. Cell Biol. 8:1247-1252, 1988.
Hill, et al., Functional Analysis of Conserved Histidines in ADP-Glucose Pyrophosphorylase from Escherichia coli, Biochem. Biophys. Res. Comm, 244:573-577, 1998.
Wacey, et al., Disentangling the perturbational effects of amino acid substitutions in DNA-binding domin of p53, Human Genetics 104:15-22, 1999.
Goldberg, et al., Localization and functionality of microsporidian iron-sulphur cluster assembly proteins, Nature 452:624-628. 2008.
Flint, et al., Studies on the synthesis of the Fe—S cluster of dihydroxy-acid dehydratase in Escherichia coli crude extract, J. Biol. Chem. 271:16053-16067, 1996.
Bandyopadhyay, et al., A Proposed Role for the Azotobacter vinelandii NfuA Protein as an Intermediate Iron-Sulfur Cluster Carrier, J. Biol. Chem. 283:14092-14099, 2008.
Foury, et al., Mitochondrial Control of Iron Homeostasis, J. Biol. Chem. 276:7762-7768, 2001.
Gerber, et al., The Yeast Scaffold Proteins Isu1p and Isu2p Are Required Inside Mitochondria for Maturation of Cytosolic Fe/S Proteins, Mal. Cell. Biol. 24:4848-4857, 2004.
Gupta, et al., Native Escherichia coil SufA, Coexpressed with SufBCDSE, Purifies as a [2Fe—2S] Protein and Acts as an Fe—S Transporter to Fe—S Target Enzymes, J. Am. Chem. Soc. 131:6149-6153, 2009.
Kaplan, et al., Iran Acquisition and Transcriptional Regulation, Chem. Rev. 109:4536-4552, 2009.
Kim, et al., Transposable Elements and Genome Organization: A Comprehensive Survey of Retrotransposons Revealed by the Complete Saccharomyces cervisiae Genome Sequence, Genome Res. 8:464-478, 1998.
Kumanovics, et al., Identification of FRA1 and FRA2 as Genes Involved in Regulating the Yeast Iron Regulon in Response to Decreased Mitochondrial Iron-Sulfur Cluster Synthesis, J. Biol. Chem. 283:10276-10286, 2008.
Li, et al., The Yeast iron Regulatory Proteins Grx3/4 and Fra2 Form Heterodimeric Complexes Containing a [2Fe—2S] Cluster with Cysteinyi and Histidyl Ligation, Biochemistry 48:9569-9561, 2009.
Li, et al., CCC1 Is a Transporter That Mediates Vacuolar Iron Storage in Yeast, J. Biol. Chem. 276:29515-29519, 2001.

(56) References Cited

OTHER PUBLICATIONS

Liu, et al., Iron-Sulfur Cluster Biosynthesis: Functional Characterization of the N- and C-Terminal Domains of Human NFU, Biochemistry 48:973-980, 2009.
Nakamura, et al., Codon usage tabulated from international DNA sequence databases: status for the year 2000, Nuc. Acids Res. 28:292, 2000.
Ojeda, et al., Role of Glutaredoxin-3 and Glutaredoxin-4 in the Iron Regulation of the Aft1 Transcriptional Activator in *Saccharomyces cervisiae*, J. Biol, Chem, 281:17661-17669, 2006.
Pujol-Carrion, et al., Glutaredoxins Grx3 and Grx4 regulate nuclear localisation of Aft1 and the oxidative stress response in *Saccharomyces cerevisiae*, J. Cell Sci. 19:4554-4564, 2006.
Rutherford, et al., Activation of the Iron Regulon by the Yeast Aft1/Aft2 Transcription Factors Depends on Mitochondrial but Not Cytosolic Iron-Sulfur Protein Biogenesis, J. Biol. Chem. 280:10135-10140, 2005.
Shakoury-Elizeh, et al., Transcriptional Remodeling in Response to Iron Deprivation in *Saccharomyces cerevisiae*, Mol. Biol. Cell 15:1233-1243, 2004.
Ueta, et al., Pse1p Mediates the Nuclear Import of the Iron-responsive Transcription Factor Aft1p in *Saccharomyces cerevisiae*, J. Biol. Chem. 278:50120-50127, 2003.
Yamaguchi-Iwai, et al., Subcellular Localization of Aft1 Transcription Factor Responds to iron Status in *Saccharornyces cerevisiae*, J. Biol. Chem. 277:18914-18918, 2002.
Yamaguchi-Iwai, et al., AFT1: a mediator of iron regulated transcriptional control in *Saccharomyces cerevisiae*, EMBO J. 14:1231-1239, 1995.
Tan et al., IscA/SufA paralogues are required for the [4Fe—4S] cluster assembly in enzymes of multiple physiological pathways in *Escherichia coli* under aerobic growth conditions, Biochem. J. 420:463-472, 2009.
Lill, et al., Maturation of Iron-Sulfur Proteins in Eukaryotes: Mechanisms, Connected Processes, and Diseases, Ann. Rev. Biochem. 77:669-700, 2008.
Ryan, et al., Subcellular Localization of Isoleucine-Valine Biosynthetic Enzymes in Yeast, J. Bacteriol. 120:631-637, 1974.
Askwith, et al., The FET3 Gene of *S. cerevisiae* Encodes a Multicopper Oxidase Required for Ferrous Iron Uptake, Cell 76:403-410,1994.
Armstrong, et al., Stereoselectivity and Stereospecificity of the alpha, beta-Dihydroxy Acid Dehydratase from *Salmonella typhimurium*, Biochimica et Biophysica Acta 498:282-293, 1977.
Armstrong, Stereochemistry of the Reductoisomerase and alpha, beta-Dihydroxyacid Dehydratase-catalysed Steps in Valine and Isoleucine Biosynthesis. Observation of a Novel Tertiary Ketol Rearrangement, J.C.S. Chem. Comm. 9:351-352, 1974.
Armstrong, et al., Structure-Activity Studies with the alpha, beta-Dihydroxyacid Dehydratase of *Salmonella typhimurium*, J. Chem. Soc. Perkin Trans. 1:691-696, 1985.
Atsumi, et al., Metabolic engineering for advanced biofuels production from *Escherichia coli*, Curr. Opin. Biotechnol. 19:414-419, 2008.
Casas, et al., The AFT1 Transcriptional Factor is Differentially Required for Expression of High-Affinity Iron Uptake Genes in *Saccharomyces cerevisiae*, Yeast 13:621-637, 1997.
Coleman, et al. Branched-chain Amino-acid Aminotransferase of *Salmonella typhimurium*: I. Crystallization and Preliminary Characterization, Biochimica et Biophysica Acta 227:56-66, 1971.
Conde, et al., KlAft, the Kluyverornyces lactis Ortholog of Aft I and Aft2, Mediates. Activation of Iron-Responsive Transcription Through the PuCACCC Aft-Type Sequence, Genetics 183:93-106, 2009.
Hausmann, et al., The eukaryotic P loop NTPase Nbp35: An essential component of the cytosolic and nuclear iron-sulfur protein assembly machinery, Proc. Natl. Acad Sci. 102:3266-3271, 2005.
Holatko, et al., Metabolic engineering of the L-valine biosynthesis pathway in Corynebacteriurn glutamicum using promoter activity modulation, J. Biotechnol, 139:203-210, 2009.
Ihrig, et al., Iron Regulation through the Back Door: Iron-Dependent Metabolite Levels Contribute to Transcriptional Adaptation to Iron Deprivation in *Saccharomyces cerevisiae*, Eukaryotic Cell 9:460-471, 2010.
Mercier, et al., Both Php4 Function and Subcellular Localization Are Regulated by Iron via a Multistep Mechanism Involving the Gluaredoxin Grx4 and the Exportin Crm 1, J. Biol. Chem. 284:20249-20262, 2009.
Mohlenhoff, et al., Cytosolic Monothiol Glutaredoxins Function in Intracellular Iron Sensing and Trafficking via Their Bound Iron-Sulfur Cluster, Cell Metabolism 12:373-385, 2010.
Ojeda, Iron Sensing in the Model Organism *Saccharomyces cerevisiae*, A dissertation submitted to the faculty of the University of Utah in partial fulfillment of the requirements for the degree of Doctor of Philosophy, The University of Utah, United States (2006).
Puig, et al., Coordinated Remodeling of Cellular Metabolism during Iron Deficiency through Targeted mRNA Degradation, Cell 120:99-110, 2005.
Rutherford, et al., A second iron-regulatory system in yeast independent of Aft1p, Proc. Natl. Acad. Sci. 98 (25):14322-14327, 2001.
Rutherford, et al., Aft1p and Aft2p Mediate iron-responsive Gene Expression in Yeast through Related Promoter Elements, J. Biol. Chem. 278:27636-27643, 2003.
Seguin, et al., Overexpression of the yeast frataxin homolog (Yfh1): Contrasting effects on iron-sulfur cluster assembly, heme synthesis and resistance to oxidative stress, Mitochondrion 9:130-138, 2009.
Stemmler, et al., Frataxin and Mitochondrial FeS Cluster Biogenesis, J. Biol. Chem. 285:26737-26743, 2010.
Twarog, Enzymes of the Isoleucine-Valine Pathway in Acinetobacter, J. Bacteriol. 111:37-46, 1972.
Wxom, et al., A Rapid Determination of Dihydroxyacid Dehydratase Activity in Microbial Cell Suspensions, Anal. Biochem. 42:262-274, 1971.
Xing, et al., Characterization of Enzymes of the Branched-Chain Amino Acid Biosynthetic Pathway in *Methanococcus* spp., J. Bacteriol. 173:2086-2092, 1991.
Alegre, et al., Transformation of Lactobacillus plantarum by electroporation with in vitro modified plasmid DNA, Fems Microbiol. Lett. 241:73-77, 2004.
Bringel, et al., Optimized transformation by electroporation of Lactobacillus plantarum strains with plasmid vectors, Appl. Microbiol. Biotechnol. 33:664-670, 1990.
Ferain, et al., Lactobacillus plantarum IdhL gene: Overexpression and Deletion, J. Bact. 176:596, 1994.
Hols, et al., Use of Homologous Expression-Secretion Signals and Vector-Free Stable Chromosomal Integration in Engineering of Lactobacillus plantarum for oL-Amylase and Levanase Expression, Appl. Environ. Microbiol. 60:1401-1403, 1994.
Horinouchi, et al., Nucleotide Sequence and Functional Map of pE194, a Plasmid That Specifies Inducible Resistance to Macrolide, Lincosamide, and Streptograrnin Type B Antibiotics, J. Bacteriol. 150:804-814, 1982.
Jang, et al., New integration vector using a cellulase gene as a screening marker for Lactobacillus, Micro. Lett. 24:191-195, 2003.
Hong, et al., Metabolic engineering of *Saccharomyces cerevisiae*: a key cell factory platform for future biorefineries, Cell. Mol. Life Sci. 69:2671-2690, 2012.
GenBank ADA64951, Dihydroxy-acid dehydratase [*Lactococcus lactis* subsp. *lactis* KF147], Jan. 30, 2014.
NCBI Reference Sequence: WP_011676306 (formerly YP_809259) Dihydroxy-acid dehydratase [*Lacococcus lactis* subsp, *cremoris* SK11], Apr. 27, 2015.
GenBank AF508808, Lactobacillus plantarum plasmid pLF1 putative integrase/recombinase, ISLP1 transposase, and cold shock protein genes, complete cds, Jun. 24, 2002.
GenBank ABH11633, Putative ABC transporter ABC5MC5 [Lactobacillus helveticus CNRZ32], Jun. 14, 2007.
UniProtKB/Swiss-Prot: Q1WS05, Iron-sulfur cluster assembly/repair protein Lactobacillus salivarius UCC118, Oct. 31, 2006.
UniProt E1TL94, Cysteine desulfurase, *Lactobacillus plantarum*, Feb. 22, 2012.
UniProt E1TPR8, NifU-like protein, *Lactobacillus plantarum*, Feb. 22, 2012.

(56) References Cited

OTHER PUBLICATIONS

NCBI Reference Sequence: NC_004567, Lactobacillus plantarum WCFS1, complete genome, Mar. 25, 2015.
UniProtKB/Swiss-Prot: Q8DRT7, Dihydroxy-acid dehydratase, ILVD_STRUM, *Streptococcus mutans*, Feb. 22, 2012.
Sequence 615 from International Patent Application No. WO 2010/0037112; Apr. 29, 2010.
UniProtKB: J3JBZ2, Dihydroxy-acid dehydratase, *Lactobacillus coryniformis* subsp.; Oct. 3, 2012.
UniProtKB/TrEMBL: I4X3T0, Dihydroxy-acid dehydratase; *Planococcus antarcticus* DSM 14505; Sep. 5, 2012.
Re-examination of U.S. Pat. No. 8,241,878, U.S. Appl. No. 95/002,167, filed Sep. 10, 2012.
Re-examination of U.S. Pat. No. 8,017,376, U.S. Appl. No. 95/001,870, filed Jan. 10, 2012.
International Search Report for corresponding international Application No. PCT/US2014/025183, dated Sep. 5, 2014.

DHAD VARIANTS AND METHODS OF SCREENING

This application is a continuation of U.S. patent application Ser. No. 14/207,823, filed on Mar. 13, 2014, now U.S. Pat. No. 9,580,705, which claims the benefit of U.S. Provisional Application No. 61/789,204, filed Mar. 15, 2013; the entire contents of each are herein incorporated by reference.

The content of the electronically submitted sequence listing, filed herewith, is incorporated herein by reference in its entirety.

STATEMENT REGARDING FEDERALLY-SPONSORED RESEARCH AND DEVELOPMENT

This invention was made with Government support under Agreement DE-AR0000006 awarded by the United States Department of Energy. The Government has certain rights in this invention.

FIELD OF THE INVENTION

The present invention relates to the field of industrial microbiology and dihydroxy-acid dehydratase variants for production pathways, including isobutanol biosynthetic pathways, in microorganisms. The invention also provides methods for screening for dihydroxy-acid dehydratase variants with improved characteristics. For example, dihydroxy-acid dehydratase variants are disclosed with increased activity compared to a parental dihydroxy-acid dehydratase.

BACKGROUND

Dihydroxy-acid dehydratase (DHAD), also called acetohydroxy acid dehydratase, catalyzes the conversion of 2,3-dihydroxyisovalerate to α-ketoisovalerate and of 2,3-dihydroxymethylvalerate to α-ketomethylvalerate. The DHAD enzyme, classified by the Enzyme Commission (EC) number 4.2.1.9, is part of the naturally occurring biosynthetic pathways that produce valine, isoleucine, leucine, and pantothenic acid (vitamin B5). DHAD-catalyzed conversion of 2,3-dihydroxyisovalerate to α-ketoisovalerate is also a common step in the multiple isobutanol biosynthetic pathways that are disclosed, for example, in U.S. Pat. No. 7,851,188. Disclosed therein is engineering of recombinant microorganisms for production of isobutanol. Isobutanol is useful as a fuel additive, and the availability of biologically-produced isobutanol can reduce the demand for petrochemical fuels.

SUMMARY OF THE INVENTION

The present invention provides, for example, isolated polypeptides and fragments thereof having dihydroxy-acid dehydratase (DHAD) activity.

One aspect of the invention is directed to an isolated polypeptide or fragment thereof having DHAD activity, wherein the polypeptide or fragment thereof comprises one or more amino acid substitutions selected from: (a) aspartic acid at a position corresponding to position 33 of *Streptococcus mutans* DHAD; (b) glutamic acid at a position corresponding to position 62 of *Streptococcus mutans* DHAD; (c) valine at a position corresponding to position 115 of *Streptococcus mutans* DHAD; (d) glutamic acid at a position corresponding to position 116 of *Streptococcus mutans* DHAD; (e) serine at a position corresponding to position 119 of *Streptococcus mutans* DHAD; (f) arginine at a position corresponding to position 158 of *Streptococcus mutans* DHAD; (g) glutamine at a position corresponding to position 176 of *Streptococcus mutans* DHAD; (h) leucine at a position corresponding to position 179 of *Streptococcus mutans* DHAD; (i) arginine at a position corresponding to position 322 of *Streptococcus mutans* DHAD; (j) serine at a position corresponding to position 425 of *Streptococcus mutans* DHAD; (k) glycine at a position corresponding to position 524 of *Streptococcus mutans* DHAD; (l) valine or leucine at a position corresponding to position 562 of *Streptococcus mutans* DHAD; (m) arginine, cysteine, or glycine at a position corresponding to position 563 of *Streptococcus mutans* DHAD; (n) glutamic acid at a position corresponding to position 564 of *Streptococcus mutans* DHAD; and (o) aspartic acid at a position corresponding to position 567 of *Streptococcus mutans* DHAD.

In an embodiment of the invention, the polypeptide or fragment thereof comprises a substitution of glutamic acid at a position corresponding to position 564 of *Streptococcus mutans* DHAD. In another embodiment, the polypeptide or fragment thereof comprises a substitution of glutamic acid at a position corresponding to position 62 of *Streptococcus mutans* DHAD, and a substitution of valine at a position corresponding to position 562 of *Streptococcus mutans* DHAD. In another embodiment, the polypeptide or fragment thereof comprises a substitution of aspartic acid at a position corresponding to position 33 of *Streptococcus mutans* DHAD, and a substitution of arginine at a position corresponding to position 563 of *Streptococcus mutans* DHAD. In another embodiment, the polypeptide or fragment thereof comprises a substitution of valine at a position corresponding to position 562 of *Streptococcus mutans* DHAD. In another embodiment, the polypeptide or fragment thereof comprises a substitution of arginine at a position corresponding to position 563 of *Streptococcus mutans* DHAD. In another embodiment, the polypeptide or fragment thereof comprises a substitution of cysteine at a position corresponding to position 563 of *Streptococcus mutans* DHAD. In another embodiment, the polypeptide or fragment thereof comprises a substitution of glycine at a position corresponding to position 563 of *Streptococcus mutans* DHAD. In yet another embodiment, the polypeptide or fragment thereof comprises a substitution of glycine at a position corresponding to position 524 of *Streptococcus mutans* DHAD, and a substitution of glycine at a position corresponding to position 563 of *Streptococcus mutans* DHAD.

In an embodiment of the invention, the polypeptide or fragment thereof comprises a substitution of valine at a position corresponding to position 115 of *Streptococcus mutans* DHAD, a substitution of arginine at a position corresponding to position 158 of *Streptococcus mutans* DHAD, and a substitution of aspartic acid at a position corresponding to position 567 of *Streptococcus mutans* DHAD. In another embodiment, the polypeptide or fragment thereof comprises a substitution of glutamic acid at a position corresponding to position 116 of *Streptococcus mutans* DHAD, and a substitution of serine at a position corresponding to position 119 of *Streptococcus mutans* DHAD. In another embodiment, the polypeptide or fragment thereof comprises a substitution of aspartic acid at a position corresponding to position 33 of *Streptococcus mutans* DHAD. In another embodiment, the polypeptide or fragment thereof comprises a substitution of glutamic acid at a position corresponding to position 62 of *Streptococcus mutans* DHAD. In another embodiment, the polypeptide or fragment thereof comprises a substitution of leucine at a position corresponding to position 562 of *Streptococcus mutans*

DHAD. In another embodiment, the polypeptide or fragment thereof comprises a substitution of glutamine at a position corresponding to position 176 of *Streptococcus mutans* DHAD, a substitution of leucine at a position corresponding to position 179 of *Streptococcus mutans* DHAD, a substitution of arginine at a position corresponding to position 322 of *Streptococcus mutans* DHAD, and a substitution of arginine at a position corresponding to position 563 of *Streptococcus mutans* DHAD. In yet another embodiment, the polypeptide or fragment thereof comprises a substitution of serine at a position corresponding to position 425 of *Streptococcus mutans* DHAD, and a substitution of arginine at a position corresponding to position 563 of *Streptococcus mutans* DHAD.

In another aspect, the invention is directed to an isolated polypeptide or fragment thereof having dihydroxy-acid dehydratase (DHAD) activity, wherein the polypeptide or fragment thereof comprises one or more amino acid substitutions selected from: (a) glycine to aspartic acid at a position corresponding to position 33 of *Streptococcus mutans* DHAD; (b) aspartic acid to glutamic acid at a position corresponding to position 62 of *Streptococcus mutans* DHAD; (c) methionine to valine at a position corresponding to position 115 of *Streptococcus mutans* DHAD; (d) glycine to glutamic acid at a position corresponding to position 116 of *Streptococcus mutans* DHAD; (e) asparagine to serine at a position corresponding to position 119 of *Streptococcus mutans* DHAD; (f) glycine to arginine at a position corresponding to position 158 of *Streptococcus mutans* DHAD; (g) histidine to glutamine at a position corresponding to position 176 of *Streptococcus mutans* DHAD; (h) histidine to leucine at a position corresponding to position 179 of *Streptococcus mutans* DHAD; (i) glutamine to arginine at a position corresponding to position 322 of *Streptococcus mutans* DHAD; (j) alanine to serine at a position corresponding to position 425 of *Streptococcus mutans* DHAD; (k) glutamic acid to glycine at a position corresponding to position 524 of *Streptococcus mutans* DHAD; (l) phenylalanine to valine or leucine at a position corresponding to position 562 of *Streptococcus mutans* DHAD; (m) tryptophan to arginine, cysteine, or glycine at a position corresponding to position 563 of *Streptococcus mutans* DHAD; (n) lysine to glutamic acid at a position corresponding to position 564 of *Streptococcus mutans* DHAD; and (o) glutamic acid to aspartic acid at a position corresponding to position 567 of *Streptococcus mutans* DHAD.

In another aspect, the invention is directed to an isolated polypeptide or fragment thereof having DHAD activity, wherein the polypeptide or fragment thereof comprises one or more amino acid substitutions selected from: (a) glycine to aspartic acid at position 33; (b) aspartic acid to glutamic acid at position 62; (c) methionine to valine at position 115; (d) glycine to glutamic acid at position 116; (e) asparagine to serine at position 119; (f) glycine to arginine at position 158; (g) histidine to glutamine at position 176; (h) histidine to leucine at position 179; (i) glutamine to arginine at position 322; (j) alanine to serine at position 425; (k) glutamic acid to glycine at position 524; (l) phenylalanine to valine or leucine at position 562; (m) tryptophan to arginine, cysteine, or glycine at position 563; (n) lysine to glutamic acid at position 564; and (o) glutamic acid to aspartic acid at position 567.

In certain embodiments, the isolated polypeptide or fragment thereof having DHAD activity is a $[2Fe-2S]^{2+}$ DHAD. In other embodiments, the isolated polypeptide or fragment thereof having DHAD activity is a $[4Fe-4S]^{2+}$ DHAD. In yet other embodiments, the isolated polypeptide or fragment thereof having DHAD activity catalyzes the conversion of 2,3-dihydroxyisovalerate to α-ketoisovalerate or catalyzes the conversion of 2,3-dihydroxymethylvalerate to α-ketomethylvalerate.

In certain embodiments of the invention, the isolated polypeptide or fragment thereof having DHAD activity has an amino acid sequence that matches the Profile Hidden Markov Model (HMM) of Table 6 with an E value of $<10^{-5}$. In another embodiment, the isolated polypeptide or fragment thereof having DHAD activity comprises three conserved cysteines corresponding to positions 56, 129, and 201 of *Streptococcus mutans* DHAD.

In other embodiments, the polypeptide or fragment thereof having DHAD activity is from a prokaryotic organism. In certain embodiments, the polypeptide or fragment thereof having DHAD activity is from bacteria, fungi, or plant. In a particular embodiment, the polypeptide or fragment thereof having DHAD activity is from *Streptococcus mutans*.

In certain embodiments of the invention, the isolated polypeptide or fragment thereof having DHAD activity comprises an amino acid sequence that is at least 90% identical to SEQ ID NO:528 and has a glutamic acid at position 564. In other embodiments, the isolated polypeptide or fragment thereof having DHAD activity comprises an amino acid sequence that is at least 95% identical to SEQ ID NO:528 and has a glutamic acid at position 564. In yet other embodiments, the isolated polypeptide or fragment thereof having DHAD activity comprises the amino acid sequence of SEQ ID NO:528.

In certain embodiments of the invention, the isolated polypeptide or fragment thereof having DHAD activity comprises an amino acid sequence that is at least 90% identical to SEQ ID NO:532 and has a glutamic acid at position 62 and a valine at position 562. In other embodiments, the isolated polypeptide or fragment thereof having DHAD activity comprises an amino acid sequence that is at least 95% identical to SEQ ID NO:532 and has a glutamic acid at position 62 and a valine at position 562. In yet other embodiments, the isolated polypeptide or fragment thereof having DHAD activity comprises the amino acid sequence of SEQ ID NO:532.

In certain embodiments of the invention, the isolated polypeptide or fragment thereof having DHAD activity comprises an amino acid sequence that is at least 90% identical to SEQ ID NO:534 and has an aspartic acid at position 33 and an arginine at position 563. In other embodiments, the isolated polypeptide or fragment thereof having DHAD activity comprises an amino acid sequence that is at least 95% identical to SEQ ID NO:534 and has an aspartic acid at position 33 and an arginine at position 563. In yet other embodiments, the isolated polypeptide or fragment thereof having DHAD activity comprises the amino acid sequence of SEQ ID NO:534.

In certain embodiments of the invention, the isolated polypeptide or fragment thereof having DHAD activity comprises an amino acid sequence that is at least 90% identical to SEQ ID NO:537 and has a valine at position 562. In other embodiments, the isolated polypeptide or fragment thereof having DHAD activity comprises an amino acid sequence that is at least 95% identical to SEQ ID NO:537 and has a valine at position 562. In yet other embodiments, the isolated polypeptide or fragment thereof having DHAD activity comprises the amino acid sequence of SEQ ID NO:537.

In certain embodiments of the invention, the isolated polypeptide or fragment thereof having DHAD activity comprises an amino acid sequence that is at least 90% identical to SEQ ID NO:540 and has an arginine at position 563. In other embodiments, the isolated polypeptide or fragment thereof having DHAD activity comprises an amino acid sequence that is at least 95% identical to SEQ ID NO:540 and has an arginine at position 563. In yet other embodiments, the isolated polypeptide or fragment thereof having DHAD activity comprises the amino acid sequence of SEQ ID NO:540.

In certain embodiments of the invention, the isolated polypeptide or fragment thereof having DHAD activity comprises an amino acid sequence that is at least 90% identical to SEQ ID NO:545 and has a cysteine at position 563. In other embodiments, the isolated polypeptide or fragment thereof having DHAD activity comprises an amino acid sequence that is at least 95% identical to SEQ ID NO:545 and has a cysteine at position 563. In yet other embodiments, the isolated polypeptide or fragment thereof having DHAD activity comprises the amino acid sequence of SEQ ID NO:545.

In certain embodiments of the invention, the isolated polypeptide or fragment thereof having DHAD activity comprises an amino acid sequence that is at least 90% identical to SEQ ID NO:572 and has a glycine at position 563. In other embodiments, the isolated polypeptide or fragment thereof having DHAD activity comprises an amino acid sequence that is at least 95% identical to SEQ ID NO:572 and has a glycine at position 563. In yet other embodiments, the isolated polypeptide or fragment thereof having DHAD activity comprises the amino acid sequence of SEQ ID NO:572.

In certain embodiments of the invention, the isolated polypeptide or fragment thereof having DHAD activity comprises an amino acid sequence that is at least 90% identical to SEQ ID NO:548 and has a glycine at position 524 and a glycine at position 563. In other embodiments, the isolated polypeptide or fragment thereof having DHAD activity comprises an amino acid sequence that is at least 95% identical to SEQ ID NO:548 and has a glycine at position 524 and a glycine at position 563. In yet other embodiments, the isolated polypeptide or fragment thereof having DHAD activity comprises the amino acid sequence of SEQ ID NO:548.

In certain embodiments of the invention, the isolated polypeptide or fragment thereof having DHAD activity comprises an amino acid sequence that is at least 90% identical to SEQ ID NO:552 and has a valine at position 115, an arginine at position 158, and an aspartic acid at position 567. In other embodiments, the isolated polypeptide or fragment thereof having DHAD activity comprises an amino acid sequence that is at least 95% identical to SEQ ID NO:552 and has a valine at position 115, an arginine at position 158, and an aspartic acid at position 567. In yet other embodiments, the isolated polypeptide or fragment thereof having DHAD activity comprises the amino acid sequence of SEQ ID NO:552.

In certain embodiments of the invention, the isolated polypeptide or fragment thereof having DHAD activity comprises an amino acid sequence that is at least 90% identical to SEQ ID NO:555 and has a glutamic acid at position 116 and a serine at position 119. In other embodiments, the isolated polypeptide or fragment thereof having DHAD activity comprises an amino acid sequence that is at least 95% identical to SEQ ID NO:555 and has a glutamic acid at position 116 and a serine at position 119. In yet other embodiments, the isolated polypeptide or fragment thereof having DHAD activity comprises the amino acid sequence of SEQ ID NO:555.

In certain embodiments of the invention, the isolated polypeptide or fragment thereof having DHAD activity comprises an amino acid sequence that is at least 90% identical to SEQ ID NO:557 and has an aspartic acid at position 33. In other embodiments, the isolated polypeptide or fragment thereof having DHAD activity comprises an amino acid sequence that is at least 95% identical to SEQ ID NO:557 and has an aspartic acid at position 33. In yet other embodiments, the isolated polypeptide or fragment thereof having DHAD activity comprises the amino acid sequence of SEQ ID NO:557.

In certain embodiments of the invention, the isolated polypeptide or fragment thereof having DHAD activity comprises an amino acid sequence that is at least 90% identical to SEQ ID NO:561 and has a glutamic acid at position 62. In other embodiments, the isolated polypeptide or fragment thereof having DHAD activity comprises an amino acid sequence that is at least 95% identical to SEQ ID NO:561 and has a glutamic acid at position 62. In yet other embodiments, the isolated polypeptide or fragment thereof having DHAD activity comprises the amino acid sequence of SEQ ID NO:561.

In certain embodiments of the invention, the isolated polypeptide or fragment thereof having DHAD activity comprises an amino acid sequence that is at least 90% identical to SEQ ID NO:563 and has a leucine at position 562. In other embodiments, the isolated polypeptide or fragment thereof having DHAD activity comprises an amino acid sequence that is at least 95% identical to SEQ ID NO:563 and has a leucine at position 562. In yet other embodiments, the isolated polypeptide or fragment thereof having DHAD activity comprises the amino acid sequence of SEQ ID NO:563.

In certain embodiments of the invention, the isolated polypeptide or fragment thereof having DHAD activity comprises an amino acid sequence that is at least 90% identical to SEQ ID NO:566 and has a glutamine at position 176, a leucine at position 179, an arginine at position 322, and an arginine at position 563. In other embodiments, the isolated polypeptide or fragment thereof having DHAD activity comprises an amino acid sequence that is at least 95% identical to SEQ ID NO:566 and has a glutamine at position 176, a leucine at position 179, an arginine at position 322, and an arginine at position 563. In yet other embodiments, the isolated polypeptide or fragment thereof having DHAD activity comprises the amino acid sequence of SEQ ID NO:566.

In certain embodiments of the invention, the isolated polypeptide or fragment thereof having DHAD activity comprises an amino acid sequence that is at least 90% identical to SEQ ID NO:569 and has a serine at position 425 and an arginine at position 563. In other embodiments, the isolated polypeptide or fragment thereof having DHAD activity comprises an amino acid sequence that is at least 95% identical to SEQ ID NO:569 and has a serine at position 425 and an arginine at position 563. In yet other embodiments, the isolated polypeptide or fragment thereof having DHAD activity comprises the amino acid sequence of SEQ ID NO:569.

In other embodiments, the isolated polypeptide or fragment thereof has DHAD activity that is increased relative to the DHAD activity of the polypeptide or fragment thereof without substitutions.

Another aspect of the invention is directed to an isolated polynucleotide molecule comprising a nucleotide sequence that encodes a polypeptide or fragment thereof having DHAD activity, wherein the polypeptide or fragment thereof comprises one or more amino acid substitutions selected from: (a) glycine to aspartic acid at a position corresponding to position 33 of *Streptococcus mutans* DHAD; (b) aspartic acid to glutamic acid at a position corresponding to position 62 of *Streptococcus mutans* DHAD; (c) methionine to valine at a position corresponding to position 115 of *Streptococcus mutans* DHAD; (d) glycine to glutamic acid at a position corresponding to position 116 of *Streptococcus mutans* DHAD; (e) asparagine to serine at a position corresponding to position 119 of *Streptococcus mutans* DHAD; (f) glycine to arginine at a position corresponding to position 158 of *Streptococcus mutans* DHAD; (g) histidine to glutamine at a position corresponding to position 176 of *Streptococcus mutans* DHAD; (h) histidine to leucine at a position corresponding to position 179 of *Streptococcus mutans* DHAD; (i) glutamine to arginine at a position corresponding to position 322 of *Streptococcus mutans* DHAD; (j) alanine to serine at a position corresponding to position 425 of *Streptococcus mutans* DHAD; (k) glutamic acid to glycine at a position corresponding to position 524 of *Streptococcus mutans* DHAD; (l) phenylalanine to valine or leucine at a position corresponding to position 562 of *Streptococcus mutans* DHAD; (m) tryptophan to arginine, cysteine, or glycine at a position corresponding to position 563 of *Streptococcus mutans* DHAD; (n) lysine to glutamic acid at a position corresponding to position 564 of *Streptococcus mutans* DHAD; and (o) glutamic acid to aspartic acid at a position corresponding to position 567 of *Streptococcus mutans* DHAD.

In an embodiment of the invention, the isolated polynucleotide molecule comprises a nucleotide sequence that encodes a polypeptide or fragment thereof comprising a substitution of glutamic acid at a position corresponding to position 564 of *Streptococcus mutans* DHAD. In another embodiment, the isolated polynucleotide molecule comprises a nucleotide sequence that encodes a polypeptide or fragment thereof comprising a substitution of glutamic acid at a position corresponding to position 62 of *Streptococcus mutans* DHAD, and a substitution of valine at a position corresponding to position 562 of *Streptococcus mutans* DHAD. In another embodiment, the isolated polynucleotide molecule comprises a nucleotide sequence that encodes a polypeptide or fragment thereof comprising a substitution of aspartic acid at a position corresponding to position 33 of *Streptococcus mutans* DHAD, and a substitution of arginine at a position corresponding to position 563 of *Streptococcus mutans* DHAD. In another embodiment, the isolated polynucleotide molecule comprises a nucleotide sequence that encodes a polypeptide or fragment thereof comprising a substitution of valine at a position corresponding to position 562 of *Streptococcus mutans* DHAD. In another embodiment, the isolated polynucleotide molecule comprises a nucleotide sequence that encodes a polypeptide or fragment thereof comprising a substitution of arginine at a position corresponding to position 563 of *Streptococcus mutans* DHAD. In another embodiment, the isolated polynucleotide molecule comprises a nucleotide sequence that encodes a polypeptide or fragment thereof comprising a substitution of cysteine at a position corresponding to position 563 of *Streptococcus mutans* DHAD. In another embodiment, the isolated polynucleotide molecule comprises a nucleotide sequence that encodes a polypeptide or fragment thereof comprising a substitution of glycine at a position corresponding to position 563 of *Streptococcus mutans* DHAD. In another embodiment, the isolated polynucleotide molecule comprises a nucleotide sequence that encodes a polypeptide or fragment thereof comprising a substitution of glycine at a position corresponding to position 524 of *Streptococcus mutans* DHAD, and a substitution of glycine at a position corresponding to position 563 of *Streptococcus mutans* DHAD.

In another embodiment of the invention, the isolated polynucleotide molecule comprises a nucleotide sequence that encodes a polypeptide or fragment thereof comprising a substitution of valine at a position corresponding to position 115 of *Streptococcus mutans* DHAD, a substitution of arginine at a position corresponding to position 158 of *Streptococcus mutans* DHAD, and a substitution of aspartic acid at a position corresponding to position 567 of *Streptococcus mutans* DHAD. In another embodiment, the isolated polynucleotide molecule comprises a nucleotide sequence that encodes a polypeptide or fragment thereof comprising a substitution of glutamic acid at a position corresponding to position 116 of *Streptococcus mutans* DHAD, and a substitution of serine at a position corresponding to position 119 of *Streptococcus mutans* DHAD. In another embodiment, the isolated polynucleotide molecule comprises a nucleotide sequence that encodes a polypeptide or fragment thereof comprising a substitution of aspartic acid at a position corresponding to position 33 of *Streptococcus mutans* DHAD. In another embodiment, the isolated polynucleotide molecule comprises a nucleotide sequence that encodes a polypeptide or fragment thereof comprising a substitution of glutamic acid at a position corresponding to position 62 of *Streptococcus mutans* DHAD. In another embodiment, the isolated polynucleotide molecule comprises a nucleotide sequence that encodes a polypeptide or fragment thereof comprising a substitution of leucine at a position corresponding to position 562 of *Streptococcus mutans* DHAD. In another embodiment, the isolated polynucleotide molecule comprises a nucleotide sequence that encodes a polypeptide or fragment thereof comprising a substitution of glutamine at a position corresponding to position 176 of *Streptococcus mutans* DHAD, a substitution of leucine at a position corresponding to position 179 of *Streptococcus mutans* DHAD, a substitution of arginine at a position corresponding to position 322 of *Streptococcus mutans* DHAD, and a substitution of arginine at a position corresponding to position 563 of *Streptococcus mutans* DHAD. In yet another embodiment, the isolated polynucleotide molecule comprises a nucleotide sequence that encodes a polypeptide or fragment thereof comprising a substitution of serine at a position corresponding to position 425 of *Streptococcus mutans* DHAD, and a substitution of arginine at a position corresponding to position 563 of *Streptococcus mutans* DHAD.

In another aspect, the invention is directed to an isolated polynucleotide molecule comprising a nucleotide sequence that encodes a polypeptide or fragment thereof having dihydroxy-acid dehydratase (DHAD) activity, wherein the polypeptide or fragment thereof comprises one or more amino acid substitutions selected from: (a) glycine to aspartic acid at position 33; (b) aspartic acid to glutamic acid at position 62; (c) methionine to valine at position 115; (d) glycine to glutamic acid at position 116; (e) asparagine to serine at position 119; (f) glycine to arginine at position 158; (g) histidine to glutamine at position 176; (h) histidine to leucine at position 179; (i) glutamine to arginine at position 322; (j) alanine to serine at position 425; (k) glutamic acid to glycine at position 524; (l) phenylalanine to valine or leucine at position 562; (m) tryptophan to arginine, cysteine, or glycine at position 563; (n) lysine to glutamic acid at position 564; and (o) glutamic acid to aspartic acid at position 567.

In certain embodiments, the isolated polynucleotide molecule comprising a nucleotide sequence that encodes a polypeptide or fragment thereof having dihydroxy-acid dehydratase (DHAD) activity comprises a sequence selected from the group consisting of: SEQ ID NO:527, SEQ ID NO:529, SEQ ID NO:530, SEQ ID NO:531, SEQ ID NO:533, SEQ ID NO:535, SEQ ID NO:536, SEQ ID NO:538, SEQ ID NO:539, SEQ ID NO:606, SEQ ID NO:541, SEQ ID NO:542, SEQ ID NO:543, SEQ ID NO:544, SEQ ID NO:546, SEQ ID NO:547, SEQ ID NO:549, SEQ ID NO:550, SEQ ID NO:551, SEQ ID NO:553, SEQ ID NO:554, SEQ ID NO:556, SEQ ID NO:558, SEQ ID NO:559, SEQ ID NO:560, SEQ ID NO:562, SEQ ID NO:564, SEQ ID NO:565, SEQ ID NO:567, SEQ ID NO:568, SEQ ID NO:570, and SEQ ID NO:571.

In other embodiments, the invention is directed to an isolated polynucleotide molecule comprising a nucleotide sequence that encodes a polypeptide or fragment thereof having dihydroxy-acid dehydratase (DHAD) activity, wherein the polypeptide or fragment thereof having DHAD activity is a $[2Fe-2S]^{2+}$ DHAD. In other embodiments, the invention is directed to an isolated polynucleotide molecule comprising a nucleotide sequence that encodes a polypeptide or fragment thereof having DHAD activity, wherein the polypeptide or fragment thereof having DHAD activity is a $[4Fe-4S]^{2+}$ DHAD. In other embodiments, the invention is directed to an isolated polynucleotide molecule comprising a nucleotide sequence that encodes a polypeptide or fragment thereof having DHAD activity, wherein the polypeptide or fragment thereof having DHAD activity catalyzes the conversion of 2,3-dihydroxyisovalerate to α-ketoisovalerate or catalyzes the conversion of 2,3-dihydroxymethylvalerate to α-ketomethylvalerate.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof has an amino acid sequence that matches the Profile Hidden Markov Model (HMM) of Table 6 with an E value of $<10^{-5}$. In another embodiment, the isolated polynucleotide molecule comprises a nucleotide sequence that encodes a polypeptide or fragment thereof having DHAD activity, wherein the polypeptide or fragment thereof comprises three conserved cysteines corresponding to positions 56, 129, and 201 of *Streptococcus mutans* DHAD.

In certain embodiments of the invention, the isolated polynucleotide molecule comprises a nucleotide sequence that encodes a polypeptide or fragment thereof having DHAD activity, wherein the polypeptide or fragment thereof having DHAD activity is from a prokaryotic organism. In certain embodiments, the isolated polynucleotide molecule comprises a nucleotide sequence that encodes a polypeptide or fragment thereof having DHAD activity from bacteria, fungi, or plant. In a particular embodiment, the isolated polynucleotide molecule comprises a nucleotide sequence that encodes a polypeptide or fragment thereof having DHAD activity from *Streptococcus mutans*.

In certain embodiments of the invention, the isolated polynucleotide molecule comprises a nucleotide sequence that encodes a polypeptide or fragment thereof having DHAD activity, wherein the polypeptide or fragment thereof having DHAD activity comprises an amino acid sequence that is at least 90% identical to SEQ ID NO:528 and has a glutamic acid at position 564. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:528 and has a glutamic acid at position 564. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:528.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:532 and has a glutamic acid at position 62 and a valine at position 562. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:532 and has a glutamic acid at position 62 and a valine at position 562. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:532.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:534 and has an aspartic acid at position 33 and an arginine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:534 and has an aspartic acid at position 33 and an arginine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:534.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:537 and has a valine at position 562. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:537 and has a valine at position 562. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:537.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:540 and has an arginine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:540 and has an arginine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:540.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:545 and has a cysteine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:545 and has a cysteine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:545.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:572 and has a glycine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:572 and has a glycine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:572.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:548 and has a glycine at position 524 and a glycine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:548 and has a glycine at position 524 and a glycine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:548.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:552 and has a valine at position 115, an arginine at position 158, and an aspartic acid at position 567. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:552 and has a valine at position 115, an arginine at position 158, and an aspartic acid at position 567. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:552.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:555 and has a glutamic acid at position 116 and a serine at position 119. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:555 and has a glutamic acid at position 116 and a serine at position 119. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:555.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:557 and has an aspartic acid at position 33. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:557 and has an aspartic acid at position 33. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:557.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:561 and has a glutamic acid at position 62. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:561 and has a glutamic acid at position 62. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:561.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:563 and has a leucine at position 562. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:563 and has a leucine at position 562. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:563.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:566 and has a glutamine at position 176, a leucine at position 179, an arginine at position 322, and an arginine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:566 and has a glutamine at position 176, a leucine at position 179, an arginine at position 322, and an arginine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:566.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 90% identical to SEQ ID NO:569 and has a serine at position 425 and an arginine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:569 and has a serine at position 425 and an arginine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:569.

In other embodiments, the isolated polynucleotide molecule comprises a nucleotide sequence that encodes a polypeptide or fragment thereof having dihydroxy-acid dehydratase (DHAD) activity, wherein the polypeptide or fragment has DHAD activity that is increased relative to the DHAD activity of the polypeptide or fragment thereof without substitutions.

In certain embodiments, the isolated polynucleotide molecule is operatively linked to a promoter sequence. In other embodiments, the isolated polynucleotide molecule is comprised within a vector.

The invention also provides polypeptides encoded by the isolated nucleic acid molecules described herein.

Another aspect of the invention is directed to a recombinant host cell comprising the isolated nucleic acid molecules of the invention or a vector of the invention. In certain embodiments, the DHAD encoded by the isolated nucleic acid molecule is heterologous to the recombinant host cell. In other embodiments, the DHAD encoded by the isolated nucleic acid molecule is over-expressed in the recombinant host cell.

In still other embodiments, the recombinant host cell of the invention is a bacterial cell or a yeast cell. In some embodiments, the recombinant host cell of the invention is a bacterial cell, and the bacterial cell is a member of a genus of bacteria selected from *Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Lactococcus, Leuconostoc, Oenococcus, Pediococcus*, and *Streptococcus*. In other embodiments, the recombinant host cell of the invention is a yeast cell, and the yeast cell is a member of a genus of yeast selected from *Saccharomyces, Schizosaccharomyces, Hansenula, Kluyveromyces, Candida, Pichia*, and *Yarrowia*. In other embodiments, the recombinant host cell of the invention is *Saccharomyces cerevisiae, Schizosaccharomyces pombe, Kluyveromyces lactis, Kluyveromyces thermotolerans, Candida glabrata, Candida albicans, Pichia stipitis*, or *Yarrowia lipolytica*. In another embodiment, the recombinant host cell of the invention is *Saccharomyces cerevisiae*.

In some embodiments, the recombinant host cell of the invention is a yeast cell and the yeast cell further comprises a disruption in an endogenous ILV3 gene that encodes mitochondrial DHAD. In other embodiments, the yeast cell further comprises a disruption in one or more endogenous genes affecting iron-sulfur cluster biosynthesis selected from FRA2, GRX3, and GRX4. In yet other embodiments, the yeast cell has been further genetically engineered to upregulate the activity of at least one gene selected from AFT1 and AFT2.

In some embodiments, the recombinant host cell of the invention is a bacterial cell, and the bacterial cell is a *Lactobacillus*. In other embodiments, the *Lactobacillus* further comprises at least one recombinant genetic expression element encoding iron-sulfur (Fe—S) cluster forming proteins. In yet other embodiments, the recombinant genetic expression element encoding iron-sulfur cluster forming proteins contains coding regions of an operon selected from Isc, Suf, and Nif operons. In some embodiments, the Suf operon comprises at least one coding region selected from SufC, SufD, SufS, SufU, SufB, SufA, and yseH. In some embodiments, the Suf operon is derived from *Lactococcus lactis* or *Lactobacillus plantarum*. In some embodiments, the Isc operon comprises at least one coding region selected from IscS, IscU, IscA, IscX, HscA, HscB, and Fdx. In some embodiments, the Isc operon is derived from *Escherichia coli*. In some embodiments, the Nif operon comprises at least one coding region selected from NifS and NifU. In some embodiments, the Nif operon is derived from *Wolinella succinogenes*.

In some embodiments, the recombinant host cell of the invention produces butanol, for example, isobutanol. In other embodiments, the recombinant host cell of the invention comprises an isobutanol biosynthetic pathway. In some embodiments, the isobutanol biosynthetic pathway comprises genes encoding acetolactate synthase, acetohydroxy acid isomeroreductase, DHAD, α-keto acid decarboxylase, and alcohol dehydrogenase. In another embodiment, the isobutanol biosynthetic pathway comprises the following substrate to product conversions: (i) pyruvate to acetolactate; (ii) acetolactate to 2,3-dihydroxyisovalerate; (iii) 2,3-dihydroxyisovalerate to α-ketoisovalerate; (iv) α-ketoisovalerate to isobutyraldehyde; and (v) isobutyraldehyde to isobutanol.

The substrate to product conversion of pyruvate to acetolactate can be catalyzed in some embodiments by an acetolactate synthase. The substrate to product conversion of acetolactate to 2,3-dihydroxyisovalerate can be catalyzed in some embodiments by a ketol-acid reductoisomerase. The substrate to product conversion of 2,3-dihydroxyisovalerate to α-ketoisovalerate can be catalyzed in some embodiments by a DHAD. The substrate to product conversion of α-ketoisovalerate to isobutyraldehyde can be catalyzed in some embodiments by an α-keto acid decarboxylase. The substrate to product conversion of isobutyraldehyde to isobutanol can be catalyzed in some embodiments by an alcohol dehydrogenase.

In some embodiments, two or more of: acetolactate synthase, ketol-acid reductoisomerase, and α-keto acid decarboxylase are heterologous to the recombinant host cell. In other embodiments, two or more of: acetolactate synthase, ketol-acid reductoisomerase, and α-keto acid decarboxylase are over-expressed in the recombinant host cell.

In some embodiments, the recombinant host cell comprising an isolated nucleic acid molecule of the invention produces an isobutanol titer that is increased as compared to a recombinant host cell that does not contain a polypeptide or fragment thereof having DHAD activity comprising one or more amino acid substitutions. In some embodiments, the recombinant host cell comprising the isolated nucleic acid molecule produces isobutanol at a rate that is increased by from about 10% to about 300% as compared to a recombinant host cell that does not contain a polypeptide or fragment thereof having DHAD activity comprising one or more amino acid substitutions. In some embodiments, the recombinant host cell comprising the isolated nucleic acid molecules produces isobutanol at a rate that is increased by at least about 10%, at least about 20%, at least about 30%, at least about 40%, or at least about 50% as compared to a recombinant host cell that does not contain a polypeptide or fragment thereof having DHAD activity comprising one or more amino acid substitutions. In other embodiments, the polypeptide or fragment thereof having DHAD activity is expressed in the cytosol, or the polypeptide or fragment thereof having DHAD activity and the ketol-acid reductoisomerase are expressed in the cytosol.

Another aspect of the invention is directed to a method for the production of butanol, for example, isobutanol, comprising providing a recombinant host cell comprising an isolated nucleic acid molecule of the invention; culturing the recombinant host cell in a fermentation medium under suitable conditions to produce isobutanol from pyruvate; and recovering the isobutanol. In some embodiments, the isobutanol is produced at a titer that is increased as compared to a recombinant host cell that does not contain a polypeptide or fragment thereof having DHAD activity comprising one or more amino acid substitutions. In other embodiments, the isobutanol is produced at a rate that is increased by from about 10% to about 300% as compared to a recombinant host cell that does not contain a polypeptide or fragment thereof having DHAD activity comprising one or more amino acid substitutions. In other embodiments, the isobutanol is produced at a rate that is increased by at least about 10%, at least about 20%, at least about 30%, at least about 40%, or at least about 50% as compared to a recombinant host cell that does not contain a polypeptide or fragment thereof having DHAD activity comprising one or more amino acid substitutions. In another embodiment, the concentration of isobutanol in the fermentation medium is greater than or equal to about 20 mM. In another embodiment, the concentration of isobutanol in the fermentation medium is from about 30 mM to about 50 mM.

Another aspect of the invention is directed to a method of converting 2,3-dihydroxyisovalerate to α-ketoisovalerate or 2,3-dihydroxymethylvalerate to α-ketomethylvalerate, comprising providing an isolated polypeptide or fragment thereof of the invention, wherein the isolated polypeptide or fragment thereof catalyzes the conversion of 2,3-dihydroxyisovalerate to α-ketoisovalerate or 2,3-dihydroxymethylvalerate to α-ketomethylvalerate. In some embodiments of the method to convert 2,3-dihydroxyisovalerate to α-ketoisovalerate or 2,3-dihydroxymethylvalerate to α-ketomethylvalerate, the isolated polypeptide or fragment thereof is comprised within a recombinant host cell.

In some embodiments of the method to convert 2,3-dihydroxyisovalerate to α-ketoisovalerate or 2,3-dihydroxymethylvalerate to α-ketomethylvalerate, the recombinant host cell is cultured in a fermentation medium under suitable conditions to produce isobutanol from pyruvate, and the isobutanol is recovered. In some embodiments, the isobutanol is recovered by distillation, liquid-liquid extraction, adsorption, decantation, pervaporation, or combinations thereof. In some embodiments, solids are removed from the fermentation medium. In some embodiments, solids are removed from the fermentation medium by centrifugation, filtration, decantation, or combinations thereof. In other embodiments, the solids are removed before the isobutanol is recovered. In other embodiments, the conversion of 2,3-dihydroxyisovalerate to α-ketoisovalerate or 2,3-dihydroxymethylvalerate to α-ketomethylvalerate is improved as compared to a control conversion under the same conditions with a control polypeptide having DHAD activity which does not comprise an amino acid substitution.

Another aspect of the invention is directed to a composition comprising one or more recombinant host cells of the invention, and a fermentable carbon substrate.

Another aspect of the invention is directed to a composition comprising one or more recombinant host cells of the invention, and isobutanol. In other embodiments, the composition further comprises an extractant.

In some embodiments of the method of screening DHAD protein variants, the weak promoter is a truncated Leu2 promoter. In certain embodiments, the truncated Leu2 promoter is SEQ ID NO:575. In other embodiments of the method of screening DHAD protein variants, the weak promoter is a truncated FBA promoter. In certain embodiments, the truncated FBA promoter is SEQ ID NO:576.

In some embodiments of the method of screening DHAD protein variants, the low copy number plasmid has a copy number of one or two in yeast. In certain embodiments, the low copy number plasmid is pRS413.

In other embodiments of the method of screening DHAD protein variants, the growth of the strain is under oxygen limiting conditions. In yet other embodiments, the yeast strain is further transformed with genes encoding acetolactate synthase, acetohydroxy acid isomeroreductase, α-keto acid decarboxylase, and alcohol dehydrogenase. In certain embodiments of the method of screening DHAD protein variants, the method further comprises determining the rate of isobutanol production of the transformants.

Another aspect of the invention is directed to isolated polynucleotides comprising a nucleic acid sequence encoding a DHAD variant obtained by the methods of screening DHAD protein variants described herein. The invention is also directed to isolated DHAD variant polypeptides encoded by these nucleic acid sequences.

Another aspect of the invention is directed to recombinant host cells transformed with an isolated nucleic acid molecule comprising the nucleic acid sequence of SEQ ID NO:573. Another aspect of the invention is directed to recombinant host cells transformed with an isolated nucleic acid molecule comprising the nucleic acid sequence of SEQ ID NO:574.

DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DESCRIPTION OF THE INVENTION

Figure 1:
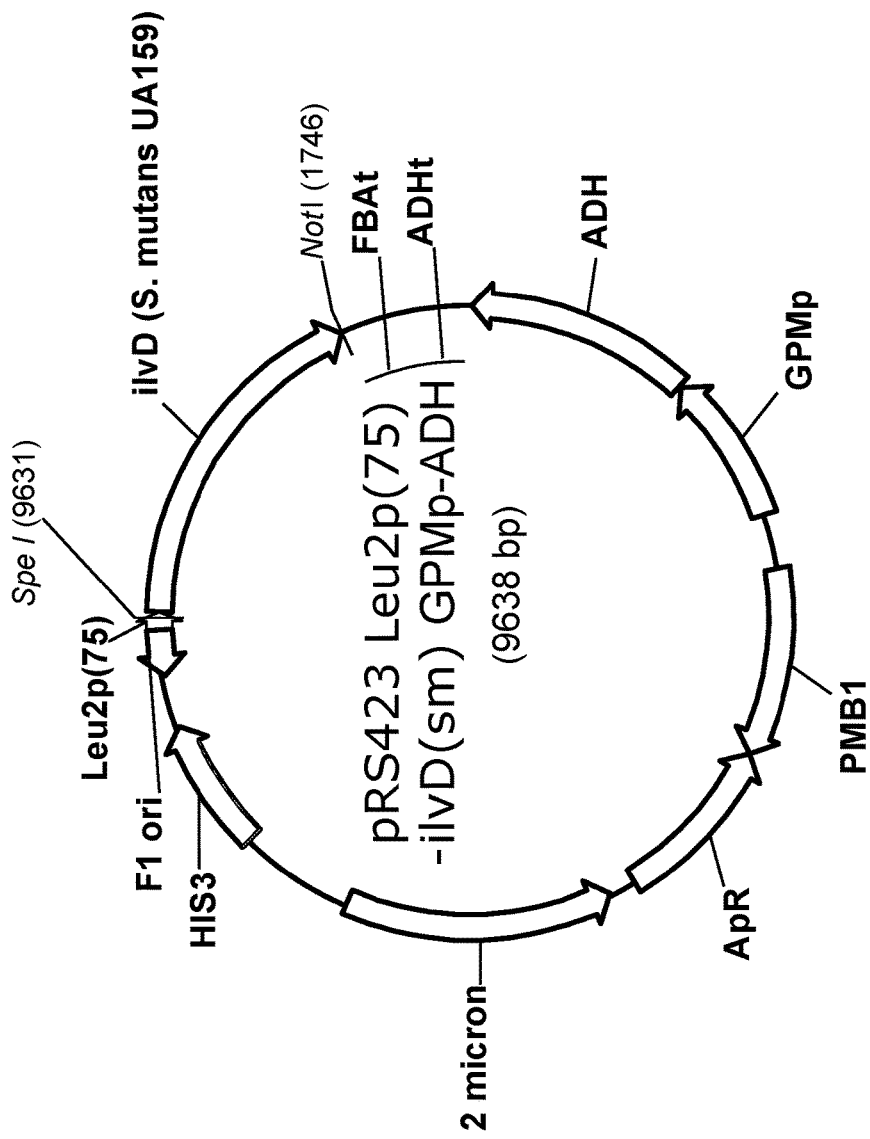
FIG. 1 is a schematic diagram of plasmid pRS423 Leu2p (75)-IlvD (sm) GPMp-ADH (SEQ ID NO:549).

For improved production of compounds synthesized in pathways including dihydroxy-acid dehydratase (DHAD), it is desirable to express a heterologous DHAD enzyme that provides this enzymatic activity in the production host of interest. However, there exists a need for alternative DHAD enzymes and DHAD variants that display increased activity as compared to a parental DHAD enzyme in heterologous organisms and for screening methods to identify such enzymes and variants. Such enzymes and variants can be employed for production of compounds from DHAD-requiring biosynthetic pathways.

The present invention satisfies these and other needs, and provides further related advantages, as will be made apparent by the description of the embodiments that follow.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

Definitions

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

Also, the indefinite articles "a" and "an" preceding an element or component of the invention are intended to be nonrestrictive regarding the number of instances, that is, occurrences of the element or component. Therefore, "a" or "an" should be read to include one or at least one, and the singular word form of the element or component also includes the plural unless the number is obviously meant to be singular.

The terms "invention" or "present invention" as used herein are non-limiting terms and are not intended to refer to any single embodiment of the particular invention but encompass all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value; in another embodiment, within 5% of the reported numerical value.

The term "alcohol" as used herein refers to any of a series of hydroxyl compounds, the simplest of which are derived from saturated hydrocarbons, having the general formula $C_nH_{2n}+1OH$. Examples of alcohol include ethanol and butanol.

The term "butanol" as used herein refers to n-butanol, 2-butanol, isobutanol, tert-butyl alcohol, individually or any mixtures thereof. Butanol can be from a biological source (i.e., biobutanol), for example.

The term "[2Fe-2S]$^{2+}$ DHAD" refers to DHAD enzymes having a bound [2Fe-2S]$^{2+}$ iron-sulfur cluster.

The term "[4Fe-4S]$^{2+}$ DHAD" refers to DHAD enzymes having a bound [4Fe-4S]$^{2+}$ iron-sulfur cluster.

The term "acetohydroxy acid dehydratase" and "dihydroxy-acid dehydratase" ("DHAD") refers to a polypeptide having enzyme activity that catalyzes the conversion of 2,3-dihydroxyisovalerate to α-ketoisovalerate or the conversion of 2,3-dihydroxymethylvalerate to α-ketomethylvalerate. Example dihydroxy-acid dehydratases are known by the EC number 4.2.1.9. Such enzymes are available from a vast array of microorganisms including, but not limited to, *Escherichia coli* (GenBank Nos: YP_026248, NC_000913), *Saccharomyces cerevisiae* (GenBank Nos: NP_012550, NC_001142), *Methanococcus maripaludis* (GenBank Nos: CAF29874, BX957219), *Bacillus subtilis* (GenBank Nos: CAB14105, Z99115), *Lactobacillus lactis*, and *Neurospora crassa*. U.S. Patent Application Publication No. 2010/0081154 and U.S. Pat. No. 7,851,188, both of which are incorporated herein by reference, describe dihydroxy-acid dehydratases including a dihydroxy-acid dehydratase from *Streptococcus mutans* (nucleic acid: SEQ ID NO:167; amino acid: SEQ ID NO:168). Dihydroxy-acid dehydratases also include, for example, the variant dihydroxy-acid dehydratases described herein.

"Increased" or "improved" properties of the DHAD variants of the invention is assessed in comparison to other DHAD enzymes, for example, a wild type DHAD, a parent DHAD, a non-substituted DHAD, or other reference DHAD. Such assessments include, but are not limited to, enzyme stability, solubility, activity, expression level, substrate to product conversion and/or isobutanol production. Methods for making these assessments are known and described in the present application.

The term "isobutanol biosynthetic pathway" as used herein refers to an enzyme pathway to produce isobutanol from pyruvate.

The terms "acetohydroxyacid synthase," "acetolactate synthase," and "acetolactate synthetase" (abbreviated "ALS") are used interchangeably herein to refer to a polypeptide having enzyme activity that catalyzes the conversion of pyruvate to acetolactate and $CO_2$. Example acetolactate synthases are known by the EC number 2.2.1.6 (Enzyme Nomenclature 1992, Academic Press, San Diego). These enzymes are available from a number of sources including, but not limited to, *Bacillus subtilis* (GenBank Nos. CAB07802.1, CAB15618, and Z99122, NCBI (National Center for Biotechnology Information) amino acid sequence, NCBI nucleotide sequence, respectively), *Klebsiella pneumoniae* (GenBank Nos. AAA25079 and M73842), and *Lactococcus lactis* (GenBank Nos. AAA25161 and L16975).

The terms "ketol-acid reductoisomerase" ("KARI"), "acetohydroxy acid reductoisomerase," and "acetohydroxy acid isomeroreductase" are used interchangeably herein to refer a polypeptide having enzyme activity that catalyzes the reaction of (S)-acetolactate to 2,3-dihydroxyisovalerate. Example KARI enzymes are classified as EC number 1.1.1.86 (Enzyme Nomenclature 1992, Academic Press, San Diego), and are available from a vast array of microorganisms including, but not limited to, *Escherichia coli* (GenBank Nos. NP_418222 and NC_000913), *Saccharomyces cerevisiae* (GenBank Nos. NP_013459 and NC_001144), *Methanococcus maripaludis* (GenBank Nos. CAF30210 and BX957220), and *Bacillus subtilis* (GenBank Nos. CAB14789 and Z99118). KARIs include, for example, *Anaerostipes caccae* KARI variants "K9G9," "K9D3," and "K9JB4P" (SEQ ID NO:569). k9jb4pKARI enzymes are also described in U.S. Pat. Nos. 7,910,342 and 8,129,162, U.S. Patent Application Publication No. 2010/0197519, and PCT Application Publication Nos. WO2011/041415 and WO2012/129555, all of which are incorporated herein by reference. Examples of KARIs disclosed therein include those from *Lactococcus lactis, Vibrio cholera, Pseudomonas aeruginosa* PAO1, *Pseudomonas fluorescens* PF5, and *Anaerostipes caccae*. In some embodiments, the KARI may utilize NADH (reduced nicotinamide adenine dinucleotide). In some embodiments, the KARI may utilize NADPH (reduced nicotinamide adenine dinucleotide phosphate).

The terms "branched-chain α-keto acid decarboxylase," "α-ketoacid decarboxylase," "α-ketoisovalerate decarboxylase," and "2-ketoisovalerate decarboxylase" ("KIVD") are used interchangeably herein to refer to a polypeptide having enzyme activity that catalyzes the conversion of α-ketoisovalerate to isobutyraldehyde and $CO_2$. Example branched-chain α-keto acid decarboxylases are known by the EC number 4.1.1.72 and are available from a number of sources including, but not limited to, *Lactococcus lactis* (GenBank Nos. AAS49166, AY548760, CAG34226, and AJ746364), *Salmonella typhimurium* (GenBank Nos. NP_461346 and NC_003197), *Clostridium acetobutylicum* (GenBank Nos. NP_149189 and NC_001988), *Macrococcus caseolyticus*, and *Listeria grayi*.

The terms "branched-chain alcohol dehydrogenase" and "alcohol dehydrogenase" ("ADH") are used interchangeably herein to refer to a polypeptide having enzyme activity that catalyzes the conversion of isobutyraldehyde to isobutanol. Example branched-chain alcohol dehydrogenases are known by the EC number 1.1.1.265, but can also be classified under other alcohol dehydrogenases (e.g., EC numbers 1.1.1.1 or 1.1.1.2). Alcohol dehydrogenases can be, for example, NADPH dependent or NADH dependent. Such enzymes are available from a number of sources including, but not limited to, *Saccharomyces cerevisiae* (GenBank Nos. NP_010656, NC_001136, NP_014051, and NC_001145), *Escherichia coli* (GenBank Nos. NP_417484 and NC_000913), and *Clostridium acetobutylicum* (GenBank Nos. NP_349892, NC_003030, NP_349891, and NC_003030). U.S. Pat. No. 8,188,250 (incorporated herein by reference) describes SadB, an alcohol dehydrogenase (ADH) from *Achromobacter xylosoxidans*. Alcohol dehydrogenases also include horse liver ADH and *Beijerinkia indica* ADH (as described in U.S. Patent Application Publication No. 2011/0269199, which is incorporated herein by reference).

The terms "carbon substrate" and "fermentable carbon substrate" are used interchangeably herein to refer to a carbon source capable of being metabolized by host organisms of the present invention and particularly carbon sources selected from the group consisting of monosaccharides, oligosaccharides, polysaccharides, and one-carbon substrates or mixtures thereof. Carbon substrates can include six-carbon (C6) and five-carbon (C5) sugars and mixtures thereof, such as, for example, glucose, sucrose, or xylose.

The term "polynucleotide" as used herein encompasses a singular nucleic acid as well as plural nucleic acids, and refers to a nucleic acid molecule or construct, for example, messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. "Polynucleotide" embraces chemically, enzymatically, or metabolically modified forms.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene can comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, the term "coding region" refers to a DNA sequence that codes for a specific amino acid sequence. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, translation leader sequences, introns, polyadenylation recognition sequences, RNA processing site, effector binding site and stem-loop structure.

"Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, enhancers, operators, repressors, transcription termination signals, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters can be derived in their entirety from a native gene, or composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from the nucleic acid fragment of the invention. Expression can also refer to translation of mRNA into a polypeptide.

The term "over-expression" as used herein refers to expression that is higher than endogenous expression of the same or related polynucleotide or gene. A heterologous polynucleotide or gene is also over-expressed if its expression is higher than that of a comparable endogenous gene, or if its expression is higher than that of the same polynucleotide or gene introduced by a means that does not over-express the polynucleotide or gene. For example, a polynucleotide can be expressed in a host cell from a low copy number plasmid, which is present in only limited or few copies, and the same polynucleotide can be over-expressed in a host cell from a high copy number plasmid or a plasmid with a copy number that can be regulated, which is present in multiple copies. Any means can be used to over-express a polynucleotide, so long as it increases the copies of the polynucleotide in the host cell. In addition to using a high copy number plasmid or a plasmid with a copy number that can be regulated, a polynucleotide can be over-expressed by multiple chromosomal integrations.

Expression or over-expression of a polypeptide of the invention in a recombinant host cell can be quantified according to any number of methods known to the skilled artisan and can be represented, for example, by a percent of total cell protein. The percent of total protein can be an amount selected from greater than about 0.001% of total cell protein; greater than about 0.01% of total cell protein; greater than about 0.1% of total cell protein; greater than about 0.5% of total cell protein; greater than about 1.0% of total cell protein; greater than about 2.0% of total cell protein; greater than about 3.0% of total cell protein; greater than about 4.0% of total cell protein; greater than about 5.0% of total cell protein; greater than about 6.0% of total cell protein; greater than about 7.0% of total cell protein; greater than about 8.0% of total cell protein; greater than about 9.0% of total cell protein; greater than about 10% of total cell protein; or greater than about 20% of total cell protein. In one embodiment, the amount of polypeptide expressed is greater than about 0.5% of total cell protein. In another embodiment, the amount of polypeptide expressed is greater than about 1.0% of total cell protein or greater than about 2.0% of total cell protein.

As used herein, the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein refer to an extra chromosomal element often carrying genes which are not part of the central metabolism of the cell, and usually in the form of circular double-stranded DNA molecules. Such elements can be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "recombinant host cell" is defined as a host cell that has been genetically manipulated to express a biosynthetic production pathway, wherein the host cell either produces a biosynthetic product in greater quantities relative to an unmodified host cell or produces a biosynthetic product that is not ordinarily produced by an unmodified host cell.

The term "engineered" as applied to a isobutanol biosynthetic pathway refers to the isobutanol biosynthetic pathway that is manipulated, such that the carbon flux from pyruvate through the engineered isobutanol biosynthetic pathway is maximized, thereby producing an increased amount of isobutanol directly from the fermentable carbon substrate. Such engineering includes expression of heterologous polynucleotides or polypeptides, over-expression of endogenous polynucleotides or polypeptides, cytosolic localization of proteins that do not naturally localize to cytosol, increased cofactor availability, decreased activity of competitive pathways, etc.

The term "codon optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F)<br>TTC Phe (F)<br>TTA Leu (L)<br>TTG Leu (L) | TCT Ser (S)<br>TCC Ser (S)<br>TCA Ser (S)<br>TCG Ser (S) | TAT Tyr (Y)<br>TAC Tyr (Y)<br>TAA Stop<br>TAG Stop | TGT Cys (C)<br>TGC Cys (C)<br>TGA Stop<br>TGG Trp (W) |
| C | CTT Leu (L)<br>CTC Leu (L)<br>CTA Leu (L)<br>CTG Leu (L) | CCT Pro (P)<br>CCC Pro (P)<br>CCA Pro (P)<br>CCG Pro (P) | CAT His (H)<br>CAC His (H)<br>CAA Gln (Q)<br>CAG Gln (Q) | CGT Arg (R)<br>CGC Arg (R)<br>CGA Arg (R)<br>CGG Arg (R) |
| A | ATT Ile (I)<br>ATC Ile (I)<br>ATA Ile (I)<br>ATG Met (M) | ACT Thr (T)<br>ACC Thr (T)<br>ACA Thr (T)<br>ACG Thr (T) | AAT Asn (N)<br>AAC Asn (N)<br>AAA Lys (K)<br>AAG Lys (K) | AGT Ser (S)<br>AGC Ser (S)<br>AGA Arg (R)<br>AGG Arg (R) |
| G | GTT Val (V)<br>GTC Val (V)<br>GTA Val (V)<br>GTG Val (V) | GCT Ala (A)<br>GCC Ala (A)<br>GCA Ala (A)<br>GCG Ala (A) | GAT Asp (D)<br>GAC Asp (D)<br>GAA Glu (E)<br>GAG Glu (E) | GGT Gly (G)<br>GGC Gly (G)<br>GGA Gly (G)<br>GGG Gly (G) |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, an "isolated nucleic acid fragment" or "isolated nucleic acid molecule" are used interchangeably herein and mean a polymer of RNA or DNA that is single- or double-stranded, optionally containing synthetic, non-natural, or altered nucleotide bases. An isolated nucleic acid fragment in the form of a polymer of DNA can be comprised of one or more segments of cDNA, genomic DNA, or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified, for example, in Sambrook, J., Fritsch, E. F. and Maniatis, T. Molecular Cloning: A Laboratory Manual, 2nd ed., Cold Spring Harbor Laboratory: Cold Spring Harbor, N.Y. (1989), particularly Chapter 11 and Table 11.1 therein (incorporated herein by reference in its entirety). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1× SSC, 0.1% SDS at 65° C. An additional set of stringent conditions include hybridization at 0.1×SSC, 0.1% SDS, 65° C. and washes with 2×SSC, 0.1% SDS followed by 0.1× SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook, et al., supra, 9.50-9.51). For hybridizations with shorter nucleic acids, for example, oligonucleotides, the position of mismatches becomes more important, and the length of the oligonucleotide determines its specificity (see Sambrook, et al., supra, 11.7-11.8). In one embodiment, the length for a hybridizable nucleic acid is at least about 10 nucleotides. Preferably, a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration can be adjusted as necessary according to factors such as length of the probe.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, the term "variant" refers to a polypeptide differing from a specifically recited polypeptide of the invention, such as DHAD, by amino acid insertions, deletions, mutations, and substitutions, created using, for example, recombinant DNA techniques, such as mutagenesis. A variant also includes "silent" substitutions or "silent" mutations whereby a substitution of one or more nucleotide bases in a polynucleotide does not change the resulting amino acid sequence, but results in improved properties of the resulting polypeptide. Guidance in determining which amino acid residues can be replaced, added, or deleted without abolishing activities of interest, can be found by comparing the sequence of the particular polypeptide with that of homologous polypeptides, for example, yeast or bacterial, and minimizing the number of amino acid sequence changes made in regions of high homology (conserved regions) or by replacing amino acids with consensus sequences.

Alternatively, recombinant polynucleotide variants encoding these same or similar polypeptides can be synthesized or selected by making use of the "redundancy" in the genetic code. Various codon substitutions, such as silent changes which produce various restriction sites, can be introduced to optimize cloning into a plasmid or viral vector for expression. Mutations in the polynucleotide sequence can be reflected in the polypeptide or domains of other peptides added to the polypeptide to modify the properties of any part of the polypeptide.

Amino acid "substitutions" can be the result of replacing one amino acid with another amino acid having similar structural and/or chemical properties, for example, conservative amino acid replacements, or they can be the result of replacing one amino acid with an amino acid having different structural and/or chemical properties, for example, non-conservative amino acid replacements. "Conservative" amino acid substitutions can be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions can be made by selecting the differences in polarity, charge, solubility, hydrophobicity, hydrophilicity, or the amphipathic nature of any of these amino acids. "Insertions" or "deletions" can be within the range of variation as structurally or functionally tolerated by the recombinant proteins. The variation allowed can be experimentally determined by systematically making insertions, deletions, or substitutions of amino acids in a polypeptide molecule using recombinant DNA techniques and assaying the resulting recombinant variants for activity.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, et al., J. Mol. Biol., 215:403-410, 1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides can be used in sequence-dependent methods of gene identification (e.g., Southern hybridization) and isolation (e.g., in situ hybridization of bacterial colonies or bacteriophage plaques). In addition, short oligonucleotides of 12-15 bases can be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, can now use all or a substantial portion of the disclosed sequences for purposes known to those skilled in this art. Accordingly, the instant invention comprises the complete sequences as reported in the accompanying Sequence Listing, as well as substantial portions of those sequences as defined herein.

The term "complementary" is used to describe the relationship between nucleotide bases that are capable of hybridizing to one another. For example, with respect to DNA, adenosine is complementary to thymine and cytosine is complementary to guanine.

The term "percent identity," as known in the art, is a relationship between two or more polypeptide sequences or two or more polynucleotide sequences, as determined by comparing the sequences. In the art, "identity" or "sequence identity" also means the degree of sequence relatedness between polypeptide or polynucleotide sequences, as the case may be, as determined by the match between strings of such sequences. "Identity" and "similarity" can be readily calculated by known methods, including but not limited to those described in: (1) Computational Molecular Biology (Lesk, A. M., Ed.) Oxford University: NY (1988); (2) Biocomputing: Informatics and Genome Projects (Smith, D. W., Ed.) Academic: NY (1993); (3) Computer Analysis of Sequence Data, Part I (Griffin, A. M., and Griffin, H. G., Eds.) Humania: NJ (1994); (4) Sequence Analysis in Molecular Biology (von Heinje, G., Ed.) Academic (1987); and (5) Sequence Analysis Primer (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations can be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, CABIOS. 5:151-153, 1989; Higgins, et al., Comput. Appl. Biosci. 8:189-191, 1992) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids, these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally, the "Clustal W method of alignment" is available and corresponds to the alignment method labeled Clustal W (described by Higgins and Sharp, CABIOS. 5:151-153, 1989; Higgins, et al., Comput. Appl. Biosci. 8:189-191, 1992; Thompson, et al., Nuc. Acid Res. 22: 4673 4680, 1994) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a percent identity by viewing the sequence distances table in the same program.

It is well understood by one skilled in the art that many levels of sequence identity are useful in identifying polypeptides, from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% is useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. Sequence analysis software can be commercially available or independently developed. Typical sequence analysis software will include, but is not limited to: (1) the GCG suite of programs (Wisconsin Package Version 9.0, Genetics Computer Group (GCG), Madison, Wis.); (2) BLASTP, BLASTN, BLASTX (Altschul, et al., J. Mol. Biol. 215:403-410, 1990); (3) DNASTAR (DNASTAR, Inc. Madison, Wis.); (4) Sequencher (Gene Codes Corporation, Ann Arbor, Mich.); and (5) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application, it will be understood that where sequence analysis software is used for analysis, that the results of the analysis will be based on the "default values" of the program referenced, unless otherwise specified. As used herein, "default values" means any set of values or parameters that originally load with the software when first initialized.

Standard recombinant DNA and molecular cloning techniques used herein are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Press, Cold Spring Harbor, N.Y. (1984); and by Ausubel, F. M. et al., Current Protocols in Molecular Biology, published by Greene Publishing Assoc. and Wiley-Interscience (1987). Additional methods used herein are in Methods in Enzymology, Volume 194, Guide to Yeast Genetics and Molecular and Cell Biology (Part A, 2004, Christine Guthrie and Gerald R. Fink (Eds.), Elsevier Academic Press, San Diego, Calif.).

"Fermentation medium" as used herein means a mixture of water, fermentable carbon substrates, dissolved solids, fermentation product and all other constituents of the material held in the fermentation vessel in which the fermentation product is being made by the reaction of fermentable carbon substrates to fermentation products, water and carbon dioxide ($CO_2$) by the microorganisms present. From time to time, as used herein, the term "fermentation broth" and "fermentation mixture" can be used synonymously with "fermentation medium."

The term "aerobic conditions" as used herein means conditions in the presence of oxygen.

The term "oxygen limiting conditions" or "microaerobic conditions" as used herein means conditions with low levels of dissolved oxygen. For example, the oxygen level may be less than about 1% of air saturation.

The term "anaerobic conditions" as used herein means conditions in the absence of oxygen. It will be understood that in many fermentation processes, an initial amount of oxygen is present at the onset of the process, but such oxygen is depleted over the course of the fermentation such that the majority of the process takes place in the absence of detectable oxygen.

As used herein, the term "yield" refers to the amount of product in grams per amount of carbon source in grams (g/g). The yield can be exemplified, for example, for glucose as the carbon source. It is understood, unless otherwise noted, that yield is expressed as a percentage of the theoretical yield. In reference to a microorganism or metabolic pathway, "theoretical yield" is defined as the maximum amount of product that can be generated per total amount of substrate as dictated by the stoichiometry of the metabolic pathway used to make the product. For example, the theoretical yield for one typical conversion of glucose to isopropanol is 0.33 g/g. As such, a yield of isopropanol from glucose of 0.297 g/g would be expressed as 90% of theoretical or 90% theoretical yield. It is understood that while in the present disclosure the yield is exemplified for glucose as a carbon source, the invention can be applied to other carbon sources and the yield can vary depending on the carbon source used. One skilled in the art can calculate yields on various carbon sources.

The term "titer" as used herein refers to the total amount of butanol isomer produced by fermentation per liter of fermentation medium. The total amount of butanol isomer includes: (i) the amount of butanol in the fermentation medium; (ii) the amount of butanol isomer recovered from the organic extractant; and (iii) the amount of butanol isomer recovered from the gas phase, if gas stripping is used.

DHAD Variants

As described herein, dihydroxy-acid dehydratase (DHAD), also called acetohydroxy acid dehydratase, catalyzes the conversion of 2,3-dihydroxyisovalerate to α-ketoisovalerate and of 2,3-dihydroxymethylvalerate to α-ketomethylvalerate. The DHAD enzyme is part of naturally occurring biosynthetic pathways producing valine, isoleucine, leucine and pantothenic acid (vitamin B5). DHAD catalyzed conversion of 2,3-dihydroxyisovalerate to α-ketoisovalerate is also a step in the multiple isobutanol biosynthetic pathways that are disclosed in commonly owned U.S. Pat. No. 7,851,188 (incorporated herein by reference). For production of compounds synthesized in pathways including DHAD, it is desirable to express a heterologous DHAD enzyme that provides DHAD enzymatic activity in a host cell. A consideration for functional expression of dihydroxy-acid dehydratases in a heterologous host is the enzyme's requirement for an iron-sulfur (Fe—S) cluster, which involves availability and proper loading of the cluster into the DHAD apo-protein.

The present invention is based, in part, on the discovery that certain variants of DHAD have DHAD activity, and, in some embodiments, improved performance compared to the parental DHAD molecule. DHAD variants are desirable for production of products produced by DHAD containing biosynthetic pathways, particularly isobutanol.

The present invention includes DHAD variants comprising amino acid substitutions that result in improved DHAD activity as indicated by increased isobutanol production. For the purposes of the present invention, amino acid substitutions were made in the *Streptococcus mutans* DHAD enzyme (SEQ ID NO:168), however, equivalent substitutions can be made in the homologous regions of DHAD enzymes from other organisms. A list of other DHAD enzymes that can be used to produce the DHAD variants of the invention is included below in Tables 3-5. Amino acids are described herein using either the full name of the amino acid or the 1-letter or 3-letter abbreviation of the amino acid, as indicated in Table 2.

TABLE 2

Amino Acids and their Abbreviations

| Amino Acid | 1-Letter Symbol | 3-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Pyroglutamic acid | pQ | pGlu |
| Glycine | G | Gly |
| Histidine | H | His |
| Hydroxylysine | | Hyl |
| Hydroxyproline, 4(R)-L- | O | Hyp |
| Isoleucine | I | Ile |
| Leucine | L | Leu |
| Lysine | K | Lys |
| Methionine | M | Met |
| Phenylalaine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acid changes that were made and/or contemplated by the present invention to produce alternative, active DHAD enzymes are described herein, for example, by a three character code that begins with the 1-letter abbreviation of the native amino acid, followed by the amino acid position number, and followed by the 1-letter abbreviation of the identity of the substituted amino acid. For example, "K564E" refers to a lysine to glutamic acid substitution of position 564 of the DHAD.

One aspect of the invention is directed to an isolated polypeptide or fragment thereof having dihydroxy-acid dehydratase (DHAD) activity, wherein the polypeptide or fragment thereof comprises one or more amino acid substitutions (e.g., as compared to the native sequence other specifically identified sequence). In some embodiments, the isolated polypeptide or fragment thereof comprises one or more amino acid substitutions at an amino acid position selected from: (a) an amino acid corresponding to position 33 of *Streptococcus mutans* DHAD; (b) an amino acid corresponding to position 62 of *Streptococcus mutans* DHAD; (c) an amino acid corresponding to position 115 of *Streptococcus mutans* DHAD; (d) an amino acid corresponding to position 116 of *Streptococcus mutans* DHAD; (e) an amino acid corresponding to position 119 of *Streptococcus mutans* DHAD; (f) an amino acid corresponding to position 158 of *Streptococcus mutans* DHAD; (g) an amino acid corresponding to position 176 of *Streptococcus mutans* DHAD; (h) an amino acid corresponding to position 179 of *Streptococcus mutans* DHAD; (i) an amino acid corresponding to position 322 of *Streptococcus mutans* DHAD; (j) an amino acid corresponding to position 425 of *Streptococcus mutans* DHAD; (k) an amino acid corresponding to position 524 of *Streptococcus mutans* DHAD; (l) an amino acid corresponding to position 562 of *Streptococcus mutans* DHAD; (m) an amino acid corresponding to position 563 of *Streptococcus mutans* DHAD; (n) an amino acid corresponding to position 564 of *Streptococcus mutans* DHAD; and (o) an amino acid corresponding to position 567 of *Streptococcus mutans* DHAD.

In some embodiments, the invention is directed to an isolated polypeptide or fragment thereof having DHAD activity, wherein the polypeptide or fragment thereof comprises one or more amino acid substitutions selected from: (a) aspartic acid or glutamic acid at a position corresponding to position 33 of *Streptococcus mutans* DHAD; (b) aspartic acid or glutamic acid at a position corresponding to position 62 of *Streptococcus mutans* DHAD; (c) glycine, alanine, valine, leucine, isoleucine, or proline at a position corresponding to position 115 of *Streptococcus mutans* DHAD; (d) aspartic acid or glutamic acid at a position corresponding to position 116 of *Streptococcus mutans* DHAD; (e) serine, threonine, cysteine, methionine, asparagine, or glutamine at a position corresponding to position 119 of *Streptococcus mutans* DHAD; (f) arginine, lysine, or histidine at a position corresponding to position 158 of *Streptococcus mutans* DHAD; (g) serine, threonine, cysteine, methionine, asparagine, or glutamine at a position corresponding to position 176 of *Streptococcus mutans* DHAD; (h) glycine, alanine, valine, leucine, isoleucine, or proline at a position corresponding to position 179 of *Streptococcus mutans* DHAD; (i) arginine, lysine, or histidine at a position corresponding to position 322 of *Streptococcus mutans* DHAD; (j) serine, threonine, cysteine, methionine, asparagine, or glutamine at a position corresponding to position 425 of *Streptococcus mutans* DHAD; (k) glycine, alanine, valine, leucine, isoleucine, or proline at a position corresponding to position 524 of *Streptococcus mutans* DHAD; (l) glycine, alanine, valine, leucine, isoleucine, or proline at a position corresponding to position 562 of *Streptococcus mutans* DHAD; (m) arginine, lysine, histidine, cysteine, serine, threonine, methionine, asparagine, glutamine, glycine, alanine, valine, leucine, isoleucine, or proline at a position corresponding to position 563 of *Streptococcus mutans* DHAD; (n) aspartic acid or glutamic acid at a position corresponding to position 564 of *Streptococcus mutans* DHAD; and (o) aspartic acid or glutamic acid at a position corresponding to position 567 of *Streptococcus mutans* DHAD.

In another embodiment, the invention is directed to an isolated polypeptide or fragment thereof having DHAD activity, wherein the polypeptide or fragment thereof comprises one or more amino acid substitutions selected from: (a) aspartic acid at a position corresponding to position 33 of *Streptococcus mutans* DHAD; (b) glutamic acid at a position corresponding to position 62 of *Streptococcus mutans* DHAD; (c) valine at a position corresponding to position 115 of *Streptococcus mutans* DHAD; (d) glutamic acid at a position corresponding to position 116 of *Streptococcus mutans* DHAD; (e) serine at a position corresponding to position 119 of *Streptococcus mutans* DHAD; (f) arginine at a position corresponding to position 158 of *Streptococcus mutans* DHAD; (g) glutamine at a position corresponding to position 176 of *Streptococcus mutans* DHAD; (h) leucine at a position corresponding to position 179 of *Streptococcus mutans* DHAD; (i) arginine at a position corresponding to position 322 of *Streptococcus mutans* DHAD; (j) serine at a position corresponding to position 425 of *Streptococcus mutans* DHAD; (k) glycine at a position corresponding to position 524 of *Streptococcus mutans* DHAD; (l) valine or leucine at a position corresponding to position 562 of *Streptococcus mutans* DHAD; (m) arginine, cysteine, or glycine at a position corresponding to position 563 of *Streptococcus mutans* DHAD; (n) glutamic acid at a position corresponding to position 564 of *Streptococcus mutans* DHAD; and aspartic acid at a position corresponding to position 567 of *Streptococcus mutans* DHAD.

In an embodiment of the invention, the polypeptide or fragment thereof comprises a substitution of glutamic acid at a position corresponding to position 564 of *Streptococcus mutans* DHAD. In another embodiment, the polypeptide or fragment thereof comprises a substitution of glutamic acid at a position corresponding to position 62 of *Streptococcus mutans* DHAD, and a substitution of valine at a position corresponding to position 562 of *Streptococcus mutans* DHAD. In another embodiment, the polypeptide or fragment thereof comprises a substitution of aspartic acid at a position corresponding to position 33 of *Streptococcus mutans* DHAD, and a substitution of arginine at a position corresponding to position 563 of *Streptococcus mutans* DHAD. In another embodiment, the polypeptide or fragment thereof comprises a substitution of valine at a position corresponding to position 562 of *Streptococcus mutans* DHAD. In another embodiment, the polypeptide or fragment thereof comprises a substitution of arginine at a position corresponding to position 563 of *Streptococcus mutans* DHAD. In another embodiment, the polypeptide or fragment thereof comprises a substitution of cysteine at a position corresponding to position 563 of *Streptococcus mutans* DHAD. In another embodiment, the polypeptide or fragment thereof comprises a substitution of glycine at a position corresponding to position 563 of *Streptococcus mutans* DHAD. In yet another embodiment, the polypeptide or fragment thereof comprises a substitution of glycine at a position corresponding to position 524 of *Streptococcus mutans* DHAD, and a substitution of glycine at a position corresponding to position 563 of *Streptococcus mutans* DHAD.

In an embodiment of the invention, the polypeptide or fragment thereof comprises a substitution of valine at a position corresponding to position 115 of *Streptococcus mutans* DHAD, a substitution of arginine at a position corresponding to position 158 of *Streptococcus mutans* DHAD, and a substitution of aspartic acid at a position corresponding to position 567 of *Streptococcus mutans* DHAD. In another embodiment, the polypeptide or fragment thereof comprises a substitution of glutamic acid at a position corresponding to position 116 of *Streptococcus mutans* DHAD, and a substitution of serine at a position corresponding to position 119 of *Streptococcus mutans* DHAD. In another embodiment, the polypeptide or fragment thereof comprises a substitution of aspartic acid at a position corresponding to position 33 of *Streptococcus mutans* DHAD. In another embodiment, the polypeptide or fragment thereof comprises a substitution of glutamic acid at a position corresponding to position 62 of *Streptococcus mutans* DHAD. In another embodiment, the polypeptide or fragment thereof comprises a substitution of leucine at a position corresponding to position 562 of *Streptococcus mutans* DHAD. In another embodiment, the polypeptide or fragment thereof comprises a substitution of glutamine at a position corresponding to position 176 of *Streptococcus mutans* DHAD, a substitution of leucine at a position corresponding to position 179 of *Streptococcus mutans* DHAD, a substitution of arginine at a position corresponding to position 322 of *Streptococcus mutans* DHAD, and a substitution of arginine at a position corresponding to position 563 of *Streptococcus mutans* DHAD. In yet another embodiment, the polypeptide or fragment thereof comprise a substitution of serine at a position corresponding to position 425 of *Streptococcus mutans* DHAD, and a substitution of arginine at a position corresponding to position 563 of *Streptococcus mutans* DHAD.

The invention is also directed to an isolated polypeptide or fragment thereof having dihydroxy-acid dehydratase (DHAD) activity, wherein the polypeptide or fragment thereof comprises one or more amino acid substitutions selected from: (a) glycine to aspartic acid or glutamic acid at a position corresponding to position 33 of *Streptococcus mutans* DHAD; (b) aspartic acid to glutamic acid at a position corresponding to position 62 of *Streptococcus mutans* DHAD; (c) methionine to valine, glycine, alanine, leucine, isoleucine, or proline at a position corresponding to position 115 of *Streptococcus mutans* DHAD; (d) glycine to glutamic acid or aspartic acid at a position corresponding to position 116 of *Streptococcus mutans* DHAD; (e) asparagine to serine, threonine, cysteine, methionine, asparagine, or glutamine at a position corresponding to position 119 of *Streptococcus mutans* DHAD; (f) glycine to arginine, histidine, or lysine at a position corresponding to position 158 of *Streptococcus mutans* DHAD; (g) histidine to glutamine, asparagine, methionine, cysteine, threonine, or serine at a position corresponding to position 176 of *Streptococcus mutans* DHAD; (h) histidine to leucine, isoleucine, proline, glycine, alanine, or valine at a position corresponding to position 179 of *Streptococcus mutans* DHAD; (i) glutamine to arginine, histidine, or lysine at a position corresponding to position 322 of *Streptococcus mutans* DHAD; (j) alanine to serine, threonine, cysteine, methionine, asparagine, or glutamine at a position corresponding to position 425 of *Streptococcus mutans* DHAD; (k) glutamic acid to glycine, alanine, valine, leucine, isoleucine, or proline at a position corresponding to position 524 of *Streptococcus mutans* DHAD; (l) phenylalanine to glycine, alanine, valine, leucine, isoleucine, or proline at a position corresponding to position 562 of *Streptococcus mutans* DHAD; (m) tryptophan to arginine, lysine, histidine, cysteine, serine, threonine, methionine, asparagine, glutamine, glycine, alanine, valine, leucine, isoleucine, or proline at a position corresponding to position 563 of *Streptococcus mutans* DHAD; (n) lysine to glutamic acid or aspartic acid at a position corresponding to position 564 of *Streptococcus mutans* DHAD; and (o) glutamic acid to aspartic acid at a position corresponding to position 567 of *Streptococcus mutans* DHAD.

The invention is also directed to an isolated polypeptide or fragment thereof having dihydroxy-acid dehydratase (DHAD) activity, wherein the polypeptide or fragment thereof comprises one or more amino acid substitutions selected from: (a) glycine to aspartic acid at a position corresponding to position 33 of *Streptococcus mutans* DHAD; (b) aspartic acid to glutamic acid at a position corresponding to position 62 of *Streptococcus mutans* DHAD; (c) methionine to valine at a position corresponding to position 115 of *Streptococcus mutans* DHAD; (d) glycine to glutamic acid at a position corresponding to position 116 of *Streptococcus mutans* DHAD; (e) asparagine to serine at a position corresponding to position 119 of *Streptococcus mutans* DHAD; (f) glycine to arginine at a position corresponding to position 158 of *Streptococcus mutans* DHAD; (g) histidine to glutamine at a position corresponding to position 176 of *Streptococcus mutans* DHAD; (h) histidine to leucine at a position corresponding to position 179 of *Streptococcus mutans* DHAD; (i) glutamine to arginine at a position corresponding to position 322 of *Streptococcus mutans* DHAD; (j) alanine to serine at a position corresponding to position 425 of *Streptococcus mutans* DHAD; (k) glutamic acid to glycine at a position corresponding to position 524 of *Streptococcus mutans* DHAD; (l) phenylalanine to valine or leucine at a position corresponding to position 562 of *Streptococcus mutans* DHAD; (m) tryptophan to arginine, cysteine, or glycine at a position corresponding to position 563 of *Streptococcus mutans* DHAD; (n) lysine to glutamic acid at a position corresponding to position 564 of *Streptococcus mutans* DHAD; and (o) glutamic acid to aspartic acid at a position corresponding to position 567 of *Streptococcus mutans* DHAD.

In another aspect, the invention is directed to an isolated polypeptide or fragment thereof having dihydroxy-acid dehydratase (DHAD) activity, wherein the polypeptide or fragment thereof comprises one or more amino acid substitutions selected from: (a) glycine to aspartic acid or glutamic acid at position 33 of *Streptococcus mutans* DHAD; (b) aspartic acid to glutamic acid at position 62 of *Streptococcus mutans* DHAD; (c) methionine to valine, glycine, alanine, leucine, isoleucine, or proline at position 115 of *Streptococcus mutans* DHAD; (d) glycine to glutamic acid or aspartic acid at position 116 of *Streptococcus mutans* DHAD; (e) asparagine to serine, threonine, cysteine, methionine, asparagine, or glutamine at position 119 of *Streptococcus mutans* DHAD; (f) glycine to arginine, histidine, or lysine at position 158 of *Streptococcus mutans* DHAD; (g) histidine to glutamine, asparagine, methionine, cysteine, threonine, or serine at position 176 of *Streptococcus mutans* DHAD; (h) histidine to leucine, isoleucine, proline, glycine, alanine, or valine at position 179 of *Streptococcus mutans* DHAD; (i) glutamine to arginine, histidine, or lysine at position 322 of *Streptococcus mutans* DHAD; (j) alanine to serine, threonine, cysteine, methionine, asparagine, or glutamine at position 425 of *Streptococcus mutans* DHAD; (k) glutamic acid to alanine, valine, leucine, isoleucine, proline, or glycine at position 524 of *Streptococcus mutans* DHAD; (l) phenylalanine to alanine, valine, leucine, isoleucine, proline, or glycine at position 562 of *Streptococcus mutans* DHAD; (m) tryptophan to arginine, lysine, histidine, cysteine, serine, threonine, methionine, asparagine, glutamine, glycine, alanine, valine, leucine, isoleucine, or proline at position 563 of *Streptococcus mutans* DHAD; (n) lysine to glutamic acid or aspartic acid at position 564 of *Streptococcus mutans* DHAD; and (o) glutamic acid to aspartic acid at position 567 of *Streptococcus mutans* DHAD.

In another aspect, the invention is directed to an isolated polypeptide or fragment thereof having DHAD activity, wherein the polypeptide or fragment thereof comprises one or more amino acid substitutions selected from: (a) glycine to aspartic acid at position 33 of *Streptococcus mutans* DHAD; (b) aspartic acid to glutamic acid at position 62 of *Streptococcus mutans* DHAD; (c) methionine to valine at position 115 of *Streptococcus mutans* DHAD; (d) glycine to glutamic acid at position 116 of *Streptococcus mutans* DHAD; (e) asparagine to serine at position 119 of *Streptococcus mutans* DHAD; (f) glycine to arginine at position 158 of *Streptococcus mutans* DHAD; (g) histidine to glutamine at position 176 of *Streptococcus mutans* DHAD; (h) histidine to leucine at position 179 of *Streptococcus mutans* DHAD; (i) glutamine to arginine at position 322 of *Streptococcus mutans* DHAD; (j) alanine to serine at position 425 of *Streptococcus mutans* DHAD; (k) glutamic acid to glycine at position 524 of *Streptococcus mutans* DHAD; (l) phenylalanine to valine or leucine at position 562 of *Streptococcus mutans* DHAD; (m) tryptophan to arginine, cysteine, or glycine at position 563 of *Streptococcus mutans* DHAD; (n) lysine to glutamic acid at position 564 of *Streptococcus mutans* DHAD; and (o) glutamic acid to aspartic acid at position 567 of *Streptococcus mutans* DHAD.

The amino acid substitutions described herein can be made in any polypeptide or fragment thereof having DHAD activity at any corresponding position in the sequence. Exemplary DHAD enzymes that can be substituted are listed in Tables 3-5, below. Sequence alignment software can be used to identify the amino acids in the DHAD enzyme of interest that corresponds to a recited amino acid in the *Streptococcus mutans* DHAD sequence (SEQ ID NO:168). In some embodiments, the isolated polypeptide or fragment thereof having DHAD activity is a $[2Fe-2S]^{2+}$ DHAD. In other embodiments, the isolated polypeptide or fragment thereof having DHAD activity is a $[4Fe-4S]^{2+}$ DHAD. In yet other embodiments, the isolated polypeptide or fragment thereof having DHAD activity catalyzes the conversion of 2,3-dihydroxyisovalerate to α-ketoisovalerate or catalyzes the conversion of 2,3-dihydroxymethylvalerate to α-ketomethylvalerate.

In certain embodiments of the invention, the amino acid substitutions described herein can be made in an isolated polypeptide or fragment thereof having DHAD activity and having an amino acid sequence that matches the Profile Hidden Markov Model (HMM) of Table 6 with an E value of $<10^{-5}$. Table 6 is a table of the Profile Hidden Markov Model (HMM) for dihydroxy-acid dehydratases based on enzymes with assayed function. Table 6 may be found on pages 108-155.

In another embodiment, the isolated polypeptide or fragment thereof having DHAD activity comprises three conserved cysteines corresponding to positions 56, 129, and 201 of *Streptococcus mutans* DHAD.

Amino acid substitutions can be made in polypeptides or fragment thereof having DHAD activity from prokaryotic organisms or eukaryotic organisms. In certain embodiments, the polypeptide or fragment thereof having DHAD activity is from bacteria, fungi, or plant. In a particular embodiment, the polypeptide or fragment thereof having DHAD activity is from *Streptococcus mutans*.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:528 and has a glutamic acid or aspartic acid at position 564. In certain embodiments, the isolated polypeptide or fragment thereof having DHAD activity comprises an amino acid sequence that is at least 95% identical to SEQ ID NO:528 and has a glutamic acid or aspartic acid at position 564. In yet other embodiments, the isolated polypeptide or fragment thereof having DHAD activity comprises the amino acid sequence of SEQ ID NO:528.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:532 and has a glutamic acid at position 62 and a glycine, alanine, valine, leucine, isoleucine, or proline at position 562. In certain embodiments, the isolated polypeptide or fragment thereof having DHAD activity comprises an amino acid sequence that is at least 95% identical to SEQ ID NO:532 and has a glutamic acid at position 62 and a glycine, alanine, valine, leucine, isoleucine, or proline at position 562. In yet other embodiments, the isolated polypeptide or fragment thereof having DHAD activity comprises the amino acid sequence of SEQ ID NO:532.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:534 and has an aspartic acid at position 33 and an arginine at position 563. In certain embodiments, the isolated polypeptide or fragment thereof having DHAD activity comprises an amino acid sequence that is at least 95% identical to SEQ ID NO:534 and has an aspartic acid or glutamic acid at position 33 and an arginine, lysine, histidine, cysteine, serine, threonine, methionine, asparagine, glutamine, glycine, alanine, valine, leucine, isoleucine, or proline at position 563. In yet other embodiments, the isolated polypeptide or fragment thereof having DHAD activity comprises the amino acid sequence of SEQ ID NO:534.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:537 and has a glycine, alanine, valine, leucine, isoleucine, or proline at position 562. In certain embodiments, the isolated polypeptide or fragment thereof having DHAD activity comprises an amino acid sequence that is at least 95% identical to SEQ ID NO:537 and has a glycine, alanine, valine, leucine, isoleucine, or proline at position 562. In yet other embodiments, the isolated polypeptide or fragment thereof having DHAD activity comprises the amino acid sequence of SEQ ID NO:537.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:540 and has an arginine, lysine, histidine, cysteine, serine, threonine, methionine, asparagine, glutamine, glycine, alanine, valine, leucine, isoleucine, or proline at position 563. In certain embodiments, the isolated polypeptide or fragment thereof having DHAD activity comprises an amino acid sequence that is at least 95% identical to SEQ ID NO:540 and has an arginine, lysine, histidine, cysteine, serine, threonine, methionine, asparagine, glutamine, glycine, alanine, valine, leucine, isoleucine, or proline at position 563. In yet other embodiments, the isolated polypeptide or fragment thereof having DHAD activity comprises the amino acid sequence of SEQ ID NO:540.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:545 and has a arginine, lysine, histidine, cysteine, serine, threonine, methionine, asparagine, glutamine, glycine, alanine, valine, leucine, isoleucine, or proline at position 563. In certain embodiments, the isolated polypeptide or fragment thereof having DHAD activity comprises an amino acid sequence that is at least 95% identical to SEQ ID NO:545 and has a arginine, lysine, histidine, cysteine, serine, threonine, methionine, asparagine, glutamine, glycine, alanine, valine, leucine, isoleucine, or proline at position 563. In yet other embodiments, the isolated polypeptide or fragment thereof having DHAD activity comprises the amino acid sequence of SEQ ID NO:545.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:572 and has an arginine, lysine, histidine, cysteine, serine, threonine, methionine, asparagine, glutamine, glycine, alanine, valine, leucine, isoleucine, or proline at position 563. In certain embodiments, the isolated polypeptide or fragment thereof having DHAD activity comprises an amino acid sequence that is at least 95% identical to SEQ ID NO:572 and has an arginine, lysine, histidine, cysteine, serine, threonine, methionine, asparagine, glutamine, glycine, alanine, valine, leucine, isoleucine, or proline at position 563. In yet other embodiments, the isolated polypeptide or fragment thereof having DHAD activity comprises the amino acid sequence of SEQ ID NO:572.

In certain embodiments of the invention, the isolated polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:548 and has a glycine, alanine, valine, leucine, isoleucine, or proline at position 524 and an arginine, lysine, histidine, cysteine, serine, threonine, methionine, asparagine, glutamine, glycine, alanine, valine, leucine, isoleucine, or proline at position 563. In certain embodiments, the isolated polypeptide or fragment thereof having DHAD activity comprises an amino acid sequence that is at least 95% identical to SEQ ID NO:548 and has a glycine, alanine, valine, leucine, isoleucine, or proline at position 524 and an arginine, lysine, histidine, cysteine, serine, threonine, methionine, asparagine, glutamine, glycine, alanine, valine, leucine, isoleucine, or proline at position 563. In yet other embodiments, the isolated polypeptide or fragment thereof having DHAD activity comprises the amino acid sequence of SEQ ID NO:548.

In certain embodiments of the invention, the isolated polypeptide or fragment thereof having DHAD activity comprises an amino acid sequence that is at least 90% identical to SEQ ID NO:552 and has a valine, alanine, glycine, leucine, isoleucine, or proline at position 115, an arginine, lysine, or histidine at position 158, and an aspartic acid or glutamic acid at position 567. In other embodiments, the isolated polypeptide or fragment thereof having DHAD activity comprises an amino acid sequence that is at least 95% identical to SEQ ID NO:552 and has a valine, alanine, glycine, leucine, isoleucine, or proline at position 115, an arginine, lysine, or histidine at position 158, and an aspartic acid or glutamic acid at position 567. In yet other embodiments, the isolated polypeptide or fragment thereof having DHAD activity comprises the amino acid sequence of SEQ ID NO:552.

In certain embodiments of the invention, the isolated polypeptide or fragment thereof having DHAD activity comprises an amino acid sequence that is at least 90% identical to SEQ ID NO:555 and has a glutamic acid or aspartic acid at position 116 and a serine, threonine, cysteine, methionine, asparagine, or glutamine at position 119. In other embodiments, the isolated polypeptide or fragment thereof having DHAD activity comprises an amino acid sequence that is at least 95% identical to SEQ ID NO:555 and has a glutamic acid or aspartic acid at position 116 and a serine, threonine, cysteine, methionine, asparagine, or glutamine at position 119. In yet other embodiments, the isolated polypeptide or fragment thereof having DHAD activity comprises the amino acid sequence of SEQ ID NO:555.

In certain embodiments of the invention, the isolated polypeptide or fragment thereof having DHAD activity comprises an amino acid sequence that is at least 90% identical to SEQ ID NO:557 and has an aspartic acid or glutamic acid at position 33. In other embodiments, the isolated polypeptide or fragment thereof having DHAD activity comprises an amino acid sequence that is at least 95% identical to SEQ ID NO:557 and has an aspartic acid or glutamic acid at position 33. In yet other embodiments, the isolated polypeptide or fragment thereof having DHAD activity comprises the amino acid sequence of SEQ ID NO:557.

In certain embodiments of the invention, the isolated polypeptide or fragment thereof having DHAD activity comprises an amino acid sequence that is at least 90% identical to SEQ ID NO:561 and has a glutamic acid or aspartic acid at position 62. In other embodiments, the isolated polypeptide or fragment thereof having DHAD activity comprises an amino acid sequence that is at least 95% identical to SEQ ID NO:561 and has a glutamic acid or aspartic acid at position 62. In yet other embodiments, the isolated polypeptide or fragment thereof having DHAD activity comprises the amino acid sequence of SEQ ID NO:561.

In certain embodiments of the invention, the isolated polypeptide or fragment thereof having DHAD activity comprises an amino acid sequence that is at least 90% identical to SEQ ID NO:563 and has a leucine, glycine, alanine, valine, isoleucine, or proline at position 562. In other embodiments, the isolated polypeptide or fragment thereof having DHAD activity comprises an amino acid sequence that is at least 95% identical to SEQ ID NO:563 and has a leucine, glycine, alanine, valine, isoleucine, or proline at position 562. In yet other embodiments, the isolated polypeptide or fragment thereof having DHAD activity comprises the amino acid sequence of SEQ ID NO:563.

In certain embodiments of the invention, the isolated polypeptide or fragment thereof having DHAD activity comprises an amino acid sequence that is at least 90% identical to SEQ ID NO:566 and has a glutamine, asparagine, methionine, serine, threonine, or cysteine at position 176, a leucine, glycine, alanine, valine, isoleucine, or proline at position 179, an arginine, lysine, or histidine at position 322, and an arginine, lysine, or histidine at position 563. In other embodiments, the isolated polypeptide or fragment thereof having DHAD activity comprises an amino acid sequence that is at least 95% identical to SEQ ID NO:566 and has a glutamine, asparagine, methionine, serine, threonine, or cysteine at position 176, a leucine, glycine, alanine, valine, isoleucine, or proline at position 179, an arginine, lysine, or histidine at position 322, and an arginine, lysine, or histidine at position 563. In yet other embodiments, the isolated polypeptide or fragment thereof having DHAD activity comprises the amino acid sequence of SEQ ID NO:566.

In certain embodiments of the invention, the isolated polypeptide or fragment thereof having DHAD activity comprises an amino acid sequence that is at least 90% identical to SEQ ID NO:569 and has a glutamine, asparagine, methionine, serine, threonine, or cysteine at position 425 and an arginine, lysine, or histidine at position 563. In other embodiments, the isolated polypeptide or fragment thereof having DHAD activity comprises an amino acid sequence that is at least 95% identical to SEQ ID NO:569 and has a glutamine, asparagine, methionine, serine, threonine, or cysteine at position 425 and an arginine, lysine, or histidine at position 563. In yet other embodiments, the isolated polypeptide or fragment thereof having DHAD activity comprises the amino acid sequence of SEQ ID NO:569.

The isolated polypeptides or fragments thereof having DHAD activity of the invention display increased DHAD activity compared to DHAD proteins without the amino acid substitutions. The phrase "increased activity" refers to any alteration in the protein that results in improved growth of a strain relative to a control strain expressing the parental DHAD enzyme, or an improved yield of a product made from a DHAD requiring pathway, such as isobutanol. "Increased activity" can result from a number of alterations in the function of the polypeptide or fragment thereof having DHAD activity including, but not limited to: improved stability of the protein, faster catalytic activity, increased binding to substrate, increased stability of the mRNA leading to more translation into protein, more efficient translation of the mRNA, or improved binding to a $[4Fe-4S]^{2+}$ cluster or a $[2Fe-2S]^{2+}$ cluster. In some embodiments, DHAD variant proteins expressed in yeast cytosol have a specific activity of greater than about 0.10 units/mg, greater than about 0.15 units/mg, greater than about 0.20 units/mg, greater than about 0.25 units/mg, greater than about 0.30 units/mg, greater than about 0.35 units/mg, or greater than about 0.40 units/mg. In some embodiments, DHAD variant proteins expressed in yeast cytosol have a specific activity of about 0.10 units/mg to about 0.40 units/mg, or any range of values therein, for example, about 0.10 units/mg to about 0.35 units/mg, about 0.10 units/mg to about 0.30 units/mg, about 0.10 units/mg to about 0.25 units/mg, about 0.10 units/mg to about 0.20 units/mg, about 0.10 units/mg to about 0.15 units/mg.

The invention is also directed to isolated polynucleotide molecules comprising a nucleic acid sequence that encodes the DHAD variant polypeptides described herein.

In certain embodiments of the invention, the isolated polynucleotide molecule comprises a nucleotide sequence that encodes a polypeptide or fragment thereof having DHAD activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:528 and has a glutamic acid or aspartic acid at position 564. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:528 and has a glutamic acid or aspartic acid at position 564. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:528. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:527 and encodes a polypeptide or fragment thereof having DHAD activity. In a specific embodiment, the polynucleotide sequence comprises the nucleic acid sequence of SEQ ID NO:527. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:529 and encodes a polypeptide or fragment thereof having DHAD activity. In a specific embodiment, the polynucleotide sequence comprises the nucleic acid sequence of SEQ ID NO:529. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:530 and encodes a polypeptide or fragment thereof having DHAD activity. In a specific embodiment, the polynucleotide sequence comprises the nucleic acid sequence of SEQ ID NO:530.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:532 and has a glutamic acid at position 62 and a glycine, alanine, valine, leucine, isoleucine, or proline at position 562. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:532 and has a glutamic acid at position 62 and a glycine, alanine, valine, leucine, isoleucine or proline at position 562. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:532. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:531 and encodes a polypeptide or fragment thereof having DHAD activity. In a specific embodiment, the polynucleotide sequence comprises the nucleic acid sequence of SEQ ID NO:531.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:534 and has an aspartic acid or glutamic acid at position 33 and an arginine, lysine, histidine, cysteine, serine, threonine, methionine, asparagine, glutamine, glycine, alanine, valine, leucine, isoleucine, or proline at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:534 and has an aspartic acid or glutamic acid at position 33 and an arginine, lysine, histidine, cysteine, serine, threonine, methionine, asparagine, glutamine, glycine, alanine, valine, leucine, isoleucine, or proline at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:534. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:533 and encodes a polypeptide or fragment thereof having DHAD activity. In a specific embodiment, the polynucleotide sequence comprises the nucleic acid sequence of SEQ ID NO:533. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:535 and encodes a polypeptide or fragment thereof having DHAD activity. In a specific embodiment, the polynucleotide sequence comprises the nucleic acid sequence of SEQ ID NO:535.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:537 and has a glycine, alanine, valine, leucine, isoleucine, or proline at position 562. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:537 and has a glycine, alanine, valine, leucine, isoleucine, or proline at position 562. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:537. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:536 and encodes a polypeptide or fragment thereof having DHAD activity. In a specific embodiment, the polynucleotide sequence comprises the nucleic acid sequence of SEQ ID NO:536. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:538 and encodes a polypeptide or fragment thereof having DHAD activity. In a specific embodiment, the polynucleotide sequence comprises the nucleic acid sequence of SEQ ID NO:538.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:540 and has an arginine, lysine, histidine, cysteine, serine, threonine, methionine, asparagine, glutamine, glycine, alanine, valine, leucine, isoleucine, or proline at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:540 and has an arginine, lysine, histidine, cysteine, serine, threonine, methionine, asparagine, glutamine, glycine, alanine, valine, leucine, isoleucine, or proline at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:540. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:539 and encodes a polypeptide or fragment thereof having DHAD activity. In a specific embodiment, the polynucleotide sequence comprises the nucleic acid sequence of SEQ ID NO:539. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:606 and encodes a polypeptide or fragment thereof having DHAD activity. In a specific embodiment, the polynucleotide sequence comprises the nucleic acid sequence of SEQ ID NO:606. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:541 and encodes a polypeptide or fragment thereof having DHAD activity. In a specific embodiment, the polynucleotide sequence comprises the nucleic acid sequence of SEQ ID NO:541. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:542 and encodes a polypeptide or fragment thereof having DHAD activity. In a specific embodiment, the polynucleotide sequence comprises the nucleic acid sequence of SEQ ID NO:542. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:543 and encodes a polypeptide or fragment thereof having DHAD activity. In a specific embodiment, the polynucleotide sequence comprises the nucleic acid sequence of SEQ ID NO:543.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:545 and has an arginine, lysine, histidine, cysteine, serine, threonine, methionine, asparagine, glutamine, glycine, alanine, valine, leucine, isoleucine, or proline at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:545 and has an arginine, lysine, histidine, cysteine, serine, threonine, methionine, asparagine, glutamine, glycine, alanine, valine, leucine, isoleucine, or proline at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:545. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:544 and encodes a polypeptide or fragment thereof having DHAD activity. In a specific embodiment, the polynucleotide sequence comprises the nucleic acid sequence of SEQ ID NO:544. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:546 and encodes a polypeptide or fragment thereof having DHAD activity. In a specific embodiment, the polynucleotide sequence comprises the nucleic acid sequence of SEQ ID NO:546.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:572 and has an arginine, lysine, histidine, cysteine, serine, threonine, methionine, asparagine, glutamine, glycine, alanine, valine, leucine, isoleucine, or proline at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:572 and has an arginine, lysine, histidine, cysteine, serine, threonine, methionine, asparagine, glutamine, glycine, alanine, valine, leucine, isoleucine, or proline at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:572. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:571 and encodes a polypeptide or fragment thereof having DHAD activity. In a specific embodiment, the polynucleotide sequence comprises the nucleic acid sequence of SEQ ID NO:571.

In certain embodiment of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:548 and has a glycine, alanine, valine, leucine, isoleucine, or proline at position 524 and an arginine, lysine, histidine, cysteine, serine, threonine, methionine, asparagine, glutamine, glycine, alanine, valine, leucine, isoleucine, or proline at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:548 and has a glycine, alanine, valine, leucine, isoleucine, or proline at position 524 and an arginine, lysine, histidine, cysteine, serine, threonine, methionine, asparagine, glutamine, glycine, alanine, valine, leucine, isoleucine, or proline at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:548. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:547 and encodes a polypeptide or fragment thereof having DHAD activity. In a specific embodiment, the polynucleotide sequence comprises the nucleic acid sequence of SEQ ID NO:547. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:549 and encodes a polypeptide or fragment thereof having DHAD activity. In a specific embodiment, the polynucleotide sequence comprises the nucleic acid sequence of SEQ ID NO:549. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:550 and encodes a polypeptide or fragment thereof having DHAD activity. In a specific embodiment, the polynucleotide sequence comprises the nucleic acid sequence of SEQ ID NO:550.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:552 and has a valine, alanine, glycine, leucine, isoleucine, or proline at position 115, an arginine, lysine, or histidine at position 158, and an aspartic acid or glutamic acid at position 567. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:552 and has a valine, alanine, glycine, leucine, isoleucine, or proline at position 115, an arginine, lysine, or histidine at position 158, and an aspartic acid or glutamic acid at position 567. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:552. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:551 and encodes a polypeptide or fragment thereof having DHAD activity. In a specific embodiment, the polynucleotide sequence comprises the nucleic acid sequence of SEQ ID NO:551. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:553 and encodes a polypeptide or fragment thereof having DHAD activity. In a specific embodiment, the polynucleotide sequence comprises the nucleic acid sequence of SEQ ID NO:553.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:555 and has a glutamic acid or aspartic acid at position 116 and a serine, threonine, cysteine, methionine, asparagine, or glutamine at position 119. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:555 and has a glutamic acid or aspartic acid at position 116 and a serine, threonine, cysteine, methionine, asparagine, or glutamine at position 119. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:555. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:554 and encodes a polypeptide or fragment thereof having DHAD activity. In a specific embodiment, the polynucleotide sequence comprises the nucleic acid sequence of SEQ ID NO:554.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:557 and has an aspartic acid or glutamic acid at position 33. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:557 and has an aspartic acid or glutamic acid at position 33. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:557. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:556 and encodes a polypeptide or fragment thereof having DHAD activity. In a specific embodiment, the polynucleotide sequence comprises the nucleic acid sequence of SEQ ID NO:556. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:558 and encodes a polypeptide or fragment thereof having DHAD activity. In a specific embodiment, the polynucleotide sequence comprises the nucleic acid sequence of SEQ ID NO:558. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:559 and encodes a polypeptide or fragment thereof having DHAD activity. In a specific embodiment, the polynucleotide sequence comprises the nucleic acid sequence of SEQ ID NO:559.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:561 and has a glutamic acid or aspartic acid at position 62. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:561 and has a glutamic acid or aspartic acid at position 62. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:561. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:560 and encodes a polypeptide or fragment thereof having DHAD activity. In a specific embodiment, the polynucleotide sequence comprises the nucleic acid sequence of SEQ ID NO:560.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:563 and has a leucine, glycine, alanine, valine, isoleucine, or proline at position 562. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:563 and has a leucine, glycine, alanine, valine, isoleucine, or proline at position 562. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:563. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:562 and encodes a polypeptide or fragment thereof having DHAD activity. In a specific embodiment, the polynucleotide sequence comprises the nucleic acid sequence of SEQ ID NO:562. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:564 and encodes a polypeptide or fragment thereof having DHAD activity. In a specific embodiment, the polynucleotide sequence comprises the nucleic acid sequence of SEQ ID NO:564.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:566 and has a glutamine, asparagine, methionine, serine, threonine, or cysteine at position 176, a leucine, glycine, alanine, valine, isoleucine, or proline at position 179, an arginine, lysine, or histidine at position 322, and an arginine, lysine, or histidine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:566 and has a glutamine, asparagine, methionine, serine, threonine, or cysteine at position 176, a leucine, glycine, alanine, valine, isoleucine, or proline at position 179, an arginine, lysine, or histidine at position 322, and an arginine, lysine, or histidine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:566. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:565 and encodes a polypeptide or fragment thereof having DHAD activity. In a specific embodiment, the polynucleotide sequence comprises the nucleic acid sequence of SEQ ID NO:565. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:567 and encodes a polypeptide or fragment thereof having DHAD activity. In a specific embodiment, the polynucleotide sequence comprises the nucleic acid sequence of SEQ ID NO:567.

In certain embodiments of the invention, the isolated polynucleotide molecule comprises a nucleotide sequence that encodes a polypeptide or fragment thereof having dihydroxy-acid dehydratase (DHAD) activity, wherein the polypeptide or fragment thereof having DHAD activity comprises an amino acid sequence that is at least 50%, 55%, 60%, 65%, 70%, 75%, 80%, 85%, 90%, 95%, 96%, 97%, 98%, or 99% identical to SEQ ID NO:569 and has a glutamine, asparagine, methionine, serine, threonine, or cysteine at position 425 and an arginine, lysine, or histidine at position 563. In other embodiments, the isolated polynucleotide molecule comprises a nucleotide sequence that encodes a polypeptide or fragment thereof having DHAD activity, wherein the polypeptide or fragment thereof having DHAD activity is at least 95% identical to SEQ ID NO:569 and has a glutamine, asparagine, methionine, serine, threonine, or cysteine at position 425 and an arginine, lysine, or histidine at position 563. In yet other embodiments, the isolated polynucleotide molecule comprises a nucleotide sequence that encodes a polypeptide or fragment thereof having DHAD activity, wherein the polypeptide or fragment thereof having DHAD activity comprises the amino acid sequence of SEQ ID NO:569. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:568 and encodes a polypeptide or fragment thereof having DHAD activity. In a specific embodiment, the polynucleotide sequence comprises the nucleic acid sequence of SEQ ID NO:568. In certain embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:570 and encodes a polypeptide or fragment thereof having DHAD activity. In a specific embodiment, the polynucleotide sequence comprises the nucleic acid sequence of SEQ ID NO:570.

In other embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:573 and encodes a polypeptide or fragment thereof having DHAD activity. In a specific embodiment, the polynucleotide sequence comprises the nucleic acid sequence of SEQ ID NO:573. In another embodiments, the polynucleotide sequence comprises a nucleic acid sequence that is at least 50%, 55%, 60%, 65%, 70%, 75%, 80%, 85%, 90%, 95%, 96%, 97%, 98%, or 99% identical to the nucleic acid sequence of SEQ ID NO:574 and encodes a polypeptide or fragment thereof having DHAD activity. In a specific embodiment, the polynucleotide sequence comprises the nucleic acid sequence of SEQ ID NO:574.

DHAD Proteins

Any DHAD protein can be used as a parental, or starting, molecule for creating a DHAD variant polypeptide of the invention. DHADs that can be used herein can be derived from bacterial, fungal, or plant sources. DHADs that can be used can have a [4Fe-4S]$^{2+}$ cluster or a [2Fe-2S]$^{2+}$ cluster bound by the apoprotein. Tables 3-5 list SEQ ID NOs for coding regions and proteins of representative DHADs that can be used in the present invention. Proteins with at least about 95% identity to those listed sequences have been omitted for simplification, but it is understood that omitted proteins with at least about 95% sequence identity to any of the proteins listed in Tables 3-5 and having DHAD activity can be used as disclosed herein. Additional DHAD proteins and their encoding sequences can be identified by BLAST searching of public databases, as well known to one skilled in the art. Typically BLAST (described herein) searching of publicly available databases with known DHAD sequences, such as those provided herein, is used to identify DHADs and their encoding sequences that can be expressed in the present cells. For example, DHAD proteins having amino acid sequence identities of at least about 80-85%, at least about 85-90%, at least about 90-95%, or at least about 98% sequence identity to any of the DHAD proteins disclosed herein can be expressed in the present cells. Identities are based on the Clustal W method of alignment using the default parameters of GAP PENALTY=10, GAP LENGTH PENALTY=0.1, and Gonnet 250 series of protein weight matrix.

TABLE 3

SEQ ID NOs of Representative Bacterial [2Fe—2S]$^{2+}$ DHAD Proteins and Encoding Sequences

| Organism of derivation | SEQ ID NO: Nucleic Acid | SEQ ID NO: Peptide |
|---|---|---|
| Mycobacterium sp. MCS | 1 | 2 |
| Mycobacterium gilvum PYR-GCK | 3 | 4 |
| Mycobacterium smegmatis str. MC2 155 | 5 | 6 |
| Mycobacterium vanbaalenii PYR-1 | 7 | 8 |
| Nocardia farcinica IFM 10152 | 9 | 10 |
| Rhodococcus sp. RHA1 | 11 | 12 |
| Mycobacterium ulcerans Agy99 | 13 | 14 |
| Mycobacterium avium subsp. paratuberculosis K-10 | 15 | 16 |
| Mycobacterium tuberculosis H37Ra | 17 | 18 |
| Mycobacterium leprae TN * | 19 | 20 |
| Kineococcus radiotolerans SRS30216 | 21 | 22 |
| Janibacter sp. HTCC2649 | 23 | 24 |
| Nocardioides sp. JS614 | 25 | 26 |
| Renibacterium salmoninarum ATCC 33209 | 27 | 28 |
| Arthrobacter aurescens TC1 | 29 | 30 |
| Leifsonia xyli subsp. xyli str. CTCB07 | 31 | 32 |
| marine actinobacterium PHSC20C1 | 33 | 34 |
| Clavibacter michiganensis subsp. michiganensis NCPPB 382 | 35 | 36 |
| Saccharopolyspora erythraea NRRL 2338 | 37 | 38 |
| Acidothermus cellulolyticus 11B | 39 | 40 |
| Corynebacterium efficiens YS-314 | 41 | 42 |
| Brevibacterium linens BL2 | 43 | 44 |
| Tropheryma whipplei TW08/27 | 45 | 46 |
| Methylobacterium extorquens PA1 | 47 | 48 |
| Methylobacterium nodulans ORS 2060 | 49 | 50 |
| Rhodopseudomonas palustris BisB5 | 51 | 52 |
| Rhodopseudomonas palustris BisB18 | 53 | 54 |
| Bradyrhizobium sp. ORS278 | 55 | 56 |
| Bradyrhizobium japonicum USDA 110 | 57 | 58 |
| Fulvimarina pelagi HTCC2506 | 59 | 60 |
| Aurantimonas sp. SI85-9A1 | 61 | 62 |
| Hoeflea phototrophica DFL-43 | 63 | 64 |
| Mesorhizobium loti MAFF303099 | 65 | 66 |
| Mesorhizobium sp. BNC1 | 67 | 68 |
| Parvibaculum lavamentivorans DS-1 | 69 | 70 |
| Loktanella vestfoldensis SKA53 | 71 | 72 |
| Roseobacter sp. CCS2 | 73 | 74 |
| Dinoroseobacter shibae DFL 12 | 75 | 76 |
| Roseovarius nubinhibens ISM | 77 | 78 |
| Sagittula stellata E-37 | 79 | 80 |
| Roseobacter sp. AzwK-3b | 81 | 82 |
| Roseovarius sp. TM1035 | 83 | 84 |
| Oceanicola batsensis HTCC2597 | 85 | 86 |
| Oceanicola granulosus HTCC2516 | 87 | 88 |
| Rhodobacterales bacterium HTCC2150 | 89 | 90 |
| Paracoccus denitrificans PD1222 | 91 | 92 |
| Oceanibulbus indolifex HEL-45 | 93 | 94 |
| Sulfitobacter sp. EE-36 | 95 | 96 |
| Roseobacter denitrificans OCh 114 | 97 | 98 |
| Jannaschia sp. CCS1 | 99 | 100 |
| Caulobacter sp. K31 | 101 | 102 |
| Candidatus Pelagibacter ubique HTCC1062 | 103 | 104 |
| Erythrobacter litoralis HTCC2594 | 105 | 106 |
| Erythrobacter sp. NAP1 | 107 | 108 |
| Comamonas testosterone KF-1 | 109 | 110 |
| Sphingomonas wittichii RW1 | 111 | 112 |
| Burkholderia xenovorans LB400 | 113 | 114 |
| Burkholderia phytofirmans PsJN | 115 | 116 |
| Bordetella petrii DSM 12804 | 117 | 118 |
| Bordetella bronchiseptica RB50 | 119 | 120 |
| Bradyrhizobium sp. ORS278 | 121 | 122 |

TABLE 3-continued

SEQ ID NOs of Representative Bacterial [2Fe—2S]$^{2+}$ DHAD Proteins and Encoding Sequences

| Organism of derivation | SEQ ID NO: Nucleic Acid | SEQ ID NO: Peptide |
|---|---|---|
| Bradyrhizobium sp. BTAi1 | 123 | 124 |
| Bradyrhizobium japonicum | 125 | 126 |
| Sphingomonas wittichii RW1 | 127 | 128 |
| Rhodobacterales bacterium HTCC2654 | 129 | 130 |
| Solibacter usitatus Ellin6076 | 131 | 132 |
| Roseiflexus sp. RS-1 | 133 | 134 |
| Rubrobacter xylanophilus DSM 9941 | 135 | 136 |
| Salinispora tropica CNB-440 | 137 | 138 |
| Acidobacteria bacterium Ellin345 | 139 | 140 |
| Thermus thermophilus HB27 | 141 | 142 |
| Maricaulis maris MCS10 | 143 | 144 |
| Parvularcula bermudensis HTCC2503 | 145 | 146 |
| Oceanicaulis alexandrii HTCC2633 | 147 | 148 |
| Plesiocystis pacifica SIR-1 | 149 | 150 |
| Bacillus sp. NRRL B-14911 | 151 | 152 |
| Oceanobacillus iheyensis HTE831 | 153 | 154 |
| Staphylococcus saprophyticus subsp. saprophyticus ATCC 15305 | 155 | 156 |
| Bacillus selenitireducens MLS10 | 157 | 158 |
| Streptococcus pneumoniae SP6-BS73 | 159 | 160 |
| Streptococcus sanguinis SK36 | 161 | 162 |
| Streptococcus thermophilus LMG 18311 | 163 | 164 |
| Streptococcus suis 89/1591 | 165 | 166 |
| Streptococcus mutans UA159 | 167 | 168 |
| Leptospira borgpetersenii serovar Hardjo-bovis L550 | 169 | 170 |
| Candidatus Vesicomyosocius okutanii HA | 171 | 172 |
| Candidatus Ruthia magnifica str. Cm (Calyptogena magnifica) | 173 | 174 |
| Methylococcus capsulatus str. Bath | 175 | 176 |
| uncultured marine bacterium EB80_02D08 | 177 | 178 |
| uncultured marine gamma proteobacterium EBAC31A08 | 179 | 180 |
| uncultured marine gamma proteobacterium EBAC20E09 | 181 | 182 |
| uncultured gamma proteobacterium eBACHOT4E07 | 183 | 184 |
| Alcanivorax borkumensis SK2 | 185 | 186 |
| Chromohalobacter salexigens DSM 3043 | 187 | 188 |
| Marinobacter algicola DG893 | 189 | 190 |
| Marinobacter aquaeolei VT8 | 191 | 192 |
| Marinobacter sp. ELB17 | 193 | 194 |
| Pseudoalteromonas haloplanktis TAC125 | 195 | 196 |
| Acinetobacter sp. ADP1 | 197 | 198 |
| Opitutaceae bacterium TAV2 | 199 | 200 |
| Flavobacterium sp. MED217 | 201 | 202 |
| Cellulophaga sp. MED134 | 203 | 204 |
| Kordia algicida OT-1 | 205 | 206 |
| Flavobacteriales bacterium ALC-1 | 207 | 208 |
| Psychroflexus torquis ATCC 700755 | 209 | 210 |
| Flavobacteriales bacterium HTCC2170 | 211 | 212 |
| unidentified eubacterium SCB49 | 213 | 214 |
| Gramella forsetii KT0803 | 215 | 216 |
| Robiginitalea biformata HTCC2501 | 217 | 218 |
| Tenacibaculum sp. MED152 | 219 | 220 |
| Polaribacter irgensii 23-P | 221 | 222 |
| Pedobacter sp. BAL39 | 223 | 224 |
| Flavobacteria bacterium BAL38 | 225 | 226 |
| Flavobacterium psychrophilum JIP02/86 | 227 | 228 |
| Flavobacterium johnsoniae UW101 | 229 | 230 |
| Lactococcus lactis subsp. cremoris SK11 | 231 | 232 |
| Psychromonas ingrahamii 37 | 233 | 234 |
| Microscilla marina ATCC 23134 | 235 | 236 |
| Cytophaga hutchinsonii ATCC 33406 | 237 | 238 |
| Rhodopirellula baltica SH 1 | 239 | 240 |
| Blastopirellula marina DSM 3645 | 241 | 242 |
| Planctomyces maris DSM 8797 | 243 | 244 |
| Algoriphagus sp. PR1 | 245 | 246 |
| Candidatus Sulcia muelleri str. Hc (Homalodisca coagulata) | 247 | 248 |
| Candidatus Carsonella ruddii PV | 249 | 250 |
| Synechococcus sp. RS9916 | 251 | 252 |
| Synechococcus sp. WH 7803 | 253 | 254 |

TABLE 3-continued

SEQ ID NOs of Representative Bacterial [2Fe—2S]$^{2+}$ DHAD Proteins and Encoding Sequences

| Organism of derivation | SEQ ID NO: Nucleic Acid | SEQ ID NO: Peptide |
|---|---|---|
| Synechococcus sp. CC9311 | 255 | 256 |
| Synechococcus sp. CC9605 | 257 | 258 |
| Synechococcus sp. WH 8102 | 259 | 260 |
| Synechococcus sp. BL107 | 261 | 262 |
| Synechococcus sp. RCC307 | 263 | 264 |
| Synechococcus sp. RS9917 | 265 | 266 |
| Synechococcus sp. WH 5701 | 267 | 268 |
| Prochlorococcus marinus str. MIT 9313 | 269 | 270 |
| Prochlorococcus marinus str. NATL2A | 271 | 272 |
| Prochlorococcus marinus str. MIT 9215 | 273 | 274 |
| Prochlorococcus marinus str. AS9601 | 275 | 276 |
| Prochlorococcus marinus str. MIT 9515 | 277 | 278 |
| Prochlorococcus marinus subsp. pastoris str. CCMP1986 | 279 | 280 |
| Prochlorococcus marinus str. MIT 9211 | 281 | 282 |
| Prochlorococcus marinus subsp. marinus str. CCMP1375 | 283 | 284 |
| Nodularia spumigena CCY9414 | 285 | 286 |
| Nostoc punctiforme PCC 73102 | 287 | 288 |
| Nostoc sp. PCC 7120 | 289 | 290 |
| Trichodesmium erythraeum IMS101 | 291 | 292 |
| Acaryochloris marina MBIC11017 | 293 | 294 |
| Lyngbya sp. PCC 8106 | 295 | 296 |
| Synechocystis sp. PCC 6803 | 297 | 298 |
| Cyanothece sp. CCY0110 | 299 | 300 |
| Thermosynechococcus elongatus BP-1 | 301 | 302 |
| Synechococcus sp. JA-2-3B'a(2-13) | 303 | 304 |
| Gloeobacter violaceus PCC 7421 | 305 | 306 |
| Nitrosomonas eutropha C91 | 307 | 308 |
| Nitrosomonas europaea ATCC 19718 | 309 | 310 |
| Nitrosospira multiformis ATCC 25196 | 311 | 312 |
| Chloroflexus aggregans DSM 9485 | 313 | 314 |
| Leptospirillum sp. Group II UBA | 315 | 316 |
| Leptospirillum sp. Group II UBA | 317 | 318 |
| Halorhodospira halophila SL1 | 319 | 320 |
| Nitrococcus mobilis Nb-231 | 321 | 322 |
| Alkalilimnicola ehrlichei MLHE-1 | 323 | 324 |
| Deinococcus geothermalis DSM 11300 | 325 | 326 |
| Polynucleobacter sp. QLW-P1DMWA-1 | 327 | 328 |
| Polynucleobacter necessarius STIR1 | 329 | 330 |
| Azoarcus sp. EbN1 | 331 | 332 |
| Burkholderia phymatum STM815 | 333 | 334 |
| Burkholderia xenovorans LB400 | 335 | 336 |
| Burkholderia multivorans ATCC 17616 | 337 | 338 |
| Burkholderia cenocepacia PC184 | 339 | 340 |
| Burkholderia mallei GB8 horse 4 | 341 | 342 |
| Ralstonia eutropha JMP134 | 343 | 344 |
| Ralstonia metallidurans CH34 | 345 | 346 |
| Ralstonia solanacearum UW551 | 347 | 348 |
| Ralstonia pickettii 12J | 349 | 350 |
| Limnobacter sp. MED105 | 351 | 352 |
| Herminiimonas arsenicoxydans | 353 | 354 |
| Bordetella parapertussis | 355 | 356 |
| Bordetella petrii DSM 12804 | 357 | 358 |
| Polaromonas sp. JS666 | 359 | 360 |
| Polaromonas naphthalenivorans CJ2 | 361 | 362 |
| Rhodoferax ferrireducens T118 | 363 | 364 |
| Verminephrobacter eiseniae EF01-2 | 365 | 366 |
| Acidovorax sp. JS42 | 367 | 368 |
| Delftia acidovorans SPH-1 | 369 | 370 |
| Methylibium petroleiphilum PM1 | 371 | 372 |
| gamma proteobacterium KT 71 | 373 | 374 |
| Tremblaya princeps | 375 | 376 |
| Blastopirellula marina DSM 3645 | 377 | 378 |
| Planctomyces mans DSM 8797 | 379 | 380 |
| Microcystis aeruginosa PCC 7806 | 381 | 382 |
| Salinibacter ruber DSM 13855 | 383 | 384 |
| Methylobacterium chloromethanicum | 385 | 386 |

TABLE 4

SEQ ID NOs of Representative Fungal and Plant [2Fe—2S]$^{2+}$ DHAD Proteins and Encoding Sequences

| Description | SEQ ID NO: Nucleic acid | SEQ ID NO: Peptide |
|---|---|---|
| Schizosaccharomyces pombe ILV3 | 387 | 388 |
| Saccharomyces cerevisiae ILV3 | 389 | 390 |
| Kluyveromyces lactis ILV3 | 391 | 392 |
| Candida albicans SC5314 ILV3 | 393 | 394 |
| Pichia stipitis CBS 6054 ILV3 | 395 | 396 |
| Yarrowia lipolytica ILV3 | 397 | 398 |
| Candida glabrata CBS 138 ILV3 | 399 | 400 |
| Chlamydomonas reinhardtii | 401 | 402 |
| Ostreococcus lucimarinus CCE9901 | 403 | 404 |
| Vitis vinifera (Unnamed protein product: CAO71581.1) | 405 | 406 |
| Vitis vinifera (Hypothetical protein: CAN67446.1) | 407 | 408 |
| Arabidopsis thaliana | 409 | 410 |
| Oryza sativa (indica cultivar-group) | 411 | 412 |
| Physcomitrella patens subsp. patens | 413 | 414 |
| Chaetomium globosum CBS 148.51 | 415 | 416 |
| Neurospora crassa OR74A | 417 | 418 |
| Magnaporthe grisea 70-15 | 419 | 420 |
| Gibberella zeae PH-1 | 421 | 422 |
| Aspergillus niger | 423 | 424 |
| Neosartorya fischeri NRRL 181 (XP_001266525.1) | 425 | 426 |
| Neosartorya fischeri NRRL 181 (XP_001262996.1) | 427 | 428 |
| Aspergillus niger (hypothetical protein An03g04520) | 429 | 430 |
| Aspergillus niger (Hypothetical protein An14g03280) | 431 | 432 |
| Aspergillus terreus NIH2624 | 433 | 434 |
| Aspergillus clavatus NRRL 1 | 435 | 436 |
| Aspergillus nidulans FGSC A4 | 437 | 438 |
| Aspergillus oryzae | 439 | 440 |
| Ajellomyces capsulatus NAm1 | 441 | 442 |
| Coccidioides immitis RS | 443 | 444 |
| Botryotinia fuckeliana B05.10 | 445 | 446 |
| Phaeosphaeria nodorum SN15 | 447 | 448 |
| Pichia guilliermondii ATCC 6260 | 449 | 450 |
| Debaryomyces hansenii CBS767 | 451 | 452 |
| Lodderomyces elongisporus NRRL YB-4239 | 453 | 454 |
| Vanderwaltozyma polyspora DSM 70294 | 455 | 456 |
| Ashbya gossypii ATCC 10895 | 457 | 458 |
| Laccaria bicolor S238N-H82 | 459 | 460 |
| Coprinopsis cinerea okayama7#130 | 461 | 462 |
| Cryptococcus neoformans var. neoformans JEC21 | 463 | 464 |
| Ustilago maydis 521 | 465 | 466 |
| Malassezia globosa CBS 7966 | 467 | 468 |
| Aspergillus clavatus NRRL 1 | 469 | 470 |
| Neosartorya fischeri NRRL 181 (Putative) | 471 | 472 |
| Aspergillus oryzae | 473 | 474 |
| Aspergillus niger (hypothetical protein An18g04160) | 475 | 476 |
| Aspergillus terreus NIH2624 | 477 | 478 |
| Coccidioides immitis RS (hypothetical protein CIMG_04591) | 479 | 480 |
| Paracoccidioides brasiliensis | 481 | 482 |
| Phaeosphaeria nodorum SN15 | 483 | 484 |
| Gibberella zeae PH-1 | 485 | 486 |
| Neurospora crassa OR74A | 487 | 488 |
| Coprinopsis cinerea okayama 7#130 | 489 | 490 |
| Laccaria bicolor S238N-H82 | 491 | 492 |
| Ustilago maydis 521 | 493 | 494 |

TABLE 5

SEQ ID NOs of Representative [4Fe—4S]$^{2+}$ DHAD Proteins and Encoding Sequences

| Organism | SEQ ID NO: Nucleic acid | SEQ ID NO: Peptide |
|---|---|---|
| *Escherichia coli* str. K-12 substr. MG1655 | 495 | 496 |
| *Bacillus subtilis* subsp. *subtilis* str. 168 | 497 | 498 |
| *Agrobacterium tumefaciens* str. C58 | 499 | 500 |
| *Burkholderia cenocepacia* MC0-3 | 501 | 502 |
| *Psychrobacter cryohalolentis* K5 | 503 | 504 |
| *Psychromonas* sp. CNPT3 | 505 | 506 |
| *Deinococcus radiodurans* R1 | 507 | 508 |
| *Wolinella succinogenes* DSM 1740 | 509 | 510 |
| *Zymomonas mobilis* subsp. *mobilis* ZM4 | 511 | 512 |
| *Clostridium acetobutylicum* ATCC 824 | 513 | 514 |
| *Clostridium beijerinckii* NCIMB 8052 | 515 | 516 |
| *Pseudomonas fluorescens* Pf-5 | 517 | 518 |
| *Methanococcus maripaludis* C7 | 519 | 520 |
| *Methanococcus aeolicus* Nankai-3 | 521 | 522 |
| *Vibrio fischeri* ATCC 700601 (ES114) | 523 | 524 |
| *Shewanella oneidensis* MR-1 ATCC 700550 | 525 | 526 |

Additional [2Fe-2S]$^{2+}$ DHADs can be identified using the analysis described in co-pending U.S. Patent Application Publication No. 2010/0081154, which is herein incorporated by reference. The analysis is as follows: A Profile Hidden Markov Model (HMM) was prepared based on amino acid sequences of eight functionally verified DHADs. These DHADs are from *Nitrosomonas europaea* (DNA SEQ ID NO:309; protein SEQ ID NO:310), *Synechocystis* sp. PCC6803 (DNA SEQ ID:297; protein SEQ ID NO:298), *Streptococcus mutans* (DNA SEQ ID NO:167; protein SEQ ID NO:168), *Streptococcus thermophilus* (DNA SEQ ID NO:163; protein SEQ ID NO:164), *Ralstonia metallidurans* (DNA SEQ ID NO:345; protein SEQ ID NO:346), *Ralstonia eutropha* (DNA SEQ ID NO:343; protein SEQ ID NO:344), and *Lactococcus lactis* (DNA SEQ ID NO:231; protein SEQ ID NO:232). In addition, the DHAD from *Flavobacterium johnsoniae* (DNA SEQ ID NO:229; protein SEQ ID NO:230) was found to have DHAD activity when expressed in *Escherichia coli* and was used in making the Profile.

The Profile HMM was built as follows:

Step 1. Build a Sequence Alignment

The eight sequences for the functionally verified DHADs listed above were aligned using Clustal W with default parameters.

Step 2. Build a Profile HMM

The hmmbuild program was run on the set of aligned sequences using default parameters. The hmmbuild reads the multiple sequence alignment file, builds a new Profile HMM, and saves the Profile HMM to file. Using this program, an un-calibrated profile was generated from the multiple alignment for each set of subunit sequences described herein.

The following information based on the HMMER software user guide gives some description of the way that the hmmbuild program prepares a Profile HMM. A Profile HMM is capable of modeling gapped alignments, for example, insertions and deletions, which allows the software to describe a complete conserved domain (rather than just a small ungapped motif). Insertions and deletions are modeled using insertion (I) states and deletion (D) states. All columns that contain more than a certain fraction x of gap characters will be assigned as an insert column. By default, x is set to 0.5. Each match state has an I and a D state associated with it. HMMER calls a group of three states (M/D/I) at the same consensus position in the alignment a "node." These states are interconnected with arrows called state transition probabilities. M and I states are emitters, while D states are silent. The transitions are arranged so that at each node, either the M state is used (and a residue is aligned and scored) or the D state is used (and no residue is aligned, resulting in a deletion-gap character, '-'). Insertions occur between nodes, and I states have a self-transition, allowing one or more inserted residues to occur between consensus columns.

The scores of residues in a match state (i.e., match state emission scores) or in an insert state (i.e., insert state emission scores) are proportional to Log_2 (p_x)/(null_x). Where p_x is the probability of an amino acid residue, at a particular position in the alignment, according to the Profile HMM and null_x is the probability according to the Null model. The Null model is a simple one state probabilistic model with pre-calculated set of emission probabilities for each of the 20 amino acids derived from the distribution of amino acids in the SWISS-PROT release 24.

State transition scores are also calculated as log odds parameters and are proportional to Log_2 (t_x). Where t_x is the probability of transiting to an emitter or non-emitter state.

Step 3. Calibrate the Profile HMM

The Profile HMM was read using hmmcalibrate which scores a large number of synthesized random sequences with the Profile (the default number of synthetic sequences used is 5,000), fits an extreme value distribution (EVD) to the histogram of those scores, and re-saves the HMM file now including the EVD parameters. These EVD parameters (µ and λ) are used to calculate the E-values of bit scores when the profile is searched against a protein sequence database. hmmcalibrate writes two parameters into the HMM file on a line labeled "EVD": these parameters are the µ (location) and λ (scale) parameters of an extreme value distribution (EVD) that best fits a histogram of scores calculated on randomly generated sequences of about the same length and residue composition as SWISS-PROT. This calibration was done once for the Profile HMM.

The calibrated Profile HMM for the DHAD set of sequences is provided in Table 6 (found on pages 108-155). The Profile HMM is provided in a chart that gives the probability of each amino acid occurring at each position in the amino acid sequence. The highest probability is highlighted for each position. The first line for each position reports the match emission scores: probability for each amino acid to be in that state (highest score is highlighted). The second line reports the insert emission scores, and the third line reports on state transition scores: M→M, M→I, M→D; I→M, I→I; D→M, D→D; B→M; M→E.

For example, the DHAD Profile HMM shows that methionine has a 1757 probability of being in the first position, the highest probability which is highlighted. In the second position, glutamic acid has the highest probability, which is 1356. In the third position, lysine has the highest probability, which is 1569.

Step 4. Test the Specificity and Sensitivity of the Built Profile HMMs

The Profile HMM was evaluated using hmmsearch, which reads a Profile HMM from hmmfile and searches a sequence file for significantly similar sequence matches. The sequence file searched contained 976 sequences (see above). During the search, the size of the database (Z parameter) was set to 1 billion. This size setting ensures that significant E-values against the current database will remain significant in the foreseeable future. The E-value cutoff was set at 10.

A hmmer search with the Profile HMM generated from the alignment of the eight DHADs with experimentally verified function, matched all 976 sequences with an E value $<10^{-5}$. This result indicates that members of the dehydratase superfamily share significant sequence similarity. A hmmer search with a cutoff of E value $10^{-5}$ was used to separate DHAD related dehydratases from other more remote but related proteins, as described herein.

The Profile HMM is prepared using the HMMER software package (see Durbin, et al., Biological sequence analysis: probabilistic models of proteins and nucleic acids, Cambridge University Press, 1998; Krogh, et al., J. Mol. Biol. 235:1501-1531, 1994), following the user guide which is available from HMMER (Janelia Farm Research Campus, Ashburn, Va.). The output of the HMMER software program is a Profile Hidden Markov Model (HMM) that characterizes the input sequences. The Profile HMM prepared for the eight DHAD proteins is given in Table 6 (pages 108-155).

This Profile HMM for DHADs can be used to identify DHAD related proteins. Any protein that matches the Profile HMM with an E value of $<10^{-5}$ is a DHAD related protein, which includes $[4Fe-4S]^{2+}$ DHADs, $[2Fe-2S]^{2+}$ DHADs, aldonic acid dehydratases, and phosphogluconate dehydratases.

Sequences matching the Profile HMM given herein are then analyzed for the presence of the three conserved cysteines described herein. The exact positions of the three conserved cysteines can vary, and these can be identified in the context of the surrounding sequence using multiple sequence alignments performed with the Clustal W algorithm (Thompson, et al., Nuc. Acid Res. 22: 4673-4680, 1994) employing the following parameters: 1) for pairwise alignment parameters, a Gap opening=10; Gap extend=0.1; matrix is Gonnet 250; and mode—Slow-accurate, 2) for multiple alignment parameters, Gap opening=10; Gap extension=0.2; and matrix is Gonnet series. For example, the three conserved cysteines are located at amino acid positions 56, 129, and 201 in the *Streptococcus mutans* DHAD (SEQ ID NO:168), and at amino acid positions 61, 135, and 207 in the *Lactococcus lactis* DHAD (SEQ ID NO:232). The exact positions of the three conserved cysteines in other protein sequences correspond to these positions in the *Streptococcus mutans* or the *Lactococcus lactis* amino acid sequence. One skilled in the art will readily be able to identify the presence or absence of each of the three conserved cysteines in the amino acid sequence of a DHAD protein using pairwise or multiple sequence alignments. In addition, other methods can be used to determine the presence of the three conserved cysteines, such as by visual analysis.

The DHAD Profile HMM matching proteins that have two, but not the third (position 56) conserved cysteine, include $[4Fe-4S]^{2+}$ DHADs and phosphogluconate dehydratases (EDDs). Proteins having the three conserved cysteines include arabonate dehydratases and $[2Fe-2S]^{2+}$ DHADs, and are members of a $[2Fe-2S]^{2+}$ DHAD/aldonic acid dehydratase group. The $[2Fe-2S]^{2+}$ DHADs can be distinguished from the aldonic acid dehydratases by analyzing for signature conserved amino acids found to be present in the $[2Fe-2S]^{2+}$ DHADs or in the aldonic acid dehydratases at positions corresponding to the following positions in the *Streptococcus mutans* DHAD amino acid sequence. These signature amino acids are in $[2Fe-2S]^{2+}$ DHADs or in aldonic acid dehydratases, respectively, at the following positions (with greater than 90% occurrence): 88 asparagine vs. glutamic acid; 113 not conserved vs. glutamic acid; 142 arginine or asparagine vs. not conserved; 165 not conserved vs. glycine; 208 asparagine vs. not conserved; 454 leucine vs. not conserved; 477 phenylalanine or tyrosine vs. not conserved; and 487 glycine vs. not conserved.

The disclosed methods for identification of $[2Fe-2S]^{2+}$ DHAD enzymes can be carried out on a single sequence or on a group of sequences. In an embodiment, one or more sequence databases may be queried with a Profile HMM as described herein.

Additionally, the sequences of DHAD coding regions provided herein can be used to identify other homologs in nature. Such methods are well-known in the art, and various methods that can be used to isolate genes encoding homologous proteins are described in U.S. Patent Application Publication No. 2010/0081154, which such methods are incorporated by reference herein.

DHAD variant polypeptides provided herein may be, for example, of a size of about 10 or more, about 20 or more, about 25 or more, about 50 or more, about 75 or more, about 100 or more, about 200 or more, about 500 or more, about 1,000 or more, or about 2,000 or more amino acids. Polypeptides can have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

Also provided are active fragments of the DHAD variant polypeptides. A "fragment" is a unique portion of a polypeptide or other enzyme used in the invention which is identical in sequence to but shorter in length than the parent full-length sequence. A fragment can comprise up to the entire length of the defined sequence, minus one amino acid residue. For example, a fragment can comprise from about 5 to about 1,000 contiguous amino acid residues. A fragment can be, for example, at least 5, 10, 15, 20, 25, 30, 40, 50, 60, 75, 100, 150, 250, 500, 750, or 1,000 contiguous amino acid residues in length. Fragments can be preferentially selected from certain regions of a molecule. For example, a polypeptide fragment can comprise a certain length of contiguous amino acids selected from the first 100, 200, 300, 400, or 500 amino acids of a polypeptide as shown in a certain defined sequence. Alternatively, a polypeptide fragment can comprise a certain length of contiguous amino acids selected from the last 100, 200, 300, 400, or 500 amino acids of a polypeptide as shown in a certain defined sequence. Clearly these lengths are exemplary, and any length that is supported by the specification, including the Sequence Listing, tables, and figures, can be encompassed by the present embodiments. In certain embodiments, the DHAD variant polypeptide fragments have DHAD activity, and thus are capable of catalyzing the conversion of 2,3-dihydroxyisovalerate to α-ketoisovalerate.

DHAD Activity Assays

The presence of DHAD activity in a cell engineered to express a heterologous DHAD can be confirmed using methods known in the art and/or described herein. As one example, crude extracts from cells engineered to express a bacterial DHAD can be used in a DHAD assay as described in the Examples herein or as described by Flint and Emptage (J. Biol. Chem. 263(8): 3558-64, 1988) using dinitrophenylhydrazine. In another example, DHAD activity can be assayed by the methods disclosed in U.S. Patent Application Publication No. 2010/0081154, incorporated herein by reference, in a yeast strain that lacks endogenous DHAD activity. If DHAD activity is present, the yeast strain will grow in the absence of branched-chain amino acids. DHAD activity can also be confirmed by more indirect methods, such as by assaying for a downstream product in a pathway requiring DHAD activity. Any product that has α-ketoisovalerate or α-ketomethylvalerate as a pathway intermediate can be measured in an assay for DHAD activity. A list of such products includes, but is not limited to, valine, isoleucine, leucine, pantothenic acid, 2-methyl-1-butanol, 3-methyl-1-butanol, and isobutanol.

Nucleic Acid Molecules

Provided herein are isolated nucleic acid molecules that encode the DHAD variant polypeptides described herein. The coding region of the isolated nucleic acid encoding the DHAD variant can be codon optimized for a particular target host cell, as is well known to one skilled in the art. The isolated nucleic acid molecules of the invention can be comprised in a vector. Vectors useful for the transformation of a variety of host cells are common and commercially available from companies such as Epicentre™ (Madison, Wis.), Invitrogen Corp. (Carlsbad, Calif.), Stratagene (La Jolla, Calif.), and New England Biolabs, Inc. (Beverly, Mass.). Typically, the vector contains a selectable marker and sequences allowing autonomous replication or chromosomal integration in the desired host. In addition, suitable vectors comprise a promoter region which harbors transcriptional initiation controls and a transcriptional termination control region, between which a coding region DNA fragment can be inserted, to provide expression of the inserted coding region. Both control regions can be derived from genes homologous to the transformed host cell, although it is to be understood that such control regions can also be, for example, derived from genes that are not native to the specific species chosen as a host.

Initiation control regions or promoters, which are useful to drive expression of bacterial DHAD variant coding regions in the desired bacterial host cell, are numerous and familiar to those skilled in the art. Virtually any promoter capable of driving these genetic elements is suitable for the present invention including, but not limited to, lac, ara, tet, trp, $IP_L$, $IP_R$, T7, tac, and trc promoters (useful for expression in *Escherichia coli, Alcaligenes*, and *Pseudomonas*); the amy, apr, and npr promoters, and various phage promoters useful for expression in *Bacillus subtilis, Bacillus licheniformis*, and *Paenibacillus macerans*; nisA (useful for expression Gram-positive bacteria, Eichenbaum, et al., Appl. Environ. Microbiol. 64(8):2763-2769, 1998); and the synthetic P11 promoter (useful for expression in *Lactobacillus plantarum*, Rud, et al., Microbiology 152:1011-1019, 2006). Termination control regions can also be derived from various genes native to the preferred hosts. Optionally, a termination site can be unnecessary; however, it is most preferred if included.

Certain vectors are capable of replicating in a broad range of host bacteria and can be transferred by conjugation. The complete and annotated sequence of pRK404 and three related vectors: pRK437, pRK442, and pRK442(H), are available. These derivatives have proven to be valuable tools for genetic manipulation in Gram-negative bacteria (Scott, et al., Plasmid 50(1):74-79, 2003). Several plasmid derivatives of broad-host-range Inc P4 plasmid RSF1010 are also available with promoters that can function in a range of Gram-negative bacteria. Plasmid pAYC36 and pAYC37 have active promoters along with multiple cloning sites to allow for heterologous gene expression in Gram-negative bacteria. Some vectors that are useful for transformation of *Bacillus subtilis* and *Lactobacillus* include pAMβ1 and derivatives thereof (Renault, et al., Gene 183:175-182, 1996; and O'Sullivan, et al., Gene 137:227-231, 1993); pMBB1 and pHW800, a derivative of pMBB1 (Wyckoff, et al., Appl. Environ. Microbiol. 62:1481-1486, 1996); pMG1, a conjugative plasmid (Tanimoto, et al., J. Bacteriol. 184:5800-5804, 2002); pNZ9520 (Kleerebezem, et al., Appl. Environ. Microbiol. 63:4581-4584, 1997); pAM401 (Fujimoto, et al., Appl. Environ. Microbiol. 67:1262-1267, 2001); and pAT392 (Arthur, et al., Antimicrob. Agents Chemother. 38:1899-1903, 1994). Several plasmids from *Lactobacillus plantarum* have also been reported (van Kranenburg, et al., Appl. Environ. Microbiol. 71(3):1223-1230, 2005).

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin, et al., J. Bacteriol. 174(17):5633-5638, 1992). Additionally, in vitro transposomes are available from commercial sources such as Epicentre™ to create random mutations in a variety of genomes.

Vectors suitable for expression and propagation in yeast cells are also well known. Methods for gene expression in yeast are known in the art (see, e.g., Methods in Enzymology, Volume 194, Guide to Yeast Genetics and Molecular and Cell Biology (Part A, 2004, Christine Guthrie and Gerald R. Fink (Eds.), Elsevier Academic Press, San Diego, Calif.). Expression of genes in yeast typically requires a promoter, operably linked to a coding region of interest, and a transcriptional terminator. A number of yeast promoters can be used in constructing expression cassettes for genes in yeast including, but not limited to, promoters derived from the following genes: CYC1, HIS3, GAL1, GAL10, ADH1, PGK, PHO5, GAPDH, ADC1, TRP1, URA3, LEU2, ENO, TPI, CUP1, FBA, GPD, GPM, and AOX1. Suitable transcriptional terminators include, but are not limited to, FBAt, GPDt, GPMt, ERG10t, GAL1t, CYC1, and ADH1.

Suitable promoters, transcriptional terminators, and a DHAD variant coding regions can be cloned into *Escherichia coli* (*E. coli*)-yeast shuttle vectors, and transformed into yeast cells, for example. These vectors allow strain propagation in both *E. coli* and yeast strains. Typically, the vector used contains a selectable marker and sequences allowing autonomous replication or chromosomal integration in the desired host. Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2p, origin of replication, and a marker for nutritional selection. The selection markers for these four vectors are His3 (vector pRS423), Trp1 (vector pRS424), Leu2 (vector pRS425), and Ura3 (vector pRS426). Construction of expression vectors with a chimeric gene encoding the described DHAD variants can be performed, for example, by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a 21 bp sequence at both the 5' and the 3' ends that sequentially overlap with each other, and with the 5' and 3' terminus of the vector DNA. For example, to construct a yeast expression vector for "Gene X", a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, for example, TOP10, followed by mini preps and restriction mapping to further verify the plasmid construct. Finally, the construct can be verified by sequence analysis.

Like the gap repair technique, integration into the yeast genome also takes advantage of the homologous recombination system in yeast. Typically, a cassette containing a coding region plus control elements (promoter and terminator) and auxotrophic marker is PCR-amplified with a high-fidelity DNA polymerase using primers that hybridize to the cassette and contain 40-70 base pairs of sequence homology to the regions 5' and 3' of the genomic area where insertion is desired. The PCR product is then transformed into yeast and plated on medium containing the appropriate compound mixtures that allow selection for the integrated auxotrophic marker. For example, to integrate "Gene X" into chromosomal location "Y," the promoter-coding region X-terminator construct is PCR amplified from a plasmid DNA construct and joined to an autotrophic marker (such as URA3) by either SOE PCR or by common restriction digests and cloning. The full cassette, containing the promoter-coding region X-terminator-URA3 region, is PCR amplified with primer sequences that contain 40-70 base pairs (bps) of homology to the regions 5' and 3' of location "Y" on the yeast chromosome. The PCR product is transformed into yeast and selected on growth media lacking uracil. Transformants can be verified either by colony PCR or by direct sequencing of chromosomal DNA.

Recombinant Host Cells

The isolated nucleic acid molecules and vectors of the invention can be transformed into a host cell for DHAD expression and activity. Suitable host cells include any cell capable of genetic manipulation, and include bacteria, cyanobacteria, filamentous fungi, and yeasts.

The microbial hosts selected for the production of isobutanol are preferably tolerant to isobutanol and should be able to convert carbohydrates to isobutanol. The criteria for selection of suitable microbial hosts include, for example, the following: intrinsic tolerance to isobutanol, high rate of glucose utilization, availability of genetic tools for gene manipulation, and the ability to generate stable chromosomal alterations.

Yeast Cells

Yeast cells that can be hosts for expression of a DHAD variant of the invention are any yeast cells that are amenable to genetic manipulation and include, but are not limited to, *Saccharomyces*, *Schizosaccharomyces*, *Hansenula*, *Candida*, *Kluyveromyces*, *Yarrowia*, and *Pichia*. Suitable strains include, but are not limited to, *Saccharomyces cerevisiae*, *Schizosaccharomyces pombe*, *Kluyveromyces lactis*, *Kluyveromyces thermotolerans*, *Candida glabrata*, *Candida albicans*, *Pichia stipitis*, and *Yarrowia lipolytica*. In some embodiments, the yeast host is *Saccharomyces cerevisiae*. *Saccharomyces cerevisiae* yeast are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *Saccharomyces cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

Expression is achieved by transforming the host cell with a gene comprising a sequence encoding any of the DHAD variants of the invention. The coding region for the DHAD to be expressed can be codon optimized for the yeast cell, as is well known to one skilled in the art.

In some embodiments, reducing production of an endogenous iron-sulfur (Fe—S) protein in a yeast host cell may result in an improvement in activity of an expressed heterologous Fe—S cluster protein, such as the variant DHAD enzymes of the invention. For example, in the yeast *Saccharomyces cerevisiae*, the native DHAD is encoded by ILV3, and is a mitochondrially-localized protein. Thus, in any of the yeast hosts described herein, an endogenous ILV3 gene can be inactivated to reduce endogenous Fe—S protein expression. ILV3 encodes mitochondrial DHAD that is involved in branched chain amino acid biosynthesis. Mitochondrial DHAD is encoded by a nuclear gene, and has a mitochondrial targeting signal sequence so that it is transported to and localized in the mitochondrion. Any ILV3 gene can be inactivated in a yeast host cell of this disclosure. Examples of yeast ILV3 inactivation target genes and their encoded proteins are those from *Saccharomyces cerevisiae* YJM78 (coding SEQ ID NO:389; protein SEQ ID NO:390), *Schizosaccharomyces pombe* (coding SEQ ID NO:387; protein SEQ ID NO:3884), *Candida galbrata* strain CBS 138 (coding SEQ ID NO:399; protein SEQ ID NO:400), *Candida albicans* SC5314 (coding SEQ ID NO:393; protein SEQ ID NO:394), *Kluyveromyces lactis* (coding SEQ ID NO:391; protein SEQ ID NO:392), *Yarrowia lipolytica* (coding SEQ ID NO:397; protein SEQ ID NO:398), and *Pichia stipitis* CBS 6054 (coding SEQ ID NO:395; protein SEQ ID NO:396).

In addition, in some embodiments, over-expression of the transcriptional activator genes AFT1 and/or AFT2 or homologs thereof in a recombinant yeast microorganism improves DHAD activity. Thus, the invention also provides recombinant yeast host cells comprising the isolated nucleic acid molecules of the invention, further genetically engineered to have increased heterologous or native expression of AFT1 and/or AFT2 or homologs thereof. Grx3, Grx4, and Fra2 are proteins involved in iron-sulfur cluster biosynthesis in yeast. Grx3 and Grx4 are monothiol glutaredoxins that have been shown to be involved in cellular Fe content modulation and delivery in yeast. Glutaredoxins are glutathione-dependent thiol-disulfide oxidoreductases that function in maintaining the cellular redox homeostasis. *Saccharomyces cerevisiae* has two dithiol glutaredoxins (Grx1 and Grx2) and three monothiol glutaredoxins (Grx3, Grx4, and Grx5). The monothiol glutaredoxins are believed to reduce mixed disulfides formed between a protein and glutathione in a process known as deglutathionylation. Thus, the invention is also directed to a recombinant host described herein (e.g., yeast) further genetically modified to disrupt a gene encoding an endogenous Fra2, Grx3, and/or Grx4 or a homolog thereof. In some embodiments, increases in DHAD activity may be observed in yeast cells with disruptions in FRA2, GRX3, and/or GRX4.

In some embodiments, the invention is also directed to a recombinant host described herein (e.g., yeast) further genetically modified to disrupt (e.g., delete) a gene encoding pyruvate decarboxylase (PDC). In some embodiments, the PDC is PDC1, PDC5, PDC6, or combinations thereof.

Bacterial Cells

In some embodiments, the recombinant host cell is a prokaryotic cell. In certain embodiments, the recombinant host cell is a bacterial cell. In other embodiments, the bacterial cell is a lactic acid bacterial (LAB) cell selected from the group consisting of Lactococcus, Lactobacillus, Leuconostoc, Oenococcus, Pediococcus, and Streptococcus. In still other embodiments, the bacterial host cell is the lactic acid bacteria Lactobacillus. In some embodiments, the bacterial host cell is Lactobacillus plantarum.

Bacterial cells that can be hosts for expression of a heterologous bacterial $[2Fe-2S]^{2+}$ DHAD include, but are not limited to, Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Lactococcus, Leuconostoc, Oenococcus, Pediococcus, and Streptococcus. Engineering expression of a heterologous DHAD variant can increase DHAD activity in a host bacterial cell that naturally expresses a $[2Fe-2S]^{2+}$ DHAD or a $[4Fe-4S]^{2+}$ DHAD. Such host cells can include, for example, Escherichia coli and Bacillus subtilis. Furthermore, engineering expression of a heterologous DHAD variant provides DHAD activity in a host bacterial cell that has no endogenous DHAD activity. Such host cells can include, for example, Lactobacillus, Enterococcus, Pediococcus, and Leuconostoc.

Specific hosts include: Escherichia coli, Alcaligenes eutrophus, Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, and Bacillus subtilis. Bacterial cells can be genetically modified for expression of DHAD variants using methods well known to one skilled in the art. Expression of DHAD variants is generally achieved by transforming suitable bacterial host cells with a sequence encoding a DHAD variant protein. Typically, the coding sequence is part of a chimeric gene used for transformation, which includes a promoter operably linked to the coding sequence as well as a ribosome binding site and a termination control region. The coding region can be from the host cell for transformation and combined with regulatory sequences that are not native to the natural gene encoding the variant DHAD. Alternatively, the coding region can be from another host cell.

Initiation control regions or promoters, which are useful to drive expression of a DHAD variant coding region in bacteria, are familiar to those skilled in the art. Some examples include the amy, apr, and npr promoters; nisA promoter (useful for expression Gram-positive bacteria (Eichenbaum, et al., Appl. Environ. Microbiol. 64(8):2763-2769, 1998); and the synthetic P11 promoter (useful for expression in Lactobacillus plantarum, Rud, et al., Microbiology 152:1011-1019, 2006). In addition, the ldhL1 and fabZ1 promoters of Lactobacillus plantarum are useful for expression of chimeric genes in bacteria. The fabZ1 promoter directs transcription of an operon with the first gene, fabZ1, encoding (3R)-hydroxymyristoyl-[acyl carrier protein] dehydratase. Termination control regions can also be derived from various genes, typically from genes native to the preferred hosts. In other embodiments, a termination site is unnecessary.

Vectors can be introduced into lactic acid bacteria (LAB) host cells using methods known in the art, such as electroporation (Cruz-Rodz, et al., Molecular Genetics and Genomics 224:1252-154, 1990; Bringel, et al., Appl. Microbiol. Biotechnol. 33:664-670, 1990; Alegre, et al., FEMS Microbiology Letters 241:73-77, 2004), and conjugation (Shrago, et al., Appl. Environ. Microbiol. 52:574-576, 1986). A chimeric DHAD gene can also be integrated into the chromosome of LAB using integration vectors (Hols, et al., Appl. Environ. Microbiol. 60:1401-1403, 1990; Jang, et al., Micro. Lett. 24:191-195, 2003).

Lactic acid bacteria are well characterized and are used commercially in a number of industrial processes. Although it is known that some lactic acid bacteria possess iron-sulfur (Fe—S) cluster requiring enzymes (Liu, et al., J. Biol. Chem. 275(17); 12367-12373, 2000) and therefore possess the genetic machinery to produce Fe—S clusters, little is known about the ability of lactic acid bacteria to insert Fe—S clusters into heterologous enzymes, and little is known about the facility with which Fe—S cluster forming proteins can be expressed in lactic acid bacteria.

To obtain high levels of product in a lactic acid bacteria from a biosynthetic pathway including DHAD activity, high expression of DHAD activity is desired. The activity of the Fe—S requiring DHAD enzyme in a host cell can be limited, for example, by the availability of Fe—S clusters in the cell. Increasing the expression of Fe—S cluster forming proteins effectively increased the activity of DHAD in LAB cells. Thus, in certain embodiments, a lactic acid bacterial host cell is genetically engineered to express at least one recombinant genetic expression element encoding Fe—S cluster forming proteins. The genetic engineering of lactic acid bacteria to express iron-sulfur cluster forming proteins is described in U.S. Patent Application Publication No. 2010/0081182, which is herein incorporated by reference.

Expression of any set of proteins for Fe—S cluster formation can be used to increase DHAD activity in LAB cells. There are three known groups of Fe—S cluster forming proteins. These proteins are encoded by three types of operons: the Suf operon, the Isc operon, and the Nif operon. U.S. Patent Application Publication No. 2010/0081182 discloses the Suf operons of Lactobacillus plantarum (L. plantarum), Lactobacillus lactis (L. lactis), and Escherichia coli (E. coli); the Isc operon of E. coli; and the Nif operon of Wolinella succinogenes.

Culture Conditions for Butanol Production

The invention also provides a method for the production of butanol (e.g., isobutanol) comprising providing recombinant host cells comprising the isolated nucleic acid molecules of the invention; culturing the recombinant host cell in a fermentation medium under suitable conditions to produce isobutanol from pyruvate; and recovering the isobutanol. In certain embodiments, the isobutanol is produced at a titer that is increased as compared to a recombinant host cell that does not contain the amino acid substitutions. In other embodiments, the isobutanol is produced at a rate that is increased by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, or at least about 300% as compared to a recombinant host cell that does not contain the amino acid substitutions. In other aspects of the method to produce isobutanol, the concentration of isobutanol in the fermentation medium is greater than or equal to about 10 mM, greater than or equal to about 20 mM, greater than or equal to about 30 mM, greater than or equal to about 40 mM, greater than or equal to about 50 mM, greater than or equal to about 60 mM, greater than or equal to about 70 mM, greater than or equal to about 80 mM, greater than or equal to about 90 mM, or greater than or equal to about 100 mM.

Recombinant host cells disclosed herein are grown in media which contains suitable carbon substrates. Additional carbon substrates can include, but are not limited to, monosaccharides such as fructose; oligosaccharides such as lactose, maltose, galactose, or sucrose; polysaccharides such as starch or cellulose; or mixtures thereof and unpurified mixtures from renewable feedstocks such as cheese whey permeate, cornsteep liquor, sugar beet molasses, and barley malt. Other carbon substrates can include, but are not limited to, ethanol, lactate, succinate, and glycerol.

Additionally the carbon substrate can also be one carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., Microb. Growth C1 Compd., [Int. Symp.], 7th (1993), 415 32, Editor(s): Murrell, J. Collin; Kelly, Don P. Publisher: Intercept, Andover, UK). Similarly, various species of *Candida* will metabolize alanine or oleic acid (Sulter, et al., Arch. Microbiol. 153:485 489, 1990). Hence, it is contemplated that the source of carbon utilized in the present invention can encompass a wide variety of carbon containing substrates and will only be limited by the choice of organism.

Although it is contemplated that all of the above mentioned carbon substrates and mixtures thereof are suitable in the present invention, in some embodiments, the carbon substrates may be glucose, fructose, and sucrose, or mixtures of these with five-carbon (C5) sugars such as xylose and/or arabinose for yeasts cells modified to use C5 sugars. Sucrose can be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Pat. No. 7,932,063, which is herein incorporated by reference. Biomass refers to any cellulosic or lignocellulosic material and includes materials comprising cellulose, and optionally further comprising hemicellulose, lignin, starch, oligosaccharides, and/or monosaccharides. Biomass can also comprise additional components, such as protein and/or lipid. Biomass can be derived from a single source, or biomass can comprise a mixture derived from more than one source; for example, biomass can comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs, bushes, vegetables, fruits, flowers, animal manure, and mixtures thereof.

In addition to an appropriate carbon source, fermentation media may contain suitable minerals, salts, cofactors, buffers, and other components, known to those skilled in the art, suitable for the growth of the cultures and promotion of an enzymatic pathway comprising a DHAD.

Typically, cells are grown at a temperature in the range of about 20° C. to about 40° C. in an appropriate medium. Suitable growth media for the present invention include, for example, common commercially prepared media such as Luria Bertani (LB) broth, Sabouraud Dextrose (SD) broth, Yeast Medium (YM) broth, or broth that includes yeast nitrogen base, ammonium sulfate, and dextrose (as the carbon/energy source) or Yeast Extract Peptone Dextrose (YPD) Medium, a blend of peptone, yeast extract, and dextrose in optimal proportions for growing most *Saccharomyces cerevisiae* strains. Other defined or synthetic growth media can also be used, and the appropriate medium for growth of the particular microorganism will be known by one skilled in the art of microbiology or fermentation science. The use of agents known to modulate catabolite repression directly or indirectly, for example, cyclic adenosine 2':3' monophosphate, can also be incorporated into the fermentation medium.

Suitable pH ranges for the fermentation are between about pH 5.0 to about pH 9.0. In one embodiment, about pH 6.0 to about pH 8.0 is used for the initial condition. Suitable pH ranges for the fermentation of yeast are typically between about pH 3.0 to about pH 9.0. In one embodiment, about pH 5.0 to about pH 8.0 is used for the initial condition. Suitable pH ranges for the fermentation of other microorganisms are between about pH 3.0 to about pH 7.5. In one embodiment, about pH 4.5 to about pH 6.5 is used for the initial condition.

Fermentations can be performed under aerobic or anaerobic conditions. In one embodiment, anaerobic or microaerobic conditions are used for fermentations.

Industrial Batch and Continuous Fermentations

Isobutanol, or other products, can be produced using a batch method of fermentation. A classical batch fermentation is a closed system where the composition of the medium is set at the beginning of the fermentation and not subject to artificial alterations during the fermentation. A variation on the standard batch system is the fed batch system. Fed batch fermentation processes are also suitable in the present invention and comprise a typical batch system with the exception that the substrate is added in increments as the fermentation progresses. Fed batch systems are useful when catabolite repression is apt to inhibit the metabolism of the cells and where it is desirable to have limited amounts of substrate in the media. Batch and fed batch fermentations are common and well known in the art, examples of which are described by Thomas D. Brock in Biotechnology: A Textbook of Industrial Microbiology, Second Edition (1989) Sinauer Associates, Inc., Sunderland, M. A., or Deshpande, Mukund V., Appl. Biochem. Biotechnol., 36:227, (1992), herein incorporated by reference.

Isobutanol, or other products, can also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of isobutanol, or other products, can be practiced using batch, fed batch, or continuous processes and that any known mode of fermentation is suitable. Additionally, it is contemplated that cells can be immobilized on a substrate as whole cell catalysts and subjected to fermentation conditions for isobutanol production.

Biosynthetic Pathways

Expression of a DHAD variant in bacteria or yeast, as described herein, provides the transformed, recombinant host cell with dihydroxy-acid dehydratase (DHAD) activity for conversion of 2,3-dihydroxyisovalerate to α-ketoisovalerate or 2,3-dihydroxymethylvalerate to α-ketomethylvalerate. Any product that has α-ketoisovalerate or α-ketomethylvalerate as a pathway intermediate can be produced in a bacterial or yeast strain disclosed herein having the described heterologous DHAD variants. A list of such products includes, but is not limited to, valine, isoleucine, leucine, pantothenic acid, 2-methyl-1-butanol, 3-methyl-1-butanol, and isobutanol.

For example, yeast biosynthesis of valine includes steps of acetolactate conversion to 2,3-dihydroxy-isovalerate by acetohydroxyacid reductoisomerase (ILV5), conversion of 2,3-dihydroxy-isovalerate to α-ketoisovalerate (also called 2-keto-isovalerate) by dihydroxy-acid dehydratase, and conversion of α-ketoisovalerate to valine by branched-chain amino acid transaminase (BAT2) and branched-chain amino acid aminotransferase (BAT1). Biosynthesis of leucine includes the same steps to α-ketoisovalerate, followed by conversion of α-ketoisovalerate to α-isopropylmalate by α-isopropylmalate synthase (LEU9, LEU4), conversion of α-isopropylmalate to beta-isopropylmalate by isopropylmalate isomerase (LEU1), conversion of beta-isopropylmalate to α-ketoisocaproate by beta-IPM dehydrogenase (LEU2), and finally conversion of α-ketoisocaproate to leucine by branched-chain amino acid transaminase (BAT2) and branched-chain amino acid aminotransferase (BAT1). The bacterial pathway is similar, involving differently named proteins and genes. Increased conversion of 2,3-dihydroxy-isovalerate to α-ketoisovalerate will increase flow in these pathways, particularly if one or more additional enzymes of a pathway is over-expressed. Thus, it is desired for production of valine or leucine to use a strain disclosed herein.

Biosynthesis of pantothenic acid includes a step performed by DHAD, as well as steps performed by ketopantoate hydroxymethyltransferase and pantothenate synthase. Engineering of expression of these enzymes for enhanced production of pantothenic acid biosynthesis in microorganisms is described, for example, in U.S. Pat. No. 6,177,264, which is incorporated by reference herein.

Figure 2:
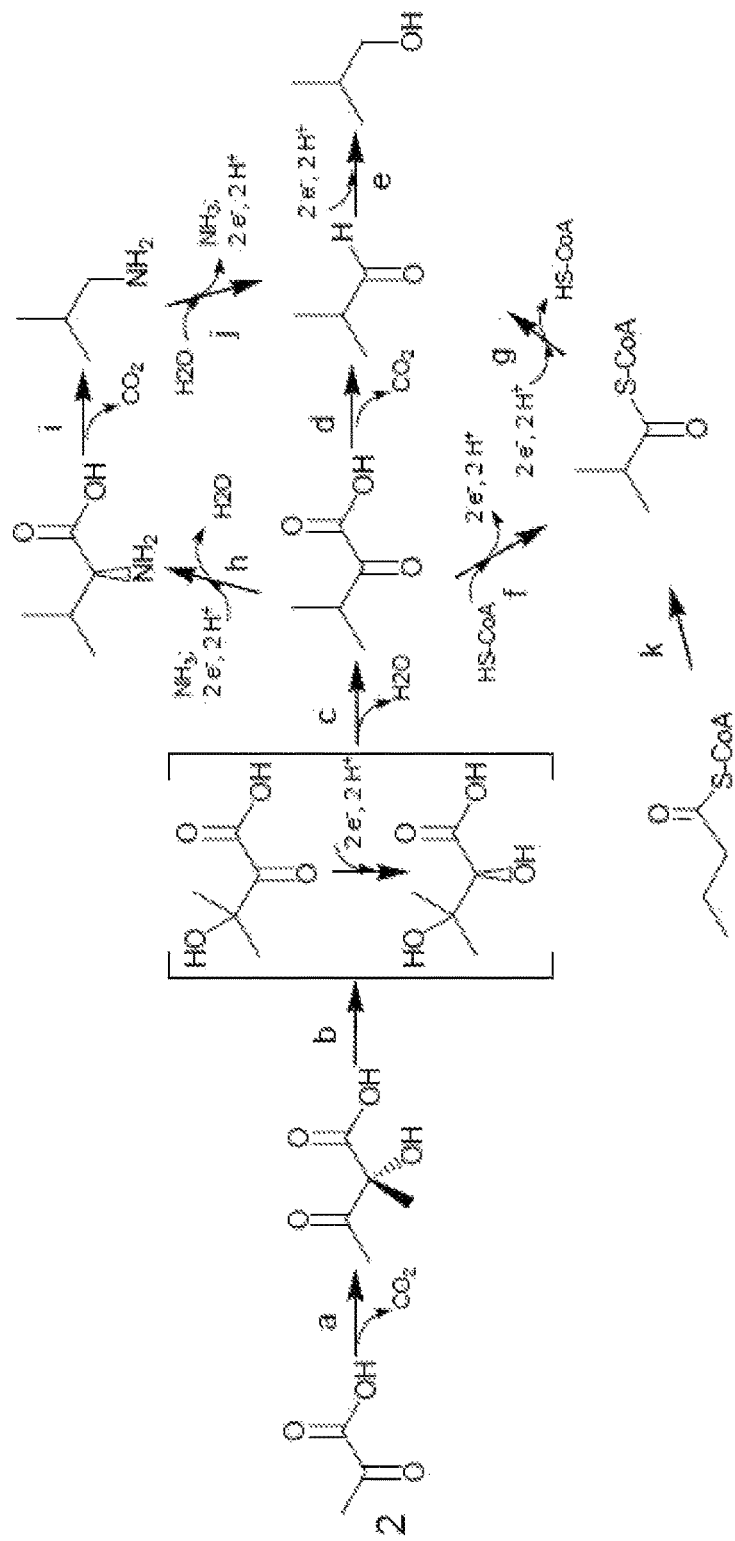
FIG. 2 shows biosynthetic pathways for isobutanol production.

The α-ketoisovalerate product of DHAD is an intermediate in isobutanol biosynthetic pathways disclosed, for example, in U.S. Pat. No. 7,851,188, which is incorporated by reference herein. A diagram of the disclosed isobutanol biosynthetic pathways is provided in FIG. 2. Production of isobutanol in a strain disclosed herein benefits from increased DHAD activity. As disclosed herein, DHAD activity is provided by expression of a variant DHAD in a bacterial or yeast cell. As described in U.S. Pat. No. 7,851,188, steps in an example isobutanol biosynthetic pathway include conversion of: pyruvate to acetolactate as catalyzed, for example, by acetolactate synthase, acetolactate to 2,3-dihydroxyisovalerate as catalyzed, for example, by acetohydroxy acid isomeroreductase; 2,3-dihydroxyisovalerate to α-ketoisovalerate as catalyzed, for example, by acetohydroxy acid dehydratase, also called dihydroxy-acid dehydratase (DHAD); α-ketoisovalerate to isobutyraldehyde as catalyzed, for example, by branched-chain α-keto acid decarboxylase; and isobutyraldehyde to isobutanol as catalyzed, for example, by branched-chain alcohol dehydrogenase. The substrate to product conversions, and enzymes involved in these reactions, are described, for example, in U.S. Pat. No. 7,851,188, which is incorporated by reference herein.

Genes that can be used for expression of the pathway step enzymes named above other than the variant DHADs disclosed herein, as well as those for two additional isobutanol pathways, are described, for example, in U.S. Pat. No. 7,851,188, which is incorporated by reference herein, and additional genes that can be used can be identified by one skilled in the art through bioinformatics or experimentally as described herein. Ketol-acid reductoisomerase (KARI) enzymes are also disclosed, for example, in U.S. Pat. No. 7,910,342 and PCT Application Publication No. WO2012/129555, both incorporated by reference herein. Examples of KARIs disclosed therein include KARIs from *Vibrio cholerae* (DNA: SEQ ID NO:599; protein SEQ ID NO:600), *Pseudomonas aeruginosa* PAO1, (DNA: SEQ ID NO:601; protein SEQ ID NO:602), *Pseudomonas fluorescens* PF5 (DNA: SEQ ID NO:603; protein SEQ ID NO:604), and *Anaerostipes caccae* (protein SEQ ID NO:605).

Additionally described in U.S. Pat. No. 7,851,188 are construction of chimeric genes and genetic engineering of bacteria and yeast for isobutanol production using the disclosed biosynthetic pathways. In some embodiments, one or more components of the biosynthetic pathways described herein can be endogenous to the host cell of choice, or can be heterologous. Additionally, in other embodiments, one or more of the genes encoding the enzymes required in the biosynthetic pathways can be over-expressed in the host cell.

Methods for Butanol Isolation from the Fermentation Medium

Methods for butanol isolation from fermentation medium have been described. For example, bioproduced isobutanol can be isolated from the fermentation medium using methods known in the art for ABE fermentations (see, e.g., Durre, Appl. Microbiol. Biotechnol. 49:639-648, 1998; Groot, et al., Process. Biochem. 27:61-75, 1992, and references therein). For example, solids may be removed from the fermentation medium by centrifugation, filtration, decantation, or the like. Then, the isobutanol can be isolated from the fermentation medium using methods such as distillation, azeotropic distillation, liquid-liquid extraction, adsorption, gas stripping, membrane evaporation, pervaporation, or combinations thereof.

Because isobutanol forms a low boiling point, azeotropic mixture with water, distillation can be used to separate the mixture up to its azeotropic composition. Distillation may be used in combination with another separation method to obtain separation around the azeotrope. Methods that can be used in combination with distillation to isolate and purify butanol include, but are not limited to, decantation, liquid-liquid extraction, adsorption, and membrane-based techniques. Additionally, butanol can be isolated using azeotropic distillation using an entrainer (see, e.g., Doherty and Malone, Conceptual Design of Distillation Systems, McGraw Hill, New York, 2001).

The butanol-water mixture forms a heterogeneous azeotrope so that distillation can be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase can be returned to the first distillation column as reflux. The isobutanol-rich decanted organic phase can be further purified by distillation in a second distillation column.

The isobutanol can also be isolated from the fermentation medium using liquid-liquid extraction in combination with distillation. In this method, the isobutanol is extracted from the fermentation broth using liquid-liquid extraction with a suitable solvent. The isobutanol-containing organic phase is then distilled to separate the butanol from the solvent.

Distillation in combination with adsorption can also be used to isolate isobutanol from the fermentation medium. In this method, the fermentation broth containing the isobutanol is distilled to near the azeotropic composition and then the remaining water is removed by use of an adsorbent, such as molecular sieves (Aden, et al., Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, June 2002).

Additionally, distillation in combination with pervaporation may be used to isolate and purify the isobutanol from the fermentation medium. In this method, the fermentation broth containing the isobutanol is distilled to near the azeotropic composition, and then the remaining water is removed by pervaporation through a hydrophilic membrane (Guo, et al., J. Membr. Sci. 245, 199-210, 2004).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches a toxic level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Application Publication No. 2009/0305370, the disclosure of which is hereby incorporated in its entirety. U.S. Patent Application Publication No. 2009/0305370 describes methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, linoleic acid, linolenic acid, myristic acid, stearic acid, methyl myristate, methyl oleate, undecanal, lauric aldehyde, 20-methylundecanal, and mixtures thereof.

In some embodiments, the alcohol can be formed by contacting the alcohol in a fermentation medium with an organic acid (e.g., fatty acids) and a catalyst capable of esterfiying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids forming organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches a toxic level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

Methods of Screening for DHAD Variants

The invention also provides yeast strains and methods of using the yeast strains to screen for DHAD variants with increased DHAD activity as compared to a parental DHAD enzyme. The premise behind the screen is to reduce DHAD expression and/or activity in a yeast strain to artificially create a system where DHAD activity is rate-limiting for growth. Introducing a mutation into the DHAD gene resulting in a DHAD variant enzyme with increased activity will overcome the rate-limiting step, allowing the strain to grow or produce an increased amount of product, such as isobutanol. Therefore, yeast isolates expressing DHAD variants with increased DHAD activity can be identified and selected based on their growth differential as compared to a control strain, or based on an increased production of a product compared to a control strain.

In certain embodiments, the invention provides a yeast strain with a defect in the genetic pathway that converts pyruvate to ethanol, such that the yeast strain cannot grow or grows poorly in fermentation medium containing glucose as the primary carbon source. The defect in the genetic pathway that converts pyruvate to ethanol can comprise a deletion of a PDC gene or a mutation in a PDC gene that reduces PDC activity. In certain embodiments, the PDC gene is PDC1, PDC5, PDC6, or a combination thereof.

The "genetic pathway that converts pyruvate to ethanol" comprises at least the following genes in *Saccharomyces cerevisiae*: PDC1, PDC5, PDC6, and ADH1. Pyruvate is first converted to acetaldehyde by pyruvate decarboxylase. Subsequently, acetaldehyde is converted to ethanol by alcohol dehydrogenase. Any defect (e.g., an insertion, deletion, mutation, or substitution in one or more pathway genes) that disrupts the ability of the yeast strain to produce ethanol from glucose but leaves intact the ability to produce isobutanol from glucose is contemplated to be a defect in the genetic pathway that converts pyruvate to ethanol.

The growth rate of the yeast strain of the invention is such that it can be modulated by increasing or decreasing the amount of DHAD activity within the cell. For example, a yeast strain of the invention that expresses very low levels of a DHAD enzyme will grow poorly or not at all when grown in fermentation medium with glucose as the primary carbon source. Thus, a "low level" of DHAD activity is defined as an amount of DHAD enzyme activity that results in no growth or poor growth of the yeast strain of the invention. "Poor growth," for the purposes of the present invention, can be considered a growth rate that is slow enough that a detectable difference in growth rates can be observed when DHAD activity is restored. Conversely, a yeast strain of the invention that expresses high levels of DHAD enzyme will grow well when grown in fermentation medium with glucose as the primary carbon source. As such, a "high level" of DHAD activity is defined as an amount of DHAD enzyme activity that results in a growth rate that is detectably improved compared to the same strain expressing a low level of DHAD activity. The growth differential between a strain with low levels of DHAD activity and a strain with high levels of DHAD activity can be determined or detected by methods known to a skilled artisan, such as calculating doubling times, determining the density of cells in culture, or simply by visually assessing the size of individual colonies grown on solid media after a given amount of time.

Numerous methods can be used to modulate the expression levels of a DHAD enzyme in the yeast strain of the invention and are well known to skilled artisans. These methods include, but are not limited to, expressing a DHAD enzyme under a weak promoter, expressing a DHAD enzyme on a low copy number plasmid, expressing a DHAD enzyme under an inducible promoter and varying the amount of inducing agent, optimizing codon usage for the organism in which it is to be expressed (to increase expression) or adjusting codon usage to be sub-optimal for the organism in which it is to be expressed (to decrease expression).

Low copy number plasmids generally exist in a cell in less than about 100 copies/cell. In certain embodiments, the low copy number plasmid exists in a cell in less than about 50, less than about 40, less than about 30, less than about 20, less than about 10, less than about 5, or less than about 2 copies/cell. In certain embodiments, the low copy number plasmid exists in a cell in about one copy per cell.

In methods to screen for DHAD variants, the yeast strain of the invention is transformed with a polynucleotide comprising a nucleic acid sequence encoding a parental DHAD enzyme under conditions wherein a low level of DHAD enzyme activity is achieved, and no growth or poor growth of the strain is seen in fermentation medium wherein glucose is the primary carbon source. This transformant is used as a control strain. A library of polynucleotides is prepared, each polynucleotide comprising a nucleic acid sequence encoding a DHAD variant. This library of DHAD variants is transformed into the yeast strain of the invention, under the same conditions as the control strain, and growth rates or product yield of individual isolates transformed with a variant is assessed. Variants that result in increased DHAD activity will grow more robustly and/or produce a higher yield of product than the control strain, and can be isolated for further analysis.

Thus, an aspect of the invention is directed to a method of screening DHAD protein variants, comprising: (a) providing a yeast strain with a defect in a genetic pathway that converts pyruvate to ethanol, wherein the yeast strain cannot grow or grows poorly in fermentation medium containing glucose as the primary carbon source; (b) transforming the yeast strain with a library of polynucleotides, each polynucleotide comprising a nucleic acid sequence encoding a DHAD variant, wherein: (i) the nucleic acid sequence encoding the DHAD variant is operably linked to a weak promoter; or (ii) the nucleic acid sequence encoding the DHAD variant is comprised within a low copy number plasmid; wherein the yeast strain cannot grow or grows poorly when transformed with a control polynucleotide comprising a nucleic acid sequence encoding a wild type DHAD, operably linked to the weak promoter or transformed with a control low copy number plasmid comprising a nucleic acid sequence encoding a wild type DHAD; and (c) selecting transformants with improved growth compared to growth of a strain transformed with the control polynucleotide. In some embodiments, the defect in the genetic pathway that converts pyruvate to ethanol comprises a deletion of a pyruvate decarboxylase (PDC) gene. In other embodiments, the defect in the genetic pathway that converts pyruvate to ethanol comprises a mutation in a PDC gene that reduces PDC activity. In certain embodiments, the PDC gene is PDC1, PDC5, PDC6, or a combination thereof.

In some embodiments of the method of screening DHAD protein variants, the weak promoter is a truncated Leu2 promoter. In certain embodiments, the truncated Leu2 promoter is SEQ ID NO:545. In other embodiments of the method of screening DHAD protein variants, the weak promoter is a truncated FBA promoter. In certain embodiments, the truncated FBA promoter is SEQ ID NO:546. Other weak promoters are known in the art, such as the Ste5 promoter, the Ura3 promoter, and the Cyc1 promoter. Other promoters that are considered strong or moderate promoters in their full-length state can be made weak by truncation or other modifications. For the purposes of the present invention, a "weak promoter" is defined as a promoter that results in a level of expression of a parental DHAD enzyme in a strain of the invention that does not allow growth or allows only poor growth on fermentation medium with glucose as the primary carbon source.

In some embodiments of the method of screening DHAD protein variants, the low copy number plasmid has a copy number of one or two in yeast. In certain embodiments, the low copy number plasmid is pRS413. Low copy number plasmids for use in yeast include the yeast integrating plasmids (Yip) and yeast centromere plasmids (YCp), as well as the pRS series of plasmids. pRS plasmids were first described by Sikorski, et al. (Genetics, 122:19-27, 1989) and include, but are not limited to, pRS303, pRS304, pRS305, pRS306, pRS313, pRS314, pRS315, and pRS316.

In other embodiments of the method of screening DHAD protein variants, the growth of the strain is under oxygen limiting conditions. In yet other embodiments, the yeast strain is further transformed with genes encoding acetolactate synthase, acetohydroxy acid isomeroreductase, α-keto acid decarboxylase, and alcohol dehydrogenase. In certain embodiments of the method of screening DHAD protein variants, the method further comprises determining the rate of isobutanol production of the transformants.

Another aspect of the invention is directed to isolated polynucleotides comprising a nucleic acid sequence encoding a DHAD variant obtained by the method of screening DHAD protein variants as described herein. The invention is also directed to isolated DHAD variant polypeptides encoded by these nucleic acid sequences.

EXAMPLES

Example 1

Construction of Yeast Strain PNY2204

The purpose of this example is to describe construction of a vector to enable integration of a gene encoding acetolactate synthase into the naturally occurring intergenic region between the PDC1 and TRX1 coding sequences in Chromosome XII. Construction of yeast strain PNY2204 is also described, for example, in U.S. Application Publication No. 2012/0237988, which is incorporated herein by reference.

Construction of Integration Vector pUC19-kan::pdc1::FBA-alsS::TRX1

The FBA-alsS-CYCt cassette was constructed by moving the 1.7 kb BbvCI/PacI fragment from pRS426::GPD::alsS::CYC (U.S. Appl. Pub. No. 2007/0092957, incorporated by reference) to pRS426::FBA::ILV5::CYC (U.S. Application Publication No. 2007/0092957, incorporated by reference, previously digested with BbvCI/PacI to release the ILV5 gene). Ligation reactions were transformed into E. coli TOP10 cells and transformants were screened by PCR using primers N98SeqF1 (SEQ ID NO:580) and N99SeqR2 (SEQ ID NO:581). The FBA-alsS-CYCt cassette was isolated from the vector using BglII and NotI for cloning into pUC19-URA3::ilvD-TRX1 (as described in U.S. Application Publication No. 2012/0156735, incorporated herein by reference, clone "B;" herein SEQ ID NO:582) at the AflII site (Klenow fragment was used to make ends compatible for ligation). Transformants containing the alsS cassette in both orientations in the vector were obtained and confirmed by PCR using primers N98SeqF4 (SEQ ID NO:583) and N1111 (SEQ ID NO:584) for configuration "A" and N98SeqF4 (SEQ ID NO:583) and N1110 (SEQ ID NO:585) for configuration "B." A geneticin selectable version of the "A" configuration vector was then made by removing the URA3 gene (1.2 kb NotI/NaeI fragment) and adding a geneticin cassette (SEQ ID NO:586 herein; previously described in U.S. Application Publication No. 2012/0156735, incorporated herein by reference) maintained in a pUC19 vector (cloned at the SmaI site). The kan gene was isolated from pUC19 by first digesting with KpnI, removal of 3' overhanging DNA using Klenow fragment (New England BioLabs, Inc., Ipswich, Mass.; Cat. No. M212), digesting with HincII, and then gel purifying the 1.8 kb gene fragment (Zymoclean™ Gel DNA Recovery Kit, Cat. No. D4001, Zymo Research, Orange, Calif.; SEQ ID NO:587). Klenow fragment was used to make all ends compatible for ligation, and transformants were screened by PCR to select a clone with the geneticin resistance gene in the same orientation as the previous URA3 marker using primers BK468 (SEQ ID NO:588) and N160SeqF5 (SEQ ID NO:589). The resulting clone was called pUC19-kan::pdc1::FBA-alsS::TRX1 (clone A) (SEQ ID NO:590).

Construction of alsS Integrant Strains and Isobutanol-Producing Derivatives

Figure 3:
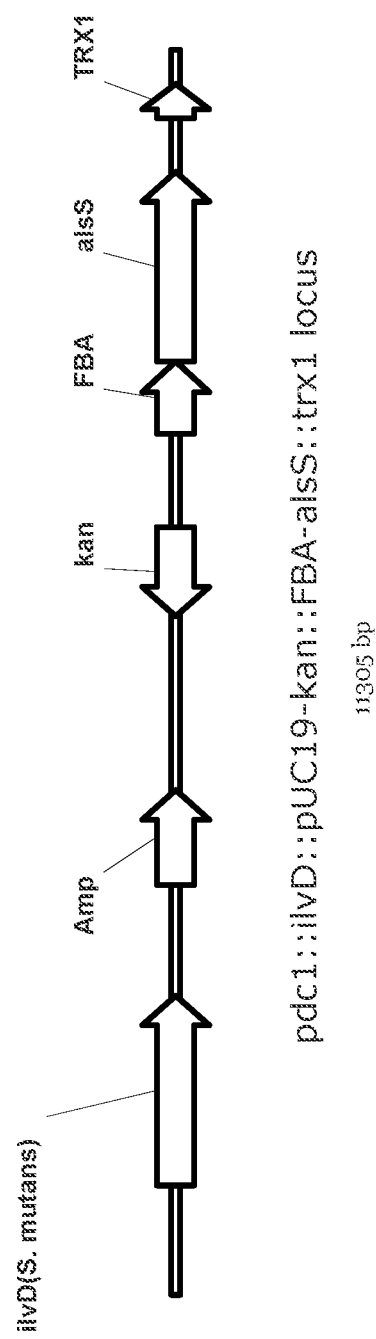
FIG. 3 is a schematic diagram of the PNY2204 locus (pdc1Δ::ilvD::pUC19-kan::FBA-alsS::TRX1).

The pUC19-kan::pdc1::FBA-alsS integration vector described above was linearized with PmeI and transformed into PNY1507 (described, for example, in U.S. Application Publication No. 2012/0156735, incorporated herein by reference). PmeI cuts the vector within the cloned pdc1-TRX1 intergenic region and thus leads to targeted integration at that location (Rothstein, Methods in Enzymology, 1991, volume 194, pp. 281-301). Transformants were selected on YPE plus 50 μg/ml G418. Patched transformants were screened by PCR for the integration event using primers N160SeqF5 (SEQ ID NO:589) and oBP512 (SEQ ID NO:591). Two transformants were tested indirectly for acetolactate synthase function by evaluating the strains ability to make isobutanol. To do this, additional isobutanol pathway genes were supplied on E. coli-yeast shuttle vectors (pYZ090ΔalsS and pBP915, described below). One clone, strain MATa ura3Δ::loxP his3Δpdc6Δpdc1Δ::P[PDC1]-DHAD|ilvD_Sm-PDC1t-pUC19-loxP-kanMX-loxP-P[FBA1]-ALS|alsS_Bs-CYC1t pdc5Δ::P[PDC5]-ADH|sadB_Ax-PDC5t gpd2Δ::loxP fra2Δadh1Δ::UAS(PGK1)P[FBA1]-kivD_Ll(y)-ADH1t was designated as PNY2204. The plasmid-free parent strain was designated PNY2204. The PNY2204 locus (pdc1Δ::ilvD:pUC19-kan::FBA-alsS::TRX1) is depicted in FIG. 3.

Isobutanol Pathway Plasmids (pYZ090ΔalsS and pBP915)

pYZ090 (SEQ ID NO:592) was digested with SpeI and NotI to remove most of the CUP1 promoter and all of the alsS coding sequence and CYC terminator. The vector was then self-ligated after treatment with Klenow fragment and transformed into E. coli Stbl3 cells, selecting for ampicillin resistance. Removal of the DNA region was confirmed for two independent clones by DNA sequencing across the ligation junction by PCR using primer N191 (SEQ ID NO:593). The resulting plasmid was named pYZ090ΔalsS (SEQ ID NO:594).

pBP915 was constructed from pLH468 (SEQ ID NO:595) by deleting the kivD gene and 957 base pairs of the TDH3 promoter upstream of kivD. pLH468 was digested with SwaI and the large fragment (12,896 bp) was purified on an agarose gel followed by a Gel Extraction kit (Qiagen, Valencia, Calif.). The isolated fragment of DNA was self-ligated with T4 DNA ligase and used to transform electro-competent TOP10 E. coli (Invitrogen; Carlsbad, Calif.). Plasmids from transformants were isolated and checked for the proper deletion by restriction analysis with the SwaI restriction enzyme. Isolates were also sequenced across the deletion site with primers oBP556 (SEQ ID NO:596) and oBP561 (SEQ ID NO:597). A clone with the proper deletion was designated pBP915 (pLH468ΔkivD) (SEQ ID NO:598).

Example 2

Expression of DHAD with a Weak Promoter for Isobutanol Production in Yeast

The use of dihydroxy-acid dehydratase (DHAD) enzymes, such as IlvD from *Streptococcus mutans*, for isobutanol production in yeast has been previously described, for example, in U.S. Application Publication No. 2012/0237988, incorporated herein by reference. In this example, yeast strain PNY2204 [MATa ura3Δ::loxP his3Δ pdc6Δ pdc1Δ::P[PDC1]-DHAD|ilvD_Sm-PDC1t-pUC19-loxP-kanMX-loxP-P [FBA1]-ALS|alsS_Bs-CYC1t pdc5Δ::P[PDC5]-ADH|sadB_Ax-PDC5t gpd2Δ::loxP fra2Δ adh1Δ::UAS(PGK1)P[FBA1]-kivD_Ll(y)-ADH1t, described above] was used as a starting point to determine the growth rate and isobutanol production rate of a strain with low levels of DHAD expression.

First, to create a control strain, yeast strain PNY2204 was transformed with plasmid pHR81 Ilv5p-K9G9 containing a KARI variant (SEQ ID NO:577). Transformants were selected on SE (-Ura) plates. The resulting strain was designated as PNY2204(K9G9). Next, plasmid pRS423 FBAp-IlvD(sm) GPMp-ADH (SEQ ID NO:578) was transformed into strain PNY2204 (K9G9) to complete the isobutanol pathway. On the plasmid pRS423 FBAp-IlvD(sm) GPMp-ADH, the DHAD gene is under the control of a strong FBA promoter. In addition, this plasmid also contained an additional ADH gene under the control of the GPM promoter to ensure a high level of activity for the downstream isobutanol pathway. Transformants were selected on agar plates with SE (-Ura -His) medium. This strain grew well on 2% glucose and produced significant amounts of isobutanol.

To create a strain with low levels of DHAD expression, strain PNY2204 (K9G9) was transformed with plasmid pRS423 Leu2p(75)-IlvD(Sm) GPMp-ADH (SEQ ID NO:579). This plasmid is identical to plasmid pRS423 FBAp-IlvD(sm) GPMp-ADH, described above, however the DHAD gene is under the control of a weak, truncated Leu2 promoter containing only 75 base pairs upstream of the ATG start site of the Leu2 coding region (SEQ ID NO:575). Transformants were selected on SE (-Ura -His) medium. The transformants obtained grew poorly on 2% glucose and made less isobutanol (lower titer) as compared to the strains containing plasmid pRS423 FBAp-IlvD(sm). This result indicated that a rate-limiting step for DHAD activity had been established using the truncated Leu2 promoter for expression.

Example 3

Construction and Screening of DHAD Mutant Libraries

Typically, pyruvate decarboxylase (PDC) deletion strains have reduced growth in the presence of 2% glucose in growth medium, especially under oxygen-limiting conditions. However, the introduction of an isobutanol pathway often results in increased growth. As shown in Example 2, DHAD enzyme activity is a rate-limiting step in the isobutanol pathway in strain PNY2204(K9G9) or PNY2204 (K9D3). One way to overcome this rate-limiting step is to improve the DHAD activity through mutagenesis of its gene ilvD. Better growth and increased isobutanol production can thus be used to screen for strains with higher DHAD activity.

Mutagenesis of the ilvD gene was carried out with the GeneMorph II Random Mutagenesis kit (Agilent Technologies, Santa Clara, Calif.). Randomly mutagenized PCR product was ligated into the pRS423 Leu2p(75) vector (SEQ ID NO:579) using the restriction sites SpeI and NotI. The ligation mixture was transformed into E. coli. Transformants were spread onto large LB plates (22 cm×23 cm) supplemented with 100 μg/ml of ampicillin. About 200,000 to 300,000 colonies were obtained per plate. Colonies were scraped from the plates, and aliquots of cell suspensions were taken for plasmid preparation. The library of randomly mutagenized pRS423 Leu2p(75) plasmids was transformed into PNY2204(K9G9) yeast strain. The transformation mixture was spread onto SE (-His, -Ura) plates to obtain about 7,000 colony forming units (CFUs) per plate. When colonies were visible following incubation, cells were scraped off the plates into SE broth. The yeast cells were allowed to grow in serum bottles containing SD liquid medium (2% glucose, -His, -Ura). After three days, 10 ml of the culture was transferred into new serum bottles with fresh SD medium to enrich the population that can grow on 2% glucose. Three passages later, an aliquot of culture was spread onto plates with YPDE medium (YPD with 0.1% ethanol) and were allowed to grow under anaerobic conditions to select individual colonies. Colonies that grew well were selected and patched onto YPDE plates. Plasmids from these strains were isolated with a yeast plasmid isolation kit (Zymoprep II Yeast Plasmid Mini Prep, Zymo Research, Orange, Calif.) and transformed into E. coli for plasmid isolation. The ilvD genes on the plasmids were sequenced to determine the sites of any mutations.

As described above, strains containing a wild type DHAD enzyme from *Streptococcus mutans* under the control of a truncated Leu2 promoter grew poorly in medium containing 2% glucose. It was expected that strains that grew well under anaerobic conditions would contain DHAD enzymes with mutations that result in increased activity. Sequencing of the mutant plasmids obtained from the above-described screen resulted in 15 DHAD variants, listed in Table 7:

TABLE 7

*Streptococcus mutans* DHAD Variants

| Variant No | Substitution | Amino Acid SEQ ID NO |
|---|---|---|
| 1 | K564E | 528 |
| 2 | D62E, F562V | 532 |
| 3 | G33D, W563R | 534 |
| 4 | F562V | 537 |
| 5 | W563R | 540 |
| 6 | W563C | 545 |
| 7 | E524G, W563G | 548 |
| 8 | M115V, G158R, E567D | 552 |
| 9 | G116E, N119S | 555 |

TABLE 7-continued

Streptococcus mutans DHAD Variants

| Variant No | Substitution | Amino Acid SEQ ID NO |
|---|---|---|
| 10 | G33D | 557 |
| 11 | D62E | 561 |
| 12 | F562L | 563 |
| 13 | H176Q, H179L, Q322R, W563R | 566 |
| 14 | A425S, W563R | 569 |
| 15 | W563G | 572 |

Many of the variants were isolated multiple times from the screen. In addition to the mutations leading to the amino acid substitutions listed in Table 7, many of the isolates also contained silent mutations. DHAD variants, the number of isolates obtained of each variant, the locations of the silent mutations in each isolate, as well as the isobutanol titer obtained from each isolate are listed in Table 8:

TABLE 8

Isolates of each Streptococcus mutans DHAD Variant

| Variant No. | Substitution | Isolate | Silent Mutation Locations | Nucleic Acid SEQ ID NO | Isobutanol (mM) |
|---|---|---|---|---|---|
| 1 | K564E | A | | 527 | |
| | | B | D257, R407 | 529 | 43.2 |
| | | C | G368 | 530 | 47.6 |
| 2 | D62E, F562V | A | | 531 | 42.8 |
| 3 | G33D, W563R | A | | 533 | |
| | | B | G218, K314, G557 | 535 | 46.3 |
| | | C | G218, K314, G557 | 535 | 48.4 |
| | | D | G218, K314, G557 | 535 | 42.4 |
| 4 | F562V | A | | 536 | |
| | | B | G199 | 538 | |
| 5 | W563R | A | | 539 | 41.2 |
| | | B | | 606 | 39.0 |
| | | C | L343 | 541 | 43.8 |
| | | D | G93, I155, D511 | 542 | 43.2 |
| | | E | G93, I155, D511 | 542 | 47.2 |
| | | F | R13, V486 | 543 | 42.9 |
| | | G | R13, V486 | 543 | 40.0 |
| | | H | R13, V486 | 543 | 30.7 |
| | | I | R13, V486 | 543 | 39.3 |
| 6 | W563C | A | | 544 | |
| | | B | G70, D395 | 546 | 45.5 |
| | | C | G70, D395 | 546 | |
| 7 | E524G, W563G | A | | 547 | |
| | | B | L253, A397 | 549 | 38.1 |
| | | C | A397 | 550 | |
| 8 | M115V, G158R, E567D | A | | 551 | |
| | | B | T49, P308 | 553 | 43.3 |
| 9 | G116E, N119S | A | | 554 | 38.0 |
| 10 | G33D | A | | 556 | |
| | | B | G218 | 558 | 44.4 |
| | | C | G218, K314, G557 | 559 | 41.2 |
| | | D | G218 | 558 | 42.9 |
| 11 | D62E | A | | 560 | |
| 12 | F562L | A | | 562 | |
| | | B | P134 | 564 | 38.5 |
| 13 | H176Q, H179L, Q322R, W563R | A | | 565 | |
| | | B | Q369, V436 | 567 | |

TABLE 8-continued

Isolates of each Streptococcus mutans DHAD Variant

| Variant No. | Substitution | Isolate | Silent Mutation Locations | Nucleic Acid SEQ ID NO | Isobutanol (mM) |
|---|---|---|---|---|---|
| 14 | A425S, W563R | A | | 568 | |
| | | B | A490 | 570 | |
| 15 | W563G | A | | 571 | |
| | | B | | 571 | |
| | | C | | 571 | |
| Control | Wild type | | | 167 | 20 |

Common mutations were clustered around the amino acids at the 562, 563, 564 positions near the C-terminus. Numerous isolates with substitutions at Trp-563 were obtained. As shown in Table 8, these results suggest that the mutations obtained in these amino acids improve DHAD function and therefore, result in increased growth on 2% glucose and increased isobutanol production. When isobutanol production was measured, the titer in these strains doubled as compared to the strain with the wild type DHAD under the truncated Leu2 promoter ("Control" in Table 8). The results obtained here successfully demonstrated the utility of a screening method employed for identification of desirable mutations in the DHAD enzyme.

Two isolates were obtained that had increased growth on 2% glucose and increased isobutanol production, but did not contain an amino acid substitution. However, both of these isolates contained silent mutations. The nucleic acid sequence of the first of these isolates is represented by SEQ ID NO:573. This Streptococcus mutans ilvD isolate has a silent mutation at proline 228 (CCG to CCA), and resulted in an isobutanol titer of 46.8 mM. The nucleic acid sequence of the second of these isolates is represented by SEQ ID NO:574. This Streptococcus mutans ilvD isolate has a silent mutation at glycine 93 (GGA to GGT), isoleucine 155 (ATT to ATC), and aspartic acid 511 (GAC to GAT), and resulted in an isobutanol titer of 47.0 mM.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

TABLE 6

```
HMMER2.0 [2.2g]                                           Program name and version
NAME  dhad_for_hmm                                        Name of the input sequence alignment file
LENG  564                                                 Length of the alignment: include indels
ALPH  Amino                                               Type of residues
MAP   yes                                                 Map of the match states to the columns of the alignment
COM   /app/public/hmmer/current/bin/hmmbuild -F dhad-exp_hmm dhad_for_hmm.aln    Commands used to generate the file: this one means that hmmbuild (default parameters) was applied to the alignment file
COM   /app/public/hmmer/current/bin/hmmcalibrate dhad-exp_hmm                     Commands used to generate the file: this one means that hmmcalibrate (default parameters) was applied to the hmm profile
NSEQ  8                                                   Number of sequences in the alignment file
DATE  Tue Jun 3 10:48:24 2008                             When was the file generated
XT    -8455 -4 -1000 -1000 -8455 -4 -8455 -4
NULT  -4 -8455                                            The transition probability distribution for the null model (single G state).
NULE  595 -1558 85 338 -294 453 -1158 197 249 902 -1085 -142 -21 -313 45 531     The symbol emission probability distribution for the null model (G state); consists of K (e.g 4 or 20) integers. The null
      201 384 -1998 -644                                  probability used to convert these back to model probabilities is 1/K.
EVD   -499.650970 0.086142                                The extreme value distribution parameters μ and lambda respectively; both floating point values. Lambda is positive and
                                                          nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 1(M) | -538 | * | -1684 | 1223 | -1477 | -1132 | 89 | -1122 | -1248 | 1757 | 1553 | -1296 | 464 | -24 | -190 | -188 | -838 | -1578 | -985 | 6 |
|  | -233 | -1296 | 99 | 43 | -381 | 399 | 106 | -626 | -466 | -720 | 275 | 394 | 45 | 96 | 359 | 117 | -369 | -294 | -249 |  |
|  | -149 | -500 | 233 | -894 | -1115 | -701 | -1378 | -538 |  |  |  |  |  |  |  |  |  |  |  |  |
|  | -29 | -6203 | -7245 |  |  |  |  |  |  |  |  |  |  |  |  |  |  |  |  |  |
| 2(E) | -220 | -1288 | 232 | 1356 | -1807 | 1016 | -70 | -1474 | -1584 | -775 | 132 | -1298 | 300 | -282 | -183 | 1140 | -1092 | -1872 | -1262 | 7 |
|  | -149 | -500 | 233 | 43 | -381 | 399 | 106 | -626 | -466 | -720 | 275 | 394 | 45 | 96 | 359 | 117 | -369 | -294 | -249 |  |
|  | -29 | -6203 | -7245 | -894 | -1115 | -701 | -1378 | * |  |  |  |  |  |  |  |  |  |  |  |  |
| 3(K) | -448 | -1932 | 1558 | 658 | -2220 | -1048 | 40 | -1983 | -1938 | -1091 | 1558 | -1319 | 450 | -193 | -278 | -419 | -1552 | -2121 | -1397 | 8 |
|  | -149 | -500 | 233 | 43 | -381 | 399 | 106 | -626 | -466 | -720 | 275 | 394 | 45 | 96 | 359 | 117 | -369 | -294 | -249 |  |
|  | -29 | -6203 | -7245 | -894 | -1115 | -701 | -1378 | * |  |  |  |  |  |  |  |  |  |  |  |  |
| 4(V) | -404 | -498 | -1497 | -939 | -588 | -1810 | -640 | 1591 | -127 | 335 | -962 | -1866 | -562 | -767 | -868 | -357 | 1720 | -1169 | -763 | 9 |
|  | -149 | -500 | 233 | 43 | -381 | 399 | 106 | -626 | -466 | -720 | 275 | 394 | 45 | 96 | 359 | 117 | -369 | -294 | -249 |  |
|  | -29 | -6203 | -7245 | -894 | -1115 | -701 | -1378 | * |  |  |  |  |  |  |  |  |  |  |  |  |
| 5(E) | -265 | -1340 | -52 | 1376 | -1572 | -1189 | 113 | -1125 | -1287 | -496 | 99 | -1321 | 505 | 198 | -218 | -205 | 597 | -1598 | -1032 | 10 |
|  | -149 | -500 | 233 | 43 | -381 | 399 | 106 | -626 | -466 | -720 | 275 | 394 | 45 | 96 | 359 | 117 | -369 | -294 | -249 |  |
|  | -29 | -6203 | -7245 | -894 | -1115 | -701 | -1378 | * |  |  |  |  |  |  |  |  |  |  |  |  |
| 6(S) | 256 | -397 | -1014 | -630 | -1841 | -646 | -862 | -1443 | -1740 | -963 | -568 | -1249 | -651 | -1007 | 2267 | 1586 | -862 | -2080 | -1672 | 11 |
|  | -149 | -500 | 233 | 43 | -381 | 399 | 106 | -626 | -466 | -720 | 275 | 394 | 45 | 96 | 359 | 117 | -369 | -294 | -249 |  |
|  | -29 | -6203 | -7245 | -894 | -1115 | -701 | -1378 | * |  |  |  |  |  |  |  |  |  |  |  |  |
| 7(M) | -990 | -889 | -2630 | 157 | -513 | -2514 | -1346 | 1309 | 820 | 3683 | -1898 | -2491 | -1496 | -1799 | -1589 | -925 | 150 | -1336 | -1041 | 12 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 8(E) | 588 | -1875 | -194 | 1536 | -2188 | -1373 | -59 | -1931 | -1890 | -977 | 904 | 292 | 393 | -162 | 483 | -372 | -1495 | -2070 | -1391 | 13 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 9(N) | -514 | -1116 | 1207 | -315 | 447 | -1650 | -304 | -778 | 825 | -277 | 1457 | -1738 | -123 | -618 | -627 | -454 | -603 | -1186 | 763 | 14 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 10(N) | -815 | -1190 | -1360 | -922 | -904 | -1967 | -797 | -442 | 381 | 1700 | 3009 | -2099 | -654 | -934 | -1051 | -791 | -445 | -1490 | -979 | 15 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

```
HMMER2.0 [2.2g]                                                    Program name and version
NAME  dhad_for_hmm                                                 Name of the input sequence alignment file
LENG  564                                                          Length of the alignment: include indels
ALPH  Amino                                                        Type of residues
MAP   yes                                                          Map of the match states to the columns of the alignment
COM   /app/public/hmmer/current/bin/hmmbuild -F dhad-exp_hmm dhad_for_hmm.aln    Commands used to generate the file: this one means that hmmbuild (default parameters) was applied to the alignment file
COM   /app/public/hmmer/current/bin/hmmcalibrate dhad-exp_hmm                   Commands used to generate the file: this one means that hmmcalibrate (default parameters) was applied to the hmm profile
NSEQ  8                                                            Number of sequences in the alignment file
DATE  Tue Jun 3 10:48:24 2008                                      When was the file generated
XT    -8455 -4 -1000 -1000 -8455 -4 -8455 -4
NULT  -4 -8455                                                     The transition probability distribution for the null model (single G state).
NULE  595 -1558 85 338 -294 453 -1158 197 249 902 -1085 -142 -21 -313 45 531    The symbol emission probability distribution for the null model (G state); consists of K (e.g 4 or 20) integers. The null
201 384 -1998 -644                                                 probability used to convert these back to model probabilities is 1/K.
EVD  -499.650970 0.086142                                          The extreme value distribution parameters μ and lambda respectively; both floating point values. Lambda is positive and
                                                                   nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 11(K) | -1530 -149 -16 | -2498 -500 -7108 | -1722 233 -8150 | -855 43 -894 | -3141 -381 -1115 | -2246 399 -701 | -428 106 -1378 | -2627 -626 * | -2404 -466 | -1656 -720 | -927 275 | 662 394 | -2 45 | 2047 96 | -1421 359 | -1337 117 | -2324 -369 | -2357 -294 | -2081 -249 | 16 |
| 12(Y) | -872 -149 -16 | -1887 -500 -7108 | -861 233 -8150 | -290 43 -894 | -1369 -381 -1115 | -1801 399 -701 | 1662 106 -1378 | -1797 -626 * | -1793 -466 | -1031 -720 | 893 275 | -1876 394 | 56 45 | 2219 96 | -812 359 | -780 117 | -1514 -369 | -1565 -294 | 2287 -249 | 17 |
| 13(S) | -830 -149 -16 | -1586 -500 -7108 | -1471 233 -8150 | -1099 43 -894 | -2717 -381 -1115 | -1642 399 -701 | -1010 106 -1378 | -2479 -626 * | -2518 -466 | -1746 -720 | -1065 275 | -2069 394 | -676 45 | 1822 96 | 2748 359 | -1000 117 | -1950 -369 | -2597 -294 | -2189 -249 | 18 |
| 14(Q) | -851 -149 -16 | -2131 -500 -7108 | -775 233 -8150 | -153 43 -894 | -2554 -381 -1115 | -1735 399 -701 | -211 106 -1378 | -2205 -626 * | -2094 -466 | -1244 -720 | -386 275 | -1802 394 | 2254 45 | 974 96 | 1001 359 | -747 117 | -1819 -369 | -2181 -294 | -1667 -249 | 19 |
| 15(T) | -405 -149 -16 | -1258 -500 -7108 | -618 233 -8150 | -100 43 -894 | -1490 -381 -1115 | -1466 399 -701 | 1158 106 -1378 | -1121 -626 * | -1299 -466 | -514 -720 | 578 275 | -1607 394 | 65 45 | -433 96 | 960 359 | 1849 117 | 343 -369 | -1677 -294 | -1143 -249 | 20 |
| 16(I) | -1772 -149 -16 | -1325 -500 -7108 | -4307 233 -8150 | -3877 43 -894 | -1405 -381 -1115 | -3993 399 -701 | -3383 106 -1378 | 2935 -626 * | 820 -466 | -217 -720 | -3632 275 | -3761 394 | -3400 45 | -3682 96 | -3260 359 | -1742 117 | 2033 -369 | -2838 -294 | -2525 -249 | 21 |
| 17(T) | -1018 -149 -16 | -1329 -500 -7108 | -2004 233 -8150 | -1771 43 -894 | -409 -381 -1115 | -1993 399 -701 | -1000 106 -1378 | -1256 -626 * | -1464 -466 | -966 -720 | -1543 275 | -2367 394 | -1428 45 | -1638 96 | -1257 359 | 3050 117 | -1090 -369 | -1012 -294 | 2448 -249 | 22 |
| 18(Q) | -1509 -149 -16 | -3056 -500 -7108 | 1970 233 -8150 | -88 43 -894 | -3310 -381 -1115 | -1666 399 -701 | -896 106 -1378 | -3242 -626 * | -3158 -466 | -2439 -720 | -322 275 | -2123 394 | 3562 45 | -1493 96 | -1259 359 | -1550 117 | -2779 -369 | -3260 -294 | -2446 -249 | 23 |
| 19(D) | -1006 -149 -16 | -2199 -500 -7108 | 2178 233 -8150 | -88 43 -894 | -3159 -381 -1115 | 1997 399 -701 | -936 106 -1378 | -2974 -626 * | -2977 -466 | -2174 -720 | -382 275 | -1960 394 | -589 45 | -1571 96 | 1295 359 | -1157 117 | -2369 -369 | -3178 -294 | -2430 -249 | 24 |
| 20(M) | 445 -149 -16 | -796 -500 -7108 | -1082 233 -8150 | -521 43 -894 | -841 -381 -1115 | -1643 399 -701 | -412 106 -1378 | -403 -626 * | -692 -466 | 2213 -720 | -646 275 | 536 394 | 1166 45 | -698 96 | -630 359 | 660 117 | 831 -369 | -1204 -294 | -767 -249 | 25 |
| 21(Q) | 741 -149 -16 | -990 -500 -7108 | -1025 233 -8150 | -507 43 -894 | -1249 -381 -1115 | -1551 399 -701 | -519 106 -1378 | -720 -626 * | -1062 -466 | -345 -720 | -635 275 | -1739 394 | 1770 45 | -713 96 | -589 359 | 1576 117 | 1129 -369 | -1559 -294 | -1097 -249 | 26 |

TABLE 6-continued

```
HMMER2.0 [2.2g]                                                    Program name and version
NAME dhad_for_hmm                                                  Name of the input sequence alignment file
LENG 564                                                           Length of the alignment
ALPH Amino                                                         Type of residues
MAP yes                                                            Map of the match states to the columns of the alignment
COM /app/public/hmmer/current/bin/hmmbuild -F dhad-exp_hmm dhad_for_hmm.aln    Commands used to generate the file: this one means that hmmbuild (default patrameters) was applied to the alignment file
COM /app/public/hmmer/current/bin/hmmcalibrate dhad-exp_hmm        Commands used to generate the file: this one means that hmmcalibrale (default parameters) was applied to the hmm profile
NSEQ 8                                                             Number of sequences in the alignment file
DATE Tue Jun 3 10:48:24 2008                                       When was the file generated
XT -8455 -4 -1000 -1000 -8455 -4 -8455 -4
NULT -4 -8455                                                      The transition probability distribution for the null model (single G state).
NULE 595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                                 probability used to convert these back to model probabilities is 1/K.
EVD -499.650970 0.086142                                           The extreme value distribution parameters µ and lambda respectively; both floating point values. Lambda is positive and
                                                                   nonzero. These values are set when the model is calibrated with hmmcalibrate.
```

| HMM | A<br>m → m | C<br>m → i | D<br>m → d | E<br>i → m | F<br>i → i | G<br>d → m | H<br>d → d | I<br>b → m | L | M | N | P | Q | R | S | T | V | W | Y | Position in alignment |
|---|---|---|---|---|---|---|---|---|---|---|---|---|---|---|---|---|---|---|---|---|
| 22(R) | -1753<br>-149<br>-16 | -2648<br>-500<br>-7108 | -2072<br>233<br>-8150 | -1047<br>43<br>-894 | -3365<br>-381<br>-1115 | -2405<br>399<br>-701 | -452<br>106<br>-1378 | -2782<br>-626<br>* | -2495<br>-466 | -1773<br>-720 | -1062<br>275 | -2379<br>394 | 2402<br>45 | 2643<br>96 | -1629<br>359 | -1506<br>117 | -2504<br>-369 | -2397<br>-294 | -2190<br>-249 | 27 |
| 23(S) | -330<br>-149<br>-16 | -1010<br>-500<br>-7108 | -1820<br>233<br>-8150 | -1628<br>-894 | -2778<br>-381<br>-1115 | -1229<br>399<br>-701 | -1652<br>106<br>-1378 | -2481<br>-626<br>* | -2691<br>-466 | -1841<br>-720 | -1273<br>275 | 2130<br>394 | -1426<br>45 | -1834<br>96 | 2449<br>359 | 1034<br>117 | -1716<br>-369 | -2961<br>-294 | -2594<br>-249 | 28 |
| 24(P) | 1882<br>-149<br>-16 | -1119<br>-500<br>-7108 | -2231<br>233<br>-8150 | -2302<br>43<br>-894 | -3062<br>-381<br>-1115 | -1360<br>399<br>-701 | -2209<br>106<br>-1378 | -2710<br>-626<br>* | -3013<br>-466 | -2243<br>-720 | -1676<br>275 | 3304<br>394 | -2117<br>45 | -2409<br>96 | -742<br>359 | -918<br>117 | -1916<br>-369 | -3263<br>-294 | -3022<br>-249 | 29 |
| 25(N) | 969<br>-149<br>-16 | -1230<br>-500<br>-7108 | -1066<br>233<br>-8150 | -915<br>-894 | -2593<br>-381<br>-1115 | -1313<br>399<br>-701 | -1196<br>106<br>-1378 | -2242<br>-626<br>* | -2447<br>-466 | -1626<br>-720 | 3197<br>275 | -1850<br>394 | -898<br>45 | -1392<br>96 | -582<br>359 | 1155<br>117 | -1644<br>-369 | -2736<br>-294 | -2256<br>-249 | 30 |
| 26(R) | -1847<br>-149<br>-16 | -2640<br>-500<br>-7108 | -2014<br>233<br>-8150 | -1161<br>-894 | -3282<br>-381<br>-1115 | -2428<br>399<br>-701 | -579<br>106<br>-1378 | -2818<br>-626<br>* | -2553<br>-466 | -1869<br>-720 | -1165<br>275 | -2462<br>394 | 2447<br>45 | 3181<br>96 | -1746<br>359 | -1630<br>117 | -2555<br>-369 | -2447<br>-294 | -2228<br>-249 | 31 |
| 27(A) | 3048<br>-149<br>-16 | -932<br>-500<br>-7108 | -2480<br>233<br>-8150 | -2533<br>-894 | -3075<br>-381<br>-1115 | -1200<br>399<br>-701 | -2274<br>106<br>-1378 | -2765<br>-626<br>* | -3071<br>-466 | -2221<br>-720 | -1658<br>275 | -1948<br>394 | -2205<br>45 | -2512<br>96 | 1225<br>359 | -739<br>117 | -1842<br>-369 | -3322<br>-294 | -3078<br>-249 | 32 |
| 28(M) | -2406<br>-149<br>-16 | -2296<br>-500<br>-7108 | -3638<br>233<br>-8150 | -3594<br>43<br>-894 | -1525<br>-381<br>-1115 | -3105<br>399<br>-701 | -2824<br>106<br>-1378 | -1047<br>-626<br>* | -596<br>-466 | 5043<br>-720 | -3293<br>275 | -3425<br>394 | -3046<br>45 | -2996<br>96 | -2911<br>359 | -2552<br>117 | -1398<br>-369 | -2513<br>-294 | -2207<br>-249 | 33 |
| 29(Y) | -1674<br>-149<br>-16 | -1506<br>-500<br>-7108 | -2863<br>233<br>-8150 | -2464<br>-894 | 596<br>-381<br>-1115 | -2872<br>399<br>-701 | 2251<br>-1378 | -972<br>-626<br>* | 2197<br>-466 | -552<br>-720 | -1986<br>275 | -2876<br>394 | -1739<br>45 | -1988<br>96 | -1987<br>359 | -1601<br>117 | -1002<br>-369 | -95<br>-294 | 2332<br>-249 | 34 |
| 30(Y) | -2013<br>-149<br>-16 | -2305<br>-500<br>-7108 | -2428<br>233<br>-8150 | -1781<br>-894 | -328<br>-381<br>-1115 | -2709<br>399<br>-701 | -654<br>106<br>-1378 | -2240<br>-626<br>* | -2064<br>-466 | -1626<br>-720 | -1631<br>275 | -2786<br>394 | -899<br>45 | 2789<br>96 | -2017<br>359 | -1896<br>117 | -2130<br>-369 | -857<br>-294 | 3434<br>-249 | 35 |
| 31(A) | 2822<br>-149<br>-16 | -1031<br>-500<br>-7108 | -2418<br>233<br>-8150 | -2539<br>-894 | -3226<br>-381<br>-1115 | 1898<br>399<br>-701 | -2364<br>106<br>-1378 | -2941<br>-626<br>* | -3229<br>-466 | -2379<br>-720 | -1722<br>275 | -2026<br>394 | -2302<br>45 | -2634<br>96 | -654<br>359 | -848<br>117 | -1983<br>-369 | -3415<br>-294 | -3226<br>-249 | 36 |
| 32(I) | -1247<br>-149<br>-16 | -941<br>-500<br>-7108 | -3569<br>233<br>-8150 | -3039<br>-894 | -1082<br>-381<br>-1115 | -3101<br>399<br>-701 | -2185<br>106<br>-1378 | 2227<br>-626<br>* | 766<br>-466 | -76<br>-720 | -2700<br>275 | -3050<br>394 | -2469<br>45 | -2697<br>96 | -2253<br>359 | 1322<br>117 | 1974<br>-369 | -1988<br>-294 | -1633<br>-249 | 37 |

TABLE 6-continued

```
HMMER2.0 [2.2g]                                                    Program name and version
NAME dhad_for_hmm                                                  Name of the input sequence alignment file
LENG 564                                                           Length of the alignment: include indels
ALPH Amino                                                         Type of residues
MAP yes                                                            Map of the match states to the columns of the alignment
COM /app/public/hmmer/current/bin/hmmbuild -F dhad-exp_hmm dhad_for_hmm.aln   Commands used to generate the file: this one means that hmmbuild (default paramaters) was applied to the alignment file
COM /app/public/hmmer/current/bin/hmmcalibrate dhad-exp_hmm        Commands used to generate the file: this one means that hmmcalibrate (default parameters) was applied to the hmm profile
NSEQ 8                                                             Number of sequences in the alignment file
DATE Tue Jun 3 10:48:24 2008                                       When was the file generated
XT -8455 -4 -1000 -1000 -8455 -4 -8455 -4
NULT -4 -8455                                                      The transition probability distribution for the null model (single G state).
NULE 595 -1558 85 338 -294 453 -1158 197 249 902 -1085 -142 -21 -313 45 531   The symbol emission probability distribution for the null model (G state); consists of K (e.g. 4 or 20) integers. The null
201 384 -1998 -644                                                 probability used to convert these back to model probabilities is 1/K.
EVD -499.650970 0.086142                                           The extreme value distribution parameters μ and lambda respectively; both floating point values. Lambda is positive and
                                                                   nonzero. These values are set when the model is calibrated with hmmcalibrate.
```

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 33(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 38 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 34(F) | -1511 | -1236 | -3511 | -3017 | 2747 | -2982 | -1069 | -260 | 992 | 2737 | -2407 | -2904 | -2088 | -2418 | -2099 | -1434 | -489 | -537 | 2056 | 39 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 35(Q) | -576 | -1869 | -401 | 92 | -2232 | 831 | -173 | -1930 | -1913 | -1042 | -186 | -1620 | 1653 | -51 | -482 | 1346 | -1534 | -2098 | -1490 | 40 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 36(D) | -1352 | -3066 | 3028 | 1349 | -3303 | -1566 | -724 | -3141 | -3043 | -2267 | -165 | -1991 | -354 | -1350 | -1086 | -1368 | -2659 | -3221 | -2356 | 41 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 37(E) | -1507 | -3288 | 2042 | 2762 | -3520 | 515 | -853 | -3401 | -3296 | -2566 | -182 | -2064 | -503 | -1753 | -1209 | -1553 | -2895 | -3486 | -2547 | 42 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 38(D) | -1445 | -2778 | 3529 | -53 | -3524 | -1590 | -1129 | -3476 | -3459 | -2774 | -396 | -2156 | -825 | -2122 | 554 | -1609 | -2880 | -3582 | -2717 | 43 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 39(F) | -2658 | -2176 | -4213 | -4000 | 3815 | -3933 | -1352 | -531 | 1121 | -19 | -3184 | -3709 | -2820 | -3296 | -3219 | -2579 | -1037 | -601 | 403 | 44 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 40(D) | -684 | -2193 | 1738 | 1460 | -2494 | -1437 | -249 | -2257 | -2199 | -1308 | -62 | -1637 | 185 | -450 | -531 | 633 | -1808 | -2374 | -1657 | 45 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 41(K) | -2620 | -2961 | -2461 | -2046 | -3743 | -2791 | -1570 | -3603 | -3387 | -2839 | -2048 | -3039 | -1260 | -465 | -2604 | -2536 | -3331 | -3001 | -2988 | 46 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 42(P) | 1882 | -1119 | -2231 | -2302 | -3062 | -1360 | -2209 | -2710 | -3013 | -2243 | -1676 | 3304 | -2117 | -2409 | -742 | -918 | -1916 | -3263 | -3022 | 47 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 43(I) | -1006 | -992 | -2347 | -1784 | -650 | -2452 | -1256 | 2372 | 77 | 2213 | -1721 | -2455 | 2030 | -1490 | -1528 | -946 | 106 | -1441 | -1111 | 48 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |

TABLE 6-continued

```
HMMER2.0 [2.2g]                                          Program name and version
NAME  dhad_for_hmm                                        Name of the input sequence alignment file
LENG  564                                                 Length of the alignment: include indels
ALPH  Amino                                               Type of residues
MAP   yes                                                 Map of the match states to the columns of the alignment
COM   /app/public/hmmer/current/bin/hmmbuild -F dhad-exp_hmm dhad_for_hmm.aln    Commands used to generate the file: this one means that hmmbuild (default parameters) was applied to the alignment file
COM   /app/public/hmmer/current/bin/hmmcalibrate dhad-exp_hmm                    Commands used to generate the file: this one means that hmmcalibrate (default parameters) was applied to the hmm profile
NSEQ  8                                                   Number of sequences in the alignment file
DATE  Tue Jun 3 10:48:24 2008                             When was the file generated
XT    -8455 -4 -1000 -1000 -8455 -4 -8455 -4
NULT  -4 -8455
NULE  595 -1558 85 338 -294 453 -1158 197 249 902 -1085 -142 -21 -313 45 531
201 384 -1998 -644                                        The transition probability distribution for the null model (single G state).
EVD   -499.650970 0.086142                                The symbol emission probability distribution for the null model (G state); consists of K (e.g 4 or 20) integers. The null
                                                          probability used to convert these back to model probabilities is 1/K.
                                                          The extreme value distribution parameters μ and lambda respectively; both floating point values. Lambda is positive and
                                                          nonzero. These values are set when the model is calibrated with hmmcalibrate.
```

| HMM | A<br>m→m | C<br>m→i | D<br>m→d | E<br>i→m | F<br>i→i | G<br>d→m | H<br>d→d | I<br>b→m | L | M | N | P | Q | R | S | T | V | W | Y | Position in alignment |
|---|---|---|---|---|---|---|---|---|---|---|---|---|---|---|---|---|---|---|---|---|
| 44(V) | -1771 | -1603 | -3750 | -3689 | -2037 | -3050 | -3231 | 403 | -1154 | -1076 | -3246 | -3399 | -3383 | -3437 | -2628 | -1917 | 3536 | -3074 | -2677 | 49 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 45(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3661 | -4222 | 50 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 46(I) | -1759 | -1303 | -4330 | -3968 | -1751 | -4051 | -3743 | 3027 | -597 | -528 | -3729 | -3875 | -3688 | -3910 | -3369 | -1751 | 2438 | -3259 | -2819 | 51 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 47(V) | 1736 | -1012 | -3546 | -3078 | -1377 | -3073 | -2434 | 2052 | -608 | -331 | -2754 | -3122 | -2619 | -2855 | -2270 | -1277 | 2193 | -2333 | -1941 | 52 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 48(N) | -686 | -1511 | -702 | -806 | -2927 | -1386 | -1339 | -2841 | -2950 | -2137 | 2702 | -1979 | -1062 | -1648 | 2444 | -971 | -2105 | -3054 | -2475 | 53 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 49(M) | -411 | -857 | -1800 | -1434 | -1528 | 1914 | -1202 | -1029 | -1347 | 2989 | -1217 | -1912 | -1119 | -1444 | -676 | 1550 | -767 | -1922 | -1539 | 54 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 50(W) | -782 | -1258 | 793 | -683 | 1193 | 346 | 2051 | -932 | -1092 | -441 | -798 | -1993 | -426 | -909 | -904 | -720 | -779 | 3163 | 1546 | 55 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 51(W) | 1009 | -798 | -1470 | -935 | -463 | -1773 | -545 | -460 | -736 | -66 | -943 | -1904 | -606 | -1002 | 1604 | -507 | -322 | 2535 | 1521 | 56 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 52(D) | -1137 | -2711 | 2125 | 1647 | -2995 | -1523 | -617 | -2786 | -2743 | -1933 | -150 | -1897 | -234 | -1165 | -924 | 2117 | -2331 | -2948 | -2141 | 57 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 53(I) | -599 | -1102 | -1031 | -829 | -1522 | 1429 | -927 | 2119 | -1369 | -699 | 1692 | -1938 | -759 | -1188 | -799 | -698 | -689 | -1887 | -1419 | 58 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 54(T) | -666 | -1412 | -954 | -984 | -2702 | -1428 | -1357 | -2418 | -2650 | -1886 | 2293 | -2000 | -1101 | -1519 | -787 | 2967 | -1835 | -2866 | -2360 | 59 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

```
HMMER2.0 [2.2g]                                                      Program name and version
NAME dhad_for_hmm                                                    Name of the input sequence alignment file
LENG 564                                                             Length of the alignment
ALPH Amino                                                           Type of residues
MAP yes                                                              Map of the match states to the columns of the alignment
COM /app/public/hmmer/current/bin/hmmbuild -F dhad-exp_hmm dhad_for_hmm.aln    Commands used to generate the file: this one means that hmmbuild (default patrameters) was applied to the alignment file
COM /app/public/hmmer/current/bin/hmmcalibrate dhad-exp_hmm                    Commands used to generate the file: this one means that hmmcalibrate (default parameters) was applied to the hmm profile
NSEQ 8                                                               Number of sequences in the alignment file
DATE Tue Jun 3 10:48:24 2008                                         When was the file generated
XT -8455 -4 -1000 -1000 -8455 -4 -8455 -4
NULT -4 -8455                                                        The transition probability distribution for the null model (single G state).
NULE 595 -1558 85 338 -294 453 -1158 197 249 902 -1085 -142 -21 -313 45 531    The symbol emission probability distribution for the null model (G state); consists of K (e.g 4 or 20) integers. The null
201 384 -1998 -644                                                   probability used to convert these back to model probabilities is 1/K.
EVD -499.650970 0.086142                                             The extreme value distribution parameters μ and lambda respectively; both floating point values. Lambda is positive and
                                                                     nonzero. These values are set when the model is calibrated with hmmcalibrate.
```

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 55(P) | -632 | -1230 | -2074 | -2144 | -2996 | -1453 | -2116 | -2631 | -2928 | -2213 | -1658 | 3610 | -2006 | -2221 | -852 | 1302 | -1931 | -3185 | -2917 | 60 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 56(C) | -2476 | 5735 | -4102 | -4358 | -3712 | -2763 | -3545 | -3518 | -3859 | -3589 | -3631 | -3363 | -4030 | -3832 | -2793 | -2860 | -3158 | -3464 | -3718 | 61 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 57(N) | -2171 | -2655 | -1458 | -1748 | -3334 | -2364 | -2267 | -3943 | -3936 | -3437 | 4205 | -2932 | -2205 | -2608 | -2224 | -2439 | -3392 | -3253 | -2909 | 62 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 58(M) | 672 | -918 | -3119 | -2578 | -742 | -2668 | -1734 | 1807 | 16 | 3713 | -2271 | -2704 | -1960 | -2216 | -1806 | -1058 | 493 | -1612 | -1306 | 63 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 59(H) | -1525 | -2164 | -1235 | -1346 | -2509 | 2296 | 4235 | -3172 | -3178 | -2523 | -1448 | -2541 | -1520 | -1760 | -1591 | -1741 | -2656 | -2681 | -2065 | 64 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 60(L) | -2478 | -2009 | -4717 | -4196 | -568 | -4424 | -3262 | 1334 | 2824 | 604 | -4085 | -3872 | -3088 | -3590 | -3717 | -2380 | -199 | -2217 | -2207 | 65 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 61(H) | -682 | -2191 | 1015 | 275 | -2485 | 396 | 2379 | -2251 | -2197 | -1307 | 1826 | -1636 | 1527 | -480 | -529 | -641 | -1803 | -2375 | -1654 | 66 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 62(D) | -575 | -1920 | 1979 | 184 | -2299 | 94 | -242 | -2029 | -2023 | -1144 | -120 | -1608 | 186 | 1063 | -469 | 1413 | -1605 | -2229 | -1561 | 67 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 63(L) | -2618 | -2139 | -4597 | -4163 | 2144 | -4285 | -2334 | -2950 | 2690 | 538 | -3771 | -3806 | -2950 | -3488 | -3563 | -2505 | -751 | -1442 | -808 | 68 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |
| 64(A) | 2657 | -1033 | -2408 | -2532 | -3233 | 2193 | -2364 | -1890 | -3237 | -2386 | -1719 | -2027 | -2301 | -2635 | -655 | -850 | -1988 | -3420 | -3231 | 69 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7106 | -8150 | -894 | -1115 | -701 | 1378 | * |  |  |  |  |  |  |  |  |  |  |  |  |
| 65(K) | -443 | -1857 | 958 | 270 | -2158 | -1393 | -66 | -626 | -442 | -957 | -36 | -1499 | 1204 | -132 | 616 | -382 | -1469 | -2048 | -1383 | 70 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | 1378 | * |  |  |  |  |  |  |  |  |  |  |  |  |

TABLE 6-continued

| | | | | | | | | | | | | | | | | | | | | | | | | |
|---|---|---|---|---|---|---|---|---|---|---|---|---|---|---|---|---|---|---|---|---|---|---|---|---|
| HMMER2.0 [2.2g] | | | | | | | | | | | | | Program name and version | | | | | | | | | | | |
| NAME dhad_for_hmm | | | | | | | | | | | | | Name of the input sequence alignment file | | | | | | | | | | | |
| LENG 564 | | | | | | | | | | | | | Length of the alignment | | | | | | | | | | | |
| ALPH Amino | | | | | | | | | | | | | Type of residues | | | | | | | | | | | |
| MAP yes | | | | | | | | | | | | | Map of the match states to the columns of the alignment | | | | | | | | | | | |
| COM /app/public/hmmer/current/bin/hmmbuild -F dhad-exp_hmm dhad_for_hmm.aln | | | | | | | | | | | | | Commands used to generate the file: this one means that hmmbuild (default patrameters) was applied to the alignment file | | | | | | | | | | | |
| COM /app/public/hmmer/current/bin/hmmcalibrate dhad-exp_hmm | | | | | | | | | | | | | Commands used to generate the file: this one means that hmmcalibrate (default parameters) was applied to the hmm profile | | | | | | | | | | | |
| NSEQ 8 | | | | | | | | | | | | | Number of sequences in the alignment file | | | | | | | | | | | |
| DATE Tue Jun 3 10:48:24 2008 | | | | | | | | | | | | | When was the file generated | | | | | | | | | | | |
| XT -8455 -4 -1000 -1000 -8455 -4 -8455 -4 | | | | | | | | | | | | | | | | | | | | | | | | |
| NULT -4 -8455 | | | | | | | | | | | | | The transition probability distribution for the null model (single G state). | | | | | | | | | | | |
| NULE 595 -1558 85 338 -294 453 -1158 197 249 902 -1085 -142 -21 -313 45 531 201 384 -1998 -644 | | | | | | | | | | | | | The symbol emission probability distribution for the null model (G state); consists of K (e.g 4 or 20) integers. The null probability used to convert these back to model probabilities is 1/K. | | | | | | | | | | | |
| EVD -499.650970 0.086142 | | | | | | | | | | | | | The extreme value distribution parameters μ and lambda respectively; both floating point values. Lambda is positive and nonzero. These values are set when the model is calibrated with hmmcalibrate. | | | | | | | | | | | |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 66(C) | 605 -149 -16 | 1553 -500 -7108 | 739 233 -8150 | -17 43 -894 | -1374 -381 -1115 | -1488 399 -701 | -182 106 -1378 | 260 -626 * | -203 -466 | -397 -720 | -263 275 | -1573 394 | 159 45 | 691 96 | -426 359 | -331 117 | -761 -369 | -1567 -294 | -1032 -249 | 71 |
| 67(A) | 2327 -149 -16 | -956 -500 -7108 | -3193 233 -8150 | -2728 43 -894 | -1289 -381 -1115 | -2677 399 -701 | -2114 106 -1378 | 1664 -626 * | -601 -466 | -288 -720 | -2403 275 | -2839 394 | -2263 45 | -2523 96 | -1871 359 | -1126 117 | 1617 -369 | -2143 -294 | -1761 -249 | 72 |
| 68(K) | -532 -149 -16 | -1656 -500 -7108 | -490 233 -8150 | 1321 43 -894 | -1891 -381 -1115 | -1527 399 -701 | -172 106 -1378 | -124 -626 * | -1591 -466 | -782 -720 | -223 275 | -1619 394 | 237 45 | -106 96 | -482 359 | -464 117 | -98 -369 | -1904 -294 | -1326 -249 | 73 |
| 69(H) | 384 -149 -16 | -1854 -500 -7108 | 936 233 -8150 | 889 43 -894 | -2165 -381 -1115 | -1363 399 -701 | 1498 106 -1378 | -1909 -626 * | -1866 -466 | -948 -720 | 1091 275 | -1464 394 | 421 45 | -131 96 | -284 359 | -342 117 | -69 -369 | -2043 -294 | -1364 -249 | 74 |
| 70(G) | 1823 -149 -16 | -932 -500 -7108 | -2330 233 -8150 | -2313 43 -894 | -3120 -381 -1115 | 2511 399 -701 | -2158 106 -1378 | -2865 -626 * | -3098 -466 | -2209 -720 | -1563 275 | -1912 394 | -2032 45 | -2419 96 | 1138 359 | -706 117 | -1883 -369 | -3328 -294 | -3077 -249 | 75 |
| 71(V) | -1760 -149 -16 | -1333 -500 -7108 | -4244 233 -8150 | -3789 43 -894 | -1262 -381 -1115 | -3902 399 -701 | -3190 106 -1378 | 1495 -626 * | 1270 -466 | -96 -720 | -3536 275 | -3677 394 | -3238 45 | -3534 96 | -3148 359 | -1725 117 | 2865 -369 | -2654 -294 | -2373 -249 | 76 |
| 72(W) | -1054 -149 -16 | -2172 -500 -7108 | -1112 233 -8150 | -403 43 -894 | -2566 -381 -1115 | -1917 399 -701 | -286 106 -1378 | -2196 -626 * | -2095 -466 | -1292 -720 | 1183 275 | -1958 394 | 140 45 | 1333 96 | -959 359 | -922 117 | -1867 -369 | 2591 -294 | -1720 -249 | 77 |
| 73(D) | 611 -149 -16 | -1995 -500 -7108 | 1525 233 -8150 | 937 43 -894 | -2295 -381 -1115 | -1400 399 -701 | -148 106 -1378 | -2043 -626 * | -2006 -466 | -1106 -720 | -37 275 | -1553 394 | 1420 45 | -312 96 | -408 359 | 1235 117 | -1609 -369 | -2193 -294 | -1499 -249 | 78 |
| 74(A) | 2716 -149 -16 | -902 -500 -7108 | -2380 233 -8150 | -2205 43 -894 | -2799 -381 -1115 | -1197 399 -701 | -1975 106 -1378 | -2459 -626 * | -2736 -466 | -1895 -720 | -1520 275 | -1895 394 | -1844 45 | -2201 96 | 1191 359 | 1299 117 | -1669 -369 | -3045 -294 | -2758 -249 | 79 |
| 75(G) | -1709 -149 -16 | -2833 -500 -7108 | 2424 233 -8150 | -409 43 -894 | -3781 -381 -1115 | 2819 399 -701 | -1457 106 1378 | -3777 -626 * | -3733 -466 | -3076 -720 | -739 275 | -2389 394 | -1180 45 | -2441 96 | -1557 359 | -1893 117 | -3158 -369 | -3660 -294 | -3038 -249 | 80 |
| 76(A) | 2529 -149 -212 -16 | -1119 -500 -2909 -7108 | -2614 233 -8150 | -2330 43 -273 -894 | -1245 -381 -2534 -1115 | -1983 399 -701 | -1829 106 -1378 | -377 -626 * | 1435 -466 | -341 -720 | -1937 275 | -2411 394 | -1873 45 | -2088 96 | -1266 359 | -1059 117 | -397 -369 | -2063 -294 | -1713 -249 | 82 |

TABLE 6-continued

| | | | | | | | | | | |
|---|---|---|---|---|---|---|---|---|---|---|
| HMMER2.0 [2.2g] | | | | | | | Program name and version | | | |
| NAME dhad_for_hmm | | | | | | | Name of the input sequence alignment file | | | |
| LENG 564 | | | | | | | Length of the alignment: include indels | | | |
| ALPH Amino | | | | | | | Type of residues | | | |
| MAP yes | | | | | | | Map of the match states to the columns of the alignment | | | |
| COM /app/public/hmmer/current/bin/hmmbuild -F dhad-exp_hmm dhad_for_hmm.aln | | | | | | | Commands used to generate the file: this one means that hmmbuild (default patrameters) was applied to the alignment file | | | |
| COM /app/public/hmmer/current/bin/hmmcalibrate dhad-exp_hmm | | | | | | | Commands used to generate the file: this one means that hmmcalibrate (default parameters) was applied to the hmm profile | | | |
| NSEQ 8 | | | | | | | Number of sequences in the alignment file | | | |
| DATE Tue Jun 3 10:48:24 2008 | | | | | | | When was the file generated | | | |
| XT -8455 -4 -1000 -1000 -8455 -4 -8455 -4 | | | | | | | | | | |
| NULT -4 -8455 | | | | | | | | | | |
| NULE 595 -1558 85 338 -294 453 -1158 197 249 902 -1085 -142 -21 -313 45 531 201 384 -1998 -644 | | | | | | | The transition probability distribution for the null model (single G state). The symbol emission probability distribution for the null model (G state); consists of K (e.g 4 or 20) integers. The null probability used to convert these back to model probabilities is 1/K. | | | |
| EVD -499.650970 0.086142 | | | | | | | The extreme value distribution parameters μ and lambda respectively; both floating point values. Lambda is positive and nonzero. These values are set when the model is calibrated with hmmcalibrate. | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 77(W) | -472 -149 -16 | -361 -500 -7108 | -2421 233 -8150 | -1812 43 -894 | -298 -381 -1115 | -1979 399 -701 | -826 106 -1378 | 1164 -626 * | -143 -466 | 2485 -720 | 873 275 | -2028 394 | -1185 45 | -1426 96 | -1048 359 | -412 117 | 1116 -369 | 2999 -294 | -454 -249 | 83 |
| 78(P) | -1198 -149 -16 | -1737 -500 -7108 | -2187 233 -8150 | -2394 43 -894 | -3665 -381 -1115 | 2006 399 -701 | -2550 106 -1378 | -3630 -626 * | -3756 -466 | -3008 -720 | -2052 275 | 3474 394 | -2495 45 | -2835 96 | -1401 359 | -1593 117 | -2736 -369 | -3511 -294 | -3519 -249 | 84 |
| 79(Q) | -999 -149 -16 | -1075 -500 -7108 | -2106 233 -8150 | -1568 43 -894 | -726 -381 -1115 | -2370 399 -701 | -1175 106 -1378 | 83 -626 * | 1373 -466 | 218 -720 | -1566 275 | -2400 394 | 2445 45 | -1340 96 | -1445 359 | -946 117 | 1441 -369 | -1501 -294 | -1146 -249 | 85 |
| 80(Q) | -885 -149 -16 | -779 -500 -7108 | -2609 233 -8150 | -2018 43 -894 | -481 -381 -1115 | -2414 399 -701 | -1253 106 -1378 | 1645 -626 * | 799 -466 | 1924 -720 | -1827 275 | -2405 394 | 2262 45 | -1752 96 | -1484 359 | -821 117 | 802 -369 | -1240 -294 | -935 -249 | 86 |
| 81(F) | -3342 -149 -16 | -2776 -500 -7108 | -4026 233 -8150 | -4232 43 -894 | 4354 -381 -1115 | -3545 399 -701 | -1431 106 -1378 | -2315 -626 * | -1801 -466 | -1900 -720 | -3299 275 | -3780 394 | -3350 45 | -3645 96 | -3490 359 | -3420 117 | -2566 -369 | -739 -294 | 341 -249 | 87 |
| 82(G) | -998 -149 -16 | -2100 -500 -7108 | -120 233 -8150 | -175 43 -894 | -2567 -381 -1115 | 2528 399 -701 | 2174 106 -1378 | -2558 -626 * | -2583 -466 | -1806 -720 | 1422 275 | -1966 394 | -461 45 | -1038 96 | -925 359 | -1088 117 | -2095 -369 | -2657 -294 | -1948 -249 | 88 |
| 83(T) | -1213 -149 -16 | -1674 -506 -7108 | -2755 233 -8150 | -2906 43 -894 | -3163 -381 -1115 | -1922 399 -701 | -2659 106 -1378 | -2698 -626 * | -3105 -466 | -2612 -720 | -2311 275 | -2600 394 | -2708 45 | -2753 96 | -1463 359 | 3819 117 | -2197 -369 | -3286 -294 | -3156 -249 | 89 |
| 84(I) | -1286 -149 -16 | -1279 -500 -7108 | -2907 233 -8150 | -2683 43 -894 | -1446 -381 -1115 | -2549 399 -701 | -2198 106 -1378 | 3290 -626 * | -726 -466 | -534 -720 | -2386 275 | 1172 394 | -2299 45 | -2437 96 | -1895 359 | -1392 117 | 283 -369 | -2302 -294 | -1913 -249 | 90 |
| 85(T) | -493 -149 -16 | -1105 -500 -7108 | -2189 233 -8150 | -2267 43 -894 | -3101 -381 -1115 | 1880 399 -701 | -2196 106 -1378 | -2791 -626 * | -3081 -466 | -2269 -720 | -1649 275 | -2058 394 | -2099 45 | -2410 96 | -719 359 | 3135 117 | -1948 -369 | -3282 -294 | -3046 -249 | 91 |
| 86(V) | -1750 -149 -16 | -1296 -500 -7108 | -4319 233 -8150 | -3957 43 -894 | -1765 -381 -1115 | -4038 399 -701 | -3733 106 -1378 | 2364 -626 * | -619 -466 | -543 -720 | -3716 275 | -3869 394 | -3685 45 | -3902 96 | -3354 359 | -1743 117 | 3012 -369 | -3265 -294 | -2817 -249 | 92 |
| 87(S) | 923 -149 -16 | -962 -500 -7108 | -2348 233 -8150 | -2422 43 -894 | -3132 -381 -1115 | -1207 399 -701 | -2248 106 -1378 | -2850 -626 * | -3140 -466 | -2285 -720 | -1624 275 | -1954 394 | -2158 45 | -2477 96 | 3171 359 | -758 117 | -1896 -369 | -3362 -294 | -3103 -249 | 93 |

TABLE 6-continued

```
HMMER2.0 [2.2g]                                              Program name and version
NAME  dhad_for_hmm                                           Name of the input sequence alignment file
LENG  564                                                    Length of the alignment: include indels
ALPH  Amino                                                  Type of residues
MAP   yes                                                    Map of the match states to the columns of the alignment
COM   /app/public/hmmer/current/bin/hmmbuild -F dhad-exp_hmm dhad_for_hmm.aln   Commands used to generate the file: this one means that hmmbuild (default parameters) was applied to the alignment file
COM   /app/public/hmmer/current/bin/hmmcalibrate dhad-exp_hmm                   Commands used to generate the file: this one means that hmmcalibrate (default parameters) was applied to the hmm profile
NSEQ  8                                                      Number of sequences in the alignment file
DATE  Tue Jun 3 10:48:24 2008                                When was the file generated
XT    -8455 -4 -1000 -1000 -8455 -4 -8455 -4
NULT  -4 -8455                                               The transition probability distribution for the null model (single G state).
NULE  595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                           probability used to convert these back to model probabilities is 1/K.
EVD   -499.650970 0.086142                                   The extreme value distribution parameters μ and lambda respectively; both floating point values. Lambda is positive and
                                                             nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 88(D) | -2784 | -3432 | 4016 | -1200 | -4140 | -2466 | -2197 | -4505 | -4365 | -3956 | -1551 | -3014 | -2039 | -3232 | -2593 | -2938 | -4046 | -3710 | -3552 | 94 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 89(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 95 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 90(I) | -1880 | -1493 | -4193 | -3724 | -953 | -3837 | -2980 | 3251 | 257 | 2372 | -3485 | -3608 | -3005 | -3310 | -3087 | -1840 | 617 | -2373 | -2155 | 96 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 91(S) | 2150 | -939 | -2407 | -2415 | -3075 | -1197 | -2205 | -2781 | -3065 | -2205 | -1613 | -1936 | -2105 | -2436 | 2652 | -729 | -1850 | -3306 | -3049 | 97 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 92(M) | -979 | -1455 | -1242 | -1122 | -1434 | -1860 | -1131 | -1171 | -1285 | 4091 | 2176 | -2226 | -1017 | -1187 | -1166 | -1086 | -1063 | -1929 | -1345 | 98 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 93(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 99 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 94(T) | -959 | -1691 | -1249 | -949 | -2563 | -1747 | -929 | -2093 | -2263 | -1554 | -995 | -2115 | -600 | -354 | -1037 | 3152 | -1726 | -2494 | -2098 | 100 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 95(E) | -572 | -1860 | -208 | 2213 | -2107 | -1461 | -191 | -1808 | -116 | -983 | -127 | 318 | 1199 | -269 | -475 | -517 | -1448 | -2078 | -1441 | 101 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 96(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 102 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 97(M) | -2406 | -2296 | -3638 | -3594 | -1525 | -3105 | -2824 | -1047 | -596 | 5043 | -3293 | -3425 | -3046 | -2996 | -2911 | -2552 | -1398 | -2513 | -2207 | 103 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 98(R) | -2097 | -2786 | -2688 | -1415 | -3622 | -2625 | -555 | -2964 | -2627 | -1957 | -1318 | -2577 | -137 | 3015 | -1979 | -1791 | -2732 | -2469 | -2363 | 104 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

| | | | | | | | | | | | | | |
|---|---|---|---|---|---|---|---|---|---|---|---|---|---|
| HMMER2.0 [2.2g] | | | | | | | | | Program name and version | | | | |
| NAME dhad_for_hmm | | | | | | | | | Name of the input sequence alignment file | | | | |
| LENG 564 | | | | | | | | | Length of the alignment: include indels | | | | |
| ALPH Amino | | | | | | | | | Type of residues | | | | |
| MAP yes | | | | | | | | | Map of the match states to the columns of the alignment | | | | |
| COM /app/public/hmmer/current/bin/hmmbuild -F dhad-exp_hmm dhad_for_hmm.aln | | | | | | | | | Commands used to generate the file: this one means that hmmbuild (default parameters) was applied to the alignment file | | | | |
| COM /app/public/hmmer/current/bin/hmmcalibrate dhad-exp_hmm | | | | | | | | | Commands used to generate the file: this one means that hmmcalibrate (default parameters) was applied to the hmm profile | | | | |
| NSEQ 8 | | | | | | | | | Number of sequences in the alignment file | | | | |
| DATE Tue Jun 3 10:48:24 2008 | | | | | | | | | When was the file generated | | | | |
| XT -8455 -4 -1000 -1000 -8455 -4 -8455 -4 | | | | | | | | | | | | | |
| NULT -4 -8455 | | | | | | | | | | | | | |
| NULE 595 -1558 85 338 -294 453 -1158 197 249 902 -1085 -142 -21 -313 45 531 | | | | | | | | | The transition probability distribution for the null model (single G state). | | | | |
| 201 384 -1998 -644 | | | | | | | | | The symbol emission probability distribution for the null model (G state); consists of K (e.g 4 or 20) integers. The null probability used to convert these back to model probabilities is 1/K. | | | | |
| EVD -499.650970 0.086142 | | | | | | | | | The extreme value distribution parameters μ and lambda respectively; both floating point values. Lambda is positive and nonzero. These values are set when the model is calibrated with hmmcalibrate. | | | | |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 99(Y) | -3615 -149 -16 | -2706 -500 -7108 | -4169 233 -8150 | -4413 43 -894 | 2626 -381 -1115 | -4044 399 -701 | -396 106 -1378 | -2535 -626 * | -1939 -466 | -1985 -720 | -2747 275 | -3930 394 | -2852 45 | -3446 96 | -3296 359 | -3494 117 | -2686 -369 | 347 -294 | 4252 -249 | 105 |
| 100(S) | -897 -149 -16 | -1462 -500 -7108 | -2333 233 -8150 | -2543 43 -894 | -3185 -381 -1115 | -1640 399 -701 | -2474 106 -1378 | -3294 -626 * | -3497 -466 | -2780 -720 | -1973 275 | -2360 394 | -2483 45 | -2703 96 | 3465 359 | -1316 117 | -2413 -369 | -3310 -294 | -3025 -249 | 106 |
| 101(L) | -2871 -149 -16 | -2457 -500 -7108 | -4231 233 -8150 | -4103 43 -894 | -1033 -381 -1115 | -3803 399 -701 | -3165 106 -1378 | -541 -626 * | 3130 -466 | -31 -720 | -3935 275 | -3797 394 | -3286 45 | -3484 96 | -3713 359 | -2869 117 | -1136 -369 | -2394 -294 | -2220 -249 | 107 |
| 102(V) | -1381 -149 -16 | -1065 -500 -7108 | -3714 233 -8150 | -3252 43 -894 | -1453 -381 -1115 | -3300 399 -701 | -2646 106 -1378 | 1872 -626 * | -615 -466 | -373 -720 | -2949 275 | -3287 394 | -2816 45 | -3039 96 | -2506 359 | 1346 117 | 2750 -369 | -2489 -294 | -2087 -249 | 108 |
| 103(S) | -897 -149 -16 | -1462 -500 -7108 | -2333 233 -8150 | -2543 43 -894 | -3185 -381 -1115 | -1640 399 -701 | -2474 106 -1378 | -3294 -626 * | -3497 -466 | -2780 -720 | -1973 275 | -2360 394 | -2483 45 | -2703 96 | 3465 359 | -1316 117 | -2413 -369 | -3310 -294 | -3025 -249 | 109 |
| 104(R) | -2957 -149 -16 | -3022 -500 -7108 | -3318 233 -8150 | -2735 43 -894 | -3796 -381 -1115 | -2998 399 -701 | -1968 106 -1378 | -3912 -626 * | -3631 -466 | -3157 -720 | -2611 275 | -3280 394 | -1724 45 | 4056 96 | -3026 359 | -2913 117 | -3650 -369 | -3096 -294 | -3185 -249 | 110 |
| 105(E) | -1719 -149 -16 | -3572 -500 -7108 | 2596 233 -8150 | 2779 43 -894 | -3767 -381 -1115 | -1632 399 -701 | -993 106 -1378 | -3700 -626 * | -3578 -466 | -2920 -720 | -234 275 | -2167 394 | -666 45 | -2090 96 | -1380 359 | -1789 117 | -3182 -369 | -3742 -294 | -2756 -249 | 111 |
| 106(V) | -1746 -149 -16 | -1296 -500 -7108 | -4303 233 -8150 | -3946 43 -894 | -1757 -381 -1115 | -4020 399 -701 | -3712 106 -1378 | 2190 -626 * | -614 -466 | -539 -720 | -3702 275 | -3858 394 | -3667 45 | -3884 96 | -3336 359 | -1740 117 | 3098 -369 | -3250 -294 | -2803 -249 | 112 |
| 107(I) | -2091 -149 -16 | -1746 -500 -7108 | -3971 233 -8150 | -3840 43 -894 | -1676 -381 -1115 | -3532 399 -701 | -3289 106 -1378 | 3684 -626 * | -659 -466 | -693 -720 | -3562 275 | -3674 394 | -3445 45 | -3521 96 | -3194 359 | -2146 117 | 449 -369 | -2877 -294 | -2493 -249 | 113 |
| 108(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3257 -466 | -2662 -720 | -2236 275 | -2447 394 | -2798 45 | -2944 96 | -1216 359 | -1387 117 | -2183 -369 | -3405 -294 | -3320 -249 | 114 |
| 109(D) | -2784 -149 -16 | -3432 -500 -7108 | 4016 233 -8150 | -1200 43 -894 | -4140 -381 -1115 | -2466 399 -701 | -2197 106 -1378 | -4505 -626 * | -4365 -466 | -3956 -720 | -1551 275 | -3014 394 | -2039 45 | -3232 96 | -2593 359 | -2938 117 | -4046 -369 | -3710 -294 | -3552 -249 | 115 |

TABLE 6-continued

| | | | | | | | | | | | | | | | | | | | | | | | |
|---|---|---|---|---|---|---|---|---|---|---|---|---|---|---|---|---|---|---|---|---|---|---|---|
| HMMER2.0 [2.2g] | | | | | | | | | | | Program name and version | | | | | | | | | | | | |
| NAME dhad_for_hmm | | | | | | | | | | | Name of the input sequence alignment file | | | | | | | | | | | | |
| LENG 564 | | | | | | | | | | | Length of the alignment | | | | | | | | | | | | |
| ALPH Amino | | | | | | | | | | | Type of residues | | | | | | | | | | | | |
| MAP yes | | | | | | | | | | | Map of the match states to the columns of the alignment | | | | | | | | | | | | |
| COM /app/public/hmmer/current/bin/hmmbuild -F dhad-exp_hmm dhad_for_hmm.aln | | | | | | | | | | | Commands used to generate the file: this one means that hmmbuild (default patrameters) was applied to the alignment file | | | | | | | | | | | | |
| COM /app/public/hmmer/current/bin/hmmcalibrate dhad-exp_hmm | | | | | | | | | | | Commands used to generate the file: this one means that hmmcalibrate (default parametrs) was applied to the hmm profile | | | | | | | | | | | | |
| NSEQ 8 | | | | | | | | | | | Number of sequences in the alignment file | | | | | | | | | | | | |
| DATE Tue Jun 3 10:48:24 2008 | | | | | | | | | | | When was the file generated | | | | | | | | | | | | |
| XT -8455 -4 -1000 -1000 -8455 -4 -8455 -4 | | | | | | | | | | | | | | | | | | | | | | | |
| NULT -4 -8455 | | | | | | | | | | | The transition probability distribution for the null model (single G state). | | | | | | | | | | | | |
| NULE 595 -1558 85 338 -294 453 -1158 197 249 902 -1085 -142 -21 -313 45 531 201 384 -1998 -644 | | | | | | | | | | | The symbol emission probability distribution for the null model (G state); consists of K (e.g 4 or 20) integers. The null probability used to convert these back to model probabilities is 1/K. | | | | | | | | | | | | |
| EVD -499.650970 0.086142 | | | | | | | | | | | The extreme value distribution parameters μ and lambda respectively; both floating point values. Lambda is positive and nonzero. These values are set when the model is calibrated with hmmcalibrate. | | | | | | | | | | | | |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 110(S) | -352 -149 -16 | 2942 -500 -7108 | -2955 233 -8150 | -2957 43 -894 | -2876 -381 -1115 | -1254 399 -701 | -2382 106 -1378 | -2573 -626 * | -2927 -466 | -2128 -720 | -1827 275 | -2001 394 | -2405 45 | -2607 96 | 3103 359 | -778 117 | -1757 -369 | -3171 -294 | -2911 -249 | 116 |
| 111(I) | -2091 -149 -16 | -1746 -500 -7108 | -3971 233 -8150 | -3840 43 -894 | -1676 -381 -1115 | -3532 394 -701 | -3289 106 -1378 | 3684 -626 * | -659 -466 | -693 -720 | -3562 275 | -3674 394 | -3445 45 | -3521 96 | -3194 359 | -2146 117 | 449 -369 | -2877 -294 | -2493 -249 | 117 |
| 112(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -4016 -466 | -3555 -720 | -1531 275 | -2959 394 | -1842 45 | -2560 96 | -2479 359 | -2750 117 | -3722 -369 | -3563 -294 | -3385 -249 | 118 |
| 113(T) | 1556 -149 -16 | -936 -500 -7108 | -2493 233 -8150 | -2457 43 -894 | -2805 -381 -1115 | -1256 394 -701 | -2159 106 -1378 | -2210 -626 * | -2681 -466 | -1932 -720 | -1656 275 | -1974 394 | -2089 45 | -2352 96 | -598 359 | 3235 117 | -1547 -369 | -3111 -294 | -2847 -249 | 119 |
| 114(C) | 1784 -149 -16 | 2119 -500 -7108 | -2013 233 -8150 | -1532 43 -894 | -1093 -381 -1115 | -1580 394 -701 | -1089 106 -1378 | -436 -626 * | -937 -466 | -273 -720 | 1093 275 | -1932 394 | -1127 45 | -1472 96 | -748 359 | -515 117 | 1585 -369 | -1536 -294 | -1163 -249 | 120 |
| 115(M) | 1831 -149 -16 | 2019 -500 -7108 | -2596 233 -8150 | -2038 43 -894 | -605 -381 -1115 | -1979 399 -701 | -1126 106 -1378 | 244 -626 * | -359 -466 | 2501 -720 | -1655 275 | -2145 394 | -1435 45 | -1683 96 | -1106 359 | -557 117 | 1087 -369 | -1153 -294 | -804 -249 | 121 |
| 116(Q) | -987 -149 -16 | -2211 -500 -7108 | -43 233 -8150 | -62 43 -894 | -2833 -381 -1115 | 2229 399 -701 | -691 106 -1378 | -2616 -626 * | -2604 -466 | -1797 -720 | 1197 275 | -1917 394 | 2260 45 | -858 96 | -880 359 | -1045 117 | -2139 -369 | -2772 -294 | -2099 -249 | 122 |
| 117(G) | 2313 -149 -16 | -1042 -500 -7108 | -2391 233 -8150 | -2526 43 -894 | -3250 -381 -1115 | 2601 394 -701 | -2372 106 -1378 | -2972 -626 * | -3257 -466 | -2407 -720 | -1721 275 | -2032 394 | -2310 45 | -2646 96 | -662 359 | -859 117 | -2003 -369 | -3434 -294 | -3247 -249 | 123 |
| 118(Q) | -914 -149 -16 | -2350 -500 -7108 | -48 233 -8150 | 1661 43 -894 | -2621 -381 -1115 | -1571 399 -701 | 2504 106 -1378 | -2400 -626 * | -2331 -466 | -1486 -720 | -201 275 | -1796 394 | 2646 45 | -351 96 | -754 359 | -865 117 | -1984 -369 | -2463 -294 | -1787 -249 | 124 |
| 119(W) | -517 -149 -16 | -1294 -500 -7108 | -733 233 -8150 | -183 43 -894 | -1062 -381 -1115 | -1605 399 -701 | -234 106 -1378 | -1037 -626 * | -1207 -466 | -456 -720 | 1435 275 | -1690 394 | 33 45 | 756 96 | 411 359 | -454 117 | -819 -369 | 3340 -294 | 1286 -249 | 125 |
| 120(M) | 410 -149 -16 | -469 -500 -7108 | -2417 233 -8150 | -1828 43 -894 | -341 -381 -1115 | -2041 399 -701 | -897 106 -1378 | 195 -626 * | -156 -466 | 3130 -720 | -1534 275 | -2102 394 | -1230 45 | -1484 96 | -1117 359 | -507 117 | 954 -369 | -894 -294 | 2253 -249 | 126 |

TABLE 6-continued

```
HMMER2.0 [2.2g]                                                    Program name and version
NAME dhad_for_hmm                                                  Name of the input sequence alignment file
LENG 564                                                           Length of the alignment
ALPH Amino                                                         Type of residues
MAP yes                                                            Map of the match states to the columns of the alignment
COM /app/public/hmmer/current/bin/hmmbuild -F dhad-exp_hmm dhad_for_hmm.aln    Commands used to generate the file: this one means that hmmbuild (default parameters) was applied to the alignment file
COM /app/public/hmmer/current/bin/hmmcalibrate dhad-exp_hmm                    Commands used to generate the file: this one means that hmmcalibrate (default parameters) was applied to the hmm profile
NSEQ 8                                                             Number of sequences in the alignment file
DATE Tue Jun 3 10:48:24 2008                                       When was the file generated
XT -8455 -4 -1000 -1000 -8455 -4 -8455 -4
NULT -4 -8455                                                      The transition probability distribution for the null model (single G state).
NULE 595 -1558 85 338 -294 453 -1158 197 249 902 -1085 -142 -21 -313 45 531    The symbol emission probability distribution for the null model (G state); consists of K (e.g. 4 or 20) integers. The null
201 384 -1998 -644                                                 probability used to convert these back to model probabilities is 1/K.
EVD -499.650970 0.086142                                           The extreme value distribution parameters μ and lambda respectively; both floating point values. Lambda is positive and
                                                                   nonzero. These values are set when the model is calibrated with hmmcalibrate.
```

| HMM | A<br>m->m | C<br>m->i | D<br>m->d | E<br>i->m | F<br>i->i | G<br>d->m | H<br>d->d | I<br>b->m | L | M | N | P | Q | R | S | T | V | W | Y | Position in alignment |
|---|---|---|---|---|---|---|---|---|---|---|---|---|---|---|---|---|---|---|---|---|
| 121(D) | -2784<br>-149<br>-16 | -3432<br>-500<br>-7108 | 4016<br>233<br>-8150 | -1200<br>43<br>-894 | -4140<br>-381<br>-1115 | -2466<br>399<br>-701 | -2197<br>106<br>-1378 | -4505<br>-626<br>* | -4365<br>-466 | -3956<br>-720 | -1551<br>275 | -3014<br>394 | -2039<br>45 | -3232<br>96 | -2593<br>359 | -2938<br>117 | -4046<br>-369 | -3710<br>-294 | -3552<br>-249 | 127 |
| 122(G) | 2142<br>-149<br>-16 | -930<br>-500<br>-7108 | -2334<br>233<br>-8150 | -2298<br>43<br>-894 | -3100<br>-381<br>-1115 | 2237<br>399<br>-701 | -2139<br>106<br>-1378 | -2842<br>-626<br>* | -3074<br>-466 | -2187<br>-720 | -1557<br>275 | -1909<br>394 | -2010<br>45 | -2397<br>96 | 1136<br>359 | -701<br>117 | -1871<br>-369 | -3308<br>-294 | -3053<br>-249 | 128 |
| 123(V) | -1514<br>-149<br>-16 | -1144<br>-500<br>-7108 | -3950<br>233<br>-8150 | -3459<br>43<br>-894 | 1821<br>-381<br>-1115 | -3487<br>399<br>-701 | -2577<br>106<br>-1378 | 2274<br>-626<br>* | -209<br>-466 | -87<br>-720 | -3112<br>275 | -3362<br>394 | -2864<br>45 | -3118<br>96 | -2680<br>359 | -1476<br>117 | 2426<br>-369 | -2194<br>-294 | -1786<br>-249 | 129 |
| 124(V) | -1743<br>-149<br>-16 | -1294<br>-500<br>-7108 | -4292<br>233<br>-8150 | -3873<br>43<br>-894 | -1511<br>-381<br>-1115 | -3988<br>399<br>-701 | -3433<br>106<br>-1378 | 2287<br>-626<br>* | 598<br>-466 | -319<br>-720 | -3626<br>275 | -3774<br>394 | -3456<br>45 | -3716<br>96 | -3260<br>359 | -1717<br>117 | 2790<br>-369 | -2931<br>-294 | -2577<br>-249 | 130 |
| 125(A) | 2911<br>-149<br>-16 | -954<br>-500<br>-7108 | -2808<br>233<br>-8150 | -2665<br>43<br>-894 | -2115<br>-381<br>-1115 | -1577<br>399<br>-701 | -2196<br>106<br>-1378 | -575<br>-626<br>* | -1646<br>-466 | -1202<br>-720 | -1906<br>275 | -2208<br>394 | -2218<br>45 | -2451<br>96 | -901<br>359 | -876<br>117 | 1294<br>-369 | -2727<br>-294 | -2394<br>-249 | 131 |
| 126(I) | -1764<br>-149<br>-16 | -1323<br>-500<br>-7108 | -4298<br>233<br>-8150 | -3936<br>43<br>-894 | -1668<br>-381<br>-1115 | -3994<br>399<br>-701 | -3655<br>106<br>-1378 | 3337<br>-626<br>* | -508<br>-466 | -462<br>-720 | -3689<br>275 | -3838<br>394 | -3608<br>45 | -3835<br>96 | -3311<br>359 | -1759<br>117 | 1847<br>-369 | -3164<br>-294 | -2747<br>-249 | 132 |
| 127(G) | -1157<br>-149<br>-16 | -1705<br>-500<br>-7108 | -2169<br>233<br>-8150 | -2375<br>43<br>-894 | -3654<br>-381<br>-1115 | 3021<br>396<br>-701 | -2534<br>106<br>-1378 | -3611<br>-626<br>* | -3741<br>-466 | -2984<br>-720 | -2024<br>275 | 2418<br>394 | -2475<br>45 | -2826<br>96 | -1361<br>359 | -1555<br>117 | -2705<br>-369 | -3513<br>-294 | -3509<br>-249 | 133 |
| 128(G) | -2594<br>-149<br>-16 | -2690<br>-500<br>-7108 | -3304<br>233<br>-8150 | -3623<br>43<br>-894 | -4328<br>-381<br>-1115 | 3747<br>399<br>-701 | -3462<br>106<br>-1378 | -4761<br>-626<br>* | -4671<br>-466 | -4212<br>-720 | -3320<br>275 | -3352<br>394 | -3748<br>45 | -3779<br>96 | -2639<br>359 | -2981<br>117 | -4004<br>-369 | -3668<br>-294 | -4222<br>-249 | 134 |
| 129(C) | -2476<br>-149<br>-16 | 5735<br>-500<br>-7108 | -4102<br>233<br>-8150 | -4358<br>43<br>-894 | -3712<br>-381<br>-1115 | -2763<br>399<br>-701 | -3545<br>106<br>-1378 | -3518<br>-626<br>* | -3859<br>-466 | -3569<br>-720 | -3631<br>275 | -3363<br>394 | -4030<br>45 | -3832<br>96 | -2793<br>359 | -2860<br>117 | -3158<br>-369 | -3464<br>-294 | -3718<br>-249 | 135 |
| 130(D) | -2784<br>-149<br>-16 | -3432<br>-500<br>-7108 | 4016<br>233<br>-8150 | -1200<br>43<br>-894 | -4140<br>-381<br>-1115 | -2466<br>399<br>-701 | -2197<br>106<br>-1378 | -4505<br>-626<br>* | -4365<br>-466 | -3956<br>-720 | -1551<br>275 | -3014<br>394 | -2039<br>45 | -3232<br>96 | -2593<br>359 | -2938<br>117 | -4046<br>-369 | -3710<br>-294 | -3552<br>-249 | 136 |
| 131(K) | -2620<br>-149<br>-16 | -2961<br>-500<br>-7108 | -2461<br>233<br>-8150 | -2046<br>43<br>-894 | -3743<br>-381<br>-1115 | -2791<br>396<br>-701 | -1570<br>106<br>-1378 | -3603<br>-626<br>* | -3387<br>-466 | -2839<br>-720 | -2048<br>275 | -3039<br>394 | -1260<br>45 | -465<br>96 | -2604<br>359 | -2536<br>117 | -3331<br>-369 | -3001<br>-294 | -2988<br>-249 | 137 |

TABLE 6-continued

```
HMMER2.0 [2.2g]                                                     Program name and version
NAME  dhad_for_hmm                                                  Name of the input sequence alignment file
LENG  564                                                           Length of the alignment: include indels
ALPH  Amino                                                         Type of residues
MAP   yes                                                           Map of the match states to the columns of the alignment
COM   /app/public/hmmer/current/bin/hmmbuild -F dhad-exp_hmm dhad_for_hmm.aln   Commands used to generate the file: this one means that hmmbuild (default patrameters) was applied to the alignment file
COM   /app/public/hmmer/current/bin/hmmcalibrate dhad-exp_hmm       Commands used to generate the file: this one means that hmmcalibrale (default parametrs) was applied to the hmm profile
NSEQ  8                                                             Number of sequences in the alignment file
DATE  Tue Jun 3 10:48:24 2008                                       When was the file generated
XT    -8455 -4 -1000 -1000 -8455 -4 -8455 -4
NULT  -4 -8455                                                      The transition probability distribution for the null model (single G state).
NULE  595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                                   probability used to convert these back to model probabilities is 1/K.
EVD   -499.650970 0.086142                                           The extreme value distribution parameters µ and lambda respectively; both floating point values. Lambda is positive and
                                                                     nonzero. These values are set when the model is calibrated with hmmcalibrate.
```

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 132(N) | -2171 -149 -16 | -2655 -500 -7108 | -1458 233 -8150 | -1748 43 -894 | -3334 -381 -1115 | -2364 399 -701 | -2267 106 -1378 | -3943 -626 * | -3936 -466 | -3437 -720 | 4205 275 | -2932 394 | -2205 45 | -2608 96 | -2224 359 | -2439 117 | -3392 -369 | -3253 -294 | -2909 -249 | 138 |
| 133(M) | -2406 -149 -16 | -2296 -500 -7108 | -3638 233 -8150 | -3594 43 -894 | -1525 -381 -1115 | -3105 399 -701 | -2824 106 -1378 | -1047 -626 * | -596 -466 | 5043 -720 | -3293 275 | -3425 394 | -3046 45 | -2996 96 | -2911 359 | -2552 117 | -1398 -369 | -2513 -294 | -2207 -249 | 139 |
| 134(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 140 |
| 135(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 141 |
| 136(A) | 2180 -149 -16 | -935 -500 -7108 | -2286 233 -8150 | -2196 43 -894 | -3057 -381 -1115 | 1098 399 -701 | -2058 106 -1378 | -2796 -626 * | -3021 -466 | -2134 -720 | -1516 275 | -1898 394 | -1906 45 | -2302 96 | 2148 359 | -689 117 | -1849 -369 | -3256 -294 | -2983 -249 | 142 |
| 137(M) | -1799 -149 -16 | -1433 -500 -7108 | -4142 233 -8150 | -3579 43 -894 | -669 -381 -1115 | -3668 399 -701 | -2608 106 -1378 | 1558 -626 * | 1235 -466 | 3799 -720 | -3296 275 | -3401 394 | -2717 45 | -3088 96 | -2843 359 | -1726 117 | 1156 -369 | -2002 -294 | -1868 -249 | 143 |
| 138(I) | -2091 -149 -16 | -1746 -500 -7108 | -3971 233 -8150 | -3840 43 -894 | -1676 -381 -1115 | -3532 399 -701 | -3289 106 -1378 | 3684 -626 * | -659 -466 | -693 -720 | -3562 275 | -3674 394 | -3445 45 | -3521 96 | -3194 359 | -2146 117 | 449 -369 | -2877 -294 | -2493 -249 | 144 |
| 139(A) | 3103 -149 -16 | -1036 -500 -7108 | -2445 233 -8150 | -2572 43 -894 | -3222 -381 -1115 | 1051 399 -701 | -2380 106 -1378 | -2930 -626 * | -3226 -466 | -2381 -720 | -1739 275 | -2034 394 | -2327 45 | -2648 96 | -664 359 | -857 117 | -1981 -369 | -3412 -294 | -3228 -249 | 145 |
| 140(M) | -2325 -149 -16 | -1891 -500 -7108 | -4598 233 -8150 | -4012 43 -894 | -498 -381 -1115 | -4222 399 -701 | -3013 106 -1378 | 1242 -626 * | 1864 -466 | 3929 -720 | -3855 275 | -3711 394 | -2910 45 | -3414 96 | -3439 359 | -2215 117 | -299 -369 | -2076 -294 | -2098 249 | 146 |
| 141(A) | 3103 -149 -16 | -1036 -500 -7108 | -2445 233 -8150 | -2572 43 -894 | -3222 -381 -1115 | 1051 399 -701 | -2380 106 -1378 | -2930 -626 * | -3226 -466 | -2381 -720 | -1739 275 | -2034 394 | -2327 45 | -2648 96 | -664 359 | -857 117 | -1981 -369 | -3412 -294 | -3228 -249 | 147 |
| 142(R) | -1588 -149 -16 | -2442 -500 -7108 | -1399 233 -8150 | -953 43 -894 | -3069 -381 -1115 | -2171 399 -701 | -708 106 -1378 | -2795 -626 * | -2625 -466 | -1916 -720 | 1858 275 | -2357 394 | -324 45 | 3294 96 | -1520 359 | -1505 117 | -2453 -369 | -2523 -294 | -2186 -249 | 148 |

TABLE 6-continued

HMMER2.0 [2.2g]  
NAME dhad_for_hmm  
LENG 564  
ALPH Amino  
MAP yes  
COM /app/public/hmmer/current/bin/hmmbuild -F dhad-exp_hmm dhad_for_hmm.aln  
COM /app/public/hmmer/current/bin/hmmcalibrate dhad-exp_hmm  
NSEQ 8  
DATE Tue Jun 3 10:48:24 2008  
XT -8455 -4 -1000 -1000 -8455 -4 -8455 -4  
NULT -4 -8455  
NULE 595 -1558 85 338 -294 453 -1158 197 249 902 -1085 -142 -21 -313 45 531 201 384 -1998 -644  
EVD -499.650970 0.086142

Program name and version  
Name of the input sequence alignment file  
Length of the alignment  
Type of residues  
Map of the match states to the columns of the alignment  
Commands used to generate the file: this one means that hmmbuild (default patrameters) was applied to the alignment file  
Commands used to generate the file: this one means that hmmcalibrate (default parameters) was applied to the hmm profile  
Number of sequences in the alignment file  
When was the file generated The transition probability distribution for the null model (single G state).  
The symbol emission probability distribution for the null model (G state); consists of K (e.g 4 or 20) integers. The null probability used to convert these back to model probabilities is 1/K.  
The extreme value distribution parameters μ and lambda respectively; both floating point values. Lambda is positive and nonzero. These values are set when the model is calibrated with hmmcalibrate.

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 143(M) | -1448 -149 -16 | -1256 -500 -7108 | -3396 233 -8150 | -2819 43 -894 | -474 -381 -1115 | -3024 399 -701 | -1923 106 -1378 | 175 -626 * | 2225 -466 | 2756 -720 | -2574 275 | -2922 394 | -2063 45 | -2375 96 | -2153 359 | 952 117 | -151 -369 | -1599 -294 | -1410 -249 | 149 |
| 144(N) | -1662 -149 -16 | -3306 -500 -7108 | 2055 233 -8150 | 78 43 -894 | -3621 -381 -1115 | -1643 399 -701 | -1040 106 -1378 | -3622 -626 * | -3531 -466 | -2870 -720 | 3477 275 | -2182 394 | -724 45 | -2071 96 | -1371 359 | -1757 117 | -3092 -369 | -3633 -294 | -2700 -249 | 150 |
| 145(I) | -1066 -149 -16 | -921 -500 -7108 | -2828 233 -8150 | -2239 43 -894 | -1041 -381 -1115 | -2675 399 -701 | -1601 106 1378 | 2235 -626 * | -455 -466 | -92 -720 | -2067 275 | -2692 394 | -1688 45 | 1701 96 | -1795 359 | -1024 117 | 1960 -359 | -1771 -294 | -1396 -249 | 151 |
| 146(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 152 |
| 147(S) | 1568 -149 -16 | -940 -500 -7108 | -2267 233 -8150 | -2192 43 -894 | -3082 -381 -1115 | 1101 399 -701 | -2068 105 -1378 | -2826 -626 * | -3049 -465 | -2159 -720 | -1515 275 | -1901 394 | -1915 45 | -2313 96 | 2603 359 | -694 117 | -1866 -369 | -3279 -294 | -3006 -249 | 153 |
| 148(I) | -1880 -149 -16 | -1492 -500 -7108 | -4195 233 -8150 | -3728 43 -894 | -963 -381 -1115 | -3841 399 -701 | -2991 106 -1378 | 3272 -626 * | 246 -466 | 2277 -720 | -3490 275 | -3613 394 | -3014 45 | -3317 96 | -3092 359 | -1841 117 | 628 -369 | -2385 -294 | -2163 -249 | 154 |
| 149(F) | -2204 -149 -16 | -1797 -500 -7108 | -3724 233 -8150 | -3473 43 -894 | 3206 -381 -1115 | -3383 399 -701 | -628 106 -1378 | -1077 -626 * | -746 -466 | 3167 -720 | -2502 275 | -3309 394 | -2372 45 | -2792 96 | -2535 359 | -2120 117 | -1245 -369 | 28 -294 | 2460 -249 | 155 |
| 150(V) | 1265 -149 -16 | -1028 -500 -710 | -3200 233 -8150 | -2994 43 -894 | -1833 -381 -1115 | -2150 399 -701 | -2480 1064 -1378 | 417 -626 * | -1122 -466 | -818 -720 | -2349 275 | -2640 394 | -2559 45 | -2766 96 | -1464 359 | -1118 117 | 3028 -369 | -2700 -294 | -2325 -249 | 156 |
| 151(Y) | -3482 -149 -16 | -2868 -500 -7108 | -3701 233 -8150 | -3919 43 -894 | 238 -381 -1115 | -3552 399 -701 | -1112 106 -1378 | -3000 -626 * | -2516 -466 | -2526 -720 | -3027 275 | -3772 394 | -3101 45 | -3341 96 | -3418 359 | -3527 117 | -3071 -369 | -441 -294 | 4711 -249 | 157 |
| 152(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 158 |
| 153(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96J | -2839 359 | -2981 117 | -4004 -369 | -3668 -294 | -4222 -249 | 159 |

TABLE 6-continued

```
HMMER2.0 [2.2g]                                              Program name and version
NAME dhad_for_hmm                                            Name of the input sequence alignment file
LENG 564                                                     Length of the alignment: include indels
ALPH Amino                                                   Type of residues
MAP yes                                                      Map of the match states to the columns of the alignment
COM /app/public/hmmer/current/bin/hmmbuild -F dhad-exp_hmm dhad_for_hmm.aln    Commands used to generate the file: this one means that hmmbuild (default patrameters) was applied to the alignment file
COM /app/public/hmmer/current/bin/hmmcalibrate dhad-exp_hmm                    Commands used to generate the file: this one means that hmmcalibrate (default parameters) was applied to the hmm profile
NSEQ 8                                                       Number of sequences in the alignment file
DATE Tue Jun 3 10:48:24 2008                                 When was the file generated
XT -8455 -4 -1000 -1000 -8455 -4 -8455 -4
NULT -4 -8455                                                The transition probability distribution for the null model (single G state).
NULE 595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                                            probability used to convert these back to model probabilities is 1/K.
EVD -499.650970 0.086142                                     The extreme value distribution parameters μ and lambda respectively; both floating point values. Lambda is positive and
                                                             nonzero. These values are set when the model is calibrated with hmmcalibrate.
```

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 154(T) | -359 | -976 | -2225 | -2229 | -2900 | -1242 | -2074 | -2560 | -2875 | -2064 | -1561 | -1958 | -1969 | -2247 | 1110 | 3375 | -1760 | -3152 | -2850 | 160 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 155(I) | -2091 | -1746 | -3971 | -3840 | -1676 | -3532 | -3289 | 3684 | -659 | -693 | -3562 | -3674 | -3445 | -3521 | -3194 | -2146 | 449 | -2877 | -2493 | 161 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 156(H) | 861 | -1924 | -384 | 1010 | -2260 | -1477 | 1767 | -1974 | -1918 | -1022 | -120 | -1566 | 362 | 697 | -417 | -459 | -1557 | -2073 | -1446 | 162 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 157(P) | -655 | -1502 | -711 | -557 | -2204 | -1463 | 2143 | -2122 | -2233 | -1445 | -688 | 2941 | -560 | -941 | 855 | -805 | -1657 | -2369 | -1763 | 163 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 158(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 164 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 159(H) | -744 | -2193 | -114 | 1118 | -2513 | -1512 | 2486 | -2252 | -2183 | -1308 | 2230 | -1689 | 180 | -233 | -598 | -687 | -1823 | -2335 | -1670 | 165 |
|  | -149 | -500 | 233 | 43 | -381 | 399 | 106 | -626 | -466 | -720 | 275 | 394 | 46 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 160(W) | -2672 | -2139 | -3850 | -3748 | 941 | -3611 | -469 | -1691 | 1047 | -1217 | -2551 | -3534 | -2514 | -2960 | -2788 | -2577 | -1799 | 4205 | 3466 | 166 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 161(K) | 386 | -1981 | 779 | 279 | -2295 | -1403 | -114 | -2043 | -1991 | -1082 | 941 | -1536 | 1263 | -211 | -384 | -457 | -1602 | -2161 | -1476 | 167 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 162(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 168 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 163(K) | -1144 | -2365 | -912 | 2048 | -2856 | -1912 | -326 | -2459 | -2295 | -1482 | -556 | -1989 | 108 | 1334 | -1013 | -1014 | -2093 | -2324 | -1881 | 169 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 164(D) | -1091 | -2610 | 2941 | 174 | -2957 | -1527 | -595 | -2750 | -2696 | -1877 | -176 | -1885 | -206 | -1006 | 740 | -1098 | -2288 | -2880 | -2105 | 170 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

```
HMMER2.0 [2.2g]                                              Program name and version
NAME  dhad_for_hmm                                           Name of the input sequence alignment file
LENG  564                                                    Length of the alignment
ALPH  Amino                                                  Type of residues
MAP   yes                                                    Map of the match states to the columns of the alignment
COM   /app/public/hmmer/current/bin/hmmbuild -F dhad-exp_hmm dhad_for_hmm.aln    Commands used to generate the file: this one means that hmmbuild (default parameters) was applied to the alignment file
COM   /app/public/hmmer/current/bin/hmmcalibrate dhad-exp_hmm                    Commands used to generate the file: this one means that hmmcalibrate (default parameters) was applied to the hmm profile
NSEQ  8                                                      Number of sequences in the alignment file
DATE  Tue Jun 3 10:48:24 2008                                When was the file generated
XT    -8455 -4 -1000 -1000 -8455 -4 -8455 -4
NULT  -4 -8455                                               The transition probability distribution for the null model (single G state).
NULE  595 -1558 85 338 -294 453 -1158 197 249 902 -1085 -142 -21 -313 45 531    The symbol emission probability distribution for the null model (G state); consists of K (e.g. 4 or 20) integers. The null
201 384 -1998 -644                                                               probability used to convert these back to model probabilities is 1/K.
EVD  -499.650970 0.086142                                                        The extreme value distribution parameters μ and lambda respectively; both floating point values. Lambda is positive and
                                                                                  nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 165(L) | -2387 | -1922 | -4674 | -4155 | -617 | -4366 | -3250 | 1889 | 2650 | 558 | -4023 | -3847 | -3098 | -3586 | -3647 | -2296 | -38 | -2247 | -2224 | 171 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 166(N) | -1021 | -2427 | 1806 | 133 | -2870 | -1499 | -635 | -2647 | -2640 | -1825 | 2171 | -1874 | -255 | -1124 | -860 | 2122 | -2184 | -2853 | -2090 | 172 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 167(I) | -1830 | -1390 | -4327 | -3873 | -1210 | -3994 | -3274 | 2967 | 1259 | -30 | -3633 | -3730 | -3283 | -3604 | -3249 | -1791 | 1570 | -2661 | -2417 | 173 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 168(V) | -1771 | -1603 | -3750 | -3689 | -2037 | -3050 | -3231 | 403 | -1154 | -1076 | -3246 | -3399 | -3383 | -3437 | -2628 | -1917 | 3536 | -3074 | -2677 | 174 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 169(S) | -897 | -1462 | -2333 | -2543 | -3185 | -1640 | -2474 | -3294 | -3497 | -2780 | -1973 | -2360 | -2483 | -2703 | 3465 | -1316 | -2413 | -3310 | -3025 | 175 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 170(A) | 2440 | -824 | -2371 | -2082 | -1993 | -1344 | -1704 | -1264 | -1832 | -1137 | -1517 | -1946 | -1674 | -2005 | 1075 | -641 | 1474 | -2390 | -2055 | 176 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 171(F) | -3342 | -2776 | -4026 | -4232 | 4354 | -3545 | -1431 | -2315 | -1801 | -1900 | -3299 | -3780 | -3350 | -3645 | -3490 | -3420 | -2566 | -739 | 349 | 177 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 172(E) | -2641 | -3308 | -896 | 3732 | -3966 | -2458 | -2043 | -4105 | -4016 | -3555 | -1531 | -2959 | -1842 | -2560 | -2479 | -2750 | -3722 | -3583 | -3385 | 178 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 173(A) | 2966 | -1031 | -2429 | -2551 | -3222 | -2368 | -2368 | -2934 | -3225 | -2377 | -1727 | -2028 | -2309 | -2637 | -656 | -850 | -1980 | -3412 | -3224 | 179 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 174(V) | -1769 | -1342 | -4255 | -3793 | -1216 | -3901 | -3162 | 1633 | 1486 | -51 | -3537 | -3667 | -3214 | -3518 | -3143 | -1731 | 2692 | -2609 | -2345 | 180 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 175(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4221 | 181 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

| HMMER2.0 [2.2g] | | Program name and version |
| NAME dhad_for_hmm | | Name of the input sequence alignment file |
| LENG 564 | | Length of the alignment |
| ALPH Amino | | Type of residues |
| MAP yes | | Map of the match states to the columns of the alignment |
| COM /app/public/hmmer/current/bin/hmmbuild -F dhad-exp_hmm dhad_for_hmm.aln | | Commands used to generate the file: this one means that hmmbuild (default parameters) was applied to the alignment file |
| COM /app/public/hmmer/current/bin/hmmcalibrate dhad-exp_hmm | | Commands used to generate the file: this one means that hmmcalibrate (default parameters) was applied to the hmm profile |
| NSEQ 8 | | Number of sequences in the alignment file |
| DATE Tue Jun 3 10:48:24 2008 | | When was the file generated |
| XT -8455 -4 -1000 -1000 -8455 -4 -8455 -4 | | |
| NULT -4 -8455 | | |
| NULE 595 -1558 85 338 -294 453 -1158 197 249 902 -1085 -142 -21 -313 45 531 201 384 -1998 -644 | | The transition probability distribution for the null model (single G state). The symbol emission probability distribution for the null model (G state); consists of K (e.g 4 or 20) integers. The null probability used to convert these back to model probabilities is 1/K. |
| EVD -499.650970 0.086142 | | The extreme value distribution parameters μ and lambda respectively; both floating point values. Lambda is positive and nonzero. These values are set when the model is calibrated with hmmcalibrate. |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| | -149 | -500 | 233 | 43 | -381 | 399 | 106 | -626 | -466 | -720 | 275 | 394 | 45 | 96 | 359 | 117 | -369 | -294 | 249 | |
| | -16 | -7108 | -8150 | -894 | -1115 | -701 | -1378 | * | | | | | | | | | | | | |
| 176(Q) | -729 | -2116 | -413 | 1096 | -2484 | -1587 | 1599 | -2186 | -2094 | -1219 | -223 | -1698 | 2418 | 90 | -599 | -649 | -1770 | -2213 | -1615 | 182 |
| 177(W) | -1652 | -1707 | -2340 | -1879 | 1996 | -2733 | 2013 | -1398 | -1386 | -938 | -1641 | -2751 | -1364 | -1762 | -1780 | -1577 | -1325 | 3577 | 2136 | 183 |
| 178(T) | -421 | -753 | -1251 | -704 | -846 | -1670 | -535 | 894 | -690 | -1 | 1376 | -1791 | -421 | -846 | 373 | 1461 | 858 | -1236 | -812 | 184 |
| 179(H) | 1498 | -1593 | -504 | 15 | -1895 | -1484 | 2279 | -1559 | -1640 | -810 | -242 | -1611 | 194 | -171 | -462 | 815 | -1231 | -1914 | -1340 | 185 |
| 180(G) | -1515 | -2130 | -1298 | -1450 | -2658 | 3285 | 2212 | -3276 | -3291 | -2638 | -1524 | -2562 | -1662 | -1925 | -1600 | -1764 | -2713 | -2804 | -2234 | 186 |
| 181(K) | -528 | -2010 | 1346 | 1082 | -2329 | -1408 | -118 | -2080 | -2018 | -1108 | 1161 | -1543 | 331 | 1052 | -394 | -471 | -1632 | -2181 | -1494 | 187 |
| 182(M) | -1894 | -1521 | -4170 | -3679 | -840 | -3793 | -2866 | 2827 | 375 | 3445 | -3437 | -3555 | -2902 | -3223 | -3028 | -1846 | 470 | -2249 | -2059 | 188 |
| 183(T) | -670 | -1758 | 1731 | -141 | -2591 | -1399 | -691 | -2319 | -2384 | -1543 | -387 | -1786 | -316 | -1016 | 1576 | 2044 | -1811 | -2624 | -1981 | 189 |
| 184(E) | 345 | -2074 | 925 | 1994 | -2378 | -1408 | -177 | -2135 | -2084 | -1183 | -38 | 641 | 264 | -356 | -444 | -536 | -1690 | -2261 | -1556 | 190 |
| 185(E) | -1493 | -2900 | 93 | 3174 | -2903 | -1743 | 1987 | -3042 | -2957 | -2238 | -411 | -2146 | -506 | -1121 | -1272 | -1503 | -2629 | -2905 | -2134 | 191 |
| 186(D) | -1293 | -2959 | 2673 | 2121 | -3219 | -1546 | -713 | -3043 | -2974 | -2191 | -158 | -1967 | -342 | -1394 | -1043 | 701 | -2567 | -3172 | -2311 | 192 |

TABLE 6-continued

| | | |
|---|---|---|
| HMMER2.0 [2.2g] | | Program name and version |
| NAME dhad_for_hmm | | Name of the input sequence alignment file |
| LENG 564 | | Length of the alignment: include indels |
| ALPH Amino | | Type of residues |
| MAP yes | | Map of the match states to the columns of the alignment |
| COM /app/public/hmmer/current/bin/hmmbuild -F dhad-exp_hmm dhad_for_hmm.aln | | Commands used to generate the file: this one means that hmmbuild (default parameters) was applied to the alignment file |
| COM /app/public/hmmer/current/bin/hmmcalibrate dhad-exp_hmm | | Commands used to generate the file: this one means that hmmcalibrate (default parameters) was applied to the hmm profile |
| NSEQ 8 | | Number of sequences in the alignment file |
| DATE Tue Jun 3 10:48:24 2008 | | When was the file generated |
| XT -8455 -4 -1000 -1000 -8455 -4 -8455 -4 | | |
| NULT -4 -8455 | | |
| NULE 595 -1558 85 338 -294 453 -1158 197 249 902 -1085 -142 -21 -313 45 531 201 384 -1998 -644 | | The transition probability distribution for the null model (single G state). The symbol emission probability distribution for the null model (G state); consists of K (e.g 4 or 20) integers. The null probability used to convert these back to model probabilities is 1/K. |
| EVD -499.650970 0.086142 | | The extreme value distribution parameters μ and lambda respectively; both floating point values. Lambda is positive and nonzero. These values are set when the model is calibrated with hmmcalibrate. |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 187(F) | -1137 -149 -16 | -905 -500 -7108 | -3250 233 -8150 | -2707 43 -894 | 2365 -381 -1115 | -2647 399 -701 | -1016 106 -1378 | -34 -626 * | 1239 -466 | 267 -720 | -2150 275 | -2626 394 | -1861 45 | -2133 96 | -1752 359 | -1069 117 | 1461 -369 | -599 -294 | 1844 -249 | 193 |
| 188(K) | -479 -149 -16 | -1713 -500 -7108 | -409 233 -8150 | 1031 43 -894 | -1925 -381 -1115 | -1467 399 -701 | 1755 106 -1378 | -1650 -626 * | -349 -466 | -827 -720 | -140 275 | -1556 394 | 319 45 | -75 96 | -403 359 | -411 117 | -1301 -369 | -1900 -294 | 843 -249 | 194 |
| 189(G) | 433 -149 -16 | -2144 -500 -7108 | 52 233 -8150 | 1047 43 -894 | -2717 -381 -1115 | 2303 399 -701 | -615 106 -1378 | -2467 -626 * | -2482 -466 | -1655 -720 | 1123 275 | -1828 394 | -233 45 | -995 96 | -763 359 | -923 117 | -2000 -369 | -2710 -294 | -2005 -249 | 195 |
| 190(V) | -1752 -149 -16 | -1320 -500 -7108 | -4254 233 -8150 | -3806 43 -894 | -1311 -381 -1115 | -3916 399 -701 | -3232 106 -1378 | 1701 -626 * | 1188 -466 | -140 -720 | -3551 275 | -3693 394 | -3280 45 | -3568 96 | -3166 359 | -1718 117 | 2833 -369 | -2703 -294 | -2409 -249 | 196 |
| 191(E) | -1199 -149 -16 | -1750 -500 -7108 | -734 233 -8150 | 2668 43 -894 | -1820 -381 -1115 | -2038 399 -701 | -1068 106 -1378 | 1892 -626 * | -1273 -466 | -897 -720 | -922 275 | -2295 394 | -797 45 | -1238 96 | -1340 359 | -1197 117 | -425 -369 | -2325 -294 | -1789 -249 | 197 |
| 192(C) | -1182 -149 -16 | 3528 -500 -7108 | -1398 233 -8150 | -620 43 -894 | -2541 -381 -1115 | -2038 399 -701 | -358 106 -1378 | -2093 -626 * | -2037 -466 | -1272 -720 | -747 275 | -2070 394 | 1553 45 | 2213 96 | -1123 359 | -1038 117 | -1817 -369 | -2142 -294 | -1774 -249 | 198 |
| 193(N) | -1478 -149 -16 | -2527 -500 -7108 | -261 233 -8150 | -403 43 -894 | -2011 -381 -1115 | -1837 399 -701 | 2032 106 -1378 | -2925 -626 * | -2845 -466 | -2195 -720 | 3635 275 | -2259 394 | -721 45 | -1085 96 | -1352 359 | -1546 117 | -2522 -369 | -2307 -294 | -1431 -249 | 199 |
| 194(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3257 -466 | -2662 -720 | -2236 275 | -2447 394 | -2798 45 | -2944 96 | -1216 359 | -1387 117 | -2183 -369 | -3405 -294 | -3320 -249 | 200 |
| 195(C) | -1220 -149 -16 | 4911 -500 -7108 | -3609 233 -8150 | -3314 43 -894 | -1440 -381 -1115 | -2525 399 -701 | -2482 106 -1378 | 1565 -626 * | -706 -466 | -544 -720 | -2678 275 | -2896 394 | -2710 45 | -2836 96 | -1869 359 | -1375 117 | 379 -369 | -2371 -294 | -1957 -249 | 201 |
| 196(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 202 |
| 197(G) | -477 -149 -16 | -1115 -500 -7108 | -1983 233 -8150 | -2189 43 -894 | -3315 -381 -1115 | 3154 399 -701 | -2272 106 -1378 | -3172 -626 * | -3387 -466 | -2522 -720 | -1599 275 | -2042 394 | -2177 45 | -2583 96 | 1217 359 | -905 117 | -2130 -369 | -3477 -294 | -3225 -249 | 203 |

TABLE 6-continued

| | | | | | | | | | | | | | | | | | | | | | | | | |
|---|---|---|---|---|---|---|---|---|---|---|---|---|---|---|---|---|---|---|---|---|---|---|---|---|
| HMMER2.0 [2.2g] | | | | | | | | | | | | | | Program name and version | | | | | | | | | | |
| NAME dhad_for_hmm | | | | | | | | | | | | | | Name of the input sequence alignment file | | | | | | | | | | |
| LENG 564 | | | | | | | | | | | | | | Length of the alignment | | | | | | | | | | |
| ALPH Amino | | | | | | | | | | | | | | Type of residues | | | | | | | | | | |
| MAP yes | | | | | | | | | | | | | | Map of the match states to the columns of the alignment | | | | | | | | | | |
| COM /app/public/hmmer/current/bin/hmmbuild -F dhad-exp_hmm dhad_for_hmm.aln | | | | | | | | | | | | | | Commands used to generate the file: this one means that hmmbuild (default parameters) was applied to the alignment file | | | | | | | | | | |
| COM /app/public/hmmer/current/bin/hmmcalibrate dhad-exp_hmm | | | | | | | | | | | | | | Commands used to generate the file: this one means that hmmcalibrate (default parameters) was applied to the hmm profile | | | | | | | | | | |
| NSEQ 8 | | | | | | | | | | | | | | Number of sequences in the alignment file | | | | | | | | | | |
| DATE Tue Jun 3 10:48:24 2008 | | | | | | | | | | | | | | When was the file generated | | | | | | | | | | |
| XT -8455 -4 -1000 -1000 -8455 -4 -8455 -4 | | | | | | | | | | | | | | | | | | | | | | | | |
| NULT -4 -8455 | | | | | | | | | | | | | | The transition probability distribution for the null model (single G state). | | | | | | | | | | |
| NULE 595 -1558 85 338 -294 453 -1158 197 249 902 -1085 -142 -21 -313 45 531 | | | | | | | | | | | | | | The symbol emission probability distribution for the null model (G state); consists of K (e.g. 4 or 20) integers. The null | | | | | | | | | | |
| 201 384 -1998 -644 | | | | | | | | | | | | | | probability used to convert these back to model probabilities is 1/K. | | | | | | | | | | |
| EVD -499.650970 0.086142 | | | | | | | | | | | | | | The extreme value distribution parameters μ and lambda respectively; both floating point values. Lambda is positive and | | | | | | | | | | |
| | | | | | | | | | | | | | | nonzero. These values are set when the model is calibrated with hmmcalibrate. | | | | | | | | | | |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 198(A) | 1653 | -1347 | -705 | -249 | -1969 | -1385 | -477 | -1629 | -1759 | -935 | -434 | 1285 | 1404 | -586 | -450 | 1019 | -1243 | -2070 | -1522 | 204 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 199(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 205 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 200(S) | 1870 | -938 | -2270 | -2183 | -3068 | 1488 | -2056 | -2810 | -3032 | -2144 | -1511 | -1898 | -1901 | -2300 | 2236 | -690 | -1857 | -3265 | -2990 | 206 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 201(C) | -2476 | 5735 | -4102 | -4358 | -3712 | -2763 | -3545 | -3518 | -3859 | -3569 | -3631 | -3363 | -4030 | -3832 | -2793 | -2860 | -3158 | -3464 | -3718 | 207 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 202(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 208 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 203(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 209 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 204(M) | -2406 | -2296 | -3638 | -3594 | -1525 | -3105 | -2824 | -1047 | -596 | 5043 | -3293 | -3425 | -3046 | -2996 | -2911 | -2552 | -1398 | -2513 | -2207 | 210 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 205(Y) | -3590 | -2700 | -4146 | -4379 | 2092 | -4028 | -404 | -2517 | -1928 | -1973 | -2744 | -3921 | -2845 | -3431 | -3284 | -3474 | -2669 | 336 | 4423 | 211 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 206(T) | -1213 | -1674 | -2755 | -2906 | -3163 | -1922 | -2659 | -2698 | -3105 | -2612 | -2311 | -2600 | -2708 | -2753 | -1463 | 3819 | -2197 | -3286 | -3156 | 212 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 207(A) | 3438 | -1472 | -2846 | -3040 | -3287 | -1726 | -2735 | -2840 | -3257 | -2662 | -2236 | -2447 | -2798 | -2944 | -1216 | -1387 | -2183 | -3405 | -3320 | 213 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 208(N) | -2171 | -2655 | -1458 | -1748 | -3334 | -2364 | -2267 | -3943 | -3936 | -3437 | 4205 | -2932 | -2205 | -2608 | -2224 | -2439 | -3392 | -3253 | -2909 | 214 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |

TABLE 6-continued

| HMMER2.0 [2.2g] | | | | | | | | | | | | Program name and version |
| NAME dhad_for_hmm | | | | | | | | | | | | Name of the input sequence alignment file |
| LENG 564 | | | | | | | | | | | | Length of the alignment: include indels |
| ALPH Amino | | | | | | | | | | | | Type of residues |
| MAP yes | | | | | | | | | | | | Map of the match states to the columns of the alignment |
| COM /app/public/hmmer/current/bin/hmmbuild -F dhad-exp_hmm dhad_for_hmm.aln | | | | | | | | | | | | Commands used to generate the file: this one means that hmmbuild (default patrameters) was applied to the alignment file |
| COM /app/public/hmmer/current/bin/hmmcalibrate dhad-exp_hmm | | | | | | | | | | | | Commands used to generate the file: this one means that hmmcalibrate (default parameters) was applied to the hmm profile |
| NSEQ 8 | | | | | | | | | | | | Number of sequences in the alignment file |
| DATE Tue Jun 3 10:48:24 2008 | | | | | | | | | | | | When was the file generated |
| XT -8455 -4 -1000 -1000 -8455 -4 -8455 -4 | | | | | | | | | | | | |
| NULT -4 -8455 | | | | | | | | | | | | |
| NULE 595 -1558 85 338 -294 453 -1158 197 249 902 -1085 -142 -21 -313 45 531 201 384 -1998 -644 | | | | | | | | | | | | The transition probability distribution for the null model (single G state). The symbol emission probability distribution for the null model (G state); consists of K (e.g 4 or 20) integers. The null probability used to convert these back to model probabilities is 1/K. |
| EVD -499.650970 0.086142 | | | | | | | | | | | | The extreme value distribution parameters μ and lambda respectively; both floating point values. Lambda is positive and nonzero. These values are set when the model is calibrated with hmmcalibrate. |

| HMM | A m->m m->i m->d | C | D | E | F | G | H | I | | | | | | | | | | | | | | Position in |
|---|---|---|---|---|---|---|---|---|---|---|---|---|---|---|---|---|---|---|---|---|---|---|---|
| | | | | | i->m i->i | d->m d->i | d->d | b->m | L | M | N | P | Q | R | S | T | V | W | Y | | | alignment |
| 209(T) | -1213 -149 -16 | -1674 -500 -7108 | -2755 233 -8150 | -2906 43 -894 | -3163 -381 -1115 | -1922 399 -701 | -2659 106 -1378 | -2698 -626 * | -3105 -466 | -2612 -720 | -2311 275 | -2600 394 | -2708 45 | -2753 96 | -1463 359 | 3819 117 | -2197 -369 | -3286 -294 | -3156 -249 | | | 215 |
| 210(M) | -2355 -149 -16 | -1988 -500 -7108 | -4343 233 -8150 | -3834 43 -894 | -504 -381 -1115 | -4051 399 -701 | -2868 106 -1378 | 105 -626 * | 1451 -466 | 4460 -720 | -3680 275 | -3671 394 | -2806 45 | -3171 96 | -3327 359 | -2274 117 | -474 -369 | -2039 -294 | -1925 -249 | | | 216 |
| 211(S) | 2150 -149 -16 | -939 -500 -7108 | -2407 233 -8150 | -2415 43 -894 | -3075 -381 -1115 | -1197 399 -701 | -2205 106 -1378 | -2781 -626 * | -3065 -466 | -2205 -720 | -1613 275 | -1936 394 | -2105 45 | -2436 96 | 2652 359 | -729 117 | -1850 -369 | -3306 -294 | -3049 -249 | | | 217 |
| 212(S) | -344 -149 -16 | -979 -500 -7108 | -2190 233 -8150 | -2162 43 -894 | -2959 -381 -1115 | -1227 399 -701 | -2042 106 -1378 | -2651 -626 * | -2934 -466 | -2100 -720 | -1526 275 | -1941 394 | -1909 45 | -2222 96 | 2940 359 | 1775 117 | -1804 -369 | -3187 -294 | -2882 -249 | | | 218 |
| 213(A) | 3048 -149 -16 | -932 -500 -7108 | -2480 233 -8150 | -2533 43 -894 | -3075 -381 -1115 | -1200 399 -701 | -2274 106 -1378 | -2765 -626 * | -3071 -466 | -2221 -720 | -1658 275 | -1948 394 | -2205 45 | -2512 96 | 1225 359 | -739 117 | -1842 -369 | -3322 -294 | -3078 -249 | | | 219 |
| 214(I) | -1924 -149 -16 | -1546 -500 -7108 | -4067 233 -8150 | -3658 43 -894 | 2312 -381 -1115 | -3663 399 -701 | -2081 106 -1378 | 3030 -626 * | 150 -466 | 99 -720 | -3197 275 | -3492 394 | -2821 45 | -3179 96 | -2894 359 | -1877 117 | 293 -369 | -1445 -294 | -692 -249 | | | 220 |
| 215(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -4016 -466 | -3555 -720 | -1531 275 | -2959 394 | -1842 45 | -2560 96 | -2479 359 | -2750 117 | -3722 -369 | -3563 -294 | -3385 -249 | | | 221 |
| 216(A) | 2389 -149 -16 | -814 -500 -7108 | -2506 233 -8150 | -2162 43 -894 | -1696 -381 -1115 | -1545 399 -701 | -1698 106 -1378 | -499 -626 * | -1393 -466 | -813 -720 | -1640 275 | -2076 394 | -1723 45 | -2027 96 | -806 359 | 1148 117 | 1559 -369 | -2200 -294 | -1856 -249 | | | 222 |
| 217(M) | -2576 -149 -16 | -2118 -500 -7108 | -4725 233 -8150 | -4165 43 -894 | -461 -381 -1115 | -4430 399 -701 | -3165 106 -1378 | -4761 -626 * | -4016 -466 | 3454 -720 | -4075 275 | -3839 394 | -2978 45 | -3488 96 | -3704 359 | -2457 117 | -591 -369 | -2111 -294 | -2145 -249 | | | 223 |
| 218(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | | | 224 |
| 219(M) | -2313 -149 -16 | -1968 -500 -7108 | -4258 233 -8150 | -3765 43 -894 | -518 -381 -1115 | -3966 399 -701 | -2806 106 -1378 | 98 -626 * | 1292 -466 | 4523 -720 | -3599 275 | -3636 394 | -2769 45 | -3097 96 | -3249 359 | -2243 117 | -457 -369 | -2026 -294 | -1874 -249 | | | 225 |

TABLE 6-continued

| | | | | | | | | | | | | | | | | | | | | | | | | |
|---|---|---|---|---|---|---|---|---|---|---|---|---|---|---|---|---|---|---|---|---|---|---|---|---|
| HMMER2.0 [2.2g] | | | | | | | | | | | Program name and version | | | | | | | | | | | | | |
| NAME dhad_for_hmm | | | | | | | | | | | Name of the input sequence alignment file | | | | | | | | | | | | | |
| LENG 564 | | | | | | | | | | | Length of the alignment | | | | | | | | | | | | | |
| ALPH Amino | | | | | | | | | | | Type of residues | | | | | | | | | | | | | |
| MAP yes | | | | | | | | | | | Map of the match states to the columns of the alignment | | | | | | | | | | | | | |
| COM /app/public/hmmer/current/bin/hmmbuild -F dhad-exp_hmm dhad_for_hmm.aln | | | | | | | | | | | Commands used to generate the file: this one means that hmmbuild (default parameters) was applied to the alignment file | | | | | | | | | | | | | |
| COM /app/public/hmmer/current/bin/hmmcalibrate dhad-exp_hmm | | | | | | | | | | | Commands used to generate the file: this one means that hmmcalibrate (default parameters) was applied to the hmm profile | | | | | | | | | | | | | |
| NSEQ 8 | | | | | | | | | | | Number of sequences in the alignment file | | | | | | | | | | | | | |
| DATE Tue Jun 3 10:48:24 2008 | | | | | | | | | | | When was the file generated | | | | | | | | | | | | | |
| XT -8455 -4 -1000 -1000 -8455 -4 -8455 -4 | | | | | | | | | | | | | | | | | | | | | | | | |
| NULT -4 -8455 | | | | | | | | | | | The transition probability distribution for the null model (single G state). | | | | | | | | | | | | | |
| NULE 595 -1558 85 338 -294 453 -1158 197 249 902 -1085 -142 -21 -313 45 531 | | | | | | | | | | | The symbol emission probability distribution for the null model (G state); consists of K (e.g 4 or 20) integers. The null probability used to convert these back to model probabilities is 1/K. | | | | | | | | | | | | | |
| 201 384 -1998 -644 | | | | | | | | | | | The extreme value distribution parameters μ and lambda respectively; both floating point values. Lambda is positive and | | | | | | | | | | | | | |
| EVD -499.650970 0.086142 | | | | | | | | | | | nonzero. These values are set when the model is calibrated with hmmcalibrate. | | | | | | | | | | | | | |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 220(S) | -897 -149 -16 | -1462 -500 -7108 | -2333 233 -8150 | -2543 43 -894 | -3185 -381 -1115 | -1640 399 -701 | -2474 106 -1378 | -3294 -626 * | -3497 -466 | -2780 -720 | -1973 275 | -2360 394 | -2483 45 | -2703 96 | 3465 359 | -1316 117 | -2413 -369 | -3310 -294 | -3025 -249 | 226 |
| 221(L) | -2631 -149 -16 | -2159 -500 -7108 | -4786 233 -8150 | -4228 43 -894 | -462 -381 -1115 | -4506 399 -701 | -3231 106 -1378 | 96 -626 * | 2828 -466 | 2482 -720 | -41157 275 | -3880 394 | -3016 45 | -3541 96 | -3793 359 | -2509 117 | -608 -369 | -2134 -294 | -2182 -249 | 227 |
| 222(P) | -1501 -149 -16 | -1778 -500 -7108 | -2473 233 -8150 | -2371 43 -894 | -1710 -381 -1115 | -2311 399 -701 | -2045 106 -1378 | -1321 -626 * | 827 -466 | -1068 -720 | -2173 275 | 3594 394 | -2082 45 | -2130 96 | -1799 359 | -1699 117 | -1373 -369 | -2373 -294 | -1942 -249 | 228 |
| 223(Y) | -1068 -149 -16 | -1670 -500 -7108 | -865 233 -8150 | -836 43 -894 | -631 -381 -1115 | 1198 399 -701 | -767 106 -1378 | -1828 -626 * | -1914 -466 | -1304 -720 | 692 275 | -2203 394 | -906 45 | -1387 96 | -1136 359 | -1163 117 | -1566 -369 | -1185 -294 | 3670 -249 | 229 |
| 224(S) | -897 -149 -16 | -1462 -500 -7108 | -2333 233 -8150 | -2543 43 -894 | -3185 -381 -1115 | -1640 399 -701 | -2474 106 -1378 | -3294 -626 * | -3497 -466 | -2780 -720 | -1973 275 | -2360 394 | -2483 45 | -2703 96 | 3465 359 | -1316 117 | -2413 -369 | -3310 -294 | -3025 -249 | 230 |
| 225(S) | 1172 -149 -16 | -954 -500 -7108 | -2367 233 -8150 | -2422 43 -894 | -3120 -381 -1115 | -1204 396 -701 | -2237 106 -1378 | -2835 -626 * | -3122 -466 | -2265 -720 | -1621 275 | -1948 394 | -2145 45 | -2467 96 | 3107 359 | -749 117 | -1884 -369 | -3349 -294 | -3092 -249 | 231 |
| 226(S) | -342 -149 -16 | -975 -500 -7108 | -2176 233 -8150 | -2124 43 -894 | -2912 -381 -1115 | -1229 399 -701 | -2003 106 -1378 | -2594 -626 * | -2878 -466 | -2048 -720 | -1510 275 | -1936 394 | -1866 45 | -2184 96 | 2553 359 | 2492 117 | -1773 -369 | -3143 -294 | -2833 -249 | 232 |
| 227(M) | -720 -149 -16 | -1440 -500 -7108 | -710 233 -8150 | -343 43 -894 | -1228 -381 -1115 | -1693 399 -701 | 2436 106 -1378 | -1209 -626 * | -1364 -466 | 3099 -720 | 1904 275 | -1852 394 | -183 45 | -458 96 | -776 359 | -680 117 | -1004 -369 | -1540 -294 | -890 -249 | 233 |
| 228(P) | 2240 -149 -16 | -1100 -500 -7108 | -2241 233 -8150 | -2293 43 -894 | -3037 -381 -1115 | -1346 399 -701 | -2188 106 -1378 | -2683 -626 * | -2986 -466 | -2210 -720 | -1663 275 | 3041 394 | -2093 45 | -2391 96 | -722 359 | -895 117 | -1893 -369 | -3243 -294 | -2998 -249 | 234 |
| 229(A) | 2958 -149 -16 | -1235 -500 -7108 | -1299 233 -8150 | -1377 43 -894 | -2868 -381 -1115 | -1345 399 -701 | -1673 106 -1378 | -2580 -626 * | -2843 -466 | -2054 -720 | 1555 275 | -1995 394 | -1468 45 | -1921 96 | -715 359 | -888 117 | -1871 -369 | -3064 -294 | -2630 -249 | 235 |
| 230(E) | -509 -149 -16 | -1046 -500 -7108 | -884 233 -8150 | 1564 43 -894 | -1116 -381 -1115 | -1669 399 -701 | -441 106 -1378 | -485 -626 * | 250 -466 | -206 -720 | -577 275 | 689 394 | -200 45 | -656 96 | -670 359 | -459 117 | 1290 -369 | -1467 -294 | -995 -249 | 236 |

TABLE 6-continued

```
HMMER2.0 [2.2g]                                                      Program name and version
NAME  dhad_for_hmm                                                   Name of the input sequence alignment file
LENG  564                                                            Length of the alignment: include indels
ALPH  Amino                                                          Type of residues
MAP   yes                                                            Map of the match states to the columns of the alignment
COM   /app/public/hmmer/current/bin/hmmbuild -F dhad-exp_hmm dhad_for_hmm.aln   Commands used to generate the file: this one means that hmmbuild (default patrameters) was applied to the alignment file
COM   /app/public/hmmer/current/bin/hmmcalibrate dhad-exp_hmm        Commands used to generate the file: this one means that hmmcalibrate (default parameters) was applied to the hmm profile
NSEQ  8                                                              Number of sequences in the alignment file
DATE  Tue Jun 3 10:48:24 2008                                        When was the file generated
XT    -8455 -4 -1000 -1000 -8455 -4 -8455 -4
NULT  -4 -8455                                                       The transition probability distribution for the null model (single G state).
NULE  595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                                   probability used to convert these back to model probabilities is 1/K.
EVD   -499.650970 0.086142                                           The extreme value distribution parameters μ and lambda respectively; both floating point values. Lambda is positive and
                                                                     nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 231(D) | -1203 -149 -16 | -2412 -500 -7108 | 2595 233 -8150 | -117 43 -894 | -3286 -381 -1115 | -1536 399 -701 | -1057 106 -1378 | -3176 -626 * | -3186 -466 | -2436 -720 | -428 275 | -2068 394 | -736 45 | -1824 96 | 2377 359 | -1366 117 | -2578 -369 | -3334 -294 | -2552 -249 | 237 |
| 232(Q) | 954 -149 -16 | -1983 -500 -7108 | -100 233 -8150 | 971 43 -894 | -2337 -381 -1115 | 177 399 -701 | -267 106 -1378 | -2067 -626 * | -2060 -466 | -1189 -720 | -125 275 | -1637 394 | 2600 45 | -418 96 | -514 359 | -597 117 | -1649 -369 | -2268 -294 | -1597 -249 | 238 |
| 233(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -4016 -466 | -3555 -720 | -1531 275 | -2959 394 | -1842 45 | -2560 96 | -2479 359 | -2750 117 | -3722 -369 | -3563 -294 | -3385 -249 | 239 |
| 234(K) | -2620 -149 -16 | -2961 -500 -7108 | -2461 233 -8150 | -2046 43 -894 | -3743 -381 -1115 | -2791 399 -701 | -1570 106 -1378 | -3603 -626 * | -3387 -466 | -2839 -720 | -2048 275 | -3039 394 | -1260 45 | -465 96 | -2604 359 | -2536 117 | -3331 -369 | -3001 -294 | -2988 -249 | 240 |
| 235(R) | 377 -149 -16 | -1802 -500 -7108 | -415 233 -8150 | 988 43 -894 | -2095 -381 -1115 | -1474 399 -701 | -95 106 -1378 | -1786 -626 * | -1785 -466 | -911 -720 | -1351 275 | -1560 394 | 343 45 | 1551 96 | -409 359 | -431 117 | 376 -369 | -1986 -294 | -1371 -249 | 241 |
| 236(D) | 1083 -149 -16 | -1565 -500 -7108 | 2662 233 -8150 | -244 43 -894 | -1941 -381 -1115 | -1573 399 -701 | -679 106 -1378 | 612 -626 * | -1651 -466 | -980 -720 | -490 275 | -1869 394 | -358 45 | -1003 96 | -771 359 | -766 117 | -903 -369 | -2208 -294 | -1633 -249 | 242 |
| 237(E) | -1225 -149 -16 | -2868 -500 -7108 | 1894 233 -8150 | 1948 43 -894 | -3149 -381 -1115 | -1532 399 -701 | -671 106 -1378 | -2975 -626 * | -2902 -466 | -2101 -720 | -150 275 | -1935 394 | -293 45 | -1299 96 | 1884 359 | -1241 117 | -2496 -369 | -3093 -294 | -2248 -249 | 243 |
| 238(C) | 1375 -149 -16 | 3262 -500 -7108 | -2620 233 -8150 | -2108 43 -894 | -827 -381 -1115 | -1866 399 -701 | -1267 106 -1378 | 1631 -626 * | -599 -466 | -10 -720 | -1674 275 | -2137 394 | -1531 45 | -1786 96 | -1034 359 | 790 117 | 249 -369 | -1361 -294 | -1010 -249 | 244 |
| 239(E) | 635 -149 -16 | -1796 -500 -7108 | 1055 233 -8150 | 1761 43 -894 | -2018 -381 -1115 | -1464 399 -701 | -263 106 -1378 | 1191 -626 * | -1767 -466 | -946 -720 | -148 275 | -1637 394 | 135 45 | -481 96 | -520 359 | -553 117 | -1300 -369 | -2077 -294 | -1441 -249 | 245 |
| 240(E) | 593 -149 -16 | -2044 -500 -7108 | -252 233 -8150 | 2548 43 -894 | -2437 -381 -1115 | -1542 399 -701 | -329 106 -1378 | -2133 -626 * | -2120 -466 | -1274 -720 | -244 275 | -1738 394 | 89 45 | 946 96 | -646 359 | -717 117 | -1734 -369 | -2305 -294 | -1686 -249 | 246 |
| 241(S) | 1884 -149 -16 | -835 -500 -7108 | -1962 233 -8150 | -1576 43 -894 | -1634 -381 -1115 | -1436 399 -701 | -1320 106 -1378 | 1041 -626 * | -1453 -466 | -781 -720 | -1293 275 | -1922 394 | -1241 45 | -1606 96 | 1973 359 | -597 117 | -669 -369 | -2036 -294 | -1656 -249 | 247 |

TABLE 6-continued

| HMMER2.0 [2.2g] | | Program name and version |
| NAME dhad_for_hmm | | Name of the input sequence alignment file |
| LENG 564 | | Length of the alignment |
| ALPH Amino | | Type of residues |
| MAP yes | | Map of the match states to the columns of the alignment |
| COM /app/public/hmmer/current/bin/hmmbuild -F dhad-exp_hmm dhad_for_hmm.aln | | Commands used to generate the file: this one means that hmmbuild (default patrameters) was applied to the alignment file |
| COM /app/public/hmmer/current/bin/hmmcalibrate dhad-exp_hmm | | Commands used to generate the file: this one means that hmmcalibrate (default parameters) was applied to the hmm profile |
| NSEQ 8 | | Number of sequences in the alignment file |
| DATE Tue Jun 3 10:48:24 2008 | | When was the file generated |
| XT -8455 -4 -1000 -1000 -8455 -4 -8455 -4 | | |
| NULT -4 -8455 | | |
| NULE 595 -1558 85 338 -294 453 -1158 197 249 902 -1085 -142 -21 -313 45 531 201 384 -1998 -644 | | The transition probability distribution for the null model (single G state). The symbol emission probability distribution for the null model (G state); consists of K (e.g 4 or 20) integers. The null probability used to convert these back to model probabilities is 1/K. |
| EVD -499.650970 0.086142 | | The extreme value distribution parameters μ and lambda respectively; both floating point values. Lambda is positive and nonzero. These values are set when the model is calibrated with hmmcalibrate. |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| | 2267 -149 -16 | -1043 -500 -7108 | -2388 233 -8150 | -2526 43 -894 | -3253 -381 -1115 | 2642 399 -701 | -2373 106 -1378 | -2975 -626 * | -3260 -466 | -2410 -720 | -1722 275 | -2033 394 | -2311 45 | -2648 96 | -663 359 | -860 117 | -2005 -369 | -3436 -294 | -3250 -249 | |
| 242(G) | | | | | | | | | | | | | | | | | | | | 248 |
| | -876 -149 -16 | -2087 -500 -7108 | -829 233 -8150 | 1490 43 -894 | -2474 -381 -1115 | -1766 399 -701 | -229 105 -1378 | -2106 -626 * | -44 -466 | -1198 -720 | -424 275 | -1829 394 | 205 45 | 2225 96 | -775 359 | -768 117 | -1753 -369 | -2143 -294 | -1647 -249 | |
| 243(R) | | | | | | | | | | | | | | | | | | | | 249 |
| | 2339 -149 -16 | -967 -500 -7108 | -2970 233 -8150 | -2766 43 -894 | -1878 -381 -1115 | -1847 399 -701 | -2252 106 -1378 | 32 -626 * | -1299 -466 | -918 -720 | -2087 275 | -2399 394 | -2316 45 | -2545 96 | -1157 359 | -971 117 | 2345 -369 | -2605 -294 | -2251 -249 | |
| 244(V) | | | | | | | | | | | | | | | | | | | | 250 |
| | -1827 -149 -16 | -1398 -500 -7108 | -4307 233 -8150 | -3831 43 -894 | -1099 -381 -1115 | -3939 399 -701 | -3142 106 -1378 | 2286 -626 * | 1835 -466 | 69 -720 | -3579 275 | -3671 394 | -3177 45 | -3511 96 | -3178 359 | -1781 117 | 1918 -369 | -2524 -294 | -2310 -249 | |
| 245(I) | | | | | | | | | | | | | | | | | | | | 251 |
| | -1178 -149 -16 | -1448 -500 -7108 | -1943 233 -8150 | -1452 43 -894 | -1776 -381 -1115 | -2261 399 -701 | -1140 106 -1378 | -227 -626 * | -1260 -466 | -816 -720 | -1444 275 | -2448 394 | -902 45 | -540 96 | -1496 359 | -1176 117 | 2697 -369 | -2161 -294 | -1764 -249 | |
| 246(V) | | | | | | | | | | | | | | | | | | | | 252 |
| | -508 -149 -16 | -1976 -500 -7108 | 840 233 -8150 | 1547 43 -894 | -2280 -381 -1115 | -1393 399 -701 | -117 106 -1378 | -2029 -626 * | -1981 -466 | -1077 -720 | 1158 275 | -1531 394 | 330 45 | -2531 96 | -3781 359 | -4541 117 | 2621 -369 | -2161 -294 | -1471 -249 | |
| 247(E) | | | | | | | | | | | | | | | | | | | | 253 |
| | 1703 -149 -16 | -991 -500 -7108 | -2901 233 -8150 | -2342 43 -894 | -528 -381 -1115 | -2567 399 701 | -1550 106 -1378 | 166 -626 * | 1544 -466 | 2668 -720 | -2104 275 | -2591 394 | -1715 45 | -2010 96 | -1685 359 | -1052 117 | -12 -369 | -1442 -294 | -1177 -249 | |
| 248(M) | | | | | | | | | | | | | | | | | | | | 254 |
| | -1947 -149 -16 | -1516 -500 -7108 | -4385 233 -8150 | -3885 43 -894 | -916 -381 -1115 | -4013 399 -701 | -3118 106 -1378 | 2193 -626 * | 2186 -466 | 257 -720 | -3656 275 | -3687 394 | -3109 45 | -3494 96 | -3250 359 | -1889 117 | 1383 -369 | -2397 -294 | -2258 -249 | |
| 249(I) | | | | | | | | | | | | | | | | | | | | 255 |
| | -1322 -149 -16 | -2647 -500 -7108 | -272 233 -8150 | 2491 43 -894 | -3071 -381 -1115 | -1811 399 -701 | -576 106 -1378 | -2759 -626 * | -2633 -466 | -1854 -720 | -464 275 | -2066 394 | -175 45 | -177 96 | -1144 359 | -1256 117 | -2368 -369 | -2692 -294 | -2140 -249 | |
| 250(E) | | | | | | | | | | | | | | | | | | | | 256 |
| | -1395 -149 -16 | -2059 -500 -7108 | -1711 233 -8150 | -1014 43 -894 | -2215 -381 -1115 | -2218 399 -701 | -641 106 -1378 | -1709 -626 * | -1652 -466 | 2578 -720 | -1075 275 | -2303 394 | -282 45 | 287 96 | -1423 359 | -1283 117 | -1603 -369 | -2159 -294 | -1803 -249 | |
| 251(K) | | | | | | | | | | | | | | | | | | | | 257 |
| | -1285 -149 -16 | -2888 -500 -7108 | 2677 233 -8150 | 176 43 -894 | -3210 -381 -1115 | 1189 399 -701 | -737 106 -1378 | -3047 -626 * | -2977 -466 | -2195 -720 | -190 275 | -1979 394 | 2106 45 | -1379 96 | -1050 359 | -1315 117 | -2564 -369 | -3161 -294 | -2320 -249 | |
| 252(D) | | | | | | | | | | | | | | | | | | | | 258 |

TABLE 6-continued

| | | | | | | | | | | | | | | | | | | | | | | | |
|---|---|---|---|---|---|---|---|---|---|---|---|---|---|---|---|---|---|---|---|---|---|---|---|
| HMMER2.0 [2.2g] | | | | | | | | | | | Program name and version | | | | | | | | | | | | |
| NAME dhad_for_hmm | | | | | | | | | | | Name of the input sequence alignment file | | | | | | | | | | | | |
| LENG 564 | | | | | | | | | | | Length of the alignment | | | | | | | | | | | | |
| ALPH Amino | | | | | | | | | | | Type of residues | | | | | | | | | | | | |
| MAP yes | | | | | | | | | | | Map of the match states to the columns of the alignment | | | | | | | | | | | | |
| COM /app/public/hmmer/current/bin/hmmbuild -F dhad-exp_hmm dhad_for_hmm.aln | | | | | | | | | | | Commands used to generate the file: this one means that hmmbuild (default patrameters) was applied to the alignment file | | | | | | | | | | | | |
| COM /app/public/hmmer/current/bin/hmmcalibrate dhad-exp_hmm | | | | | | | | | | | Commands used to generate the file: this one means that hmmcalibrate (default parametrs) was applied to the hmm profile | | | | | | | | | | | | |
| NSEQ 8 | | | | | | | | | | | Number of sequences in the alignment file | | | | | | | | | | | | |
| DATE Tue Jun 3 10:48:24 2008 | | | | | | | | | | | When was the file generated | | | | | | | | | | | | |
| XT -8455 -4 -1000 -1000 -8455 -4 -8455 -4 | | | | | | | | | | | | | | | | | | | | | | | |
| NULT -4 -8455 | | | | | | | | | | | The transition probability distribution for the null model (single G state). | | | | | | | | | | | | |
| NULE 595 -1558 85 338 -294 453 -1158 197 249 902 -1085 -142 -21 -313 45 531 | | | | | | | | | | | The symbol emission probability distribution for the null model (G state); consists of K (e.g 4 or 20) integers. The null | | | | | | | | | | | | |
| 201 384 -1998 -644 | | | | | | | | | | | probability used to convert these back to model probabilities is 1/K. | | | | | | | | | | | | |
| EVD -499.650970 0.086142 | | | | | | | | | | | The extreme value distribution parameters μ and lambda respectively; both floating point values. Lambda is positive and nonzero. These values are set when the model is calibrated with hmmcalibrate. | | | | | | | | | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 253(I) | -2073 -149 -16 | -1632 -500 -7108 | -4434 233 -8150 | -3975 43 -894 | -911 -381 -1115 | -4130 399 -701 | -3238 106 -1378 | 3164 -626 * | 1451 -456 | 244 -720 | -3779 275 | -3785 394 | -3187 45 | -3557 96 | -3413 359 | -2021 117 | 546 -369 | -2449 -294 | -2273 -249 | 259 |
| 254(K) | -1570 -149 -16 | -2144 -500 -7108 | -1887 233 -8150 | -1191 43 -894 | -2098 -381 -1115 | -2363 399 -701 | -750 106 -1378 | -1603 -626 * | 938 -466 | -1112 -720 | -1231 275 | -2436 394 | -408 45 | 215 96 | -1616 359 | -1443 117 | -1580 -369 | -2166 -294 | -1804 -249 | 260 |
| 255(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 261 |
| 256(R) | -928 -149 -16 | -1705 -500 -7108 | -1507 233 -8150 | -1055 43 -894 | -2761 -381 -1115 | -1730 399 -701 | -896 106 -1378 | -2490 -626 * | -2489 -466 | -1723 -720 | -1042 275 | -2102 394 | -543 45 | 2614 96 | 2258 359 | -1053 117 | -1998 -369 | -2546 -294 | -2158 -249 | 262 |
| 257(D) | -1280 -149 -16 | -2865 -500 -7108 | 3154 233 -8150 | 175 43 -894 | -3194 -381 -1115 | -1547 399 -701 | -743 106 -1378 | -3034 -626 * | -2971 -466 | -2194 -720 | -190 275 | -1979 394 | 1342 45 | -1391 96 | 553 359 | -1316 117 | -2552 -369 | -3161 -294 | -2317 -249 | 263 |
| 258(I) | -1997 -149 -16 | -1562 -500 -7108 | -4355 233 -8150 | -3927 43 -894 | -1042 -381 -1115 | -4066 399 -701 | -3261 106 -1378 | 3343 -626 * | 937 -466 | 97 -720 | -3718 275 | -3783 394 | -3239 45 | -3555 96 | -3364 359 | -1959 117 | 702 -369 | -2549 -294 | -2295 -249 | 264 |
| 259(M) | -2252 -149 -16 | -1821 -500 -7108 | -4572 233 -8150 | -3991 43 -894 | -530 -381 -1115 | -4164 399 -701 | -2990 106 -1378 | 2068 -626 * | 1993 -466 | 3197 -720 | -3808 275 | -3685 394 | -2916 45 | -3406 96 | -3378 359 | -2149 117 | -172 -369 | -2084 -294 | -2091 -249 | 265 |
| 260(T) | -1213 -149 -16 | -1674 -500 -7108 | -2755 233 -8150 | -2906 43 -894 | -3163 -381 -1115 | -1922 399 -701 | -2659 106 -1378 | -2698 -626 * | -3105 -466 | -2612 -720 | -2311 275 | -2600 394 | -2708 45 | -2753 96 | -1463 359 | 3819 117 | -2197 -369 | -3286 -294 | -3156 -249 | 266 |
| 261(R) | -2131 -149 -16 | -2786 -500 -7108 | -2704 233 -8150 | -1460 43 -894 | -3618 -381 -1115 | -2638 399 -701 | -587 106 -1378 | -2976 -626 * | -2645 -465 | -1985 -720 | -1353 275 | -2603 394 | -173 45 | 3492 96 | -2020 359 | -1828 117 | -2748 -369 | -2484 -294 | -2384 -249 | 267 |
| 262(K) | -1349 -149 -16 | -2635 -500 -7108 | -381 233 -8150 | 2083 43 -894 | -3083 -381 -1115 | -1857 399 -701 | -565 106 -1378 | -2750 -626 * | -2612 -466 | -1837 -720 | -514 275 | -2090 394 | -161 45 | -61 96 | -1178 359 | -1271 117 | -2369 -369 | -2655 -294 | -2138 -249 | 268 |
| 263(A) | 2821 -149 -16 | -932 -500 -7108 | -2451 233 -8150 | -2472 43 -894 | -3065 -381 -1115 | -1198 399 -701 | -2233 106 -1378 | -2763 -626 * | -3056 -466 | -2201 -720 | -1633 275 | -1940 394 | -2147 45 | -2468 96 | 1831 359 | -730 117 | -1840 -369 | -3305 -294 | -3055 -249 | 269 |

TABLE 6-continued

```
HMMER2.0 [2.2g]                                          Program name and version
NAME  dhad_for_hmm                                       Name of the input sequence alignment file
LENG  564                                                Length of the alignment
ALPH  Amino                                              Type of residues
MAP   yes                                                Map of the match states to the columns of the alignment
COM   /app/public/hmmer/current/bin/hmmbuild -F dhad-exp_hmm dhad_for_hmm.aln   Commands used to generate the file: this one means that hmmbuild (default parameters) was applied to the alignment file
COM   /app/public/hmmer/current/bin/hmmcalibrate dhad-exp_hmm                   Commands used to generate the file: this one means that hmmcalibrate (default parameters) was applied to the hmm profile
NSEQ  8                                                  Number of sequences in the alignment file
DATE  Tue Jun 3 10:48:24 2008                            When was the file generated
XT    -8455 -4 -1000 -1000 -8455 -4 -8455 -4
NULT  -4 -8455                                           The transition probability distribution for the null model (single G state).
NULE  595 -1558 85 338 -294 453 -1158 197 249 902 -1085 -142 -21 -313 45 531    The symbol emission probability distribution for the null model (G state); consists of K (e.g. 4 or 20) integers. The null
201 384 -1998 -644                                       probability used to convert these back to model probabilities is 1/K.
EVD   -499.650970 0.086142                               The extreme value distribution parameters μ and lambda respectively; both floating point values. Lambda is positive and
                                                         nonzero. These values are set when the model is calibrated with hmmcalibrate.
```

| HMM | A m->m m->i m->d -> | C m->i m->d m->d | D m->d | E i->m i->i i->d | F i->i | G d->m d->i d->d | H d->d | I b->m | L | M | N | P | Q | R | S | T | V | W | Y | Position in alignment |
|---|---|---|---|---|---|---|---|---|---|---|---|---|---|---|---|---|---|---|---|---|
| 264(F) | -2063 -149 -16 | -1686 -500 -7108 | -4037 233 -8150 | -3677 43 -894 | 3437 -381 -1115 | -3644 399 -701 | -1706 106 -1378 | 2063 -626 * | 135 -466 | 67 -720 | -3095 275 | -3486 394 | -2739 45 | -3127 96 | -2876 359 | -2012 117 | -83 -369 | -1038 -294 | -158 -249 | 270 |
| 265(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -4016 -466 | -3555 -720 | -1531 275 | -2959 394 | -1842 45 | -2560 96 | -2479 359 | -2750 117 | -3722 -369 | -3563 -294 | -3385 -249 | 271 |
| 266(N) | -1662 -149 -16 | -3306 -500 -7108 | 2055 233 -8150 | 78 43 -894 | -3621 -381 -1115 | -1643 399 -701 | -1040 106 -1378 | -3622 -626 * | -3531 -466 | -2870 -720 | 3477 275 | -2182 394 | -724 45 | -2071 96 | -1371 359 | -1757 117 | -3092 -369 | -3633 -294 | -2700 -249 | 272 |
| 267(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3257 -466 | -2662 -720 | -2236 275 | -2447 394 | -2798 45 | -2944 96 | -1216 359 | -1387 117 | -2183 -369 | -3405 -294 | -3320 -249 | 273 |
| 268(I) | -1760 -149 -16 | -1307 -500 -7108 | -4325 233 -8150 | -3962 43 -894 | -1735 -381 -1115 | -4042 399 -701 | -3726 106 -1378 | 3135 -626 * | -579 -466 | -515 -720 | -3722 275 | -3869 394 | -3673 45 | -3896 96 | -3359 359 | -1752 117 | 2276 -369 | -3240 -294 | -2806 -249 | 274 |
| 269(T) | 1428 -149 -16 | -904 -500 -7108 | -2334 233 -8150 | -2158 43 -894 | -2747 -381 -1115 | -1206 399 -701 | -1940 106 -1378 | -2392 -626 * | -2678 -466 | -1846 -720 | -1504 275 | -1896 394 | -1809 45 | -2163 96 | 902 359 | 3001 117 | -1635 -369 | -2999 -294 | -2705 -249 | 275 |
| 270(V) | -1745 -149 -16 | -1300 -500 -7108 | -4286 233 -8150 | -3858 43 -894 | -1446 -381 -1115 | -3967 399 -701 | -3370 106 -1378 | 2358 -626 * | 852 -466 | -261 -720 | -3606 275 | -3749 394 | -3403 45 | -3673 96 | -3232 359 | -1717 117 | 2643 -369 | -2856 -294 | -2524 -249 | 276 |
| 271(V) | -1404 -149 -16 | -1072 -500 -7108 | -3766 233 -8150 | -3305 43 -894 | -1464 -381 -1115 | -3356 399 -701 | -2696 106 -1378 | 2276 -626 * | -616 -466 | -379 -720 | -3001 275 | -3325 394 | -2870 45 | -3091 96 | -2563 359 | 1344 117 | 2521 -369 | -2516 -294 | -2113 -249 | 277 |
| 272(M) | 866 -149 -16 | -1113 -500 -7108 | -2656 233 -8150 | -2412 43 -894 | -1322 -381 -1115 | -1920 399 -701 | -1883 106 -1378 | -487 -626 * | -587 -466 | 4451 -720 | -1950 275 | -2387 394 | -1928 45 | -2078 96 | -1220 359 | -1053 117 | -498 -369 | -2134 -294 | -1803 -249 | 278 |
| 273(A) | 2601 -149 -16 | -957 -500 -7108 | -2898 233 -8150 | -2711 43 -894 | -1943 -381 -1115 | -1740 399 -701 | -2211 106 -1378 | -165 -626 * | -1406 -466 | -1001 -720 | -2008 275 | -2320 394 | -2260 45 | -2494 96 | -1053 359 | -929 117 | 1990 -369 | -2626 -294 | -2279 -249 | 279 |
| 274(L) | -1171 -149 -16 | -983 -500 -7108 | -3266 233 -8150 | -2733 43 -894 | -796 -381 -1115 | -2795 399 -701 | -1888 106 -1378 | 590 -626 * | 2001 -466 | 198 -720 | -2418 275 | -2816 394 | -2106 45 | -2362 96 | -1944 359 | 965 117 | 1777 -369 | -1724 -294 | -1426 -249 | 280 |

TABLE 6-continued

```
HMMER2.0 [2.2g]                                                          Program name and version
NAME  dhad_for_hmm                                                       Name of the input sequence alignment file
LENG  564                                                                Length of the alignment
ALPH  Amino                                                              Type of residues
MAP   yes                                                                Map of the match states to the columns of the alignment
COM   /app/public/hmmer/current/bin/hmmbuild -F dhad-exp_hmm dhad_for_hmm.aln   Commands used to generate the file: this one means that hmmbuild (default patrameters) was applied to the alignment file
COM   /app/public/hmmer/current/bin/hmmcalibrate dhad-exp_hmm             Commands used to generate the file: this one means that hmmcalibrale (default parametrs) was applied to the hmm profile
NSEQ  8                                                                  Number of sequences in the alignment file
DATE  Tue Jun 3 10:48:24 2008                                            When was the file generated
XT    -8455 -4 -1000 -1000 -8455 -4 -8455 -4
NULT  -4 -8455                                                           The transition probability distribution for the null model (single G state).
NULE  595 -1558 85 338 -294 453 -1158 197 249 902 -1085 -142 -21 -313 45 531    The symbol emission probability distribution for the null model (G state); consists of K (e.g 4 or 20) integers. The null
201 384 -1998 -644                                                               probability used to convert these back to model probabilities is 1/K.
EVD   -499.650970 0.086142                                               The extreme value distribution parameters μ and lambda respectively; both floating point values. Lambda is positive and
                                                                         nonzero. These values are set when the model is calibrated with hmmcalibrate.
```

| HMM | A<br>m->m | C<br>m->i | D<br>m->d | E<br>i->m | F<br>i->i | G<br>d->m | H<br>d->d | I<br>b->m | L | M | N | P | Q | R | S | T | V | W | Y | Position in alignment |
|---|---|---|---|---|---|---|---|---|---|---|---|---|---|---|---|---|---|---|---|---|
| 275(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 281 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 276(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 282 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 277(S) | -897 | -1462 | -2333 | -2543 | -3185 | -1640 | -2474 | -3294 | -3497 | -2780 | -1973 | -2360 | -2483 | -2703 | 3465 | -1316 | -2413 | -3310 | -3025 | 283 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 278(T) | -1213 | -1674 | -2755 | -2906 | -3163 | -1922 | -2659 | -2698 | -3105 | -2612 | -2311 | -2600 | -2708 | -2753 | -1463 | 3819 | -2197 | -3286 | -3156 | 284 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 279(N) | -2171 | -2655 | -1458 | -1748 | -3334 | -2364 | -2267 | -3943 | -3936 | -3437 | 4205 | -2932 | -2205 | -2608 | -2224 | -2439 | -3392 | -3253 | -2909 | 285 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 280(A) | 3134 | -934 | -2491 | -2567 | -3083 | -1203 | -2300 | -2766 | -3082 | -2237 | -1672 | -1954 | -2240 | -2537 | 874 | -747 | -1844 | -3333 | -3093 | 286 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 281(V) | -984 | -1045 | -3169 | -2909 | -1709 | -2304 | -2404 | 531 | -988 | -697 | -2378 | -2722 | -2480 | -2661 | -1601 | 1504 | 3014 | -2588 | -2201 | 287 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 282(L) | -2631 | -2159 | -4786 | -4228 | -462 | -4506 | -3231 | 96 | 2828 | 2482 | -4157 | -3880 | -3016 | -3541 | -3793 | -2509 | -608 | -2134 | -2182 | 288 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 283(H) | -3205 | -3079 | -2723 | -2890 | -2110 | -3046 | 5295 | -4135 | -3813 | -3561 | -2886 | -3482 | -2833 | -2620 | -3291 | -3356 | -3895 | -2397 | -1681 | 289 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 284(L) | -1623 | -1338 | -3726 | -3164 | -251 | -3255 | -1820 | 1373 | 2371 | 514 | -2785 | -3086 | -2281 | -2613 | -2389 | -1543 | -161 | -1311 | 1782 | 290 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | 701 | -1378 | * |  |  |  |  |  |  |  |  |  |  |  |  |
| 285(L) | -2333 | -1873 | -4640 | -4127 | -650 | -4326 | -3241 | 2176 | 2519 | 523 | -3982 | -3833 | -3105 | -3579 | -3604 | -2247 | 56 | -2268 | -2230 | 291 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

| | | | | | | | | | | | | | | | | | | | | | | | |
|---|---|---|---|---|---|---|---|---|---|---|---|---|---|---|---|---|---|---|---|---|---|---|---|

HMMER2.0 [2.2g]    Program name and version
NAME dhad_for_hmm    Name of the input sequence alignment file
LENG 564    Length of the alignment
ALPH Amino    Type of residues
MAP yes    Map of the match states to the columns of the alignment
COM /app/public/hmmer/current/bin/hmmbuild -F dhad-exp_hmm dhad_for_hmm.aln    Commands used to generate the file: this one means that hmmbuild (default parameters) was applied to the alignment file
COM /app/public/hmmer/current/bin/hmmcalibrate dhad-exp_hmm    Commands used to generate the file: this one means that hmmcalibrate (default parameters) was applied to the hmm profile
NSEQ 8    Number of sequences in the alignment file
DATE Tue Jun 3 10:48:24 2008    When was the file generated
XT -8455 -4 -1000 -1000 -8455 -4 -8455 -4
NULT -4 -8455    The transition probability distribution for the null model (single G state).
NULE 595 -1558 85 338 -294 453 -1158 197 249 902 -1085 -142 -21 -313 45 531    The symbol emission probability distribution for the null model (G state); consists of K (e.g 4 or 20) integers. The null
201 384 -1998 -644    probability used to convert these back to model probabilities is 1/K.
EVD -499.650970 0.086142    The extreme value distribution parameters μ and lambda respectively; both floating point values. Lambda is positive and nonzero. These values are set when the model is calibrated with hmmcalibrate.

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 286(A) | 3438 | -1472 | -2846 | -3040 | -3287 | -1726 | -2735 | -2840 | -3257 | -2662 | -2236 | -2447 | -2798 | -2944 | -1216 | -1387 | -2183 | -3405 | -3320 | 292 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 287(M) | -1886 | -1507 | -4178 | -3693 | -877 | -3806 | -2901 | 3008 | 335 | 3109 | -3451 | -3570 | -2934 | -3251 | -3044 | -1840 | 524 | -2288 | -2089 | 293 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 288(A) | 3438 | -1472 | -2846 | -3040 | -3287 | -1726 | -2735 | -2840 | -3257 | -2662 | -2236 | -2447 | -2798 | -2944 | -1216 | -1387 | -2183 | -3405 | -3320 | 294 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 289(H) | -1490 | -2484 | -362 | -476 | -1816 | -1880 | 4320 | -2854 | -2770 | -2133 | 2185 | -2285 | -728 | -1000 | -1377 | -1550 | -2475 | -2146 | -1255 | 295 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 290(A) | 2439 | -911 | -2326 | -2131 | -2811 | -1197 | -1934 | -2480 | -2745 | -1898 | -1490 | -1888 | -1785 | -2153 | 1898 | 1073 | -1682 | -3044 | -2749 | 296 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 291(I) | 2038 | -985 | -3388 | -2919 | -1320 | -2893 | -2277 | 2155 | -587 | -297 | -2593 | -2992 | -2450 | -2697 | -2087 | -1208 | 1681 | -2229 | -1846 | 297 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 292(G) | -1243 | -2769 | 311 | 1902 | -3172 | 1980 | -744 | -2992 | -2936 | -2152 | 1923 | -1974 | -377 | -1331 | -1030 | -1284 | -2506 | -3125 | -2308 | 298 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 293(V) | -1738 | -1298 | -4281 | -3921 | -1737 | -3979 | -3665 | 1917 | -601 | -528 | -3671 | -3834 | -3628 | -3843 | -3293 | -1735 | 3205 | -3215 | -2770 | 299 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 294(E) | -833 | -2344 | 1092 | 2412 | -2643 | -1464 | -386 | -2413 | -2369 | -1505 | -96 | 562 | 29 | -717 | -666 | 862 | -1966 | -2562 | -1818 | 300 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 295(W) | -1380 | -1116 | -3614 | -3026 | 1322 | -2981 | -1582 | 1956 | 1775 | 556 | -2562 | -2865 | -2117 | -2424 | -2098 | -1302 | -187 | 2908 | -629 | 301 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 296(T) | -350 | -973 | -2204 | -2178 | -2893 | -1236 | -2035 | -2561 | -2862 | -2043 | -1536 | -1946 | -1916 | -2214 | 1618 | 3198 | -1758 | -3137 | -2831 | 302 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |

TABLE 6-continued

| | | | | | | | | | | | | | | | | | | | | | | | | |
|---|---|---|---|---|---|---|---|---|---|---|---|---|---|---|---|---|---|---|---|---|---|---|---|---|
| HMMER2.0 [2.2g] | | | | | | | | | Program name and version | | | | | | | | | | | | | | | |
| NAME dhad_for_hmm | | | | | | | | | Name of the input sequence alignment file | | | | | | | | | | | | | | | |
| LENG 564 | | | | | | | | | Length of the alignment: include indels | | | | | | | | | | | | | | | |
| ALPH Amino | | | | | | | | | Type of residues | | | | | | | | | | | | | | | |
| MAP yes | | | | | | | | | Map of the match states to the columns of the alignment | | | | | | | | | | | | | | | |
| COM /app/public/hmmer/current/bin/hmmbuild -F dhad-exp_hmm dhad_for_hmm.aln | | | | | | | | | Commands used to generate the file: this one means that hmmbuild (default patrameters) was applied to the alignment file | | | | | | | | | | | | | | | |
| COM /app/public/hmmer/current/bin/hmmcalibrate dhad-exp_hmm | | | | | | | | | Commands used to generate the file: this one means that hmmcalibrate (default parametrs) was applied to the hmm profile | | | | | | | | | | | | | | | |
| NSEQ 8 | | | | | | | | | Number of sequences in the alignment file | | | | | | | | | | | | | | | |
| DATE Tue Jun 3 10:48:24 2008 | | | | | | | | | When was the file generated | | | | | | | | | | | | | | | |
| XT -8455 -4 -1000 -1000 -8455 -4 -8455 -4 | | | | | | | | | | | | | | | | | | | | | | | | |
| NULT -4 -8455 | | | | | | | | | The transition probability distribution for the null model (single G state). | | | | | | | | | | | | | | | |
| NULE 595 -1558 85 338 -294 453 -1158 197 249 902 -1085 -142 -21 -313 45 531 201 384 -1998 -644 | | | | | | | | | The symbol emission probability distribution for the null model (G state); consists of K (e.g 4 or 20) integers. The null probability used to convert these back to model probabilities is 1/K. | | | | | | | | | | | | | | | |
| EVD -499.650970 0.086142 | | | | | | | | | The extreme value distribution parameters μ and lambda respectively; both floating point values. Lambda is positive and nonzero. These values are set when the model is calibrated with hmmcalibrate. | | | | | | | | | | | | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 297(L) | -1443 -149 -16 | -1269 -500 -7108 | -3144 233 -8150 | -2576 43 -894 | -528 -381 -1115 | -3014 399 -701 | -1816 106 -1378 | 1945 -626 * | 2102 -466 | 508 -720 | -2422 275 | -2899 394 | 1193 45 | -2133 96 | -2129 359 | -1369 117 | -50 -369 | -1616 -294 | -1384 -249 | 303 |
| 298(D) | -1826 -149 -16 | -3682 -500 -7108 | 3559 233 -8150 | 1199 43 -894 | -3883 -381 -1115 | -1662 399 -701 | -1073 106 -1378 | -3846 -626 * | -3720 -466 | -3110 -720 | -272 275 | -2222 394 | -760 45 | -2283 96 | -1471 359 | -1913 117 | -3321 -369 | -3864 -294 | -2864 -249 | 304 |
| 299(D) | -2784 -149 -16 | -3432 -500 -7108 | 4016 233 -8150 | -1200 43 -894 | -4140 -381 -1115 | -2466 399 -701 | -2197 106 -1378 | -4505 -626 * | -4365 -466 | -3956 -720 | -1551 275 | -3014 394 | -2039 45 | -3232 96 | -2593 359 | -2938 117 | -4046 -369 | -3710 -294 | -3552 -249 | 305 |
| 300(F) | -3342 -149 -16 | -2776 -500 -7108 | -4026 233 -8150 | -4232 43 -894 | 4354 -381 -1115 | -3545 399 -701 | -1431 106 -1378 | -2315 -626 * | -1801 -466 | -1900 -720 | -3299 275 | -3780 394 | -3350 45 | -3645 96 | -3490 359 | -3420 117 | -2566 -369 | -739 -294 | 349 -249 | 306 |
| 301(Q) | -1048 -149 -16 | -2608 -500 -7108 | 205 233 -8150 | 2170 43 -894 | -2893 -381 -1115 | -1535 399 -701 | -505 106 -1378 | -2680 -626 * | -2604 -466 | -1769 -720 | 1814 275 | -1849 394 | 2272 45 | -789 96 | -848 359 | -1028 117 | -2228 -369 | -2770 -294 | -2013 -249 | 307 |
| 302(R) | 1083 -149 -16 | -1687 -500 -7108 | 691 233 -8150 | 135 43 -894 | -2058 -381 -1115 | -1406 399 -701 | -178 106 -1378 | -1755 -626 * | -1793 -466 | -924 -720 | -145 275 | -1553 394 | 247 45 | 1670 96 | -383 359 | 1217 117 | -1367 -369 | -2031 -294 | -1404 -249 | 308 |
| 303(I) | -1915 -149 -16 | -1536 -500 -7108 | -4077 233 -8150 | -3667 43 -894 | 2027 -381 -1115 | -3678 399 -701 | -2155 106 -1378 | 3137 -626 * | 144 -466 | 94 -720 | -3225 275 | -3506 394 | -2848 45 | -3202 96 | -2914 359 | -1871 117 | 345 -369 | -1522 -294 | -791 -249 | 309 |
| 304(R) | -689 -149 -16 | -2015 -500 -7108 | -494 233 -8150 | 24 43 -894 | -2395 -381 -1115 | -1582 399 -701 | -184 106 -1378 | -2087 -626 * | -2020 -466 | -1151 -720 | 1161 275 | -1687 394 | 1832 45 | 2131 96 | 626 359 | -614 117 | -1684 -369 | -2156 -294 | -1573 -249 | 310 |
| 305(D) | 387 -149 -16 | -1967 -500 -7108 | 1600 233 -8150 | 1359 43 -894 | -2275 -381 -1115 | -1391 399 -701 | 1561 106 -1378 | -2025 -626 * | -1976 -466 | -1067 -720 | -25 275 | -1525 394 | 342 45 | 1024 96 | -369 359 | -443 117 | -1584 -369 | -2152 -294 | -1462 -249 | 311 |
| 306(R) | -1460 -149 -16 | -2315 -500 -7108 | -1793 233 -8150 | -887 43 -894 | -2832 -381 -1115 | -2237 399 -701 | -431 106 -1378 | -2288 -626 * | -2199 -466 | -1473 -720 | -946 275 | -2245 394 | -20 45 | 2706 96 | -1394 359 | -1275 117 | 591 -369 | -2248 -294 | -1961 -249 | 312 |
| 307(V) | -941 -149 -16 | -1027 -500 -7108 | -3099 233 -8150 | -2832 43 -894 | -1692 -381 -1115 | -2234 399 -701 | -2324 106 -1378 | 470 -626 * | -1001 -466 | -695 -720 | -2305 275 | -2663 394 | -2399 45 | -2587 96 | -1527 359 | 1858 117 | 2876 -369 | -2536 -294 | -2152 -249 | 313 |

TABLE 6-continued

| | | | | | | | | | | | | | | | | | | | | | | | | |
|---|---|---|---|---|---|---|---|---|---|---|---|---|---|---|---|---|---|---|---|---|---|---|---|---|
| HMMER2.0 [2.2g] | | | | | | | | | Program name and version | | | | | | | | | | | | | | | |
| NAME dhad_for_hmm | | | | | | | | | Name of the input sequence alignment file | | | | | | | | | | | | | | | |
| LENG 564 | | | | | | | | | Length of the alignment | | | | | | | | | | | | | | | |
| ALPH Amino | | | | | | | | | Type of residues | | | | | | | | | | | | | | | |
| MAP yes | | | | | | | | | Map of the match states to the columns of the alignment | | | | | | | | | | | | | | | |
| COM /app/public/hmmer/current/bin/hmmbuild -F dhad-exp_hmm dhad_for_hmm.aln | | | | | | | | | Commands used to generate the file: this one means that hmmbuild (default parameters) was applied to the alignment file | | | | | | | | | | | | | | | |
| COM /app/public/hmmer/current/bin/hmmcalibrate dhad-exp_hmm | | | | | | | | | Commands used to generate the file: this one means that hmmcalibrate (default parameters) was applied to the hmm profile | | | | | | | | | | | | | | | |
| NSEQ 8 | | | | | | | | | Number of sequences in the alignment file | | | | | | | | | | | | | | | |
| DATE Tue Jun 3 10:48:24 2008 | | | | | | | | | When was the file generated | | | | | | | | | | | | | | | |
| XT -8455 -4 -1000 -1000 -8455 -4 -8455 -4 | | | | | | | | | | | | | | | | | | | | | | | | |
| NULT -4 -8455 | | | | | | | | | The transition probability distribution for the null model (single G state). | | | | | | | | | | | | | | | |
| NULE 595 -1558 85 338 -294 453 -1158 197 249 902 -1085 -142 -21 -313 45 531 201 384 -1998 -644 | | | | | | | | | The symbol emission probability distribution for the null model (G state); consists of K (e.g 4 or 20) integers. The null probability used to convert these back to model probabilities is 1/K. | | | | | | | | | | | | | | | |
| EVD -499.650970 0.086142 | | | | | | | | | The extreme value distribution parameters μ and lambda respectively; both floating point values. Lambda is positive and nonzero. These values are set when the model is calibrated with hmmcalibrate. | | | | | | | | | | | | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 308(P) | -2931 -149 -16 | -2878 -500 -7108 | -3420 233 -6150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 314 |
| 309(V) | -1090 -149 -16 | -1215 -500 -7108 | -2097 233 -8150 | -1824 43 -894 | -819 -381 -1115 | -2221 399 -701 | 2699 106 -1378 | -287 -626 * | -1027 -466 | -591 -720 | -1674 275 | -2482 394 | -1446 45 | -1482 96 | -1482 359 | -1143 117 | 2879 -369 | -1420 -294 | -707 -249 | 315 |
| 310(L) | -2439 -149 -16 | -1972 -500 -7108 | -4702 233 -8150 | -4181 43 -894 | -588 -381 -1115 | -4401 399 -701 | -3258 106 -1378 | 1582 -626 * | 2757 -466 | 587 -720 | -4061 275 | -3862 394 | -3093 45 | -3590 96 | -3689 359 | -2344 117 | -130 -369 | -2230 -294 | -2217 -249 | 316 |
| 311(C) | 2157 -149 -16 | 4166 -500 -7108 | -3012 233 -8150 | -2973 43 -894 | -2780 -381 -1115 | 1022 399 -701 | -2337 106 -1378 | -2398 -626 * | -2744 -466 | -1930 -720 | -1786 275 | -1943 394 | -2372 45 | -2623 96 | -540 359 | -692 117 | -1624 -369 | -3091 -294 | -2881 -249 | 317 |
| 312(D) | -1732 -149 -16 | -3453 -500 -7108 | 3468 233 -8150 | 99 43 -894 | -3733 -381 -1115 | -1645 399 -701 | -1066 106 -1378 | -3747 -626 * | -3641 -466 | -3008 -720 | 1690 275 | -2201 394 | -755 45 | -2209 96 | -1416 359 | -1833 117 | -3208 -369 | -3752 -294 | -2776 -249 | 318 |
| 313(L) | -2477 -149 -16 | -2023 -500 -7108 | -4713 233 -8150 | -4122 43 -894 | 1592 -381 -1115 | -4329 399 -701 | -2920 106 -1378 | 72 -626 * | 2593 -466 | 2472 -720 | -3948 275 | -3754 394 | -2914 45 | -3466 96 | -3550 359 | -2350 117 | -634 -369 | -1927 -294 | -1830 -249 | 319 |
| 314(K) | -2620 -149 -16 | -2961 -500 -7108 | -2461 233 -8150 | -2046 43 -894 | -3743 -381 -1115 | -2791 399 -701 | -1570 106 -1378 | -3603 -626 * | -3387 -466 | -2839 -720 | -2048 275 | -3039 394 | -1260 45 | -465 96 | -2604 359 | -2536 117 | -3331 -369 | -3001 -294 | -2988 -249 | 320 |
| 315(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 321 |
| 316(S) | -897 -149 -16 | -1462 -500 -7108 | -2333 233 -8150 | -2543 43 -894 | -3185 -381 -1115 | -1640 394 -701 | -2474 106 -1378 | -3294 -626 * | -3497 -466 | -2780 -720 | -1973 275 | -2360 394 | -2483 45 | -2703 96 | 3465 359 | -1316 117 | -2413 -369 | -3310 -294 | -3025 -249 | 322 |
| 317(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 323 |
| 318(K) | 2 -149 -16 | -2257 -500 -7108 | -1073 233 -8150 | -374 43 -894 | -2740 -381 -1115 | -1908 399 -701 | -278 106 -1378 | -2339 -626 * | -2192 -466 | -1373 -720 | -562 275 | -1953 394 | 2273 45 | 1344 96 | -952 359 | -933 117 | -1980 -369 | -2234 -294 | -1799 -249 | 324 |

TABLE 6-continued

| | | | | | | | | | | | |
|---|---|---|---|---|---|---|---|---|---|---|---|
| HMMER2.0 [2.2g] | | | | | | Program name and version | | | | | |
| NAME dhad_for_hmm | | | | | | Name of the input sequence alignment file | | | | | |
| LENG 564 | | | | | | Length of the alignment: include indels | | | | | |
| ALPH Amino | | | | | | Type of residues | | | | | |
| MAP yes | | | | | | Map of the match states to the columns of the alignment | | | | | |
| COM /app/public/hmmer/current/bin/hmmbuild -F dhad-exp_hmm dhad_for_hmm.aln | | | | | | Commands used to generate the file: this one means that hmmbuild (default patrameters) was applied to the alignment file | | | | | |
| COM /app/public/hmmer/current/bin/hmmcalibrate dhad-exp_hmm | | | | | | Commands used to generate the file: this one means that hmmcalibrate (default parameters) was applied to the hmm profile | | | | | |
| NSEQ 8 | | | | | | Number of sequences in the alignment file | | | | | |
| DATE Tue Jun 3 10:48:24 2008 | | | | | | When was the file generated | | | | | |
| XT -8455 -4 -1000 -1000 -8455 -4 -8455 -4 | | | | | | | | | | | |
| NULT -4 -8455 | | | | | | | | | | | |
| NULE 595 -1558 85 338 -294 453 -1158 197 249 902 -1085 -142 -21 -313 45 531 201 384 -1998 -644 | | | | | | The transition probability distribution for the null model (single G state). The symbol emission probability distribution for the null model (G state); consists of K (e.g 4 or 20) integers. The null probability used to convert these back to model probabilities is 1/K. | | | | | |
| EVD -499.650970 0.086142 | | | | | | The extreme value distribution parameters μ and lambda respectively; both floating point values. Lambda is positive and nonzero. These values are set when the model is calibrated with hmmcalibrate. | | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 319(Y) | -3482 -149 -16 | -2868 -500 -7108 | -3701 233 -8150 | -3919 43 -894 | 238 -381 -1115 | -3552 399 -701 | -1112 106 -1378 | -3000 -626 * | -2516 -466 | -2526 -720 | -3027 275 | -3772 394 | -3101 45 | -3341 96 | -3418 359 | -3527 117 | -3071 -369 | -441 -294 | 4711 -249 | 325 |
| 320(M) | -1559 -149 -16 | -1267 -500 -7108 | -3829 233 -8150 | -3380 43 -894 | -1103 -381 -1115 | -3357 399 -701 | -2655 106 -1378 | 805 -626 * | -64 -466 | 3046 -720 | -3065 275 | -3326 394 | -2779 45 | -3011 96 | -2591 359 | -1556 117 | 2855 -369 | -2312 -294 | -1998 -249 | 326 |
| 321(M) | 1225 -149 -16 | -469 -500 -7108 | -2256 233 -8150 | -1679 43 -894 | 1656 -381 -1115 | -1926 399 -701 | -870 106 -1378 | 90 -626 * | -210 -466 | 2763 -720 | -1424 275 | -2028 394 | -1129 45 | -1411 96 | -1008 359 | 712 117 | 154 -369 | -951 -294 | -586 -249 | 327 |
| 322(T) | -738 -149 -16 | -2094 -500 -7108 | -84 233 -8150 | 1704 43 -894 | -2416 -381 -1115 | -1495 399 -701 | -317 106 -1378 | -2135 -626 * | -2127 -466 | -1275 -720 | -163 275 | -1704 394 | 1857 45 | -405 96 | -613 359 | 1930 117 | -1734 -369 | -2331 -294 | -1668 -249 | 328 |
| 323(D) | -1746 -149 -16 | -3458 -500 -7108 | 3540 233 -8150 | 90 43 -894 | -3744 -381 -1115 | -1650 399 -701 | -1081 106 -1378 | -3767 -626 * | -3662 -466 | -3036 -720 | 1386 275 | -2211 394 | -772 45 | -2239 96 | -1429 359 | -1850 117 | -3226 -369 | -3765 -294 | -2789 -249 | 329 |
| 324(L) | -2451 -149 -16 | -1983 -500 -7108 | -4707 233 -8150 | -4186 43 -894 | -582 -381 -1115 | -4409 399 -701 | -3259 106 -1378 | 1510 -626 * | 2778 -466 | 592 -720 | -4069 275 | -3865 394 | -3091 45 | -3590 96 | -3698 359 | -2355 117 | -150 -369 | -2226 -294 | -2214 -249 | 330 |
| 325(H) | -2923 -149 -16 | -2573 -500 -7108 | -2959 233 -8150 | -2926 43 -894 | 826 -381 -1115 | -3449 399 -701 | 4553 106 -1378 | -2508 -626 * | -2054 -466 | -1948 -720 | -2279 275 | -3499 394 | -2191 45 | -2397 96 | -2761 359 | -2855 117 | -2540 -369 | 123 -294 | 2920 -249 | 331 |
| 326(K) | 373 -149 -16 | -1957 -500 -7108 | -342 233 -8150 | 1025 43 -894 | -2297 -381 -1115 | -1472 396 -701 | -98 106 -1378 | -2018 -626 * | -1954 -466 | -1056 -720 | 906 275 | -1570 394 | 352 45 | 685 96 | -424 359 | -473 117 | -1592 -369 | -2105 -294 | -1469 -249 | 332 |
| 327(V) | 1739 -149 -16 | -1008 -500 -7108 | -3509 233 -8150 | -3043 43 -894 | -1376 -381 -1115 | -3028 399 -701 | -2406 106 -1378 | 1765 -626 * | -615 -466 | -334 -720 | -2718 275 | -3093 394 | -2585 45 | -2823 96 | -2226 359 | -1263 117 | 2376 -369 | -2322 -294 | -1931 -249 | 333 |
| 328(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 334 |
| 329(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 335 |

TABLE 6-continued

```
HMMER2.0 [2.2g]                                    Program name and version
NAME dhad_for_hmm                                  Name of the input sequence alignment file
LENG 564                                           Length of the alignment
ALPH Amino                                         Type of residues
MAP yes                                            Map of the match states to the columns of the alignment
COM /app/public/hmmer/current/bin/hmmbuild -F dhad-exp_hmm dhad_for_hmm.aln   Commands used to generate the file: this one means that hmmbuild (default parameters) was applied to the alignment file
COM /app/public/hmmer/current/bin/hmmcalibrate dhad-exp_hmm                   Commands used to generate the file: this one means that hmmcalibrate (default parameters) was applied to the hmm profile
NSEQ 8                                             Number of sequences in the alignment file
DATE Tue Jun 3 10:48:24 2008                       When was the file generated
XT -8455 -4 -1000 -1000 -8455 -4 -8455 -4
NULT -4 -8455                                      The transition probability distribution for the null model (single G state).
NULE 595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                 probability used to convert these back to model probabilities is 1/K.
EVD -499.650970 0.086142                           The extreme value distribution parameters μ and lambda respectively; both floating point values. Lambda is positive and
                                                   nonzero. These values are set when the model is calibrated with hmmcalibrate.
```

| HMM | A m→m m→i m→d | C m→m m→i m→d | D m→d m→i d→d | E i→m i→i | F i→i i→d | G d→m d→i | H d→d d→d | I b→m b→d | L | M | N | P | Q | R | S | T | V | W | Y | Position in alignment |
|---|---|---|---|---|---|---|---|---|---|---|---|---|---|---|---|---|---|---|---|---|
| 330(I) | -1758 -149 -16 | -1302 -500 -7108 | -4331 233 -8150 | -3970 43 -894 | -1756 -381 -1115 | -4054 399 -701 | -3748 106 -1378 | 2976 -626 * | -603 -466 | -533 -720 | -3731 275 | -3877 394 | -3693 45 | -3914 96 | -3372 359 | -1750 117 | 2505 -369 | -3265 -294 | -2824 -249 | 336 |
| 331(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 337 |
| 332(Q) | 1795 -149 -16 | -1440 -500 -7108 | -730 233 -8150 | -492 43 -894 | -2453 -381 -1115 | 682 399 -701 | -812 106 -1378 | -2151 -626 * | -2256 -466 | -1426 -720 | -624 275 | -1796 394 | 2666 45 | -901 96 | -590 359 | -689 117 | -1636 -369 | -2510 -294 | -1971 -249 | 338 |
| 333(V) | -1771 -149 -16 | -1603 -500 -7108 | -3750 233 -8150 | -3689 43 -894 | -2037 -381 -1115 | -3050 399 -701 | -3231 106 -1378 | 403 -626 * | -1154 -466 | -1076 -720 | -3246 275 | -3399 394 | -3383 45 | -3437 96 | -2628 359 | -1917 117 | 3536 -369 | -3074 -294 | -267 -249 | 339 |
| 334(M) | -2355 -149 -16 | -1988 -500 -7108 | -4343 233 -8150 | -3834 43 -894 | -504 -381 -1115 | -4051 399 -701 | -2868 106 -1378 | 105 -626 * | 1451 -466 | 4460 -720 | -3680 275 | -3671 394 | -2806 45 | -3171 96 | -3327 359 | -2274 117 | -474 -369 | -2039 -294 | -1925 -249 | 340 |
| 335(K) | -2620 -149 -16 | -2961 -500 -7108 | -2461 236 -8150 | -2046 43 -894 | -3743 -381 -1115 | -2791 399 -701 | -1570 106 -1378 | -3603 -626 * | -3387 -466 | -2839 -720 | -2048 275 | -3039 394 | -1260 45 | -465 96 | -2604 359 | -2536 117 | -3331 -369 | -3001 -294 | -2988 -249 | 341 |
| 336(Y) | -1187 -149 -16 | -974 -500 -7108 | -3186 233 -8150 | -2638 46 -894 | -117 -381 -1115 | -2732 396 -701 | -1255 106 -1378 | 1905 -626 * | 73 -466 | 1977 -720 | -2217 275 | -2699 394 | -1882 45 | -2144 96 | -1841 359 | -1124 117 | 71 -369 | -907 -294 | 3254 -249 | 342 |
| 337(L) | -2871 -149 -16 | -2457 -500 -7108 | -4231 233 -8150 | -4103 43 -894 | -1033 -381 -1115 | -3803 399 -701 | -3165 106 -1378 | -541 -626 * | 3130 -466 | -31 -720 | -3935 275 | -3797 394 | -3286 45 | -3484 96 | -3713 359 | -2869 117 | -1136 -369 | -2394 -294 | -2220 -249 | 343 |
| 338(L) | -2871 -149 -16 | -2457 -500 -7108 | -4231 233 -8150 | -4103 43 -894 | -1033 -381 -1115 | -3803 399 -701 | -3165 106 -1378 | -541 -626 * | 3130 -466 | -31 -720 | -3935 275 | -3797 394 | -3286 45 | -3484 96 | -3713 359 | -2869 117 | -1136 -369 | -2394 -294 | -2220 -249 | 344 |
| 339(K) | -864 -149 -16 | -1785 -500 -7108 | -860 233 -8150 | -366 43 -894 | -2128 -381 -1115 | -1763 399 -701 | -407 106 -1378 | -1612 -626 * | -1800 -466 | -1045 -720 | 629 275 | -1900 394 | -28 45 | 62 96 | -851 359 | -805 117 | 1127 -369 | -2064 -294 | -1581 -249 | 345 |
| 340(N) | 602 -149 -16 | -1686 -500 -7108 | -275 233 -8150 | 1008 43 -894 | -1926 -381 -1115 | -1415 399 -701 | 1528 106 -1378 | -1618 -626 * | -1673 -466 | -815 -720 | 1897 275 | -1530 394 | 299 45 | -244 96 | -371 359 | -391 117 | 322 -369 | -1934 -294 | -1306 -249 | 346 |

TABLE 6-continued

```
HMMER2.0 [2.2g]                                                          Program name and version
NAME  dhad_for_hmm                                                       Name of the input sequence alignment file
LENG  564                                                                Length of the alignment: include indels
ALPH  Amino                                                              Type of residues
MAP   yes                                                                Map of the match states to the columns of the alignment
COM   /app/public/hmmer/current/bin/hmmbuild -F dhad-exp_hmm dhad_for_hmm.aln   Commands used to generate the file: this one means that hmmbuild (default patrameters) was applied to the alignment file
COM   /app/public/hmmer/current/bin/hmmcalibrate dhad-exp_hmm             Commands used to generate the file: this one means that hmmcalibrate (default parameters) was applied to the hmm profile
NSEQ  8                                                                  Number of sequences in the alignment file
DATE  Tue Jun 3 10:48:24 2008                                            When was the file generated
XT    -8455 -4 -1000 -1000 -8455 -4 -8455 -4
NULT  -4 -8455                                                           The transition probability distribution for the null model (single G state).
NULE  595 -1558 85 338 -294 453 -1158 197 249 902 -1085 -142 -21 -313 45 531    The symbol emission probability distribution for the null model (G state); consists of K (e.g 4 or 20) integers. The null
201 384 -1998 -644                                                       probability used to convert these back to model probabilities is 1/K.
EVD   -499.650970 0.086142                                               The extreme value distribution parameters μ and lambda respectively; both floating point values. Lambda is positive and
                                                                         nonzero. These values are set when the model is calibrated with hmmcalibrate.
```

| HMM | A m->m | C m->i | D m->d | E i->m | F i->i | G d->m | H d->d | I b->m | | L | M | N | P | Q | R | S | T | V | W | Y | Position in alignment |
|---|---|---|---|---|---|---|---|---|---|---|---|---|---|---|---|---|---|---|---|---|---|
| 341(G) | -1709 | -2639 | 1362 | -690 | -3785 | 3257 | -1671 | -3805 | | -3792 | -3137 | -980 | -2480 | -1424 | -2576 | -1630 | -1936 | -3150 | -3628 | -3155 | 347 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 342(F) | -942 | -799 | -2828 | -2226 | 1797 | -2476 | -1269 | 1109 | | 1793 | 516 | -1952 | -2453 | -1557 | -1815 | -1558 | -875 | 52 | -1138 | -794 | 348 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 343(L) | -2451 | -1983 | -4707 | -4186 | -582 | -4409 | -3259 | 1510 | | 27781 | 592 | -4069 | -3865 | -3091 | -3590 | -3698 | -2355 | -150 | -2226 | -2214 | 349 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 344(H) | -3205 | -3079 | -2723 | -2890 | -2110 | -3046 | 5295 | -4135 | | -3813 | -3561 | -2886 | -3482 | -2833 | -2620 | -3291 | -3356 | -3895 | -2397 | -1681 | 350 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 345(G) | -2594 | -2690 | -3304 | -3623 | -4328 | 3747 | -3462 | -4761 | | -4671 | -4212 | -3320 | -3352 | -3748 | -3779 | -2839 | -2981 | -4004 | -3668 | -4222 | 351 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 346(D) | -2784 | -3432 | 4016 | -1200 | -4140 | -2466 | -2197 | -4505 | | -4365 | -3956 | -1551 | -3014 | -2039 | -3232 | -2593 | -2938 | -4046 | -3710 | -3552 | 352 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 347(C) | 774 | 4452 | -2162 | -1688 | -1962 | -1478 | -1302 | -1474 | | -1796 | -1088 | -1351 | -1979 | -1147 | 1684 | -732 | -719 | -1116 | -2225 | -1881 | 353 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 348(L) | -2387 | -1922 | -4674 | -4155 | -617 | -4366 | -3250 | 1889 | | 2650 | 558 | -4023 | -3847 | -3098 | -3586 | -3647 | -2296 | -38 | -2247 | -2224 | 354 |
|  | -149 | -500 | 233 | 43 | -381 | 399 | 106 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 349(T) | -1213 | -1674 | -2755 | -2906 | -3163 | -1922 | -2659 | -2698 | | -3105 | -2612 | -2311 | -2600 | -2708 | -2753 | -1463 | 3819 | -2197 | -3286 | -3156 | 355 |
|  | -149 | -500 | 233 | 43 | -381 | 399 | 106 | -626 | | -465 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 350(C) | -1489 | 2972 | -4007 | -3563 | -1524 | -3541 | -2939 | 2612 | | -617 | -413 | -3224 | -3470 | -3129 | -3335 | -2770 | -1475 | 2269 | -2657 | -2248 | 356 |
|  | -149 | -500 | 233 | 43 | -381 | 399 | 105 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |
| 351(T) | -364 | -979 | -2232 | -2250 | -2904 | -1245 | -2090 | -2559 | | -2881 | -2075 | -1571 | -1964 | -1991 | -2260 | 905 | 3428 | -1762 | -3159 | -2858 | 357 |
|  | -149 | -500 | 233 | 43 | -381 | 399 | 105 | -626 | | -466 | -720 | 275 | 394 | 45 | 96 | 359 | 117 | -369 | -294 | -249 |  |
|  | -16 | -7108 | -8150 | -894 | -1115 | -701 | -1378 | * | | | | | | | | | | | | |  |

TABLE 6-continued

```
HMMER2.0 [2.2g]                                              Program name and version
NAME  dhad_for_hmm                                           Name of the input sequence alignment file
LENG  564                                                    Length of the alignment: include indels
ALPH  Amino                                                  Type of residues
MAP   yes                                                    Map of the match states to the columns of the alignment
COM   /app/public/hmmer/current/bin/hmmbuild -F dhad-exp_hmm dhad_for_hmm.aln    Commands used to generate the file: this one means that hmmbuild (default patrameters) was applied to the alignment file
COM   /app/public/hmmer/current/bin/hmmcalibrate dhad-exp_hmm                    Commands used to generate the file: this one means that hmmcalibrate (default parameters) was applied to the hmm profile
NSEQ  8                                                      Number of sequences in the alignment file
DATE  Tue Jun 3 10:48:24 2008                                When was the file generated
XT    -8455 -4 -1000 -1000 -8455 -4 -8455 -4
NULT  -4 -8455
NULE  595 -1558 85 338 -294 453 -1158 197 249 902 -1085 -142 -21 -313 45 531    The transition probability distribution for the null model (single G state).
201 384 -1998 -644                                           The symbol emission probability distribution for the null model (G state); consists of K (e.g 4 or 20) integers. The null
EVD   -499.650970 0.086142                                                      probability used to convert these back to model probabilities is 1/K.
                                                             The extreme value distribution parameters μ and lambda respectively; both floating point values. Lambda is positive and
                                                             nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 352(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 358 |
| 353(K) | -1716 -149 -16 | -2632 -500 -7108 | -2004 233 -8150 | -1008 43 -894 | -3336 -381 -1115 | -2379 399 -701 | -444 106 -1378 | -2764 -626 * | -2484 -466 | -1756 -720 | -1035 275 | -2357 394 | 2151 45 | 1811 96 | -1592 359 | -1477 117 | -2481 -369 | -2391 -294 | -2172 -249 | 359 |
| 354(T) | -1213 -149 -16 | -1674 -500 -7108 | -2755 233 -8150 | -2906 43 -894 | -3163 -381 -1115 | -1922 399 -701 | -2659 106 -1378 | -2698 -626 * | -3105 -466 | -2612 -720 | -2311 275 | -2600 394 | -2708 45 | -2753 96 | -1463 359 | 3819 117 | -2197 -369 | -3286 -294 | -3158 -249 | 360 |
| 355(V) | -1771 -149 -16 | -1339 -500 -7108 | -4275 233 -8150 | -3816 43 -894 | -1235 -381 -1115 | -3919 399 -701 | -3194 106 -1378 | 2139 -626 * | 1520 -466 | -66 -720 | -3558 275 | -3681 394 | -3244 45 | -3547 96 | -3164 359 | -1733 117 | 2390 -369 | -2634 -294 | -2369 -249 | 361 |
| 356(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3257 -466 | -2662 -720 | -2236 275 | -2447 394 | -2798 45 | -2944 96 | -1216 359 | -1387 117 | -2183 -369 | -3405 -294 | -3320 -249 | 362 |
| 357(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -4016 -466 | -3555 -720 | -1531 275 | -2959 394 | -1842 45 | -2560 96 | -2479 359 | -2750 117 | -3722 -369 | -3563 -294 | -3385 -249 | 363 |
| 358(N) | -823 -149 -16 | -1917 -500 -7108 | -96 233 -8150 | 1188 43 -894 | -2187 -381 -1115 | -1547 399 -701 | -506 106 -1378 | -1711 -626 * | -1955 -466 | -1191 -720 | 2711 275 | -1815 394 | -144 45 | -747 96 | -757 359 | -815 117 | 1140 -369 | -2297 -294 | -1666 -249 | 364 |
| 359(L) | -2153 -149 -16 | -1779 -500 -7108 | -4360 233 -8150 | -3884 43 -894 | -675 -381 -1115 | -3965 399 -701 | -3012 106 -1378 | 392 -626 * | 2726 -466 | 467 -720 | -3673 275 | -3662 394 | -2955 45 | -3355 96 | -3239 359 | -2102 117 | 1281 -369 | -2207 -294 | -2099 -249 | 365 |
| 360(E) | 1136 -149 -16 | -2084 -500 -7108 | -175 233 -8150 | 2027 43 -894 | -2436 -381 -1115 | -1510 399 -701 | -274 106 -1378 | -2147 -626 * | -2118 -466 | -1254 -720 | -175 275 | -1692 394 | 152 45 | -251 96 | -593 359 | -670 117 | -1736 -369 | -2296 -294 | -1650 -249 | 366 |
| 361(H) | 893 -149 -16 | -1761 -500 -7108 | 1357 233 -8150 | 214 43 -894 | -2092 -381 -1115 | -1387 399 -701 | 1862 106 -1378 | -1810 -626 * | -1825 -466 | -942 -720 | -83 275 | -1527 394 | 293 45 | -273 96 | 640 359 | 793 117 | -1409 -369 | -2050 -294 | -1397 -249 | 367 |
| 362(I) | 608 -149 -16 | -458 -500 -7108 | -2776 233 -8150 | -2176 43 -894 | 1666 -381 -1115 | -2202 399 -701 | -1113 106 -1378 | 1712 -626 * | -222 -466 | 338 -720 | -1782 275 | -2245 394 | -1512 45 | -1731 96 | -1292 359 | 867 117 | 1366 -369 | -1036 -294 | -684 -249 | 368 |

TABLE 6-continued

```
HMMER2.0 [2.2g]                                           Program name and version
NAME dhad_for_hmm                                         Name of the input sequence alignment file
LENG 564                                                  Length of the alignment: include indels
ALPH Amino                                                Type of residues
MAP yes                                                   Map of the match states to the columns of the alignment
COM /app/public/hmmer/current/bin/hmmbuild -F dhad-exp_hmm dhad_for_hmm.aln   Commands used to generate the file: this one means that hmmbuild (default patrameters) was applied to the alignment file
COM /app/public/hmmer/current/bin/hmmcalibrate dhad-exp_hmm                   Commands used to generate the file: this one means that hmmcalibrale (default parameters) was applied to the hmm profile
NSEQ 8                                                    Number of sequences in the alignment file
DATE Tue Jun 3 10:48:24 2008                              When was the file generated
XT -8455 -4 -1000 -1000 -8455 -4 -8455 -4
NULT -4 -8455                                             The transition probability distribution for the null model (single G state).
NULE 595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                        probability used to convert these back to model probabilities is 1/K.
EVD -499.650970 0.086142                                  The extreme value distribution parameters μ and lambda respectively; both floating point values. Lambda is positive and
                                                          nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 363(P) | -922 | -1912 | 1681 | -141 | -2123 | -1604 | -687 | -1787 | 187 | -1245 | -427 | 2677 | -363 | -1049 | -882 | -947 | -1524 | -2338 | -1711 | 369 |
|  | -144 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 364(D) | -1692 | -3605 | 3364 | 1256 | -3770 | -1599 | -957 | -3700 | -3569 | -2909 | 1025 | -2138 | -628 | -2083 | -1346 | -1761 | -3174 | -3765 | -2738 | 370 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 365(Q) | -877 | -1646 | -633 | 499 | -1610 | -1781 | -505 | -1210 | 1648 | -649 | -558 | -1931 | 2241 | -360 | -907 | -814 | -1097 | -1882 | -1385 | 371 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 366(P) | -648 | -2019 | 1139 | 203 | -2354 | -1436 | -285 | -2089 | -2086 | -1217 | -114 | 1965 | 1445 | -492 | -529 | 1244 | -1672 | -2300 | -1616 | 372 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -1646 | -894 | -1115 | -701 | -1378 | * |  |  |  |  |  |  |  |  |  |  |  |  |
| 367(R) | -422 | -1009 | -851 | -304 | 1406 | -1496 | -183 | -740 | -894 | -230 | -440 | 775 | 21 | 2009 | -539 | -381 | -568 | -1136 | -521 | 373 |
|  | -149 | -500 | 233 | 43 | -381 | 399 | 106 | -626 | -466 | -720 | 275 | 394 | 45 | 96 | 359 | 117 | -369 | -294 | -249 |  |
|  | -23 | -6560 | -7602 | -894 | -1115 | -701 | -2249 | * |  |  |  |  |  |  |  |  |  |  |  |  |
| 368(D) | 1472 | -1668 | 1835 | -70 | -2356 | -1385 | -511 | -2062 | -2128 | -1275 | -318 | 1353 | -118 | -746 | -526 | 425 | -1602 | -2380 | -1752 | 374 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 369(G) | -1044 | -2230 | 2141 | -100 | -3222 | 2291 | -982 | -3045 | -3050 | -2258 | -395 | -1985 | -644 | -1669 | 858 | -1207 | -2428 | -3250 | -2493 | 375 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 370(Q) | -2562 | -2904 | -1886 | -1971 | -3251 | -2661 | -2079 | -3690 | -3469 | -3081 | -2107 | -3091 | 4371 | -1665 | -2585 | -2674 | -3411 | -3077 | -2821 | 376 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 371(D) | -1275 | -2955 | 2862 | 1330 | -3205 | -1556 | -670 | -3029 | -2936 | -2141 | -158 | -1955 | -290 | -1213 | -1025 | -1281 | -2554 | -3111 | -2272 | 377 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 372(V) | -1738 | -1298 | -4281 | -3921 | -1737 | -3979 | -3665 | 1917 | -601 | -528 | -3671 | -3834 | -3628 | -3843 | -3293 | -1735 | 3205 | -3215 | -2770 | 378 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 373(I) | -2091 | -1746 | -3971 | -3840 | -1676 | -3532 | -3289 | 3684 | -659 | -693 | -3562 | -3674 | -3445 | -3521 | -3194 | -2146 | 449 | -2877 | -2493 | 379 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

| | | | | | | | | | | | | |
|---|---|---|---|---|---|---|---|---|---|---|---|---|
| HMMER2.0 [2.2g] | | | | | | | Program name and version | | | | | |
| NAME dhad_for_hmm | | | | | | | Name of the input sequence alignment file | | | | | |
| LENG 564 | | | | | | | Length of the alignment | | | | | |
| ALPH Amino | | | | | | | Type of residues | | | | | |
| MAP yes | | | | | | | Map of the match states to the columns of the alignment | | | | | |
| COM /app/public/hmmer/current/bin/hmmbuild -F dhad-exp_hmm dhad_for_hmm.aln | | | | | | | Commands used to generate the file: this one means that hmmbuild (default patrameters) was applied to the alignment file | | | | | |
| COM /app/public/hmmer/current/bin/hmmcalibrate dhad-exp_hmm | | | | | | | Commands used to generate the file: this one means that hmmcalibrate (default parametrs) was applied to the hmm profile | | | | | |
| NSEQ 8 | | | | | | | Number of sequences in the alignment file | | | | | |
| DATE Tue Jun 3 10:48:24 2008 | | | | | | | When was the file generated | | | | | |
| XT -8455 -4 -1000 -1000 -8455 -4 -8455 -4 | | | | | | | | | | | | |
| NULT -4 -8455 | | | | | | | | | | | | |
| NULE 595 -1558 85 338 -294 453 -1158 197 249 902 -1085 -142 -21 -313 45 531 201 384 -1998 -644 | | | | | | | The transition probability distribution for the null model (single G state). The symbol emission probability distribution for the null model (G state); consists of K (e.g 4 or 20) integers. The null probability used to convert these back to model probabilities is 1/K. | | | | | |
| EVD -499.650970 0.086142 | | | | | | | The extreme value distribution parameters μ and lambda respectively; both floating point values. Lambda is positive and nonzero. These values are set when the model is calibrated with hmmcalibrate. | | | | | |

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 374(M) | -584 -149 -16 | -1354 -500 -7108 | -847 233 -8150 | -246 43 -894 | -1467 -381 -1115 | -1659 399 -701 | 2505 106 -1378 | -1087 -626 * | -374 -466 | 2571 -720 | -449 275 | -1729 394 | 1171 45 | 1074 96 | -634 359 | -507 117 | -876 -369 | -1617 -294 | -1128 -249 | 380 |
| 375(P) | -910 -149 -16 | -2031 -500 -7108 | -73 233 -8150 | 1195 43 -894 | -2792 -381 -1115 | -1488 399 -701 | -794 106 -1378 | -2539 -626 * | -2588 -466 | -1788 -720 | -401 275 | 3005 394 | -439 45 | -1131 96 | 612 359 | -1014 117 | -2050 -369 | -2815 -294 | -2151 -249 | 381 |
| 376(W) | -1588 -149 -16 | -1300 -500 -7108 | -3783 233 -8150 | -3197 43 -894 | -329 -381 -1115 | -3245 399 -701 | -1926 106 -1378 | 2071 -626 * | 1901 -466 | 558 -720 | -2822 275 | -3072 394 | -2297 45 | -2616 96 | -2381 359 | -1508 117 | -111 -369 | 3483 -294 | -1042 -249 | 382 |
| 377(E) | -1024 -149 -16 | -2640 -500 -7108 | 1844 233 -8150 | 2310 43 -894 | -2908 -381 -1115 | -1498 399 -701 | -505 106 -1378 | -2711 -626 * | -2636 -466 | -1791 -720 | -107 275 | -1824 394 | 1521 45 | -957 96 | 207 359 | -1011 117 | -2243 -369 | -2817 -294 | -2021 -249 | 383 |
| 378(N) | -826 -149 -16 | -2349 -500 -7108 | 1089 233 -8150 | 227 43 -894 | -2651 -381 -1115 | -1487 399 -701 | -341 106 -1378 | -2416 -626 * | -2346 -466 | -1475 -720 | 2601 275 | -1724 394 | 1005 45 | -522 96 | -657 359 | -787 117 | -1968 -369 | -2511 -294 | -1791 -249 | 384 |
| 379(P) | 1932 -149 -16 | -1116 -500 -7108 | -2232 233 -8150 | -2301 43 -894 | -3058 -381 -1115 | -1358 399 -701 | -2206 106 -1378 | -2706 -626 * | -3009 -466 | -2238 -720 | -1674 275 | 3274 394 | -2114 45 | -2406 96 | -739 359 | -914 117 | -1913 -369 | -3260 -294 | -3019 -249 | 385 |
| 380(V) | -914 -149 -16 | -773 -500 -7108 | -2713 233 -8150 | -2129 43 -894 | -712 -381 -1115 | -2505 399 -701 | -1388 106 -1378 | 1452 -626 * | 1324 -466 | 204 -720 | -1926 275 | -2507 394 | -1580 45 | -1808 96 | -1591 359 | -859 117 | 1713 -369 | -1424 -294 | -1081 -249 | 386 |
| 381(Y) | -1484 -149 -16 | -2331 -500 -7108 | -1762 233 -8150 | -887 43 -894 | -2436 -381 -1115 | -2254 399 -701 | -420 106 -1378 | -2325 -626 * | -2195 -466 | -1475 -720 | -949 275 | -2258 394 | -39 45 | 1983 96 | -1411 359 | -1295 117 | -2075 -369 | -2087 -294 | 2868 -249 | 387 |
| 382(E) | 1256 -149 -16 | -1890 -500 -7108 | -206 233 -8150 | 1353 43 -894 | -2196 -381 -1115 | -1401 399 -701 | -89 106 -1378 | -1930 -626 * | -1898 -466 | -996 -720 | -45 275 | 547 394 | 1252 45 | -162 96 | -356 359 | -414 117 | -1507 -369 | -2083 -294 | -1416 -249 | 388 |
| 383(Q) | -752 -149 -16 | -2272 -500 -7108 | 1586 233 -8150 | 1407 43 -894 | -2561 -381 -1115 | -1448 399 -701 | -308 106 -1378 | -2329 -626 * | -2276 -466 | -1396 -720 | -71 275 | -1677 394 | 1749 45 | -577 96 | -590 359 | 1569 117 | -1881 -369 | -2459 -294 | -1727 -249 | 389 |
| 384(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 390 |

TABLE 6-continued

```
HMMER2.0 [2.2g]                                            Program name and version
NAME  dhad_for_hmm                                         Name of the input sequence alignment file
LENG  564                                                  Length of the alignment: include indels
ALPH  Amino                                                Type of residues
MAP   yes                                                  Map of the match states to the columns of the alignment
COM   /app/public/hmmer/current/bin/hmmbuild -F dhad-exp_hmm dhad_for_hmm.aln   Commands used to generate the file: this one means that hmmbuild (default parameters) was applied to the alignment file
COM   /app/public/hmmer/current/bin/hmmcalibrate dhad-exp_hmm                    Commands used to generate the file: this one means that hmmcalibrate (default parameters) was applied to the hmm profile
NSEQ  8                                                    Number of sequences in the alignment file
DATE  Tue Jun 3 10:48:24 2008                              When was the file generated
XT   -8455 -4 -1000 -1000 -8455 -4 -8455 -4
NULT -4 -8455
NULE 595 -1558 85 338 -294 453 -1158 197 249 902 -1085 -142 -21 -313 45 531
201 384 -1998 -644                                         The transition probability distribution for the null model (single G state).
EVD  -499.650970 0.086142                                  The symbol emission probability distribution for the null model (G state); consists of K (e.g 4 or 20) integers. The null
                                                           probability used to convert these back to model probabilities is 1/K.
                                                           The extreme value distribution parameters μ and lambda respectively; both floating point values. Lambda is positive and
                                                           nonzero. These values are set when the model is calibrated with hmmcalibrate.
```

| HMM | A m→m | C m→i | D m→d | E i→m | F i→i | G d→m | H d→d | I b→m | L | M | N | P | Q | R | S | T | V | W | Y | Position in alignment |
|---|---|---|---|---|---|---|---|---|---|---|---|---|---|---|---|---|---|---|---|---|
| 385(H) | -964 -149 -16 | -2089 -500 -7108 | -200 233 -8150 | -136 43 -894 | -2264 -381 -1115 | -1600 399 -701 | 3833 106 -1378 | -2320 -626 * | -2338 -466 | -1558 -720 | 1362 275 | 1479 394 | -276 45 | -699 96 | -881 359 | -992 117 | -1924 -369 | -2364 -294 | -1652 -249 | 391 |
| 386(L) | -2451 -149 -16 | -1983 -500 -7108 | -4707 233 -8150 | -4186 43 -894 | -582 -381 -1115 | -4409 399 -701 | -3259 106 -1378 | 1510 -626 * | 2778 -466 | 592 -720 | -4069 275 | -3865 394 | -3091 45 | -3590 96 | -3698 359 | -2355 117 | -150 -369 | -2226 -294 | -2214 -249 | 392 |
| 387(Q) | 1643 -149 -16 | -1017 -500 -7108 | -1196 233 -8150 | -721 43 -894 | -1189 -381 -1115 | -1714 399 -701 | -668 106 -1378 | 1336 -626 * | -907 -466 | -297 -720 | -823 275 | -1893 394 | 2044 45 | -794 96 | -784 359 | -569 117 | -339 -369 | -1579 -294 | -1135 -249 | 393 |
| 388(I) | -1760 -149 -16 | -1308 -500 -7108 | -4323 233 -8150 | -3961 43 -894 | -1730 -381 -1115 | -4039 399 -701 | -3721 106 -1378 | 3156 -626 * | -575 -466 | -512 -720 | -3720 275 | -3867 394 | -3669 45 | -3893 96 | -3356 359 | -1753 117 | 2241 -369 | -3236 -294 | -2802 -249 | 394 |
| 389(L) | -2871 -149 -16 | -2457 -500 -7108 | -4231 233 -8150 | -4103 43 -894 | -1033 -381 -1115 | -3803 399 -701 | -3165 106 -1378 | -541 -626 * | 3130 -466 | -31 -720 | -3935 275 | -3797 394 | -3286 45 | -3484 96 | -3713 359 | -2869 117 | -1136 -369 | -2394 -294 | -2220 -249 | 395 |
| 390(K) | -1259 -149 -16 | -2115 -500 -7108 | -1267 233 -8150 | -676 43 -894 | -970 -381 -1115 | -2105 399 -701 | 1794 106 -1378 | -2040 -626 * | -1955 -466 | -1282 -720 | -808 275 | -2165 394 | -167 45 | 114 96 | -1192 359 | -1140 117 | -1801 -369 | -1301 -294 | 2517 -249 | 396 |
| 391(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 397 |
| 392(N) | -2171 -149 -16 | -2655 -500 -7108 | -1458 233 -8150 | -1748 43 -894 | -3334 -381 -1115 | -2364 399 -701 | -2267 106 -1378 | -3943 -626 * | -3936 -466 | -3437 -720 | 4205 275 | -2932 394 | -2205 45 | -2608 96 | -2224 359 | -2439 117 | -3392 -369 | -3253 -294 | -2909 -249 | 398 |
| 393(L) | -2871 -149 -16 | -2457 -506 -7108 | -4231 233 -8150 | -4103 43 -894 | -1033 -381 -1115 | -3803 399 -701 | -3165 106 -1378 | -541 -626 * | 3130 -466 | -31 -720 | -3935 275 | -3797 394 | -3286 45 | -3484 96 | -3713 359 | -2869 117 | -1136 -369 | -2394 -294 | -2221 -249 | 399 |
| 394(A) | 3121 -149 -16 | -934 -500 -7108 | -2489 233 -8150 | -2561 43 -894 | -3081 -381 -1115 | -1203 399 -701 | -2295 106 -1378 | -2766 -626 * | -3080 -466 | -2234 -720 | -1669 275 | -1953 394 | -2234 45 | -2533 96 | 936 359 | -746 117 | -1844 -369 | -3331 -294 | -3090 -249 | 400 |
| 395(E) | -522 -149 -16 | -1773 -500 -7108 | -240 233 -8150 | 1676 43 -894 | -2248 -381 -1115 | -1396 399 -701 | -289 106 -1378 | -1968 -626 * | -1989 -466 | -1115 -720 | -174 275 | 1198 394 | 131 45 | -448 96 | 1226 359 | 677 117 | -1538 -369 | -2214 -294 | -1565 -249 | 401 |

TABLE 6-continued

| | | | | | | | | | |
|---|---|---|---|---|---|---|---|---|---|
| HMMER2.0 [2.2g] | | | | | | | | Program name and version | |
| NAME dhad_for_hmm | | | | | | | | Name of the input sequence alignment file | |
| LENG 564 | | | | | | | | Length of the alignment | |
| ALPH Amino | | | | | | | | Type of residues | |
| MAP yes | | | | | | | | Map of the match states to the columns of the alignment | |
| COM /app/public/hmmer/current/bin/hmmbuild -F dhad-exp_hmm dhad_for_hmm.aln | | | | | | | | Commands used to generate the file: this one means that hmmbuild (default patrameters) was applied to the alignment file | |
| COM /app/public/hmmer/current/bin/hmmcalibrate dhad-exp_hmm | | | | | | | | Commands used to generate the file: this one means that hmmcalibrate (default parameters) was applied to the hmm profile | |
| NSEQ 8 | | | | | | | | Number of sequences in the alignment file | |
| DATE Tue Jun 3 10:48:24 2008 | | | | | | | | When was the file generated | |
| XT -8455 -4 -1000 -1000 -8455 -4 -8455 -4 | | | | | | | | | |
| NULT -4 -8455 | | | | | | | | | |
| NULE 595 -1558 85 338 -294 453 -1158 197 249 902 -1085 -142 -21 -313 45 531 201 384 -1998 -644 | | | | | | | | The transition probability distribution for the null model (single G state). The symbol emission probability distribution for the null model (G state); consists of K (e.g. 4 or 20) integers. The null probability used to convert these back to model probabilities is 1/K. | |
| EVD -499.650970 0.086142 | | | | | | | | The extreme value distribution parameters μ and lambda respectively; both floating point values. Lambda is positive and nonzero. These values are set when the model is calibrated with hmmcalibrate. | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 396(E) | -1481 -149 -16 | -3230 -500 -7108 | 1425 233 -8150 | 2936 43 -894 | -3481 -381 -1115 | 751 399 -701 | -843 106 -1378 | -3354 -626 * | -3256 -466 | -2520 -720 | -187 275 | -2057 394 | -492 45 | -1711 96 | -1193 359 | -1527 117 | -2852 -369 | -3445 -294 | -2523 -249 | 402 |
| 397(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 403 |
| 398(A) | 2847 -149 -16 | -932 -500 -7108 | -2454 233 -8150 | -2477 43 -894 | -3066 -381 -1115 | -1198 399 -701 | -2236 106 -1378 | -2763 -626 * | -3057 -466 | -2202 -720 | -1635 275 | -1940 394 | -2152 45 | -2471 96 | 1777 359 | -731 117 | -1840 -369 | -3306 -294 | -3056 -249 | 404 |
| 399(V) | -1771 -146 -16 | -1603 -500 -7108 | -3750 233 -8150 | -3689 43 -894 | -2037 -381 -1115 | -3050 399 -701 | -3231 106 -1378 | 403 -626 | -1154 -466 | -1076 -720 | -3246 275 | -3399 394 | -3383 45 | -3437 96 | -2628 359 | -1917 117 | 3536 -369 | -3074 -294 | -2677 -249 | 405 |
| 400(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3257 -466 | -2662 -720 | -2236 275 | -2447 394 | -2798 45 | -2944 96 | -1216 359 | -1387 117 | -2183 -369 | -3405 -294 | -3320 -249 | 406 |
| 401(K) | -2620 -149 -16 | -2961 -500 -7108 | -2461 233 -8150 | -2046 43 -894 | -3743 -381 -1115 | -2791 399 -701 | -1570 106 -1378 | -3603 -626 * | -3387 -466 | -2839 -720 | -2048 275 | -3039 394 | -1260 45 | -465 96 | -2604 359 | -2536 117 | -3331 -369 | -3001 -294 | -2988 -249 | 407 |
| 402(I) | -1761 -149 -16 | -1312 -500 -7108 | -4317 233 -8150 | -3954 43 -894 | -1713 -381 -1115 | -4027 399 -701 | -3703 106 -1378 | 3225 -626 | -556 -466 | -498 -720 | -3712 275 | -3859 394 | -3653 45 | -3877 96 | -3344 359 | -1754 117 | 2110 -369 | -3216 -294 | -2787 -249 | 408 |
| 403(S) | -348 -149 -16 | -981 -500 -7108 | -2200 233 -8150 | -2194 43 -894 | -2989 -381 -1115 | -1227 399 -701 | -2073 106 -1378 | -2686 -626 * | -2970 -466 | -2136 -720 | -1541 275 | -1946 394 | -1946 45 | -2253 96 | 3060 359 | 1398 117 | -1824 -369 | -3217 -294 | -2916 -249 | 409 |
| 404(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 410 |
| 405(V) | -917 -149 -16 | -809 -500 -7108 | -2556 233 -8150 | -1976 43 -894 | -827 -381 -1115 | -2491 399 -701 | -1367 106 -1378 | 1339 -626 | 721 -466 | 94 -720 | -1841 275 | -2501 394 | -1487 45 | -1710 96 | -1570 359 | -863 117 | 2038 -369 | -1514 -294 | -1151 -249 | 411 |
| 406(K) | -1386 -149 -16 | -2643 -500 -7108 | -447 233 -8150 | 1824 43 -894 | -3108 -381 -1115 | -1893 399 -701 | -570 106 -1378 | -2762 -626 * | -2616 -466 | -1848 -720 | -552 275 | -2117 394 | -166 45 | -3 96 | -1217 359 | -1300 117 | -2388 -369 | -2647 -294 | -2154 -249 | 412 |

TABLE 6-continued

| HMMER2.0 [2.2g] | | | | | | | | | | | Program name and version |
|---|---|---|---|---|---|---|---|---|---|---|---|
| NAME dhad_for_hmm | | | | | | | | | | | Name of the input sequence alignment file |
| LENG 564 | | | | | | | | | | | Length of the alignment: include indels |
| ALPH Amino | | | | | | | | | | | Type of residues |
| MAP yes | | | | | | | | | | | Map of the match states to the columns of the alignment |
| COM /app/public/hmmer/current/bin/hmmbuild -F dhad-exp_hmm dhad_for_hmm.aln | | | | | | | | | | | Commands used to generate the file: this one means that hmmbuild (default patrameters) was applied to the alignment file |
| COM /app/public/hmmer/current/bin/hmmcalibrate dhad-exp_hmm | | | | | | | | | | | Commands used to generate the file: this one means that hmmcalibrate (default parameters) was applied to the hmm profile |
| NSEQ 8 | | | | | | | | | | | Number of sequences in the alignment file |
| DATE Tue Jun 3 10:48:24 2008 | | | | | | | | | | | When was the file generated |
| XT -8455 -4 -1000 -1000 -8455 -4 -8455 -4 | | | | | | | | | | | |
| NULT -4 -8455 | | | | | | | | | | | |
| NULE 595 -1558 85 338 -294 453 -1158 197 249 902 -1085 -142 -21 -313 45 531 201 384 -1998 -644 | | | | | | | | | | | The transition probability distribution for the null model (single G state). The symbol emission probability distribution for the null model (G state); consists of K (e.g 4 or 20) integers. The null probability used to convert these back to model probabilities is 1/K. |
| EVD -499.650970 0.086142 | | | | | | | | | | | The extreme value distribution parameters μ and lambda respectively; both floating point values. Lambda is positive and nonzero. These values are set when the model is calibrated with hmmcalibrate. |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 407(N) | -537 -149 -16 | -1563 -500 -7108 | -449 233 -8150 | -36 43 -894 | -1889 -381 -1115 | 1143 399 -701 | -307 106 -1378 | -1529 -626 * | -1655 -466 | -844 -720 | 1794 275 | -1658 394 | 73 45 | -356 96 | -518 359 | -516 117 | 924 -369 | -1962 -294 | -1392 -249 | 413 |
| 408(P) | -894 -149 -16 | -2181 -500 -7108 | -369 233 -8150 | 1705 43 -894 | -2576 -381 -1115 | -1650 399 -701 | -357 106 -1378 | -2268 -626 * | -2210 -466 | -1375 -720 | -330 275 | 2093 394 | 63 45 | 1619 96 | -774 359 | -835 117 | -1876 -369 | -2347 -294 | -1769 -249 | 414 |
| 409(V) | -419 -149 -16 | -634 -500 -7108 | -1376 233 -8150 | -807 43 -894 | 1053 -381 -1115 | -1737 399 -701 | -499 106 -1378 | -198 -626 * | -505 -466 | 178 -720 | 600 275 | -1807 394 | -475 45 | 475 96 | 313 359 | -360 117 | 1389 -369 | -1016 -294 | 1303 -249 | 415 |
| 410(I) | -1282 -149 -16 | -1082 -500 -7108 | -3022 233 -8150 | -2555 43 -894 | 2426 -381 -1115 | -2683 399 -701 | 1767 106 -1378 | 2555 -626 * | -443 -466 | -88 -720 | -2038 275 | -2692 394 | -1794 45 | -2075 96 | -1793 359 | -1220 117 | -317 -369 | -361 -294 | 552 -249 | 416 |
| 411(T) | -499 -149 -16 | -1595 -500 -7108 | -431 233 -8150 | 966 43 -894 | -1830 -381 -1115 | -1487 399 -701 | -185 106 -1378 | -1449 -626 * | -1574 -466 | -754 -720 | -207 275 | -1601 394 | 213 45 | -206 96 | -458 359 | 2067 117 | 159 -369 | -1877 -294 | -1296 -249 | 417 |
| 412(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 418 |
| 413(P) | -632 -149 -16 | -1230 -500 -7108 | -2074 233 -8150 | -2144 43 -894 | -2996 -381 -1115 | -1453 399 -701 | -2116 106 -1378 | -2631 -626 * | -2928 -466 | -2213 -720 | -1658 275 | 3610 394 | -2006 45 | -2221 96 | -852 359 | 1302 117 | -1931 -369 | -3185 -294 | -2917 -249 | 419 |
| 414(A) | 3438 -149 -16 | -1472 -500 -7108 | -2846 233 -8150 | -3040 43 -894 | -3287 -381 -1115 | -1726 399 -701 | -2735 106 -1378 | -2840 -626 * | -3257 -466 | -2662 -720 | -2236 275 | -2447 394 | -2798 45 | -2944 96 | -1216 359 | -1387 117 | -2183 -369 | -3405 -294 | -3320 -249 | 420 |
| 415(R) | -1454 -149 -16 | -2316 -500 -7108 | -1780 233 -8150 | -878 43 -894 | -2834 -381 -1115 | -2232 399 -701 | -428 106 -1378 | -2292 -626 * | -2200 -466 | -1473 -720 | -940 275 | -2240 394 | -17 45 | 2627 96 | -1386 359 | -1270 117 | 588 -369 | -2249 -294 | -1960 -249 | 421 |
| 416(V) | -1771 -149 -16 | -1603 -500 -7108 | -3750 233 -8150 | -3689 43 -894 | -2037 -381 -1115 | -3050 399 -701 | -3231 106 -1378 | 403 -626 * | -1154 -466 | -1076 -720 | -3246 275 | -3399 394 | -3383 45 | -3437 96 | -2628 359 | -1917 117 | 3536 -369 | -3074 -294 | -2677 -249 | 422 |
| 417(F) | -3342 -149 -16 | -2776 -500 -7108 | -4026 233 -8150 | -4232 43 -894 | 4354 -381 -1115 | -3545 399 -701 | -1431 106 -1378 | -2315 -626 * | -1801 -466 | -1900 -720 | -3299 275 | -3780 394 | -3350 45 | -3645 96 | -3490 359 | -3420 117 | -2566 -369 | -739 -294 | 349 -249 | 423 |

TABLE 6-continued

```
HMMER2.0 [2.2g]                                                    Program name and version
NAME dhad_for_hmm                                                  Name of the input sequence alignment file
LENG 564                                                           Length of the alignment: include indels
ALPH Amino                                                         Type of residues
MAP yes                                                            Map of the match states to the columns of the alignment
COM /app/public/hmmer/current/bin/hmmbuild -F dhad-exp_hmm dhad_for_hmm.aln   Commands used to generate the file: this one means that hmmbuild (default patrameters) was applied to the alignment file
COM /app/public/hmmer/current/bin/hmmcalibrate dhad-exp_hmm        Commands used to generate the file: this one means that hmmcalibrate (default parameters) was applied to the hmm profile
NSEQ 8                                                             Number of sequences in the alignment file
DATE Tue Jun 3 10:48:24 2008                                       When was the file generated
XT -8455 -4 -1000 -1000 -8455 -4 -8455 -4
NULT -4 -8455                                                      The transition probability distribution for the null model (single G state).
NULE 595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                                 probability used to convert these back to model probabilities is 1/K.
EVD -499.650970 0.086142                                           The extreme value distribution parameters μ and lambda respectively; both floating point values. Lambda is positive and
                                                                   nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 418(D) | -1572 | -3426 | 2573 | 2447 | -3613 | -1583 | -879 | -3513 | -3393 | -2684 | 1292 | -2085 | -535 | -1855 | -1253 | -1623 | -3000 | -3585 | -2609 | 424 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 419(S) | -879 | -1989 | 1498 | -177 | -3045 | 1600 | -939 | -2843 | -2867 | -2046 | -438 | -1922 | -591 | -1483 | 2171 | -1044 | -2226 | -3072 | -2372 | 425 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 420(E) | -2641 | -3308 | -896 | 3732 | -3966 | -2458 | -2043 | -4105 | -4016 | -3555 | -1531 | -2959 | -1842 | -2560 | -2479 | -2750 | -3722 | -3563 | -3385 | 426 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 421(Q) | -705 | -1925 | -199 | 2112 | 917 | -1534 | -288 | -1824 | -1842 | -1054 | -210 | -1709 | 2163 | -420 | -611 | -656 | -1502 | -1997 | -1291 | 427 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 422(H) | -569 | -2048 | 1450 | 1526 | -2349 | -1405 | 1830 | -2103 | -2058 | -1157 | -37 | -1569 | 272 | -349 | 713 | 620 | -1662 | -2240 | -1537 | 428 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 423(C) | 1626 | 2878 | -2671 | -2107 | 1264 | -1968 | -1091 | 233 | -334 | 250 | -1672 | -2128 | -1459 | -1691 | -1096 | -529 | 1209 | -1066 | -704 | 429 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 424(M) | -2042 | -1634 | -4379 | -3826 | -659 | -3976 | -2899 | 2765 | 1204 | 3085 | -3605 | -3604 | -2896 | -3318 | -3183 | -1961 | 195 | -2135 | -2058 | 430 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 425(E) | 412 | -2447 | 1356 | 2379 | -2747 | -1477 | -445 | -2527 | -2477 | -1622 | -107 | 855 | -36 | -831 | -730 | -894 | -2073 | -2668 | -1906 | 431 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 426(A) | 2822 | -1031 | -2418 | -2539 | -3226 | 1898 | -2364 | -2941 | -3229 | -2379 | -1722 | -2026 | -2302 | -2634 | -654 | -848 | -1983 | -3415 | -3226 | 432 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 427(I) | -1772 | -1325 | -4307 | -3877 | -1405 | -3993 | -3383 | 2935 | 820 | -217 | -3632 | -3761 | -3400 | -3682 | -3260 | -1742 | 2033 | -2838 | -2525 | 433 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 428(L) | -875 | -1634 | -575 | 959 | -1581 | -1769 | -525 | -1179 | 1884 | -625 | -547 | -1931 | 1405 | -450 | -909 | -816 | -1074 | -1883 | -1383 | 434 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

| | | | | | | | | | | | |
|---|---|---|---|---|---|---|---|---|---|---|---|
| HMMER2.0 [2.2g] | | | | | | | Program name and version | | | | |
| NAME dhad_for_hmm | | | | | | | Name of the input sequence alignment file | | | | |
| LENG 564 | | | | | | | Length of the alignment | | | | |
| ALPH Amino | | | | | | | Type of residues | | | | |
| MAP yes | | | | | | | Map of the match states to the columns of the alignment | | | | |
| COM /app/public/hmmer/current/bin/hmmbuild -F dhad-exp_hmm dhad_for_hmm.aln | | | | | | | Commands used to generate the file: this one means that hmmbuild (default parameters) was applied to the alignment file | | | | |
| COM /app/public/hmmer/current/bin/hmmcalibrate dhad-exp_hmm | | | | | | | Commands used to generate the file: this one means that hmmcalibrate (default parameters) was applied to the hmm profile | | | | |
| NSEQ 8 | | | | | | | Number of sequences in the alignment file | | | | |
| DATE Tue Jun 3 10:48:24 2008 | | | | | | | When was the file generated | | | | |
| XT -8455 -4 -1000 -1000 -8455 -4 -8455 -4 | | | | | | | | | | | |
| NULT -4 -8455 | | | | | | | The transition probability distribution for the null model (single G state). | | | | |
| NULE 595 -1558 85 338 -294 453 -1158 197 249 902 -1085 -142 -21 -313 45 531 201 384 -1998 -644 | | | | | | | The symbol emission probability distribution for the null model (G state); consists of K (e.g 4 or 20) integers. The null probability used to convert these back to model probabilities is 1/K. | | | | |
| EVD -499.650970 0.086142 | | | | | | | The extreme value distribution parameters μ and lambda respectively; both floating point values. Lambda is positive and nonzero. These values are set when the model is calibrated with hmmcalibrate. | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 429(A) | 1705 -149 -16 | -1826 -500 -7108 | -180 233 -8150 | 949 43 -894 | -2318 -381 -1115 | -1410 399 -701 | -359 106 -1378 | -2041 -626 * | -2067 -466 | -1204 -720 | 1001 275 | -1652 394 | 52 45 | -561 96 | 1232 359 | -595 117 | -1609 -369 | -2298 -294 | -1643 -249 | 435 |
| 430(D) | -1074 -149 -16 | -2458 -500 -7108 | 2381 233 -8150 | 80 43 -894 | -2921 -381 -1115 | 1927 399 -701 | -658 106 -1378 | -2710 -626 * | -2675 -466 | -1860 -720 | -271 275 | -1918 394 | -276 45 | 866 96 | -915 359 | -1100 117 | -2245 -369 | -2845 -294 | -2124 -249 | 436 |
| 431(K) | -688 -149 -16 | -2117 -500 -7108 | 785 233 -8150 | 888 43 -894 | -2469 -381 -1115 | -1529 399 -701 | -187 106 -1378 | -2189 -626 * | -2106 -466 | -1221 -720 | -162 275 | -1661 394 | 256 45 | 1134 96 | -553 359 | -619 117 | -1760 -369 | -2240 -294 | -1607 -249 | 437 |
| 432(I) | -2019 -149 -16 | -1582 -500 -7108 | -4380 233 -8150 | -3941 43 -894 | -1000 -381 -1115 | -4086 399 -701 | -3253 106 -1378 | 3295 -626 * | 1100 -466 | 145 -720 | -3736 275 | -3783 394 | -3222 45 | -3556 96 | -3378 359 | -1976 117 | 657 -369 | -2517 -294 | -2289 -249 | 438 |
| 433(Q) | -490 -149 -16 | -1797 -500 -7108 | -369 233 -8150 | 171 43 -894 | -2078 -381 -1115 | -1457 399 -701 | 1762 106 -1378 | -1779 -626 * | -1780 -466 | -905 -720 | 1165 275 | -1550 394 | 1798 45 | -48 96 | -396 359 | -422 117 | 725 -369 | -1986 -294 | -1366 -249 | 439 |
| 434(A) | 1954 -149 -16 | -1836 -500 -7108 | 1733 233 -8150 | -180 43 -894 | -2714 -381 -1115 | -1429 399 -701 | -806 106 -1378 | -2438 -626 * | -2518 -466 | -1698 -720 | -430 275 | 1775 394 | -448 45 | -1211 96 | -736 359 | -894 117 | -1923 -369 | -2765 -294 | -2117 -249 | 440 |
| 435(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 441 |
| 436(D) | -1736 -149 -16 | -3455 -500 -7108 | 3490 233 -8150 | -3874 43 -894 | -3737 -381 -1115 | -1646 399 -701 | -1070 106 -1378 | -3753 -626 * | -3647 -466 | -3016 -720 | 1602 275 | -2204 394 | -760 45 | -2218 96 | -1420 359 | -1838 117 | -3213 -369 | -3756 -294 | -2780 -249 | 442 |
| 437(V) | -1721 -149 -16 | -1302 -500 -7108 | -4229 233 -8150 | 97 43 -894 | -1705 -381 -1115 | -3894 399 -701 | -3582 106 -1378 | 1607 -626 * | -582 -466 | -513 -720 | -3610 275 | -3786 394 | -3559 45 | -3767 96 | -3209 359 | -1725 117 | 3294 -369 | -3158 -294 | -2712 -249 | 443 |
| 438(V) | 594 -149 -16 | -988 -500 -7108 | -3391 233 -8150 | -2911 43 -894 | -1164 -381 -1115 | -2888 399 -701 | -2187 106 -1378 | 845 -626 * | 765 -466 | -154 -720 | -2576 275 | -2962 394 | -2387 45 | -2622 96 | -2074 359 | -1205 117 | 2800 -369 | -2084 -294 | -1724 -249 | 444 |
| 439(V) | -1771 -149 -16 | -1603 -500 -7108 | -3750 233 -8150 | -3689 43 -894 | -2037 -381 -1115 | -3050 399 -701 | -3231 106 -1378 | 403 -626 * | -1154 -466 | -1076 -720 | -3246 275 | -3399 394 | -3383 45 | -3437 96 | -2628 359 | -1917 117 | 3536 -369 | -3074 -294 | -2677 -249 | 445 |

TABLE 6-continued

| HMMER2.0 [2.2g] | | | | | | | | | | | | | Program name and version |
|---|---|---|---|---|---|---|---|---|---|---|---|---|---|
| NAME dhad_for_hmm | | | | | | | | | | | | | Name of the input sequence alignment file |
| LENG 564 | | | | | | | | | | | | | Length of the alignment: include indels |
| ALPH Amino | | | | | | | | | | | | | Type of residues |
| MAP yes | | | | | | | | | | | | | Map of the match states to the columns of the alignment |
| COM /app/public/hmmer/current/bin/hmmbuild -F dhad-exp_hmm dhad_for_hmm.aln | | | | | | | | | | | | | Commands used to generate the file: this one means that hmmbuild (default patrameters) was applied to the alignment file |
| COM /app/public/hmmer/current/bin/hmmcalibrate dhad-exp_hmm | | | | | | | | | | | | | Commands used to generate the file: this one means that hmmcalibrale (default parametrs) was applied to the hmm profile |
| NSEQ 8 | | | | | | | | | | | | | Number of sequences in the alignment file |
| DATE Tue Jun 3 10:48:24 2008 | | | | | | | | | | | | | When was the file generated |
| XT -8455 -4 -1000 -1000 -8455 -4 -8455 -4 | | | | | | | | | | | | | |
| NULT -4 -8455 | | | | | | | | | | | | | The transition probability distribution for the null model (single G state). |
| NULE 595 -1558 85 338 -294 453 -1158 197 249 902 -1085 -142 -21 -313 45 531 201 384 -1998 -644 | | | | | | | | | | | | | The symbol emission probability distribution for the null model (G state); consists of K (e.g 4 or 20) integers. The null probability used to convert these back to model probabilities is 1/K. |
| EVD -499.650970 0.086142 | | | | | | | | | | | | | The extreme value distribution parameters μ and lambda respectively; both floating point values. Lambda is positive and nonzero. These values are set when the model is calibrated with hmmcalibrate. |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 440(I) | -1754 -149 -16 | -1308 -500 -7108 | -4295 233 -8150 | -3867 43 -894 | -1434 -381 -1115 | -3978 399 -701 | -3377 106 -1378 | 2661 -626 * | 862 -466 | -247 -720 | -3617 275 | -3754 394 | -3406 45 | -3679 96 | -3243 359 | -1725 117 | 2373 -369 | -2852 -294 | -2526 -249 | 446 |
| 441(R) | -2957 -149 -16 | -3022 -500 -7108 | -3318 233 -8150 | -2735 43 -894 | -3796 -381 -1115 | -2998 399 -701 | -1968 106 -1378 | -3912 -626 * | -3631 -466 | -3157 -720 | -2611 275 | -3280 394 | -1724 45 | 4056 96 | -3026 359 | -2913 117 | -3650 -369 | -3096 -294 | -3185 -249 | 447 |
| 442(Y) | -1321 -149 -16 | -1438 -500 -7108 | -1994 233 -8150 | -1608 43 -894 | 2186 -381 -1115 | 527 399 -701 | -450 106 -1378 | -1117 -626 * | -1211 -466 | -693 -720 | 1178 275 | -2522 394 | -1217 45 | -1665 96 | -1518 359 | -1275 117 | -1021 -369 | -198 -294 | 3178 -249 | 448 |
| 443(C) | -675 -149 -16 | 2205 -500 -7108 | -2544 233 -8150 | 972 43 -894 | -572 -381 -1115 | -2236 399 -701 | -1121 106 -1378 | 1373 -626 * | 679 -466 | 261 -720 | -1700 275 | -2270 394 | -1403 45 | -1668 96 | -1311 359 | -621 117 | 1601 -369 | -1150 -294 | -790 -249 | 449 |
| 444(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 450 |
| 445(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 451 |
| 446(K) | -1060 -149 -16 | -2058 -500 -7108 | -1088 233 -8150 | -460 43 -894 | -2432 -381 -1115 | -1917 399 -701 | -357 106 -1378 | -1970 -626 * | -1978 -466 | -1220 -720 | -632 275 | -1990 394 | 1339 45 | 367 96 | -999 359 | -946 117 | 536 -369 | -2145 -294 | -1717 -249 | 452 |
| 447(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 453 |
| 448(G) | -2594 -149 -16 | -2690 -500 -7108 | -3304 233 -8150 | -3623 43 -894 | -4328 -351 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 454 |
| 449(P) | -2931 -149 -16 | -2878 -500 -7108 | -3420 233 -8150 | -3706 43 -894 | -4181 -381 -1115 | -2925 399 -701 | -3468 106 -1378 | -4621 -626 * | -4490 -466 | -4165 -720 | -3491 275 | 4225 394 | -3781 45 | -3695 96 | -3182 359 | -3279 117 | -4087 -369 | -3594 -294 | -4064 -249 | 455 |
| 450(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 456 |

TABLE 6-continued

| | | | | | | | | | | | | | | | | | | | | | | | | | |
|---|---|---|---|---|---|---|---|---|---|---|---|---|---|---|---|---|---|---|---|---|---|---|---|---|---|
| HMMER2.0 [2.2g] | | | | | | | | | | Program name and version | | | | | | | | | | | | | | | |
| NAME dhad_for_hmm | | | | | | | | | | Name of the input sequence alignment file | | | | | | | | | | | | | | | |
| LENG 564 | | | | | | | | | | Length of the alignment | | | | | | | | | | | | | | | |
| ALPH Amino | | | | | | | | | | Type of residues | | | | | | | | | | | | | | | |
| MAP yes | | | | | | | | | | Map of the match states to the columns of the alignment | | | | | | | | | | | | | | | |
| COM /app/public/hmmer/current/bin/hmmbuild -F dhad-exp_hmm dhad_for_hmm.aln | | | | | | | | | | Commands used to generate the file: this one means that hmmbuild (default parameters) was applied to the alignment file | | | | | | | | | | | | | | | |
| COM /app/public/hmmer/current/bin/hmmcalibrate dhad-exp_hmm | | | | | | | | | | Commands used to generate the file: this one means that hmmcalibrate (default parameters) was applied to the hmm profile | | | | | | | | | | | | | | | |
| NSEQ 8 | | | | | | | | | | Number of sequences in the alignment file | | | | | | | | | | | | | | | |
| DATE Tue Jun 3 10:48:24 2008 | | | | | | | | | | When was the file generated | | | | | | | | | | | | | | | |
| XT -8455 -4 -1000 -1000 -8455 -4 -8455 -4 | | | | | | | | | | | | | | | | | | | | | | | | | |
| NULT -4 -8455 | | | | | | | | | | The transition probability distribution for the null model (single G state). | | | | | | | | | | | | | | | |
| NULE 595 -1558 85 338 -294 453 -1158 197 249 902 -1085 -142 -21 -313 45 531 | | | | | | | | | | The symbol emission probability distribution for the null model (G state); consists of K (e.g 4 or 20) integers. The null probability used to convert these back to model probabilities is 1/K. | | | | | | | | | | | | | | | |
| 201 384 -1998 -644 | | | | | | | | | | The extreme value distribution parameters μ and lambda respectively; both floating point values. Lambda is positive and nonzero. These values are set when the model is calibrated with hmmcalibrate. | | | | | | | | | | | | | | | |
| EVD -499.650970 0.086142 | | | | | | | | | | | | | | | | | | | | | | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 451(M) | -2406 | -2296 | -3638 | -3594 | -1525 | -3105 | -2824 | -1047 | -596 | 5043 | -3293 | -3425 | -3046 | -2996 | -2911 | -2552 | -1398 | -2513 | -2207 | 457 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 452(P) | -1659 | -2241 | -2022 | -1646 | -3185 | -2242 | -1373 | -3000 | -2936 | -2274 | -1624 | 3435 | -1065 | 2095 | -1730 | -1750 | -2593 | -2816 | -2613 | 458 |
| | -149 | -500 | 233 | -894 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 453(E) | -2641 | -3308 | -896 | 3732 | -3966 | -2458 | -2043 | -4105 | -4016 | -3555 | -1531 | -2959 | -1842 | -2560 | -2479 | -2750 | -3722 | -3563 | -3385 | 459 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 454(M) | -2406 | -2296 | -3638 | -3594 | -1525 | -3105 | -2824 | -1047 | -596 | 5043 | -3293 | -3425 | -3046 | -2996 | -2911 | -2552 | -1398 | -2513 | -2207 | 460 |
| | -149 | -500 | 233 | 43 | -381 | 399 | 106 | -626 | -466 | -720 | 276 | 394 | 45 | 96 | 359 | 117 | -369 | -294 | -249 | |
| | -16 | -7108 | -8150 | -894 | -1115 | -701 | -1378 | * | | | | | | | | | | | | |
| 455(L) | -2871 | -2457 | -4231 | -4103 | -1033 | -3803 | -3165 | -541 | 3130 | -31 | -3935 | -3797 | -3286 | -3484 | -3713 | -2869 | -1136 | -2394 | -2220 | 461 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 456(K) | 1366 | -1491 | -763 | -332 | -2319 | -1417 | -551 | -1998 | -2068 | -1221 | -500 | -1721 | -160 | -470 | 1631 | -587 | -1532 | -2299 | -1754 | 462 |
| | -149 | -500 | 233 | -894 | -381 | 399 | 106 | -626 | -466 | -726 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 457(P) | -1500 | -1738 | -2514 | -2380 | -1555 | -2358 | -2022 | -1126 | 1224 | -841 | -2189 | 3436 | -2061 | -2129 | -1822 | -1674 | -1231 | -2290 | -1878 | 463 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 458(T) | -351 | -974 | -2208 | -2185 | -2894 | -1237 | -2041 | -2561 | -2863 | -2046 | -1539 | -1948 | -1923 | -2218 | 1543 | 3230 | -1758 | -3139 | -2834 | 464 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 459(S) | -897 | -1462 | -2333 | -2543 | -3185 | -1640 | -2474 | -3294 | -3497 | -2780 | -1976 | -2360 | -2483 | -2703 | 3465 | -1316 | -2413 | -3310 | -3025 | 465 |
| | -149 | -500 | 233 | -894 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 460(M) | 2706 | -986 | -2433 | -2144 | -1502 | -1684 | -1706 | -700 | -968 | 2744 | -1705 | -2188 | -1713 | -1932 | -963 | -862 | -592 | -2145 | -1794 | 466 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |
| 461(I) | -2103 | -1659 | -4461 | -3992 | -869 | -4152 | -3233 | 3082 | 1619 | 290 | -3801 | -3788 | -3171 | -3557 | -3432 | -2046 | 487 | -2418 | -2265 | 467 |
| | -149 | -500 | 233 | 43 | -381 | 399 | 106 | -626 | -466 | -720 | 275 | 394 | 45 | 96 | 359 | 117 | -369 | -294 | -249 | |
| | -16 | -7108 | -8150 | -894 | -1115 | -701 | -1378 | * | | | | | | | | | | | | |

TABLE 6-continued

```
HMMER2.0 [2.2g]                                             Program name and version
NAME dhad_for_hmm                                           Name of the input sequence alignment file
LENG 564                                                    Length of the alignment
ALPH Amino                                                  Type of residues
MAP yes                                                     Map of the match states to the columns of the alignment
COM /app/public/hmmer/current/bin/hmmbuild -F dhad-exp_hmm dhad_for_hmm.aln    Commands used to generate the file: this one means that hmmbuild (default patrameters) was applied to the alignment file
COM /app/public/hmmer/current/bin/hmmcalibrate dhad-exp_hmm                    Commands used to generate the file: this one means that hmmcalibrale (default parameters) was applied to the hmm profile
NSEQ 8                                                      Number of sequences in the alignment file
DATE Tue Jun 3 10:48:24 2008                                When was the file generated
XT -8455 -4 -1000 -1000 -8455 -4 -8455 -4
NULT -4 -8455                                               The transition probability distribution for the null model (single G state).
NULE 595 -1558 85 338 -294 453 -1158 197 249 902 -1085 -142 -21 -313 45 531   The symbol emission probability distribution for the null model (G state); consists of K (e.g 4 or 20) integers. The null
201 384 -1998 -644                                          probability used to convert these back to model probabilities is 1/K.
EVD -499.650970 0.086142                                    The extreme value distribution parameters μ and lambda respectively; both floating point values. Lambda is positive and
                                                            nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 462(I) | -1761 -149 -16 | -1312 -500 -7108 | -4317 233 -8150 | -3954 43 -894 | -1713 -381 -1115 | -4027 399 -701 | -2703 106 -1378 | 3225 -626 * | -556 -466 | -498 -720 | -3712 275 | -3859 394 | -3653 45 | -3877 96 | -3344 359 | -1754 117 | 2110 -369 | -3216 -294 | -2787 -249 | 468 |
| 463(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 469 |
| 464(K) | 1641 -149 -16 | -2033 -500 -7108 | -323 233 -8150 | 914 43 -894 | -2415 -381 -1115 | -1565 399 -701 | -296 106 -1378 | -2097 -626 * | -2080 -466 | -1233 -720 | -257 275 | -1736 394 | 125 45 | -133 96 | -646 359 | -702 117 | -1707 -369 | -2258 -294 | -1657 -249 | 470 |
| 465(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 471 |
| 466(L) | -1699 -149 -16 | -1807 -500 -7108 | -2268 233 -8150 | -1925 43 -894 | -830 -381 -1115 | -2795 399 -701 | -1551 106 -1378 | -455 -626 * | 2510 -466 | 90 -720 | -1958 275 | -2845 394 | 1927 45 | -1308 96 | -2067 359 | -1651 117 | -846 -369 | -1841 -294 | -1454 -249 | 472 |
| 467(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 473 |
| 468(D) | -853 -149 -16 | -2415 -500 -7108 | 2115 233 -8150 | 1717 43 -894 | -2702 -381 -1115 | -1468 399 -701 | -378 106 -1378 | -2484 -626 * | -2417 -466 | -1546 -720 | -84 275 | -1732 394 | 41 45 | -699 96 | 696 359 | -824 117 | -2025 -369 | -2594 -294 | -1839 -249 | 474 |
| 469(S) | -892 -149 -16 | -1780 -500 -7108 | -931 233 -8150 | -688 43 -894 | -2757 -381 -1115 | -1643 399 -701 | -830 106 -1378 | -2472 -626 * | -2492 -466 | -1708 -720 | -799 275 | -2018 394 | -468 45 | -365 96 | 2676 359 | -1004 117 | -1981 -369 | -2598 -294 | -2130 -249 | 475 |
| 470(C) | -1135 -149 -16 | 3503 -500 -7108 | -3700 233 -8150 | -3406 43 -894 | -1670 -381 -1115 | -2549 399 -701 | -2675 106 -1378 | 653 -626 * | -916 -466 | -667 -720 | -2727 275 | -2925 394 | -2870 45 | -3030 96 | -1868 359 | -1288 117 | 2927 -369 | -2619 -294 | -2222 -249 | 476 |
| 471(A) | 2590 -149 -16 | -1035 -500 -7108 | -2404 233 -8150 | -2530 43 -894 | -3236 -381 -1115 | 2290 399 -701 | -2365 106 -1378 | -2954 -626 * | -3240 -466 | -2389 -720 | -1719 275 | -2027 394 | -2302 45 | -2637 96 | -656 359 | -851 117 | -1991 -369 | -3423 -294 | -3234 -249 | 477 |
| 472(L) | -2632 -149 -16 | -2152 -500 -7108 | -4630 233 -8150 | -4185 43 -894 | 1767 -381 -1115 | -4324 399 -701 | -2442 106 -1378 | -61 -626 * | 2789 -466 | 563 -720 | -3833 275 | -3823 394 | -2970 45 | -3513 96 | -3609 359 | -2518 117 | -738 -369 | -1527 -294 | -945 -249 | 478 |

TABLE 6-continued

```
HMMER2.0 [2.2g]                                          Program name and version
NAME  dhad_for_hmm                                       Name of the input sequence alignment file
LENG  564                                                Length of the alignment
ALPH  Amino                                              Type of residues
MAP   yes                                                Map of the match states to the columns of the alignment
COM   /app/public/hmmer/current/bin/hmmbuild -F dhad-exp_hmm dhad_for_hmm.aln    Commands used to generate the file: this one means that hmmbuild (default parameters) was applied to the alignment file
COM   /app/public/hmmer/current/bin/hmmcalibrate dhad-exp_hmm                    Commands used to generate the file: this one means that hmmcalibrate (default parameters) was applied to the hmm profile
NSEQ  8                                                  Number of sequences in the alignment file
DATE  Tue Jun 3 10:48:24 2008                            When was the file generated
XT    -8455 -4 -1000 -1000 -8455 -4 -8455 -4
NULT  -4 -8455                                           The transition probability distribution for the null model (single G state).
NULE  595 -1558 85 338 -294 453 -1158 197 249 902 -1085 -142 -21 -313 45 531    The symbol emission probability distribution for the null model (G state); consists of K (e.g. 4 or 20) integers. The null
201 384 -1998 -644                                       probability used to convert these back to model probabilities is 1/K.
EVD   -499.650970 0.086142                               The extreme value distribution parameters μ and lambda respectively; both floating point values. Lambda is positive and
                                                         nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 473(I) | -2073 -149 -16 | -1632 -500 -7108 | -4434 233 -8150 | -3975 43 -894 | -911 -381 -1115 | -4130 399 -701 | -3238 106 -1378 | 3164 -626 * | 1451 -466 | 244 -720 | -3779 275 | -3785 394 | -3187 45 | -3557 96 | -3413 359 | -2021 117 | 546 -369 | -2449 -294 | -2273 -249 | 479 |
| 474(T) | -1213 -149 -16 | -1674 -500 -7108 | -2755 233 -8150 | -2906 43 -894 | -3163 -381 -1115 | -1922 399 -701 | -2659 106 -1378 | -2698 -626 * | -3105 -466 | -2612 -720 | -2311 275 | -2600 394 | -2708 45 | -2753 96 | -1463 359 | 3819 117 | -2197 -369 | -3286 -294 | -3156 -249 | 480 |
| 475(D) | -2784 -149 -16 | -3432 -500 -7108 | 4016 233 -8150 | -1200 43 -894 | -4140 -381 -1115 | -2466 399 -701 | -2197 106 -1378 | -4505 -626 * | -4365 -466 | -3956 -720 | -1551 275 | -3014 394 | -2039 45 | -3232 96 | -2593 359 | -2938 117 | -4046 -369 | -3710 -294 | -3552 -249 | 481 |
| 476(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 482 |
| 477(R) | -2957 -149 -16 | -3022 -500 -7108 | -3318 236 -8150 | -2735 43 -894 | -3796 -381 -1115 | -2998 399 -701 | -1968 106 -1378 | -3912 -626 * | -3631 -466 | -3157 -726 | -2611 275 | -3280 394 | -1724 45 | 4056 96 | -3026 359 | -2913 117 | -3650 -369 | -3096 -294 | -3185 -249 | 483 |
| 478(F) | -3342 -149 -16 | -2776 -500 -7108 | -4026 233 -8150 | -4232 43 -894 | 4354 -381 -1115 | -3545 394 -701 | -1431 106 -1378 | -2315 -626 * | -1801 -466 | -1900 -720 | -3299 275 | -3780 394 | -3350 45 | -3645 96 | -3490 359 | -3420 117 | -2566 -369 | -739 -294 | 349 -249 | 484 |
| 479(S) | -897 -149 -16 | -1462 -500 -7108 | -2333 233 -8150 | -2543 43 -894 | -3185 -381 -1115 | -1640 399 -701 | -2474 106 -1378 | -3294 -626 * | -3497 -466 | -2780 -720 | -1973 275 | -2360 394 | -2483 45 | -2703 96 | 3465 359 | -1316 117 | -2413 -369 | -3310 -294 | -3025 -249 | 485 |
| 480(G) | -2594 -149 -16 | -2690 -500 -7108 | -3304 233 -8150 | -3623 43 -894 | -4328 -381 -1115 | 3747 395 -701 | -3462 106 -1378 | -4761 -626 * | -4671 -466 | -4212 -726 | -3320 275 | -3352 394 | -3748 45 | -3779 96 | -2839 359 | -2981 117 | -4004 -369 | -3668 -294 | -4222 -249 | 486 |
| 4811(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 354 | -2981 117 | -4004 -369 | -3668 -294 | -4222 -249 | 487 |
| 482(T) | -359 -149 -16 | -976 -500 -7108 | -2225 233 -8150 | -2229 43 -894 | -2900 -381 -1115 | -1242 394 -701 | -2074 106 -1378 | -2560 -626 * | -2875 -466 | -2064 -720 | -1561 275 | -1958 394 | -1969 45 | -2247 96 | 1110 359 | 3375 117 | -1760 -369 | -3152 -294 | -2850 -249 | 488 |
| 483(Y) | -3402 -149 -16 | -2632 -500 -7108 | -3941 233 -8150 | -4011 43 -894 | 1064 -381 -1115 | -3924 399 -701 | 3388 106 -1378 | -2526 -626 * | -1996 -466 | -1973 -720 | -2625 275 | -3821 394 | -2664 45 | -3170 96 | -3135 359 | -3280 117 | -2619 -369 | 3420 -294 | 3756 -249 | 489 |

TABLE 6-continued

| | |
|---|---|
| HMMER2.0 [2.2g] | Program name and version |
| NAME dhad_for_hmm | Name of the input sequence alignment file |
| LENG 564 | Length of the alignment: include indels |
| ALPH Amino | Type of residues |
| MAP yes | Map of the match states to the columns of the alignment |
| COM /app/public/hmmer/current/bin/hmmbuild -F dhad-exp_hmm dhad_for_hmm.aln | Commands used to generate the file: this one means that hmmbuild (default patrameters) was applied to the alignment file |
| COM /app/public/hmmer/current/bin/hmmcalibrate dhad-exp_hmm | Commands used to generate the file: this one means that hmmcalibrate (default parameters) was applied to the hmm profile |
| NSEQ 8 | Number of sequences in the alignment file |
| DATE Tue Jun 3 10:48:24 2008 | When was the file generated |
| XT -8455 -4 -1000 -1000 -8455 -4 -8455 -4 | |
| NULT -4 -8455 | |
| NULE 595 -1558 85 338 -294 453 -1158 197 249 902 -1085 -142 -21 -313 45 531 201 384 -1998 -644 | The transition probability distribution for the null model (single G state). The symbol emission probability distribution for the null model (G state); consists of K (e.g 4 or 20) integers. The null probability used to convert these back to model probabilities is 1/K. |
| EVD -499.650970 0.086142 | The extreme value distribution parameters μ and lambda respectively; both floating point values. Lambda is positive and nonzero. These values are set when the model is calibrated with hmmcalibrate. |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 484(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 490 |
| — | -149 | -500 | 233 | 43 | -381 | 359 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 485(M) | -2322 | -1904 | -4536 | -3951 | 2387 | -4112 | -2676 | 67 | 2034 | 3156 | -3710 | -3633 | -2803 | -3311 | -3309 | -2204 | -588 | -1794 | -1586 | 491 |
| — | -149 | -500 | 233 | 43 | -381 | 359 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 486(V) | -1771 | -1603 | -3750 | -3689 | -2037 | -3050 | -3231 | 403 | -1154 | -1076 | -3246 | -3399 | -3383 | -3437 | -2628 | -1917 | 3536 | -3074 | -2677 | 492 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 487(V) | -1771 | -1603 | -3750 | -3689 | -2037 | -3050 | -3231 | 403 | -1154 | -1076 | -3246 | -3399 | -3383 | -3437 | -2628 | -1917 | 3536 | -3074 | -2677 | 493 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 488(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 494 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 489(H) | -3205 | -3079 | -2723 | -2890 | -2110 | -3046 | 5295 | -4135 | -3813 | -3561 | -2886 | -3482 | -2833 | -2620 | -3291 | -3356 | -3895 | -2397 | -1681 | 495 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 490(V) | -1754 | -1297 | -4329 | -3968 | -1770 | -4053 | -3752 | 2604 | -621 | -545 | -3728 | -3878 | -3699 | -3917 | -3370 | -1746 | 2859 | -3276 | -2829 | 496 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 491(A) | 2587 | -828 | -2477 | -2155 | -1837 | -1468 | -1728 | -743 | -1564 | -954 | -1607 | -2033 | -1725 | -2034 | -738 | 1178 | 1108 | -2310 | -1972 | 497 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 492(P) | -2931 | -2878 | -3420 | -3706 | -4181 | -2925 | -3468 | -4621 | -4490 | -4165 | -3491 | 4225 | -3781 | -3695 | -3182 | -3279 | -4087 | -3594 | -4064 | 498 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 493(E) | -2641 | -3308 | -896 | 3732 | -3966 | -2458 | -2043 | -4105 | -4016 | -3555 | -1531 | -2959 | -1842 | -2560 | -2479 | -2750 | -3722 | -3563 | -3385 | 499 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |
| 494(A) | 3438 | -1472 | -2846 | -3040 | -3287 | -1726 | -2735 | -2840 | -3257 | -2662 | -2236 | -2447 | -2798 | -2944 | -1216 | -1387 | -2183 | -3405 | -3320 | 500 |
| — | -149 | -500 | 233 | 43 | -381 | 399 | 106 | -626 | -466 | -720 | 275 | 394 | 45 | 96 | 359 | 117 | -369 | -294 | -249 | |
| — | -16 | -7108 | -8150 | -894 | -1115 | -701 | -1378 | * | | | | | | | | | | | | |

TABLE 6-continued

```
HMMER2.0 [2.2g]                                                    Program name and version
NAME  dhad_for_hmm                                                 Name of the input sequence alignment file
LENG  564                                                          Length of the alignment: include indels
ALPH  Amino                                                        Type of residues
MAP   yes                                                          Map of the match states to the columns of the alignment
COM   /app/public/hmmer/current/bin/hmmbuild -F dhad-exp_hmm dhad_for_hmm.aln    Commands used to generate the file: this one means that hmmbuild (default parameters) was applied to the alignment file
COM   /app/public/hmmer/current/bin/hmmcalibrate dhad-exp_hmm                   Commands used to generate the file: this one means that hmmcalibrate (default parameters) was applied to the hmm profile
NSEQ  8                                                            Number of sequences in the alignment file
DATE  Tue Jun 3 10:48:24 2008                                      When was the file generated
XT    -8455 -4 -1000 -1000 -8455 -4 -8455 -4
NULT  -4 -8455                                                     The transition probability distribution for the null model (single G state).
NULE  595 -1558 85 338 -294 453 -1158 197 249 902 -1085 -142 -21 -313 45 531   The symbol emission probability distribution for the null model (G state); consists of K (e.g. 4 or 20) integers. The null
201 384 -1998 -644                                                 probability used to convert these back to model probabilities is 1/K.
EVD   -499.650970 0.086142                                         The extreme value distribution parameters μ and lambda respectively; both floating point values. Lambda is positive and
                                                                   nonzero. These values are set when the model is calibrated with hmmcalibrate.
```

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 495(Y) | -866 | -976 | -1863 | -1331 | 1353 | -2145 | 1318 | -556 | -771 | -173 | -1242 | -2197 | 1714 | -1301 | -1173 | -802 | 888 | -445 | 2749 | 501 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 496(D) | 417 | -1831 | 1647 | 1094 | -2065 | -1488 | -353 | -1618 | -1820 | -1019 | -189 | -1698 | 30 | -623 | -603 | -643 | 1629 | -2154 | -1520 | 502 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 497(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 503 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 498(G) | -2594 | -2690 | -3304 | -3623 | -4326 | 3747 | -3462 | -4761 | -4671 | -4212 | -3320 | -3352 | -3748 | -3779 | -2839 | -2981 | -4004 | -3668 | -4222 | 504 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 499(T) | 492 | -1190 | -706 | -181 | -1475 | 311 | -333 | -1099 | 71 | -509 | 570 | 1113 | -6 | -509 | -450 | 1123 | -835 | -1680 | -1161 | 505 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 500(I) | -2091 | -1746 | -3971 | -3840 | -1676 | -3532 | -3289 | 3684 | -659 | -693 | -3562 | -3674 | -3445 | -3521 | -3194 | -2146 | 449 | -2877 | -2493 | 506 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 501(A) | 3103 | -1036 | -2445 | -2572 | -3222 | 1051 | -2380 | -2930 | -3226 | -2381 | -1739 | -2034 | -2327 | -2648 | -664 | -857 | -1981 | -3412 | -3228 | 507 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 502(L) | -2239 | -1892 | -3711 | -3400 | 301 | -3520 | -1210 | -542 | 2564 | -35 | -2786 | -3395 | -2438 | -2750 | -2747 | -2165 | -945 | -573 | 2562 | 508 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 503(V) | -1757 | -1387 | -4101 | -3681 | -1174 | -3714 | -3031 | 880 | 1254 | -60 | -3407 | -3585 | -3094 | -3354 | -2984 | -1743 | 3014 | -2536 | -2219 | 509 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 504(Q) | -982 | -2251 | -866 | 971 | -2711 | -1822 | -252 | -2340 | -2194 | -1356 | -464 | -1885 | 2646 | 1632 | -858 | -863 | -1958 | -2245 | -1765 | 510 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 505(E) | -1162 | -2771 | 2137 | 2239 | -3046 | -1526 | -626 | -2849 | -2792 | -1983 | -145 | -1905 | -242 | -1192 | -940 | 1396 | -2385 | -2990 | -2169 | 511 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

```
HMMER2.0 [2.2g]                                                      Program name and version
NAME  dhad_for_hmm                                                   Name of the input sequence alignment file
LENG  564                                                            Length of the alignment: include indels
ALPH  Amino                                                          Type of residues
MAP   yes                                                            Map of the match states to the columns of the alignment
COM   /app/public/hmmer/current/bin/hmmbuild -F dhad-exp_hmm dhad_for_hmm.aln    Commands used to generate the file: this one means that hmmbuild (default patrameters) was applied to the alignment file
COM   /app/public/hmmer/current/bin/hmmcalibrate dhad-exp_hmm                    Commands used to generate the file: this one means that hmmcalibrate (default parameters) was applied to the hmm profile
NSEQ  8                                                              Number of sequences in the alignment file
DATE  Tue Jun 3 10:48:24 2008                                        When was the file generated
XT   -8455 -4 -1000 -1000 -8455 -4 -8455 -4
NULT -4 -8455                                                        The transition probability distribution for the null model (single G state).
NULE 595 -1558 85 338 -294 453 -1158 197 249 902 -1085 -142 -21 -313 45 531    The symbol emission probability distribution for the null model (G state); consists of K (e.g 4 or 20) integers. The null
201 384 -1998 -644                                                   probability used to convert these back to model probabilities is 1/K.
EVD -499.650970 0.086142                                             The extreme value distribution parameters μ and lambda respectively; both floating point values. Lambda is positive and
                                                                     nonzero. These values are set when the model is calibrated with hmmcalibrate.
```

| HMM | A<br>m -> m | C<br>m -> i | D<br>m -> d | E<br>i -> m | F<br>i -> i | G<br>d -> m | H<br>d -> d | I<br>b -> m | L | M | N | P | Q | R | S | T | V | W | Y | Position in alignment |
|---|---|---|---|---|---|---|---|---|---|---|---|---|---|---|---|---|---|---|---|---|
| 506(G) | -1707<br>-149<br>-16 | -2684<br>-500<br>-7108 | 1591<br>233<br>-8150 | -614<br>43<br>-894 | -3783<br>-381<br>-1115 | 3190<br>399<br>-701 | -1613<br>106<br>-1378 | -3795<br>-626<br>* | -3775<br>-466 | -3119<br>-720 | -915<br>275 | -2456<br>394 | -1358<br>45 | -2539<br>96 | -1610<br>359 | -1924<br>117 | -3150<br>-369 | -3636<br>-294 | -3124<br>-249 | 512 |
| 507(D) | -2784<br>-149<br>-16 | -3432<br>-500<br>-7108 | 4016<br>233<br>-8150 | -1200<br>-894 | -4140<br>-381<br>-1115 | -2466<br>399<br>-701 | -2197<br>106<br>-1378 | -4505<br>-626<br>* | -4365<br>-466 | -3956<br>-720 | -1551<br>275 | -3014<br>394 | -2039<br>45 | -3232<br>96 | -2593<br>359 | -2938<br>117 | -4046<br>-369 | -3710<br>-294 | -3552<br>-249 | 513 |
| 508(M) | -473<br>-149<br>-16 | -522<br>-500<br>-7108 | -1819<br>233<br>-8150 | -1236<br>-894 | -468<br>-381<br>-1115 | -1879<br>399<br>-701 | -687<br>106<br>-1378 | 1519<br>-626<br>* | 566<br>-466 | 1677<br>-720 | -1154<br>275 | -1937<br>394 | 836<br>45 | -1131<br>96 | 1079<br>359 | -413<br>117 | 102<br>-369 | -957<br>-294 | -585<br>-249 | 514 |
| 509(I) | -1761<br>-149<br>-16 | -1312<br>-500<br>-7108 | -4317<br>233<br>-8150 | -3954<br>-894 | -1713<br>-381<br>-1115 | -4027<br>399<br>-701 | -3703<br>106<br>-1378 | 3225<br>-626<br>* | -556<br>-466 | -498<br>-720 | -3712<br>275 | -3859<br>394 | -3653<br>45 | -3877<br>96 | -3344<br>359 | -1754<br>117 | 2110<br>-369 | -3216<br>-294 | -2787<br>-249 | 515 |
| 510(T) | 782<br>-149<br>-16 | -1467<br>-500<br>-7108 | -550<br>233<br>-8150 | 1029<br>-894 | -2202<br>-381<br>-1115 | -1425<br>399<br>-701 | -709<br>106<br>-1378 | -1791<br>-626<br>* | -1993<br>-466 | -1203<br>-720 | -528<br>275 | -1787<br>394 | -368<br>45 | -902<br>96 | -617<br>359 | 2685<br>117 | -1400<br>-369 | -2333<br>-294 | -1783<br>-249 | 516 |
| 511(I) | -1766<br>-149<br>-16 | -1333<br>-500<br>-7108 | -4283<br>233<br>-8150 | -3923<br>-894 | -1635<br>-381<br>-1115 | -3967<br>399<br>-701 | -3619<br>106<br>-1378 | 3388<br>-626<br>* | -473<br>-466 | -437<br>-720 | -3672<br>275 | -3822<br>394 | -3576<br>45 | -3804<br>96 | -3285<br>359 | -1764<br>117 | 1695<br>-369 | -3126<br>-294 | -2717<br>-249 | 517 |
| 512(D) | -2784<br>-149<br>-16 | -3432<br>-500<br>-7108 | 4016<br>233<br>-8150 | -1200<br>-894 | -4140<br>-381<br>-1115 | -2466<br>399<br>-701 | -2197<br>106<br>-1378 | -4505<br>-626<br>* | -4365<br>-466 | -3956<br>-726 | -1551<br>275 | -3014<br>394 | -2039<br>45 | -3232<br>96 | -2593<br>359 | -2938<br>117 | -4046<br>-369 | -3710<br>-294 | -3552<br>-249 | 518 |
| 513(A) | 2705<br>-149<br>-16 | -1451<br>-500<br>-7108 | -1036<br>233<br>-8150 | -913<br>-894 | -2506<br>-381<br>-1115 | -1504<br>399<br>-701 | -1143<br>106<br>-1378 | -2174<br>-626<br>* | -2337<br>-466 | -1613<br>-720 | -946<br>275 | -1993<br>394 | 2040<br>45 | -1061<br>96 | -809<br>359 | -910<br>117 | -1703<br>-369 | -2633<br>-294 | -2156<br>-249 | 519 |
| 514(H) | -615<br>-149<br>-16 | -1680<br>-500<br>-7108 | 1444<br>233<br>-8150 | 66<br>-894 | -1883<br>-381<br>-1115 | 168<br>399<br>-701 | 2650<br>106<br>-1378 | -1558<br>-626<br>* | -1691<br>-466 | -891<br>-720 | -223<br>275 | -1680<br>394 | 31<br>45 | -577<br>96 | -571<br>359 | -585<br>117 | 1267<br>-369 | -2007<br>-294 | -1397<br>-249 | 520 |
| 515(K) | -654<br>-149<br>-16 | -2006<br>-500<br>-7108 | -546<br>233<br>-8150 | 42<br>-894 | -2376<br>-381<br>-1115 | -1581<br>399<br>-701 | -133<br>106<br>-1378 | -2066<br>-626<br>* | -1987<br>-466 | -1107<br>-720 | 1132<br>275 | -1658<br>394 | 1043<br>45 | 1058<br>96 | -540<br>359 | 1180<br>117 | -1660<br>-369 | -2113<br>-294 | -1532<br>-249 | 521 |
| 516(N) | -933<br>-149<br>-16 | -2085<br>-500<br>-7108 | -946<br>233<br>-8150 | -284<br>-894 | -2472<br>-381<br>-1115 | -1822<br>399<br>-701 | -253<br>106<br>-1378 | -2090<br>-626<br>* | 76<br>-466 | -1204<br>-726 | 1918<br>275 | -1876<br>394 | 175<br>45 | 1799<br>96 | -841<br>359 | -817<br>117 | -1755<br>-369 | -2132<br>-294 | -1663<br>-249 | 522 |

TABLE 6-continued

| | | | | | | | | | | | | | | | | | | | | | | |
|---|---|---|---|---|---|---|---|---|---|---|---|---|---|---|---|---|---|---|---|---|---|---|
| HMMER2.0 [2.2g] | | | | | | | | | | | Program name and version | | | | | | | | | | | |
| NAME dhad_for_hmm | | | | | | | | | | | Name of the input sequence alignment file | | | | | | | | | | | |
| LENG 564 | | | | | | | | | | | Length of the alignment: include indels | | | | | | | | | | | |
| ALPH Amino | | | | | | | | | | | Type of residues | | | | | | | | | | | |
| MAP yes | | | | | | | | | | | Map of the match states to the columns of the alignment | | | | | | | | | | | |
| COM /app/public/hmmer/current/bin/hmmbuild -F dhad-exp_hmm dhad_for_hmm.aln | | | | | | | | | | | Commands used to generate the file: this one means that hmmbuild (default patrameters) was applied to the alignment file | | | | | | | | | | | |
| COM /app/public/hmmer/current/bin/hmmcalibrate dhad-exp_hmm | | | | | | | | | | | Commands used to generate the file: this one means that hmmcalibrate (default parametrs) was applied to the hmm profile | | | | | | | | | | | |
| NSEQ 8 | | | | | | | | | | | Number of sequences in the alignment file | | | | | | | | | | | |
| DATE Tue Jun 3 10:48:24 2008 | | | | | | | | | | | When was the file generated | | | | | | | | | | | |
| XT -8455 -4 -1000 -1000 -8455 -4 -8455 -4 | | | | | | | | | | | | | | | | | | | | | | |
| NULT -4 -8455 | | | | | | | | | | | The transition probability distribution for the null model (single G state). | | | | | | | | | | | |
| NULE 595 -1558 85 338 -294 453 -1158 197 249 902 -1085 -142 -21 -313 45 531 | | | | | | | | | | | The symbol emission probability distribution for the null model (G state); consists of K (e.g 4 or 20) integers. The null | | | | | | | | | | | |
| 201 384 -1998 -644 | | | | | | | | | | | probability used to convert these back to model probabilities is 1/K. | | | | | | | | | | | |
| EVD -499.650970 0.086142 | | | | | | | | | | | The extreme value distribution parameters μ and lambda respectively; both floating point values. Lambda is positive and | | | | | | | | | | | |
| | | | | | | | | | | | nonzero. These values are set when the model is calibrated with hmmcalibrate. | | | | | | | | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 517(E) | -416 -149 -16 | -987 -500 -7108 | -843 233 -8150 | 1107 48 -894 | -1070 -381 -1115 | -1583 399 -701 | -338 106 -1378 | -623 -626 * | 879 -466 | -172 -720 | -489 275 | -1679 394 | -94 45 | -565 96 | 544 359 | 813 117 | 265 -369 | -1379 -294 | -905 -249 | 523 |
| 518(I) | -2258 -149 -16 | -1804 -500 -7108 | -4588 233 -8150 | -4084 43 -894 | -706 -381 -1115 | -4269 399 -701 | -3231 106 -1378 | 2527 -626 * | 2292 -466 | 465 -720 | -3923 275 | -3814 394 | -3118 45 | -3570 96 | -3544 359 | -2181 117 | 190 -369 | -2303 -294 | -2237 -249 | 524 |
| 519(Q) | -477 -149 -16 | -1909 -500 -7108 | 958 233 -8156 | 282 43 -894 | -2211 -381 -1115 | -1389 399 -701 | 1484 106 -1378 | -1953 -626 * | -1921 -466 | -1018 -720 | -32 275 | -1517 394 | 2318 45 | -225 96 | 630 359 | 559 117 | -1525 -369 | -2110 -294 | -1430 -249 | 525 |
| 520(L) | -2127 -149 -16 | -1743 -500 -7108 | -4402 233 -8150 | -3796 43 -894 | 1257 -381 -1115 | -3918 399 -701 | -2674 106 -1378 | 149 -626 * | 2527 -466 | 2164 -720 | -3553 275 | -3509 394 | -2714 45 | -3181 96 | -3095 359 | -2019 117 | 570 -369 | -1870 -294 | -1816 -249 | 526 |
| 521(N) | -723 -149 -16 | -2217 -500 -7108 | 958 233 -8150 | 236 43 -894 | -2518 -381 -1115 | -1466 399 -701 | 1611 106 -1378 | -2279 -626 * | -2217 -466 | -1334 -720 | 2285 275 | -1666 394 | 166 45 | -401 96 | -570 359 | -677 117 | -1837 -369 | -2382 -294 | -1678 -249 | 527 |
| 522(V) | -1754 -149 -16 | -1297 -500 -7108 | -4330 233 -8150 | -3968 43 -894 | -1770 -381 -1115 | -4053 399 -701 | -3752 106 -1378 | 2623 -626 * | -620 -466 | -545 -720 | -3729 275 | -3878 394 | -3699 45 | -3918 96 | -3371 359 | -1746 117 | -2846 -369 | -3277 -294 | -2830 -249 | 528 |
| 523(S) | 1545 -149 -16 | -974 -500 -7108 | -2003 233 -8150 | -1825 43 -894 | -2867 -381 -1115 | -1206 399 -701 | -1790 106 -1378 | -2580 -626 * | -2795 -466 | -1932 -720 | -1362 275 | 1826 394 | -1586 45 | -999 96 | 2362 359 | -672 117 | -1755 -369 | -3057 -294 | -2721 -249 | 529 |
| 524(D) | -1776 -149 -16 | -3649 -500 -7108 | 3326 233 -8150 | 1869 43 -894 | -3838 -381 -1115 | -1642 399 -701 | -1031 106 -1378 | -3788 -626 * | -3660 -466 | -3029 -720 | -245 275 | -2192 394 | -711 45 | -2201 96 | -1425 359 | -1855 117 | -3264 -369 | -3821 -294 | -2816 -249 | 530 |
| 525(E) | 423 -149 -16 | -2950 -500 -7108 | 1944 233 -8150 | 2696 43 -894 | -3223 -381 -1115 | -1545 399 -701 | -718 106 -1378 | -3047 -626 * | -2979 -466 | -2196 -720 | -161 275 | -1968 394 | -347 45 | -1403 96 | -1043 359 | -1314 117 | -2569 -369 | -3177 -294 | -2316 -249 | 531 |
| 526(E) | -2641 -149 -16 | -3308 -500 -7108 | -896 233 -8150 | 3732 43 -894 | -3966 -381 -1115 | -2458 399 -701 | -2043 106 -1378 | -4105 -626 * | -4016 -466 | -3555 -720 | -1531 275 | -2959 394 | -1842 45 | -2560 96 | -2479 359 | -2750 117 | -3722 -389 | -3563 -294 | -3385 -249 | 532 |
| 527(L) | -2339 -149 -16 | -1899 -500 -7108 | -4618 233 -8150 | -4042 43 -894 | 1570 -381 -1115 | -4204 399 -701 | -2849 106 -1378 | 1440 -626 * | 2558 -466 | 676 -720 | -3825 275 | -3700 394 | -2902 45 | -3418 96 | -3418 359 | -2226 117 | -382 -369 | -1924 -294 | -1778 -249 | 533 |

TABLE 6-continued

```
HMMER2.0 [2.2g]                                              Program name and version
NAME  dhad_for_hmm                                           Name of the input sequence alignment file
LENG  564                                                    Length of the alignment: include indels
ALPH  Amino                                                  Type of residues
MAP   yes                                                    Map of the match states to the columns of the alignment
COM   /app/public/hmmer/current/bin/hmmbuild -F dhad-exp_hmm dhad_for_hmm.aln   Commands used to generate the file: this one means that hmmbuild (default parameters) was applied to the alignment file
COM   /app/public/hmmer/current/bin/hmmcalibrate dhad-exp_hmm                    Commands used to generate the file: this one means that hmmcalibrate (default parameters) was applied to the hmm profile
NSEQ  8                                                      Number of sequences in the alignment file
DATE  Tue Jun 3 10:48:24 2008                                When was the file generated
XT    -8455 -4 -1000 -1000 -8455 -4 -8455 -4
NULT  -4 -8455                                               The transition probability distribution for the null model (single G state).
NULE  595 -1558 85 338 -294 453 -1158 197 249 902 -1085 -142 -21 -313 45 531    The symbol emission probability distribution for the null model (G state); consists of K (e.g. 4 or 20) integers. The null
201 384 -1998 -644                                           probability used to convert these back to model probabilities is 1/K.
EVD   -499.650970 0.086142                                   The extreme value distribution parameters μ and lambda respectively; both floating point values. Lambda is positive and
                                                             nonzero. These values are set when the model is calibrated with hmmcalibrate.
```

| HMM | A<br>m→m<br>m→i | C<br>m→i<br>m→d | D<br>m→d<br>i→m | E<br>i→m<br>i→i | F<br>i→i<br>i→d | G<br>d→m<br>d→d | H<br>d→d<br>b→m | I<br>b→m | L | M | N | P | Q | R | S | T | V | W | Y | Position in alignment |
|---|---|---|---|---|---|---|---|---|---|---|---|---|---|---|---|---|---|---|---|---|
| 528(A) | 2338<br>-149<br>-16 | -1990<br>-500<br>-7108 | -241<br>233<br>-8150 | 938<br>43<br>-894 | -2395<br>-381<br>-1115 | -1557<br>399<br>-701 | -423<br>106<br>-1378 | -2061<br>-626<br>* | -2103<br>-466 | -1286<br>-720 | -301<br>275 | -1791<br>394 | -26<br>45 | -375<br>96 | -717<br>359 | -784<br>117 | -1691<br>-369 | -2330<br>-294 | -1728<br>-249 | 534 |
| 529(R) | 524<br>-149<br>-16 | -2098<br>-500<br>-7108 | -789<br>233<br>-8150 | -146<br>43<br>-894 | -2504<br>-381<br>-1115 | -1729<br>399<br>-701 | 1632<br>106<br>-1378 | -2153<br>-626<br>* | -2054<br>-466 | -1204<br>-720 | -379<br>275 | -1789<br>394 | 1328<br>45 | 2313<br>96 | -719<br>359 | -724<br>117 | -1774<br>-369 | -2150<br>-294 | -1637<br>-249 | 535 |
| 530(R) | -2957<br>-149<br>-16 | -3022<br>-500<br>-7108 | -3318<br>233<br>-8150 | -2735<br>43<br>-894 | -3796<br>-381<br>-1115 | -2998<br>399<br>-701 | -1968<br>106<br>-1378 | -3912<br>-626<br>* | -3631<br>-466 | -3157<br>-720 | -2611<br>275 | -3280<br>394 | -1724<br>45 | 4056<br>96 | -3026<br>359 | -2913<br>117 | -3650<br>-369 | -3096<br>-294 | -3185<br>-249 | 536 |
| 531(R) | -1895<br>-149<br>-16 | -2713<br>-500<br>-7108 | -2327<br>233<br>-8150 | -1192<br>43<br>-894 | -3484<br>-381<br>-1115 | -2502<br>399<br>-701 | -481<br>106<br>-1378 | -2856<br>-626<br>* | -2544<br>-466 | -1842<br>-720 | -1161<br>275 | -2458<br>394 | 1393<br>45 | 3023<br>96 | -1770<br>359 | -1619<br>117 | -2599<br>-369 | -2421<br>-294 | -2259<br>-249 | 537 |
| 532(A) | 2935<br>-149<br>-16 | -1714<br>-500<br>-7108 | -553<br>233<br>-8150 | 857<br>43<br>-894 | -2769<br>-381<br>-1115 | -1546<br>399<br>-701 | -1218<br>106<br>-1378 | -2333<br>-626<br>* | -2591<br>-466 | -1873<br>-720 | -809<br>275 | -2065<br>394 | -934<br>45 | -1502<br>96 | -954<br>359 | -1103<br>117 | -1872<br>-369 | -2898<br>-294 | -2374<br>-249 | 538 |
| 533(A) | 1291<br>-149<br>-16 | -1874<br>-500<br>-7108 | -176<br>233<br>-8150 | 1227<br>43<br>-894 | -2177<br>-381<br>-1115 | -1392<br>399<br>-701 | -109<br>106<br>-1378 | -1909<br>-626<br>* | -1891<br>-466 | -995<br>-720 | 1134<br>275 | -1522<br>394 | 1248<br>45 | -228<br>96 | -361<br>359 | 562<br>117 | -1492<br>-369 | -2090<br>-294 | -1419<br>-249 | 539 |
| 534(W) | -805<br>-149<br>-16 | -687<br>-500<br>-7108 | -2581<br>233<br>-8150 | -2028<br>43<br>-894 | 138<br>-381<br>-1115 | -2236<br>399<br>-701 | -697<br>106<br>-1378 | 897<br>-626<br>* | -421<br>-466 | 141<br>-720 | -1645<br>275 | -2282<br>394 | -1369<br>45 | -1627<br>96 | -1315<br>359 | 636<br>117 | -90<br>-369 | 4479<br>-294 | 1809<br>-249 | 540 |
| 535(H) | -408<br>-149<br>-16 | -1801<br>-500<br>-7108 | -274<br>233<br>-8150 | 1284<br>43<br>-894 | -2096<br>-381<br>-1115 | -1385<br>399<br>-701 | 1500<br>106<br>-1378 | -1822<br>-626<br>* | -1802<br>-466 | -899<br>-720 | -33<br>275 | -1479<br>394 | 1381<br>45 | -102<br>96 | -303<br>359 | 595<br>117 | 221<br>-369 | -1996<br>-294 | -1339<br>-249 | 541 |
| 536(Q) | -650<br>-149<br>-16 | -1737<br>-500<br>-7108 | -627<br>233<br>-8150 | -72<br>43<br>-894 | -1981<br>-381<br>-1115 | -1615<br>399<br>-701 | -209<br>106<br>-1378 | -1625<br>-626<br>* | 392<br>-466 | -866<br>-726 | -318<br>275 | 1222<br>394 | 2120<br>45 | 50<br>96 | -598<br>359 | -572<br>117 | -1326<br>-369 | -1932<br>-294 | -1394<br>-249 | 542 |
| 537(P) | -2931<br>-149<br>-324 | -2878<br>-500<br>-7108 | -3420<br>233<br>-2368 | -3706<br>43<br>-894 | -4181<br>-381<br>-1115 | -2925<br>399<br>-701 | -3468<br>106<br>-1378 | -4621<br>-626<br>* | -4490<br>-466 | -4165<br>-720 | -3491<br>275 | 4225<br>394 | -3781<br>45 | -3695<br>96 | -3182<br>359 | -3279<br>117 | -4087<br>-369 | -3594<br>-294 | -4064<br>-249 | 543 |
| 538(A) | 2195<br>-149<br>-19 | -924<br>-500<br>-6408 | -968<br>233<br>-7846 | -546<br>43<br>-894 | -1397<br>-381<br>-1115 | -1356<br>399<br>-428 | -583<br>106<br>-1961 | -812<br>-626<br>* | -1167<br>-466 | -487<br>-720 | -618<br>275 | -1660<br>394 | 1324<br>45 | -684<br>96 | -483<br>359 | -404<br>117 | 462<br>-369 | -1703<br>-294 | -1242<br>-249 | 544 |

TABLE 6-continued

| | | | | | | | | | | | |
|---|---|---|---|---|---|---|---|---|---|---|---|
| HMMER2.0 [2.2g] | | | | | | Program name and version | | | | | |
| NAME dhad_for_hmm | | | | | | Name of the input sequence alignment file | | | | | |
| LENG 564 | | | | | | Length of the alignment: include indels | | | | | |
| ALPH Amino | | | | | | Type of residues | | | | | |
| MAP yes | | | | | | Map of the match states to the columns of the alignment | | | | | |
| COM /app/public/hmmer/current/bin/hmmbuild -F dhad-exp_hmm dhad_for_hmm.aln | | | | | | Commands used to generate the file: this one means that hmmbuild (default patrameters) was applied to the alignment file | | | | | |
| COM /app/public/hmmer/current/bin/hmmcalibrate dhad-exp_hmm | | | | | | Commands used to generate the file: this one means that hmmcalibrate (default parameters) was applied to the hmm profile | | | | | |
| NSEQ 8 | | | | | | Number of sequences in the alignment file | | | | | |
| DATE Tue Jun 3 10:48:24 2008 | | | | | | When was the file generated | | | | | |
| XT -8455 -4 -1000 -1000 -8455 -4 -8455 -4 | | | | | | | | | | | |
| NULT -4 -8455 | | | | | | | | | | | |
| NULE 595 -1558 85 338 -294 453 -1158 197 249 902 -1085 -142 -21 -313 45 531 201 384 -1998 -644 | | | | | | The transition probability distribution for the null model (single G state). The symbol emission probability distribution for the null model (G state); consists of K (e.g 4 or 20) integers. The null probability used to convert these back to model probabilities is 1/K. | | | | | |
| EVD -499.650970 0.086142 | | | | | | The extreme value distribution parameters μ and lambda respectively; both floating point values. Lambda is positive and nonzero. These values are set when the model is calibrated with hmmcalibrate. | | | | | |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| | | | | | | | | | | | | | | | | | | | | |
| 539(P) | 411 -149 -16 | -1017 -500 -7108 | -1886 233 -8150 | -1616 43 -894 | -1600 -381 -1115 | -1588 399 -701 | -1411 106 -1378 | -962 -626 * | 495 -466 | -755 -720 | -1384 275 | 3156 394 | -1323 45 | -1577 96 | -847 359 | -785 117 | -783 -369 | -2111 -294 | -1716 -249 | 545 |
| 540(R) | -1612 -149 -16 | -2397 -500 -7108 | -2037 233 -8150 | -1033 43 -894 | -2897 -381 -1115 | -2352 399 -701 | -458 106 -1378 | -2365 -626 * | 665 -466 | -1520 -720 | -1051 275 | -2334 394 | -51 45 | 2602 96 | -1545 359 | -1395 117 | -2143 -369 | -2262 -294 | -2014 -249 | 546 |
| 541(Y) | 712 -149 -16 | -796 -500 -7108 | -2334 233 -8150 | -1883 43 -894 | -370 -381 -1115 | -2028 399 -701 | -986 106 -1378 | -143 -626 * | -663 -466 | -131 -720 | -1587 275 | -2243 394 | -1383 45 | -1656 96 | -1178 359 | -771 117 | 1114 -369 | -965 -294 | 3479 -249 | 547 |
| 542(T) | -527 -149 -16 | -1669 -500 -7108 | 1091 233 -8150 | -27 43 -894 | -2315 -381 -1115 | -1379 399 -701 | -443 106 -1378 | -2033 -626 * | -2081 -466 | -1218 -720 | -282 275 | 557 394 | -41 45 | -650 96 | 1128 359 | 2077 117 | -1576 -369 | -2321 -294 | -1690 -249 | 548 |
| 543(R) | -2957 -149 -16 | -3022 -506 -7108 | -3318 233 -8150 | -2735 43 -894 | -3796 -381 -1115 | -2998 399 -701 | -1968 106 -1378 | -3912 -626 * | -3631 -466 | -3157 -720 | -2611 275 | -3280 394 | -1724 45 | 4056 96 | -3026 359 | -2913 117 | -3650 -369 | -3096 -294 | -3185 -249 | 549 |
| 544(G) | -2594 -149 -16 | -2690 -500 -7108 | -3304 233 -8150 | -3623 43 -894 | -4328 -381 -1115 | 3747 399 -701 | -3462 106 -1378 | -4761 -626 * | -4671 -466 | -4212 -720 | -3320 275 | -3352 394 | -3748 45 | -3779 96 | -2839 359 | -2981 117 | -4004 -369 | -3668 -294 | -4222 -249 | 550 |
| 545(V) | -1747 -149 -16 | -1296 -500 -7108 | -4310 233 -8150 | -3948 43 -894 | -1758 -381 -1115 | -4023 399 -701 | -3716 106 -1378 | 2215 -626 * | -615 -466 | -540 -720 | -3705 275 | -3860 394 | -3670 45 | -3887 96 | -3339 359 | -1741 117 | 3087 -369 | -3252 -294 | -2806 -249 | 551 |
| 546(L) | -2871 -149 -16 | -2457 -500 -7108 | -4231 233 -8150 | -4103 43 -894 | -1033 -381 -1115 | -3803 399 -701 | -3165 106 -1378 | -541 -626 * | 3130 -466 | -31 -720 | -3935 275 | -3797 394 | -3286 45 | -3484 96 | -3713 359 | -2869 117 | -1136 -369 | -2394 -294 | -2220 -249 | 552 |
| 547(A) | 2404 -149 -16 | -890 -500 -7108 | -1926 233 -8150 | -1629 43 -894 | -1803 -381 -1115 | 1275 399 -701 | -1415 106 -1378 | -1282 -626 * | 392 -466 | -963 -720 | -1316 275 | -1930 394 | -1328 45 | -1674 96 | -654 359 | -644 117 | -952 -369 | -2187 -294 | -1810 -249 | 553 |
| 548(K) | -2620 -149 -16 | -2961 -500 -7108 | -2461 233 -8150 | -2046 43 -894 | -3743 -381 -1115 | -2791 399 -701 | -1570 106 -1378 | -3603 -626 * | -3387 -466 | -2839 -720 | -2048 275 | -3039 394 | -1260 45 | -465 96 | -2604 359 | -2536 117 | -3331 -369 | -3001 -294 | -2988 -249 | 554 |
| 549(Y) | -3621 -149 -16 | -2707 -500 -7108 | -4176 233 -8150 | -4424 43 -894 | 2950 -381 -1115 | -4049 399 -701 | -394 106 -1378 | -2539 -626 * | -1942 -466 | -1987 -720 | -2749 275 | -3933 394 | -2854 45 | -3451 96 | -3299 359 | -3499 117 | -2690 -369 | 349 -294 | 4094 -249 | 555 |

TABLE 6-continued

| | | | | | | | | | | | | | | | | | | | | | | | | |
|---|---|---|---|---|---|---|---|---|---|---|---|---|---|---|---|---|---|---|---|---|---|---|---|---|

HMMER2.0 [2.2g]      Program name and version
NAME dhad_for_hmm      Name of the input sequence alignment file
LENG 564      Length of the alignment
ALPH Amino      Type of residues
MAP yes      Map of the match states to the columns of the alignment
COM /app/public/hmmer/current/bin/hmmbuild -F dhad-exp_hmm dhad_for_hmm.aln      Commands used to generate the file: this one means that hmmbuild (default patrameters) was applied to the alignment file
COM /app/public/hmmer/current/bin/hmmcalibrate dhad-exp_hmm      Commands used to generate the file: this one means that hmmcalibrate (default parametrs) was applied to the hmm profile
NSEQ 8      Number of sequences in the alignment file
DATE Tue Jun 3 10:48:24 2008      When was the file generated
XT -8455 -4 -1000 -1000 -8455 -4 -8455 -4
NULT -4 -8455      The transition probability distribution for the null model (single G state).
NULE 595 -1558 85 338 -294 453 -1158 197 249 902 -1085 -142 -21 -313 45 531 201 384 -1998 -644      The symbol emission probability distribution for the null model (G state); consists of K (e.g 4 or 20) integers. The null probability used to convert these back to model probabilities is 1/K.
EVD -499.650970 0.086142      The extreme value distribution parameters μ and lambda respectively; both floating point values. Lambda is positive and nonzero. These values are set when the model is calibrated with hmmcalibrate.

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
| 550(A) | 3438 | -1472 | -2846 | -3040 | -3287 | -1726 | -2735 | -2840 | -3257 | -2662 | -2236 | -2447 | -2798 | -2944 | -1216 | -1387 | -2183 | -3405 | -3320 | 556 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 551(H) | -1741 | -2627 | -2070 | -1046 | -3303 | -2401 | 2713 | -2751 | -2476 | -1755 | -1061 | -2375 | -27 | 2379 | -1621 | -1497 | -2477 | -2379 | -2161 | 557 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 552(L) | -1014 | -876 | -2956 | -2408 | -582 | -2550 | -1529 | 1721 | 2042 | 345 | -2114 | -2581 | -1775 | -2028 | 454 | -980 | 286 | -1414 | -1096 | 558 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 553(V) | 933 | -842 | -2818 | -2467 | -1542 | -1870 | -1890 | 154 | -1095 | -617 | -1932 | -2326 | -1995 | -2259 | -1126 | 1070 | 2769 | -2180 | -1826 | 559 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 554(S) | -787 | -1522 | -1486 | -1172 | -2714 | -1599 | -1112 | -2500 | -2563 | -1791 | -1110 | -2067 | -796 | 1351 | 2916 | -989 | -1943 | -2648 | -2234 | 560 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 555(S) | -326 | -1010 | -1779 | -1541 | -2691 | -1234 | -1566 | -2386 | -2594 | -1749 | -1228 | 1196 | -1330 | -1747 | 2396 | 1967 | -1662 | -2876 | -2496 | 561 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 556(A) | 3121 | -934 | -2489 | -2561 | -3081 | -1203 | -2295 | -2766 | -3080 | -2234 | -1669 | -1953 | -2234 | -2533 | 936 | -746 | -1844 | -3331 | -3090 | 562 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 557(S) | -897 | -1462 | -2333 | -2543 | -3185 | -1640 | -2474 | -3294 | -3497 | -2780 | -1973 | -2360 | -2483 | -2703 | 3465 | -1316 | -2413 | -3310 | -3025 | 563 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 558(R) | -586 | -1873 | -516 | 979 | -2188 | -1543 | -123 | -1869 | -353 | -980 | -202 | -1622 | 314 | 1886 | -491 | 782 | -1495 | -2024 | -1439 | 564 |
|  | -149 | -500 | 233 | -894 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 559(G) | -2594 | -2690 | -3304 | -3623 | -4328 | 3747 | -3462 | -4761 | -4671 | -4212 | -3320 | -3352 | -3748 | -3779 | -2839 | -2981 | -4004 | -3668 | -4222 | 565 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |
| 560(C) | 2804 | 3772 | -3185 | -3198 | -2739 | -1303 | -2462 | -2065 | -2628 | -1924 | -1927 | -2044 | -2547 | -2727 | -661 | -799 | -1463 | -3099 | -2886 | 566 |
|  | -149 | -500 | 233 | 43 | -381 | 399 | 106 | -626 | -466 | -720 | 275 | 394 | 45 | 96 | 359 | 117 | -369 | -294 | -249 |  |
|  | -16 | -7108 | -8150 | -894 | -1115 | -701 | -1378 | * |  |  |  |  |  |  |  |  |  |  |  |  |

TABLE 6-continued

| HMMER2.0 [2.2g] | | Program name and version |
| NAME dhad_for_hmm | | Name of the input sequence alignment file |
| LENG 564 | | Length of the alignment: number of residues |
| ALPH Amino | | Type of residues |
| MAP yes | | Map of the match states to the columns of the alignment |
| COM /app/public/hmmer/current/bin/hmmbuild -F dhad-exp_hmm dhad_for_hmm.aln | | Commands used to generate the file: this one means that hmmbuild (default parameters) was applied to the alignment file |
| COM /app/public/hmmer/current/bin/hmmcalibrate dhad-exp_hmm | | Commands used to generate the file: this one means that hmmcalibrate (default parameters) was applied to the hmm profile |
| NSEQ 8 | | Number of sequences in the alignment file |
| DATE Tue Jun 3 10:48:24 2008 | | When was the file generated |
| XT -8455 -4 -1000 -1000 -8455 -4 -8455 -4 | | |
| NULT -4 -8455 | | The transition probability distribution for the null model (single G state). |
| NULE 595 -1558 85 338 -294 453 -1158 197 249 902 -1085 -142 -21 -313 45 531 201 384 -1998 -644 | | The symbol emission probability distribution for the null model (G state); consists of K (e.g 4 or 20) integers. The null probability used to convert these back to model probabilities is 1/K. |
| EVD -499.650970 0.086142 | | The extreme value distribution parameters μ and lambda respectively; both floating point values. Lambda is positive and nonzero. These values are set when the model is calibrated with hmmcalibrate. |

| HMM | A m->m | C m->i | D m->d | E i->m | F i->i | G d->m | H d->d | I b->m | L | M | N | P | Q | R | S | T | V | W | Y | Position in alignment |
|---|---|---|---|---|---|---|---|---|---|---|---|---|---|---|---|---|---|---|---|---|
|  | -149 | -500 | 233 | 43 | -381 | 399 | 106 | -626 | -466 | -720 | 275 | 394 | 45 | 96 | 359 | 117 | -369 | -294 | -249 | |
|  | -16 | -7108 | -8150 | -894 | -1115 | -701 | -1378 | * | | | | | | | | | | | | |
| 561(V) | -1771 | -1603 | -3750 | -3689 | -2037 | -3050 | -3231 | 403 | -1154 | -1076 | -3245 | -3399 | -3383 | -3437 | -2528 | -1917 | 3536 | -3074 | -2677 | 567 |
| 562(T) | -1213 | -1674 | -2755 | -2906 | -3163 | -1922 | -2659 | -2698 | -3105 | -2612 | -2311 | -2600 | -2708 | -2753 | -1463 | 3819 | -2197 | -3286 | -3156 | 568 |
|  | -149 | -500 | 233 | 43 | -381 | 399 | 106 | -626 | -466 | -720 | 275 | 394 | 45 | 96 | 359 | 117 | -369 | -294 | -249 | |
|  | -16 | -7108 | -8150 | -894 | -1115 | -701 | -1378 | * | | | | | | | | | | | | |
| 563(D) | -2784 | -3432 | 4016 | -1200 | -4140 | -2466 | -2197 | -4505 | -4365 | -3956 | -1551 | -3014 | -2039 | -3232 | -2593 | -2938 | -4046 | -3710 | -3552 | 569 |
|  | -149 | -500 | 233 | 43 | -381 | 399 | 106 | -626 | -466 | -720 | 275 | 394 | 45 | 96 | 359 | 117 | -369 | -294 | -249 | |
|  | -21 | -6715 | -7757 | -894 | -1115 | -701 | -1378 | * | | | | | | | | | | | | |
| 564(F) | -525 | -445 | -2202 | -1627 | 1946 | -2001 | -744 | 1247 | 952 | 561 | 1079 | -2030 | -1067 | -1362 | -1067 | -465 | 338 | -714 | -230 | 570 |
|  | * | * | * | * | * | * | * | * | * | * | * | * | * | * | * | * | * | * | * | |
|  | * | * | * | * | * | * | * | * | | | | | | | | | | | | |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10287566B2). An electronic copy of the "Sequence Listing" will also be available from the USPTO upon request and payment of the fee set forth in 37 CFR 1.19(b)(3).

What is claimed is:

1. A method for the production of isobutanol comprising
   (a) providing a recombinant host cell that comprises
      (i) an isolated polypeptide having dihydroxy-acid dehydratase (DHAD) activity, wherein the polypeptide is at least 95% identical to a *Streptococcus mutans* DHAD of SEQ ID NO: 168 and comprises amino acid substitutions at position 33 and position 563, and
      (ii) an isobutanol biosynthetic pathway, wherein the isobutanol biosynthetic pathway comprises the following substrate to product conversions:
         (1) pyruvate to acetolactate catalyzed by an acetolactate synthase,
         (2) acetolactate to 2,3-dihydroxyisovalerate catalyzed by a ketol-acid reductoisomerase,
         (3) 2,3-dihydroxyisovalerate to α-ketoisovalerate catalyzed by DHAD,
         (4) α-ketoisovalerate to isobutyraldehyde catalyzed by an α-keto acid decarboxylase, and
         (5) isobutyraldehyde to isobutanol catalyzed by an alcohol dehydrogenase;
   (b) culturing the recombinant host cell in a fermentation medium under suitable conditions to produce isobutanol; and
   (c) recovering the isobutanol.

2. The method of claim 1, wherein the recombinant host cell is a bacterial cell or a yeast cell.

3. The method of claim 2, wherein the bacterial cell is a member of a genus of bacteria selected from *Clostridium, Zymomonas, Escherichia, Salmonella, Rhodococcus, Pseudomonas, Bacillus, Lactobacillus, Enterococcus, Pediococcus, Alcaligenes, Klebsiella, Paenibacillus, Arthrobacter, Corynebacterium, Brevibacterium, Lactococcus, Leuconostoc, Oenococcus, Pediococcus*, and *Streptococcus*.

4. The method of claim 2, wherein the yeast cell is a member of a genus of yeast selected from *Saccharomyces, Schizosaccharomyces, Hansenula, Kluyveromyces, Candida, Pichia*, and *Yarrowia*.

5. The method of claim 1, wherein the recovering is by distillation, liquid-liquid extraction, adsorption, gas stripping, decantation, membrane evaporation, pervaporation, or combinations thereof.

6. The method of claim 5, wherein the recovering is by liquid-liquid extraction and the extractant is derived from biomass.

7. The method of claim 1, further comprising removing solids from the fermentation medium.

8. The method of claim 7, wherein the removing is by centrifugation, filtration, decantation, or combinations thereof.

9. The method of claim 7, wherein the removing occurs before the recovering.

10. The method of claim 1, wherein the recombinant host cell comprises the polypeptide of SEQ ID NO: 534.

11. The method of claim 1, wherein the recombinant host cell further comprises a disruption in an endogenous gene that encodes a mitochrondrial DHAD.

12. The method of claim 1, wherein the recombinant host cell further comprises a disruption in one or more endogenous genes affecting iron-sulfur cluster biosynthesis selected from FRA2, GRX3, and GRX4.

13. The method of claim 1, wherein the recombinant host cell has been further genetically engineered to upregulate the activity of at least one gene selected from AFT1 and AFT2.

14. The method of claim 1, wherein the recombinant host cell has been further genetically modified to disrupt a gene encoding pyruvate decarboxylase (PDC).

* * * * *